US008093008B2

(12) United States Patent
Murphy et al.

(10) Patent No.: US 8,093,008 B2
(45) Date of Patent: *Jan. 10, 2012

(54) CHARACTERIZATION OF GRANULOCYTIC EHRLICHIA AND METHODS OF USE

(75) Inventors: Cheryl Murphy, Hopkinton, MA (US); James Storey, Lynwood, MA (US); Gerald A. Beltz, Lexington, MA (US); Richard T. Coughlin, Portland, ME (US)

(73) Assignee: Antigenics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/859,236

(22) Filed: Aug. 18, 2010

(65) Prior Publication Data

US 2011/0045605 A1 Feb. 24, 2011

Related U.S. Application Data

(62) Division of application No. 09/792,957, filed on Feb. 26, 2001, now Pat. No. 7,863,434, which is a division of application No. 09/066,046, filed on Apr. 24, 1998, now Pat. No. 6,204,252.

(60) Provisional application No. 60/044,933, filed on Apr. 25, 1997.

(51) Int. Cl.
*G01N 33/53* (2006.01)
*A61K 39/02* (2006.01)
*A61K 39/00* (2006.01)

(52) U.S. Cl. .................... 435/7.1; 424/184.1; 424/185.1; 424/190.1; 435/7.2; 435/243; 530/300; 530/350

(58) Field of Classification Search ................... 424/9.1, 424/9.2, 184.1; 435/243, 252.1; 530/300, 530/350
See application file for complete search history.

(56) References Cited

U.S. PATENT DOCUMENTS

| | | | |
|---|---|---|---|
| 5,976,860 | A | 11/1999 | Coughlin et al. |
| 6,204,252 | B1 | 3/2001 | Murphy et al. |
| 6,207,169 | B1 | 3/2001 | Reed et al. |
| 6,231,869 | B1 | 5/2001 | Reed et al. |
| 6,277,381 | B1 | 8/2001 | Reed et al. |
| 6,284,238 | B1 | 9/2001 | Coughlin et al. |
| 6,306,394 | B1 | 10/2001 | Murphy et al. |
| 6,306,402 | B1 | 10/2001 | Reed et al. |

FOREIGN PATENT DOCUMENTS

| | | |
|---|---|---|
| WO | WO 96/39484 | 12/1996 |
| WO | WO 97/45540 | 12/1997 |
| WO | WO 98/14584 | 4/1998 |
| WO | WO 98/42740 | 10/1998 |
| WO | WO 00/00615 | 1/2000 |
| WO | WO 00/06744 | 2/2000 |

OTHER PUBLICATIONS

Anacker et al., 1987, "Neutralizing Activity of Monoclonal Antibodies to Heat-Sensitive and Heat-Resistant Epitopes of *Rickettsia rickettsii* Surface Proteins", Infect. Immun. 55:825-827.
Chen et al., 1994, "Identification of a Granulocytotropic *Ehrlichia* Species as the Etiologic Agent of Human Disease", J. Clin. Microbiol. 32:589-595.
Coughlin et al., 1995, "Protection of Dogs from Lyme Disease with a Vaccine Containing Outer Surface Protein (Osp) A, OspB, and the Saponin Adjuvant QS21", J. Infect. Dis. 171:1049-1052.
Dasch et al., 1984, "Approaches to Subunit Vaccines Against the Typhus Rickettsiae *Rickettsia typhii* and *Rickettsia prowazekii*", in: Microbiology, D. Schlessinger, ed., American Society for Microbiology, Washington, D.C., pp. 251-256.
Dumler et al., 1995, "Serologic Cross-Reactions Among *Ehrlichia equi*, *Ehrlichia phagocytophila*, and Human Granulocytic Ehrlichia", J. Clin. Microbiol. 33:1098-1103.
Dumler et al., 1991, "Identification of Ehrlichia in Human Tissue", N. Engl. J. Med. 325:1109-1110.
Eremeeva et al., 1994, "Differentiation Among Spotted Fever Group Rickettsiae Species by Analysis of Restriction Fragment Length Polymorphism of PCR-Amplified DNA", J. Clin. Microbiol. 32:803-810.
Goodman et al., 1996, "Direct Cultivation of the Causative Agent of Human Granulocytic Ehrlichiosis", N. Engl. J. Med. 334:209-215.
Mahan et al., 1994, "Molecular Cloning of a Gene Encoding the Immunogenic 21 kDa Protein of *Cowdria ruminantium*", Microbiol. 140:2135-2142.
Palmer et al., 1994, "The Immunoprotective *Anaplasma marginale* Major Surface Protein 2 is Encoded by a Polymorphic Multigene Family", Infect. Immun. 62:3808-3816. Ristic and Huxsoll, 1984, "Tribe II. Ehrlichieae Philip 1957, 948 *AL*", Bergey's Manual of Systemic Bacteriology, vol. 1, Krieg et al. Eds., Williams & Wilkins, pp. 704-709.
Spencer et al., 1984, "Nucleotide Sequence of the *sucB* Gene Encoding the Dihydrolipoamide Succinyltransferase of *Escherichia coli* K12 and Homology with the Corresponding Acetyltransferase", Eur. J. Biochem. 141:361-374.

(Continued)

*Primary Examiner* — Rodney P. Swartz

(74) *Attorney, Agent, or Firm* — Wolf, Greenfield & Sacks, P.C.

(57) ABSTRACT

The present invention relates, in general, to granulocytic ehrlichia (GE) proteins. In particular, the present invention relates to nucleic acid molecules coding for GE S2, S7, S22, S23, C6.1, C6.2, S11, E8, E46#1, and E46#2 proteins; purified GE S2, S7, S22, S23, C6.1, C6.2, S11, E8, E46#1, and E46#2 proteins and polypeptides; recombinant nucleic acid molecules; cells containing the recombinant nucleic acid molecules; antibodies having binding affinity specifically to GE S2, S7, S22, S23, C6.1, C6.2, S11, E8, E46#1, and E46#2 proteins and polypeptides; hybridomas containing the antibodies; nucleic acid probes for the detection of nucleic acids encoding GE S2, S7, S22, S23, C6.1, C6.2, S11, E8, E46#1, and E46#2 proteins; a method of detecting nucleic acids encoding GE S2, S7, S22, S23, C6.1, C6.2, S11, E8, E46#1, and E46#2 proteins or polypeptides in a sample; kits containing nucleic acid probes or antibodies; bioassays using the nucleic acid sequence, protein or antibodies of this invention to diagnose, assess, or prognose a mammal afflicted with ehrlichiosis; therapeutic uses, specifically vaccines comprising S2, S7, S22, S23, C6.1, C6.2, S11, E8, E46#1, and E46#2 proteins or polypeptides or nucleic acids; and methods of preventing or inhibiting ehrlichiosis in an animal.

15 Claims, 72 Drawing Sheets

OTHER PUBLICATIONS

Sumner et al., 1995, "Protection of Guinea-Pigs from Experimental Rocky Mountain Spotted Fever by Immunization with Baculovirus-Expressed *Rickettsia rickettsii* rOmpA Protein", Vaccine 13:29-35.

Tebele et al., 1991, "Induction of Protective Immunity by Using *Anaplasma marginale* Initial Body Membranes", Infect. Immun. 59:3199-3204.

VanVliet et al., 1994, "Molecular Cloning, Sequence Analysis, and Expression of the Gene Encoding the Immunodominant 32-Kilodalton Protein of *Cowdria ruminantium*", Infect. Immun. 62:1451-1456.

Wren, 1991, "A Family of Clostridial and Streptococcal Ligand-Binding Proteins with Conserved C-Terminal Repeat Sequences", Mol. Microbiol. 5:797-803.

Yu et al., 1996, "The Recombinant 120-Kilodalton Protein of *Ehrlichia chaffeensis*, a Potential Diagnostic Tool", J. Clin. Microbiol. 34:2853-2855.

BLAST comparison of SEQ ID Nos. 4, 6, 2, 8, 21, 22, 39, 27, 29 and 30 in U.S. Appl. No. 09/792,957 with SEQ ID No. 8 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 9 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 10 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 11 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 12 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 13 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 14 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 23 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 24 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 25 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 26 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 27 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 28 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 29 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 30 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 32 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 33 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 35 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 37 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 38 in U.S. Patent No. 6,231,869.

BLAST comparison of SEQ ID Nos. 4, 6, 2, 8, 21, 22, 39, 27, 29 and 30 in U.S. Appl. No. 09/792,957 with SEQ ID No. 50 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 51 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 52 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 53 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 54 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 55 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 56 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 57 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 58 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 59 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 60 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 61 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 62 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 63 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 64 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 65 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 66 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 67 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 68 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 69 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 70 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 71 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 72 in U.S. Patent No. 6,207,169.

BLAST comparison of SEQ ID Nos. 4, 6, 2, 8, 21, 22, 39, 27, 29 and 30 in U.S. Appl. No. 09/792,957 with SEQ ID No. 73 in U.S. Patent No. 6,207,169.

Asanovich et al., "Partial characterization of cloned genes encoding immunoreactive proteins of *Ehrlichia equi* and the agent of human granulocytic ehrlichiosis (HGE)," 96th General Meeting of the American Society for Microbiology, New Orleans, LA; May 19-23, 1996, p. 22.

Caturegli et al., "Cloning and characterization of an ankyrin-like protein antigen gene from the agent of human granulocytic ehrlichiosis," Database Genbank; Accession No. AF047896, Mar. 31, 1998.

Storey et al., "Molecular cloning and sequencing of three granulocytic *Ehrlichia* genes encoding high-molecular-weight immunoreactive proteins," Infect Immun. Apr. 1998;66(4):1356-1363.

International Search Report for International Application No. PCT/US98/08265.

Office Action mailed Nov. 2, 1999 in U.S. Appl. No. 09/066,046.
Office Action mailed Nov. 3, 1999 in U.S. Appl. No. 09/066,047.
Office Action mailed Sep. 21, 2000 in U.S. Appl. No. 09/066,047.
Office Action mailed Aug. 20, 1996 in U.S. Appl. No. 08/470,358.
Office Action mailed May 28, 1997 in U.S. Appl. No. 08/470,358.
Office Action mailed Dec. 8, 1999 in U.S. Appl. No. 08/470,358.
Office Action mailed Aug. 30, 2000 in U.S. Appl. No. 08/470,358.

Rikihisa Y. "Protection against murine potomac horse fever by an inactivated Ehrlichia risticii vaccine," Vet Microbiol. May 1991;27(3-4):339-350.

Rikihisa Y. et al., "Analyses of Ehrlichia canis and a canine granulocytic Ehrlichia infection," J Clin Microbiol. Jan. 1992;30(1):143-148.

Office Action mailed Jul. 14, 2006 in U.S. Appl. No. 09/792,957.
Office Action mailed Jan. 25, 2007 in U.S. Appl. No. 09/792,957.
Office Action mailed Sep. 11, 2007 in U.S. Appl. No. 09/792,957.
Office Action mailed Sep. 28, 2007 in U.S. Appl. No. 09/792,957.
Office Action mailed Mar. 24, 2008 in U.S. Appl. No. 09/792,957.
Office Action mailed Sep. 25, 2008 in U.S. Appl. No. 09/792,957.
Office Action mailed Mar. 17, 2009 in U.S. Appl. No. 09/792,957.

Alleman et al., 1997, Anaplasma marginale Major Surface Protein 3 Is Encoded by a Polymorphic, Multigene Family, Infection and Immunity, 65(1): 156-163.

Anderson et al., 1991, *Ehrlichia chaffeensis*, a New Species Associated with Human Ehrlichiosis, Journal of Clinical Microbiology, 29(12):2838-2842.

Asanovich et al., 1997, Antigenic Diversity of Granulocytic Ehrlichia Isolates from Humans in Wisconsin and New York and a Horse in California, The Journal of Infectious Diseases, 176:1029-1034.

Chen et al., 1994, Identification of a Granulocytotropic Ehrlichia Species as the Etiologic Agent of Human Disease, Journal of Clinical Microbiology, 32(3):589-595.

Dumler et al., 1995, Serologic Cross-Reactions among *Ehrlichia equi*, *Ehrlichia phagocytophila*, and Human Granulocytic Ehrlichia, Journal of Clinical Microbiology, 33(5):1098-1103.

Eid et al., 1996, Expression of Major Surface Protein 2 Antigenic Variants during Acute Anaplasma marginale Rickettsemia, Infection and Immunity, 64(3):836-841.

Kolbert et al., 1997, Characterization of an Immunoreactive Protein from the agent of Human Granulocytic Ehrlichiosis, Journal of Clinical Microbiology, 35(5):1172-1178.

Magnarelli et al., 1995, Coexistance of Antibodies to Tick-Borne Pathogens of Babesiosis, Erhlichiosis, and Lyme Borreliosis in Human Sera, Journal of Clinical Microbiology, 33(11):3054-3057.

Murphy et al., 1998, Major Antigenic Proteins of the Agent of Human Granulocytic Ehrlichiosis Are Encoded by Members of a Multigene Family, Infection and Immunity, 66(8):3711-3718.

Nicholson et al., 1997, An Indirect Immunofluorescence Assay Using a Cell Culture-Derived Antigen for Detection of Antibodies to the Agent of Human Granulocytic Ehrlichiosis, 35(6):1510-1516.

Ohashi et al., 1998, Immunodominant Major Outer Membrane Proteins of *Ehrlichia chaffeensis* Are Encoded by a Polymorphic Multigene Family, Infection and Immunity, 66(1):132-139.

Palmer et al., 1994, The Immunoprotective Anaplasma marginal Major Surface Protein 2 is Encoded by a Polymorphic Multigene Family, Infetion and Immunity, 62(9):3808-3816.

Storey et al., 1998, Molecular Cloning and Sequencing of Three Granulocytic Ehrlichia Genes Enclding High-Molecular-Weight Immunoreactive Proteins, 66(4):1356-1363.

Sumner et al., 1997, PRC Amplification and Comparison of Nucleotide Sequences from the groESL Heat Shock Operon of Ehrlichia Species, Journal of Clinical Microbiology, 35(8):2087-2092.

Yeh et al., 1997, Serologic and Molecular Detection of Granulocytic Ehrlichiosis in Rhode Island, Journal of Clinical Microbiology, 35(4):944-947.

Yu et al., 1996, The Recombinant 120-Kilodalton Protein of *Ehrlichia chaffeensis*, a Potential Diagnostic Tool, Journal of Clinical Microbiology, 34(11):2853-2855.

Yu et al., 1997, Cloning and sequencing of the gene for a 120-kDa immunodominant protein of *Ehrlichia chaffeensis*, Gene, 184:149-154.

Wong et al., 1997, Serological Responses to *Ehrlichia equi*, *Ehrlichia chaffeensis*, and *Borrelia burgdorferi* in Patients from New York State, Journal of Clinical Microbiology, 35(9):2198-2205.

Zhi et al., 1997, Comparison of Major Antigenic Proteins of Six Strains of the Human Granulocytic Ehrlichiosis Agent by Western Immunoblot Analysis, Journal of Clinical Microbiology, 35(10):2606-2611.

```
   1 GAATTCCTTA CCTCCCTATA TTTCGTACAG GTTATTTCGC AGTCTAGCTA TGATGCTTTA
  61 CCAGGATACG TTAAACGTTG ACGTTCTACG CTGTCATAGC CTTTTATTCT GCAAAAATAG
 121 CTTAACTGTG TCACTTCCTG AGAAAGTAAG ATACATATTT AGTTTTTGCA CAGCCAAAAA
 181 ACTTCTAGTG AACTGTGGTT TCTCTGGAAT CAATAACCTG GGTTTCGCCT GTGCGTTCTA
 241 TAACAATCTA CAGCTGTGGT TATTAGGCGT GGTTTCGCCT GATAATAAAG ATACTTTAGA
 301 GGGTATAAAC TTGGAAAAAA TAATGAAAAA CCCTCCTTAG TGCCTCCCCG TTTTTGACAA
 361 CATACTCTTA TGGAAAAGCG TTAGGGAGTT GCTTCGCTTG TCACGCGTGC GTTAGGTTTT
 421 ACGTATACGT GTCTGGGACT TCACGAAAAC TCGACGCAGG CGGATTTTGT ACTATGTTTC
 481 ACTTAACAAG GTATTATAAA TGTTTGAACA GATACATACA CAGGAACAAC
 541 TGCAGAAGGT TCTCCTGGCT TAGCAGGCGG GGATTTTAGC TTAAGTTCTA TTGACTTTAC
 601 AAGGGACTTT ACAATTGAAT CACATAGAGG AAGCTCAGCT GATGACCCAG GTTACATCAG
 661 CTTTAGGGAT CAAGACGGAA ACGTCATGTC ACGTTTTCTT GATGTGTACG TAGCTAATTT
 721 CAGCTTGCGA TGCAAGCATT CTCCCTATAA CAACGACAGA ATGGAAACAG CTGGCTTCTC
 781 TCTAACTCCC GACATAATAG AGCCTTTCTG TTTATTGCAA GAATCACATA GTACACAAAA
 841 CAATGTAGAA GAGGCAGTAC AAGTTACACG TCTTGAGTGC CCTCCATGTA ATCCAGTCCC
 901 TGCCGAGGAA GTAGCTCCTC AACCGTCTTT TCTAAGCAGA ATAATTCAGG CGTTCTTGTG
 961 GTTATTCACG CCTTCTTCTA CTACCGACAC TGCTGAAGAC AGCAAGTGTA ATAGTAGCGA
1021 TACTTCAAAA TGTACCTCTG CTAGCAGTGA GTCATTAGAG CAGCAACAAG AATCAGTGGA
1081 AGTGCAACCA TCTGTACTTA TGTCTACTGC CCCTATAGCA ACAGACCCTC AAAATGCGGT
1141 TGTTAACCAA GTAAACACTA CTGCAGTACA AGTAGAATCA TCCATTATTG TGCCAGAATC
1201 GCAACACACT GACGTTACCG TGCTCGAAGA TACTACTGAG ACGATAACTG TTGATGGGGA
1261 ATATGGACAT TTTAGTGACA TTGCTTCCAG TGAACACAAT AACGATCTGC CTGCCATGTT
1321 GTTAGATGAA GCAGACTTCA CTATGTTATT AGCGAACGAG GAGTCAAAGA CCCTGGAGTC
1381 TATGCCTTCT GATAGCCTAG AAGACAATGT TCAGGAACTA GGTACATTGC CTTTACAAGA
1441 AGGTGAAACA GTTTCTGAGG GCAACACACG AGAGTCACTA CCCACTGACG TTTCACAAGA
1501 CTCAGTTGGT GTAAGTACAG ATCTTGAAGC TCATTCTCAA GAAGTTGAAA CAGTTTCTGA
1561 GGTCAGCACA CAAGATTCAC TATCCACTAA CATTTCACAA GACTCCAGTTG GTGTAAGTAC
```

FIG. 4A

```
1621  AGATCTTGAA  GCTCATTCTA  AAGGAGTTGA  AATAGTTTCT  GAGGGCGGCA  CACAAGATTC
1681  ACTATCCGCT  GATTTTCCAA  TAAACACAGT  TGAAAGTGAA  AGTACAGATC  TTGAAGCTCA
1741  TTCTCAAGAA  GTTGAAACTG  TTTCTGAATT  CACACAAGAT  TCACTATCCA  CTAACATTTC
1801  ACAAGACTCA  GTTGGTGTAA  GTACAGATCT  TGAAGTTCAT  TCTCAAGAAG  TTGAAATAGT
1861  TTCTGAGGGC  GGCACACAAG  ATTCACTATC  CACTAACATT  CACAAGACT   CAGTTGGTGT
1921  AAGTACAGAT  CTTGAAGCTC  ATTCTCAAGA  AGTTGAAACT  GTTTCTGAAT  TCACACAAGA
1981  TTCACTATCC  ACTAACATTT  CACAAGACTC  AGTTGGTGTA  AGTACAGATC  TTGAAGTTCA
2041  TTCTCAAGAA  GTTGAAATAG  TTTCTGAGGG  CGGCACACAA  GATTCACTAT  CCACTAACAT
2101  TTCACAAGAC  TCAGTTGGTG  TAAGTACAGA  TCTTGAAGCT  CATTCTAAAG  GAGTTGAAAT
2161  AGTTTCTGAG  GGCGGCACAC  AAGATTCACT  ATCCGCTGAT  TTTCCAATAA  ACACAGTTGA
2221  AAGTGAAAGT  ACAGATCTTG  AAGCTCATTC  CCCAGAAGGT  GAAATAGTTT  CTGAGGTCAG
2281  CACACAAGAT  GCGCCATCCA  CTGGAGTAGA  GATCAGATTT  ATGGATCGTG  ATTCTGATGA
2341  TGACGTGCTC  GCGTTGTGAA  GTGATCATGG  TAGGGGAAAC  AGTTATGGCG  TAAAGACATC
2401  TTTGATGACT  TGTCTTTGCGT  GAATAAGTAG  TGCAAGTTTT  TTATGCATTG  AGTGCATGA
2461  TCATTGCCCC  TAAGAAAAGC  AGTACTAATG  GTAGTCTAAG  ATCTTATACA  GGGTTTCGGA
2521  CTACCACTTT  TGGTGTTTTA  AAACGTCTTA  TTCGCGTTGG  GTGCTTGCTT  ACAATGTACC
2581  TGTACGTGCC  CAACACTAAA  AATGGTCAGT  ATTACTTAGG  GGAGTTCGTA  GACGAGGCAT
2641  CTCGATTTAC  TCTAAGTAAG  CTACAAATAA  CTCAGTCATA  TCAAGGTAGT  TCAAGATGAA
2701  AGCAGTGCTA  TGCTTATCAT  GGAGAATTCC  TGCGGTTCTC  TTCAAAATTC  TCTTTTCCCG
2761  CAAGGGCAGA  CTCTTATTTG  TTAAAATAAC  AAAATTTCTC  TACAGGAAGC  GACATTTCAT
2821  ATCAAAGCTG  ATTGTGAAAT  AATGGCATTG  AGTATTTTTC  TCGCCCTAGA  AGATAATCAT
2881  TTCGGCACTA  TCAAAGCATT  TACGATATTC  TCCATTATCT  TGTAATCAGA  TGGCTATCTT
2941  GAAAGCAACC  AAGGATATCC  GTACATGGTA  GCTTACATAC  TGCTATCAAT  CTCCTATACG
3001  ACCTTCAATG  AAACGGTAAC  TGTTGCTGAC  AGCTTGCACA  TGCTGTGATT  CAATTCCTGG
3061  TTCCTAGATG  TTCTACTACG  TTTATCCGGT  ACTAATATTA  TTCTTTGGCG  CTCTATTATC
3121  TAGCAACTCA  GAGTCCATTA  GGAATTC    (SEQ ID NO:1)
```

FIG. 4B

```
  1  MFEHNIPDTY TGTTAEGSPG LAGGDFSLSS IDFTRDFTIE SHRGSSADDP GYISFRDQDG
 61  NVMSRFLDVY VANFSLRCKH SPYNNDRMET AAFSLTPDII EPSALLQESH STQNNVEEAV
121  QVTALECPPC NPVPAEEVAP QPSFLSRIIQ AFLWLFTPSS TTDTAEDSKC NSSDTSKCTS
181  ASSESLEQQQ ESVEVQPSVL MSTAPIATEP QNAVVNQVNT TAVQVESSII VPESQHTDVT
241  VLEDTTETIT VDGEYGHFSD IASGEHNNDL PAMLLDEADF TMLLANEESK TLESMPSDSL
301  EDNVQELGTL PLQEGETVSE GNTRESLPTD VSQDSVGVST DLEAHSQEVE TVSEVSTQDS
361  LSTNISQDSV GVSTDLEAHS KGVEIVSEGG TQDSLSADFP INTVESESTD LEAHSQEVET
421  VSEFTQDSLS TNISQDSVGV STDLEVHSQE VEIVSEGGTQ DSLSTNISQD SVGVSTDLEA
481  HSQEVETVSE FTQDSLSTNI SQDSVGVSTD LEVHSQEVEI VSEGGTQDSL STNISQDSVG
541  VSTDLEAHSK GVEIVSEGGT QDSLSADFPI NTVESESTDL EAHSPEGEIV SEVSTQDAPS
601  TGVEIRFMDR DSDDDVLAL (SEQ ID NO:2)
```

FIG. 5A

```
  1   TCGACGCAGGGCGGATTTGTACTATGTTCACTTAACAAGGTATTATAAATGTTTGAACA
                                                            M  F  E  H

61   CAATATTCCTGATACATACAGGAACAACTGCAGAAGGTTCTCCTGGCTTAGCAGGCGG
       N  I  P  D  T  Y  T  G  T  T  A  E  G  S  P  G  L  A  G  G

121   GGATTTTAGCTTAAGTTCTATTGACTTTACAAGGGACTTTACAATTGAATCACATAGAG
       D  F  S  L  S  S  I  D  F  T  R  D  F  T  I  E  S  H  R  G

181   AAGCTCAGCTGATGACCCAGGTTACATCAGTTTAGGGATCAAGACGGAAACGTCATGTC
       S  S  A  D  D  P  G  Y  I  S  F  R  D  Q  D  G  N  V  M  S

241   ACGTTTCTTGATGTGTACGTAGCTAATTCAGCTTGCGATGCAAGCATTCTCCTATAA
       R  F  L  D  V  V  A  N  F  S  L  R  C  K  H  S  P  Y  N

301   CAACGACAGAATGGAAACAGCTGCGTTCTCTCTAACTCCGACATAATAGAGCCTTCTGC
       N  D  R  M  E  T  A  A  F  S  L  T  P  D  I  I  E  P  S  A

361   TTTATTGCAAGAATCACATAGTACACAAAACATGTAGAAGAGCAGTACAAGTACAGC
       L  L  Q  E  S  H  S  T  Q  N  N  V  E  A  V  Q  V  T  A

421   TCTTGAGTGCCCTCCTAATCCAGTCCCTGCCGAGAAGTAGCCCTTCTTCAACCGTCTTT
       L  E  C  P  P  C  N  P  V  P  A  E  E  V  A  P  Q  P  S  F

481   TCTAAGCAGAATAATTCAGGCGTTCTGTGGTTATTCAGGCCCTTCTTCTACTACCGACAC
       L  S  R  I  Q  A  F  L  W  L  F  T  P  S  S  T  T  D  T

541   TGCTGAAGACAGCAAGTGTAATAGTAGCGATCTTCAAATGTACCTCTGCTAGCAGTGA
       A  E  D  S  K  C  N  S  S  D  T  S  K  C  T  S  A  S  S  E

601   GTCATTAGAGCAGCAACAACAAGAATCAGTGGAAGTGCAACCATCTGTACTTATGTCTACTGC
       S  L  E  Q  Q  Q  E  S  V  E  V  Q  P  S  V  L  M  S  T  A

661   CCCTATAGCAACAGAGCCTCAAAATGCGGTTGTTAACCAAGTAAACACTACTGCAGTACA
       P  I  A  T  E  P  Q  N  A  V  V  N  Q  V  N  T  T  A  V  Q

721   AGTAGAATCATCCATTATTGTGCCAGAATCGCAACACTGACGTTACCGTGTCGAAGA
       V  E  S  S  I  I  V  P  E  S  Q  H  T  D  V  T  V  L  E  D

781   TACTACTGAGACGATAACTGTTGATGGGAATAACATTTTAGTGACATTTGACATTGCTTCAGG
       T  T  E  T  I  T  V  D  G  E  Y  G  H  F  S  D  I  A  S  G
```

```
1681  TCTTGAAGCTCATTCTAAAGGAGTTGAAATAGTTTCTGAGGGCACACAAGATTCACT
        L  E  A  H  S  K  G  V  E  I  V  S  E  G  G  T  Q  D  S  L
1741  ATCCGCTGATTTCCAATAAACACAGTTGAAAGTACAGATCTTGAAGCTCATTC
        S  A  D  F  P  I  N  T  V  E  S  T  D  L  E  A  H  S
1801  CCCAGAAGGTGAAATAGTTTCTGAGGTCAGCACACAAGATGCCATCCACTGGAGTAGA
        P  E  G  E  I  V  S  E  V  S  T  Q  D  A  P  S  T  G  V  E
1861  GATCAGATTTATGGATCGTGATTCTGATGATGACGTGCTCGCGTTGTGAAGTGATCATGG
        I  R  F  M  D  R  D  S  D  D  D  V  L  A  L
1921  TAGGGAAA
```

FIG. 5B-3

```
   1 GGATCCCCCG GGCTGCAGGA ATTCCTAAAA AGATCTGGCG CCTGAGCGTC TGCTACAGGC
  61 AGATTGTGCG CGCTAAGATA GGTTTAGTAA GACGTGTTTT TTATTGAATA AAGGCCCCAA
 121 CAATGTTGAC AGAAGAAGAA AAGAAAAAGA GCGCCGGTGC TCTGCAAGCC ATTATCACAG
 181 GAGATTACGA GAGTGTTCAG GCGTCCGTTC AGGGAATTTC TTCCGAAGAC TTAATACTCC
 241 CGTTGATTAT GAGGGAGAA CACTACTGCA CTATGCAGCT TCATCCCGTA ATGGTAATTT
 301 CTATGGCATT CTGGTTGAAA GAGGATGTGT TACTAATATC AGAGATGCTT ATGGATTTAC
 361 TCCAGAACAA GCACGTGAGA AGGCAGGGTA TGCACGCACA CAGTGGTATG GAGCAGATGT
 421 AAATGACCCT GGTGTATCTA GGCAGTTAAT GACGCAAGCT GTTCAGCAGT CTGGAAAGG
 481 TAACATGTAT GCTGCTCTCG CTATATTAGA CCTTGTGCGT AATGACGATG CAAAACATTC
 541 AGGTCAATGA GGAAAGGGGC ATAGTGTTTT GCATCTAGCA TGTATTGAAG GCAGTAATCC
 601 ATCTTTCACT TCATCCCCTA TGCTAAAGGG TTGTTCTTTA AACATTAAGG ATGTAGATGG
 661 TAATACGCCA TTACATAGAG CTGCGTTTTC AGTAGGCAAA AATGCTTTAG GCAATCTTGA
 721 TGTACTATGC GACAAGCTCT TATAGCAGAT GTTAATGCTA AGGGACCGGG TGGAAACACT
 781 CCGCTTCATA TTGCTACGGA GCGTATGGCT CACCAGAAAG TAGAGCATCT TCTCTCAAGG
 841 TTAAGTGATA TTAGCGTTGC AAATCGATGC TGGTGAAACC GTTGCCACA TTGTTGCAAA
 901 GCAATGGCCA AGGCGGGATG TTTTACCATA ATGCAAGAAG CGGTGTCGTC
 961 AAATATTGAG GCAATGCGCG AGTGTGCAGA CATTGACAAG TTCCCGGATA AAAAGGGAT
1021 GAGTGCAGTA CAGTATGCTA TTAGAAGGCA TATACCGGAG CTGAGAAGAT CTTCGAGAAG
1081 GCCATTAACA AGTGTATGGC TTAGCTTTCTT CAGAAGTAGA ATCTCTCTTT
1141 ACATGTCCTA ATCCAGAGGA CGCATCAACG CTGGTGCATT TTGTATCTTC TAATGGGACC
1201 CCAAATTTTG ATTCTCTTGC GAAAAGGGTA TTGGAGGAAG CATATCATAG GTATGGAGAG
1261 AAACCTTTTA CTAATTTAGA TGTTGCAGGT AATGCACCTA TACATGCTGC AGCACAAAAA
1321 TCAACAGTGG GGGTTTTTGA GCAGGGGTA AGATACACTC CTGAGTCTGT TGTAAACTCA
1381 ATTAGCACCG AATGGCAAAG CGCCTATTCA CATGATAGTT GAGGATGAGC CAAGCCATAA
1441 AAGCGTAAGC ATTAAATTGC AGATGTTGAT TGGGAATGTG CGTAATATTC CATCAATCAA
1501 TGTACCATCC CCAGTGACAG GTGAAACGCT GCGGTAGCTG CGTATAAAGG GGCAACACT
```

FIG. 6A

| | | | | |
|---|---|---|---|---|
| 1561 | GAGGATGTTA | AGACTATGTT | ACGCTGTAAT | AGCATGGACG | TAGATGCTCG | GTCACATGAT |
| 1621 | GGTAGAACTA | TAATACATTA | CGCAGCAAAG | GATGGAAATT | TAGAGATATT | GCAGCAGGCT |
| 1681 | CTTGGAAGGA | AGAGTAGTTA | TTCTAAGTTT | CCTGTAAAGG | ATGGTGTTCC | TACTCCAGGT |
| 1741 | GTATATGCGA | TTCGTGAAGC | AAGTGGTGGA | AAAGTATCGC | TACAAGCACT | TGACATGTTA |
| 1801 | ATGAGATATG | AGCCTCACCC | GCAGCATGTT | GCTGTCGAGG | CAGTAAGAAC | AGGTGCAGTA |
| 1861 | GGTGTATTGG | AGCACCTTAT | TACCACTGAA | GTGATTAGTG | TAAATGAAGA | AATTACAACT |
| 1921 | CCTGAAGGAA | AAAAGACAAC | TTTGACCGCT | GAAGCACTAA | CTAGTGGTAA | ATATGGTGTA |
| 1981 | GTGAAGGCGT | TAATTAAAAA | CAGTGCTGAT | GTAAAATGCGT | CTCCAGAACC | AGCTATTACT |
| 2041 | TTGGGTATAC | AAGGAAGGTG | CTTTCAGGGG | AGTAAAGCTA | TAAAGCATTT | AAAGCGTGTT |
| 2101 | GTAGAAGCTG | GGGCACATAT | AAATACTCCT | ACCGGATCTA | TGAGCCCTTT | AGCTGCTGCA |
| 2161 | GTTCAAGCGG | CAAATGAGGC | AAGTAACCTT | AAAGAGGCTA | ATAAGATTGT | AAATTCCTT |
| 2221 | TTACATAGGG | GTGCAGATCT | TTCGTCTACG | TAGGACTGCT | GAACTCCAGC | CTTGCATTTA |
| 2281 | GCAACAGCTG | CTGGCAACCA | TAGGAGTGCT | ATGTTGCTCT | TGGATAAAAG | GGCTCCAGCA |
| 2341 | ACGCAGAGAG | ATGCTAGGGG | TAGGACGGCT | TTACATATAG | CAGCTGCTAA | TGGTGACGGT |
| 2401 | AAGCTATATA | GGATGATTGC | GAAAAAATGC | CCAGATAGCT | GTCAACCACT | CTGTTCTGAT |
| 2461 | ATGGGAGATA | CAGCGGTTACA | TGAGGCTTTA | TATTCTGATA | ATGTTACAGA | AAAAATGCTTT |
| 2521 | TTAAAGAGTC | TTAAAGAGTC | TCGAAAGCAT | TTGTCAAACT | CATCTTTTTT | CGGAGACTTG |
| 2581 | CTTAATACTC | CTCAAGAAGC | AAATGGTGAC | ACGTTACTGC | ATCTGGCTGC | ATCGCGTGGT |
| 2641 | TTCGGTAAAG | CATGTAAAAT | ACTACTAAAG | GCTGGGGCGT | CAGTATCAGT | CGTGAATGTA |
| 2701 | GAGGGAAAAA | CACCGGTAGA | TGTTGCGGAT | CCATCATTGA | AAACTCGTCC | GTGGTTTTT |
| 2761 | GGAAAGTCCG | TTGTCACAAT | GATGGCTGAA | CGTGTTCAAG | TTCCTGAAGG | GGGATTCCCA |
| 2821 | CCATATCTGC | CGCCTGAAAG | TCCAACTCCT | TCTTTAGGAT | CTAGTTTCAAG | TTTTGAGAGT |
| 2881 | GTCTCTGCGC | TATCATCCTT | GGGTAGTGGC | CTAGATACTG | CAGGAGCTGA | GGAGTCTATC |
| 2941 | TACGAAGAAA | TTAAGGATAC | AGCAAAAGGT | ACAACGGAAG | TTGAAAGCAC | ATATACAACT |
| 3001 | GTAGGAGCTG | AGGAGTCTAT | CTACGAAGAA | ATTAAGGATA | CAGCAAAAGG | TACAACGGAA |

FIG. 6B

```
3061 GTTGAAAGCA CATATACAAC TGTAGGAGCT GAAGGTCCGA GAACACCAGA AGGTGAAGAT
3121 CTGTATGCTA CTGTGGGAGC TGCAATTACT TCCGAGGCGC AAGCATCAGA TGCGGGGTCA
3181 TCTAAGGGAG AAAGGCCGGA ATCCATTTAT GCTGATCCAT TTGATATAGT GAAACCTAGG
3241 CAGGAAAGGC CTGAATCTAT CTATGCTGAC CCATTTGCTG CGGAACGAAC ATCTTCTGGA
3301 GTAACGACAT TTGGCCCTAA GGAAGAGCCG ATTTATGCAA CAGTGAAAAA GGGTCCTAAG
3361 AAGAGTGATA CTTCTCAAAA AGAAGGAACA GCTTCTGAAA AAGTCTGCTC AACAATAACT
3421 GTGATTAAGA AGAAAGTGAA ACCTCAGGTT CCAGCTAGGA CAAGTAGTTT GCCTACTAAA
3481 GAAGGTATAG GTTCTGATAA AGACCTGAGT TCAGGAACTA GTAGCTCTTT TGCAGCTGAG
3541 CTGCAAGCAC AAAGGGTAA ATTGCGTCCT GTGAAGGGAG GTGCTCCGGA TTCTACCAAA
3601 GACAAAACAG CTACTTCTAT ATTCTCCAGT AAAGAGTTCA AAAAGGAACT AACAAAAGCT
3661 GCCGAAGGAT TACAGGGAGC AGTTGAAGAA GCTCAGAAGG GTGATGGAGG AGCTGCAAAG
3721 GCAAAGCAAG ATCTTGGCAT GGAAATCTGGT CTCAACCAGA AGCTCCTCAA
3781 AGTGAAGGCC CTAAGTCTGT AAAAGGAGGT CGCGGTAGT AGAATTATAC CGAAAAATCG
3841 CTGAGGTACT TTGATCAATA TTAATTCGCGC TTCTGAGTAT TTAGGCGATG ATCTCGCCAC
3901 TTTAATAATA CCCCTTTTAG AGTACATAAC GCTCTAAAGG GGGCAGATTA TTTTAAGTAG
3961 TAGGGTTTTG ATTCTGAGAT CTTTTGAGTA CAACTATTCC TTAGTGTTTT TTTGGAATGC
4021 TATGTGCTTG ATAAAGAAAA AACTTGCTCT GGGGTGGGAT GCACTCTTGA GTACTTTCCG
4081 CGCTCTGTAT ATTCCTTTTT TTGCATCTGC ATAATCTGCT GCATATGTGA TTATGTGATA
4141 ATGACGGAAT TACCCAGAAA AGCCTTAGCG TGTGAGGCCT ATCATTCTCA GAAAGTCACA
4201 GTAGGAAACT TGCATTTTCA TCTTGTATTT TTGTAAGTTG GCTAAGAGCA CTAGCTATAA
4261 CAAATGCATC TATGGCATTT TTTGAGAGTT ATAATAATGA GAGCAACAAA GGGTGGTACT
4321 ATTGTTCAAA ATTTGTTTAT GTGCTTTGTC TCACAATGGA GTTTAAAGTC ATCTCCAGT
4381 AGTACTACGA CTTTAAGTAG AGAATACTTT GTATTTTCTT TATAGAGCTC AGAGATATAC
4441 TTCAGTATGT GTCGGAGGTT GTTCCCTTGG GAAAAAGGGC ATTTTATCAA CTGTGAACTA
4501 TCGCTACTAT GGCTGAGGAA AAGTAGATAG CAACAAAGAT AGTATTCTGG TTTTATAATC
4561 AAACCGTAAT CTTTCAACAT GTTCGAAGAT CGCTTTCACT TATCCTCGCT TTTTGACTGC
4621 CCTGCTGAAA GGGCTTTTTT GTTATGAAAC TATCCTCGCT CGATTTTCTT ATCTTTGGAT
4681 TCTATTACCA CGGATAAATGT TTGTTGAAT TATTTTAGAA GAAG
                                                            (SEQ ID NO:3)
```

FIG. 6C

```
  1 MLRCNSMDVD ARSHDGRTII HYAAKDGNLE ILQQALGRKS SYSKFPVKDG VPTPGVYAIR
 61 EASGGKVSLQ ALDMLMRYEP HPQHVAVEAV RTGAVGVLEH LITTEVISVN EEITTPEGKK
121 TTLTAEALTS GKYGVVKALI KNSADVNASP EPAITLGIQG RCFQGSKAIK HLKRVVEAGA
181 HINTPTGSMS PLAAAVQAAN EASNLKEANK IVNFLLHRGA DLSSTEHTGT PALHLATAAG
241 NHRTAMLLLD KGAPATQRDA RGRTALHIAA ANGDGKLYRM IAKKCPDSCQ PLCSDMGDTA
301 LHEALYSDNV TEKCFLKMLK ESRKHLSNSS FFGDLLNTPQ EANGDTLLHL AASRGFGKAC
361 KILLKAGASV SVVNVEGKTP VDVADPSLKT RPWFFGKSVV TMMAERVQVP EGGFPPYLPP
421 ESPTPSLGSI SSFESVSALS SLGSGLDTAG AEESIYEEIK DTAKGTTEVE STYTTVGAEE
481 SIYEEIKDTA KGTTEVESTY TTVGAEGPRT PEGEDLYATV GAAITSEAQA SDAASSKGER
541 PESIYADPFD IVKPRQERPE SIYADPFAAE RTSSGVTTFG PKEEPIYATV KKGPKKSDTS
601 QKEGTASEKV CSTITVIKKK VKPQVPARTS SLPTKEGIGS DKDLSSGTSS SFAAELQAQR
661 GKLRPVKGGA PDSTKDKTAT SIFSSKEFKK ELTKAAEGLQ GAVEEAQKGD GGAAKAKQDL
721 GMESGAPGSQ PEAPQSEGPK SVKGGRGR (SEQ ID NO: 4)
```

FIG. 7A

```
  1  TGTACCATCCCCAGTGACAGGTGAAGCGTGCGTAGCTGCGTATAAGGGGCAACACT
 61  GAGGATGTTAAGACTATGTTACGCTGTAATAGCATGGACGTAGACGTCGGTCACATGAT
              M  L  R  C  N  S  M  D  V  D  A  R  S  H  D
121  GGTAGAACTATAATACATTACGCCAGCAAGGATGGAAATTTAGAGATATTGCAGCAGGCT
       G  R  T  I  I  H  Y  A  A  K  D  G  N  L  E  I  L  Q  Q  A
181  CTTGGAAGGAAGAGTAGTATTCTAAGTTCCTGTAAAGGATGGTGTTCCTACTCCAGGT
       L  G  R  K  S  S  Y  S  K  F  P  V  K  D  G  V  P  T  P  G
241  GTATATGCGATTCGTGAAGCAAGTGGTGGGAAAGTATCCAAGCACTTGACATGTTA
       V  Y  A  I  R  E  A  S  G  G  K  V  S  L  Q  A  L  D  M  L
301  ATGAGATATGAGCCTCACCCGCAGCATGTTGCTGTGAGGCAGTAAGACAGGTGCAGTA
       M  R  Y  E  P  H  P  Q  H  V  A  V  E  A  V  R  T  G  A  V
361  GGTGTATTGGAGCAAAAGACAACTTGACCGCTGAAGCACTAGTGTAAATATGGTGTA
       G  V  L  E  H  L  I  T  T  E  V  I  S  V  N  E  E  I  T  T
421  CCTGAAGGAAAAACTTAATTAAAACGTGTTATTGCTGAAGCACTTACTAGTGGTAAATATGGTGTA
       P  E  G  K  K  T  L  T  A  E  L  T  S  G  K  Y  G  V
481  GTGAAGGCGTTAATTAAAAATGCTGATGTAATGCTAGTGTAAGCTAAGCTATTAAGGCTGATT
       V  K  A  L  I  K  N  A  D  V  N  A  S  P  E  A  I  T
541  TGGGTATACAAGGAGGTGCTTTCAGGGAGTAAGCTATACGGATCTATGCCCTTAGCTGCTGCA
       L  G  I  Q  G  R  C  F  Q  G  S  K  A  I  K  H  L  K  R  V
601  GTAGAAGCTGGGCAATGGAGGCAAATGAGCAATAACCTAAGCTAAGAGGCTAATAAGATTGTAAATTCCTT
       V  E  A  G  A  H  I  N  T  P  T  G  S  M  S  P  L  A  A  A
661  GTTCAAGGGGGTGCAGATGTCGTCTACGGAACACACTGGAACTCCAGCTTGCATTTA
       V  Q  A  N  E  A  S  N  L  K  E  A  N  K  I  V  N  P  L
721  TTACATAGGGTCCATCAAGGAGGTGCTATCTGCTCTTGATGCTCTTTGATAAGGGGTGCAGCA
       L  R  G  A  D  L  S  T  E  H  T  G  T  P  A  L  H  L
781  GCAACAGCTGCCATCATAGACACTGCTATGCTCTTGATAAGGGGCTCAGCA
       A  T  A  A  G  N  H  R  T  A  H  L  L  D  K  G  A  P  A
```

FIG. 7B-1

```
      ACGGAAGAGATCGTAGGGTAGGACGGCTTACATAGCAGCTGCTATGGTGACGGT
       T  Q  R  D  A  R  G  R  T  A  L  H  I  A  A  N  G  D  G
 841
      AAGCTATATAGGATGATTGGGAAAAATGCCCAGATAGCTGTCACCACTCGTTCTGAT
       K  L  Y  R  M  I  A  K  K  C  P  Q  S  C  Q  P  L  C  S  D
 901
      ATGGGAGATACAGGCTTACATGAGGCTTTATATTGTGATAATGTTACAGAAAATGCTTT
       M  G  D  T  A  L  H  E  A  L  Y  S  D  N  V  T  E  K  C  F
 961
      TTAAAGATCCTTAAAGAGTCTCGAAGCATTGTCAACTCATCTTTTTGGAGACTTG
       L  K  M  L  K  E  S  R  R  H  L  S  N  S  F  F  G  D  L
1021
      CTTAATACTCCTCAAGAACGAAATGGTGACAGTCTACTGCATCTGGCTGCATGCCTGT
       L  N  T  P  Q  E  A  N  G  D  T  L  L  H  L  A  A  S  R  G
1081
      TTCGGTAAAGCATGTAAAATACTACTAAAGGCTGGGGGTCAGTATCGTGAATGTA
       F  G  K  A  C  K  I  L  L  K  A  G  A  S  V  V  N  V
1141
      GAGGGAAAACACCGGGAGTAGATGTGCGGATCCATGAAACTCGTCCGTGGTTTT
       E  G  K  T  P  V  D  V  A  D  P  S  L  K  T  R  P  W  F  F
1201
      GGAAAGTCCGTTGTCACAATGGCTGAACGTGTTCAAGTTCCTGAAGGGGATTCCCA
       G  K  S  V  V  T  M  A  E  R  V  Q  V  P  E  G  G  F  P
1261
      CCATATCTGGGCTATCATCCTTGGGTAGTGGCTAGATACTGCAGGAGTCTGAGGAGTCTATC
       P  Y  L  P  P  E  S  P  T  P  S  L  G  S  I  S  F  E  S
1321
      GTCTCTGCGCTATCATCCTTGGGTACAGCAAAGTACAGCGAAGTACTTGAAGCACATACAACT
       V  S  A  L  S  S  L  G  S  G  L  D  T  A  G  A  E  E  S  I
1381
      TACGAAGAAATTAAGGATACAGCAAAGGTACAGCTTGAAGATACAGCAAAGGTTACAACGGAA
       Y  E  E  I  K  D  T  A  K  G  T  T  E  V  E  S  T  Y  T  T
1441
      GTAGGAGCTGAGGAGTCTATCTACGAAGAATTAAGGATACAGCAAAGGTTACAACGGAA
       V  G  A  E  E  S  I  Y  E  E  I  K  D  T  A  K  G  T  T  E
1501
      GTTGAAAGCACATATACAACTGTAGGAGCTGAAGGTCCGAGACCACCAGAAGGTGAAGAT
       V  E  S  T  Y  T  T  V  G  A  E  G  P  R  T  P  E  G  E  D
1561
```

FIG. 7B-2

```
1621  CTGTATGCTACTGTGGGAGCTGCAATTACTTCCGAGGCATCAGATGCGGGTCA
       L   Y   A   T   V   G   A   A   I   T   S   E   A   Q   A   S   D   A   A   S
1681  TCTAAGGGAGAAAGCCCGAATCCATTTGATGTCATTTGATATAGTGAAACCTAGG
       S   K   G   E   R   P   E   S   I   Y   A   D   P   F   D   I   V   K   P   R
1741  CAGGAAAGGCCTGAATCTATCTATGCTGACCATTGCTGCGGAACGAACATCTTCTGGA
       Q   E   R   P   E   S   I   Y   A   D   P   F   A   E   R   T   S   S   G
1801  GTAACGACATTGGCCCTAAGGAAGAGCCGATTTATGCAACAGTGAAAAGGGTCCTAAG
       V   T   T   F   G   P   K   E   E   P   I   Y   A   T   V   K   K   G   P   K
1861  AAGAGTGATACTTCTCAAAAGGAAGGAACAGCTTCTGAAAAGTCTGCTCAACAATACT
       K   S   D   T   S   Q   K   E   G   T   A   S   E   K   V   C   S   T   I   T
1921  GTGATTAAGAAGAAAGTGAAACCTCAGGTTCCAGGTACAAGTAGTAGTTGCCTACTAAA
       V   I   K   K   V   K   P   Q   V   P   A   R   T   S   S   L   P   T   K
1981  GAAGGTATAGGTTCTGATAAGGACCTGAGTTCAGGTACTAGTAGTTTTGCAGCTGAG
       E   G   I   G   S   D   K   D   L   S   S   G   T   S   S   F   A   E
2041  CTGCAAGCACAAAGGGGTAAATGCCTGTCCTGTGAAGGAGGTGCTCCGGATTCTACCAAA
       L   Q   A   Q   R   G   K   L   R   P   V   K   G   G   A   P   D   S   T   K
2101  GACAAAACAGCTACTTCTATATTCTCCAGTAAAGAGTTCAAAAGGAACTACAAAAGCT
       D   K   T   A   T   S   I   F   S   S   K   E   F   K   K   E   L   T   K   A
2161  GCCGAAGGATTACAGCAGGCAGTTGAAGCTCAAGGTGATGGAGAGCTGCAAAG
       A   E   G   L   Q   Q   A   V   E   E   A   Q   K   G   D   G   G   A   K
2221  GCAAAGCAAGATCTTGGCATGGAATCTGGTGCCCCAGGATCTCAACCAGAAGCTCCTCAA
       A   K   Q   D   L   G   M   E   S   G   A   P   G   S   Q   P   E   A   P   Q
2281  AGTGAAGGCCCTAAGTCTGTAAAGGAGGTCGGGTAGGTGAATTATACCGAAAATCG
       S   E   G   P   K   S   V   K   G   G   R   G   R
2341  CTGAGGTACT
```

```
   1  GAATTCCTGA TAGTATTTTA GAGGATAGTA GGCAATATGG TTTAGGGGAT TTCTTCGCAT
  61  ACTTGTTATC ATCGTCCTTA TTTGTGCTTA GTTGGTCGGA TATTTGTGCA AGTTGTTGTA
 121  AAATATGCAT ATTGTATGTA TAGGTGTGCA AGATATCATC TCTTTAGGTG TATCGTGTAG
 181  CACTTAAACA AATGCTGGTG AACGTAGAGG GATTAAAGGA GGATTTGCGT ATATGTATGG
 241  TATAGATATA GAGCTAAGTG ATTACAGAAT TGGTAGTGAA ACCATTTCCA GTGGAGATGA
 301  TGGCTACTAC GAAGGATGTG CTTGTGACAA AGATGCCAGC ACTAAATGCT ACTCGTATGA
 361  CAAGTAGG GTAGTACGGG GAACGTGGAG ACCGAGCGAA CTGGTTTTAT ATGTTGGTGA
 421  TGAGCATGTG GCATGTAGAG ATGTTGCTTC GGGTATGCAT CATGGTAATT TGCCAGGGAA
 481  GGTGTATTTT ATAGAGGCAG AAGCGGGCAG AGCTGCTACT GCTGAAGGTG GTGTTTATAC
 541  TACCGTTGTG GAGGCATTAT CGCTGGTGCA AGAGGAAGAG GGTACAGGTA TGTACTTGAT
 601  AAACGCACCA GAAAAAGCGG TCGTAAGGTT TTTCAAGATA GAAAAGAGTG CAGCAGAGGA
 661  ACCTCAAACA GTAGATCCTA GTGTAGTTGA GTCAGCAACA GGGTCGGGTG TAGATACGCA
 721  AGAAGAACAA GAAATAGATC AAGAAGCACC AGCAATTGAA AGCAATTGAA GAAGTTGAGA CAGAAGAGCA
 781  AGAAGTTATT CTGGAAGAAG GTACTTTGAT AGATCTTGAG CAACCTGTAG CGCAAGTACC
 841  TGTAGTAGCT GAAGCAGAAT TACCTGGTGT TGAAGCTGCA GAAGCGATTG TACCATCACT
 901  AGAAGAAAAT AAGCTTCAAG AAGTGGTAGT TGCTCCAGGA GCGCAACAAC TAGAATCAGC
 961  TCCTGAAGTT TCTGCGCCAG CACAACCTGA GTCTACAGTT CTTGGTGTTG CTGAAGGTGA
1021  TCTAAAGTCT GAAGTATCTG TAGAAGCTAA TGCTGATGTA CCGCAAAAAG AAGTAATCTC
1081  TGGTCAACAA GAGCAAGAAA TTGCAGAAGC ACTAGAGGGA ACTGAAGCTC CTGTAGAAGT
1141  AAAAGAAGAA ACAGAAGTTC TTCTAAAGGA AGATACTTTG ATAGATCTTG AGCAACCTGT
1201  AGCACAAGTA CCTGTAGTAG CTGAAGCAGA ATTACCTGGT GTTGAAGCTG CAGAAGCGAT
1261  TGTACCATCA CTAGAAGAAA ATAAGCTTCA AGAAGTGGTA GTTGCTCCAG AAGCGCAACA
1321  ACTAGAATCA GCTCCTGAAG TTTCTGCGCC AGCACAACCT GAGTCTACAG TTCTTGGTGT
```

FIG. 8A

```
1381  TACTGAAGGT GATCTGAAGT CTGAAGTATC TGTAGAAGCT GATGCTGGTA TGCAGCAAGA
1441  AGCAGGAATC TCTGATCAAG AGACACAAGC AACTGAAGAA GTTGAAAAGG TTGAAGTATC
1501  TGTAGAAACA AAAACGGAAG AGCCAGAAGT TATTCTAGAA GAAGTACTT TGATAGATCT
1561  TGAGCAACCT GTAGCGCAAG TACCTGTAGT AGCTGAAGCA GAATTACCTG GTGTTGAAGC
1621  TGCAGAAGCG ATTGTACCAT CACTAGAAGA AAATAAGCTT CAAGAAGTGG TAGTTGCTCC
1681  AGAAGCGCAA CAACTAGAAT CAGCTCCTGA AGTTCTGCG CCAGTACAAC CTGAGTCTAC
1741  AGTTCTTGGT GTTACTGAAG GTGATCTGAA AGTTCTGAAG TCTGTAGAAG CTGATGCTGG
1801  TATGCAGCAA GAAGCAGGAA TCTCTGATCA AGAGACACAA GCAACTGAAG AAGTTGAGAA
1861  GGTTGAAGTA TCTGTAGAAG CTGATGCTGG TATGCAGCAA GAGTTAGTAG ATGTTCCGAC
1921  TGCTTTGCCG TTAAAGGATC CTGACGATGA AGATGTTCTA AGTTATTAGG ATATCTTCT
1981  CGTGAAAAGT ATGGGGAAGG TTCGATGTGT TGAACCGTGC CCCATGCTTT TTCTTTAAGA
2041  TTTCTTCAAA AAGAGGTAAA ACTCTCCTAT GTTTTTTGTG AGCAGTAATT TCTTGCAGTT
2101  TTGCGACTGA GTTGTGTGTT ATTGCGAAGT TTTTCTTCTG ATTATTGGAC GAAGGTGGTG
2161  CTTGTCATGT CTGTGGTGCG TGCTTTCCAT GCTTGATAGA GCTCCCTGATT ATTTTCTTTA
2221  TACGCAAGCC AGGTAAATCG TGTATGTGGC GACTTTTCGA ATCAGTGTTT AGATTACATA
2281  GAAGTAATTG TGGCTTATAC GCTGTTAATT GCGCTGCAAT CTGTCAAAAG TGATGCAGTA
2341  ACTTCCTCTA TATGTCCTAA TGCTGTTACA TGACATGGGT AATGCATAGC ATTATCAATG
2401  GTCATGGTGT CTTTAGTAGG CATACCAGCG GTTTATATA CCAGTGATGC GCGAGCCTTG
2461  TTCTCCGCTT TCATAAAAGA TTTATTACTC AAGATATTGG TATACCTAGC GATTCACGTG
2521  TAATTTGAGT ACTTACCTGC GTATTTCGAA GGTAACGTAC TAATAGCGTA TGGTAAAACT
2581  ATCTATTATC CCAATCCCTA AGAATAAACTA TGCTGTTTTG GAGCTGTTGC ATGCTGAAAG
2641  ATGTCTTATA GCATCGCGGT TATATATTTT CACATTTTAG AGATTTTAAG AGTATAACTT
2701  TCTAGCATCT TAGAGAACTA TACTCAAAGT TAAACACAAT AAAAACATGA AGCATTAAAA
2761  CTCAAGTATA CTAAACCAGC CTTAGACCTT AAAGGAAAGT AAGGAATGCT TATCTATGTT
```

FIG. 8B

```
2821  CAATTGTGCC  ATTACTTAAA  AAGGAACCT   AACACCGAAT  TCCCCACCGA  CATAAGCCAT
2881  GGAGAAATTA  GCAATAGCAG  TATCCTTAGT  ACGACCCGCC  GGACTAGTAT  CATCTACAAG
2941  ACGTTGAGCC  GGCAGATCAT  CATAAACGCC  ATCTCCAACA  ACGCGATGAT  AGAATCCACC
3001  CGCAAAAGCG  GAGATTTCAG  GTGAGAGCTG  ATAACTCAAG  CCAGCCTTTA  ACCTCAAGCT
3061  TAGGAGTGAT  GTTCTAGACA  CCATCCGTAT  TAGTCACAGA  TTAGCTTCCT  CTCGAAGTAC
3121  AGATAACCTC  TGGAAAGTTT  TAGAAAGGAC  GGAATGTGTA  ACGCCGCTCC  GTGCCATCAA
3181  CCACGCCAAC  GAAGTTACCG  CCTAAACCAA  CACAAGCATA  AGGAACAACA  CCTAAACCTT
3241  CACTAAGAAG  ATCATAACAA  GCATTAACCA  TTACAGATGT  AGAAGAAACA  GCTCTGATCT
3301  CAACAACCTC  TCCCCCTTCA  ATAGTTTTAG  CAAGTAATCC  TGCTACTATG  GTTTTTTCAT
3361  CACGATTAAG  ACCTAATAGG  TCTTTAGCCA  TAGCGTTTGC  ATTACTATTA  GGTTCTCCCT
3421  CGACGTTTTG  ACTGCTGCCA  TTACTCCCTC  GTCCCCTAGG  CCAGTTTTTA  CCTTCACCGA
3481  CTTTCACAGT  ATTAACAAAA  CCACTCAAACG  TCTTTGGTCC  TGTCGCCCCC  GTCGTATTTC
3541  CCAAACCGCT  ACACTGTGTT  GTCTCCTCGT  TGCCGTGTGT  CGTCGACAAC  TCCGCAACAT
3601  ACTTCTTCCC  CTTAGCCTTA  GTTATAGCAG  ACAGCATTGG  CATGATCCCC  ACTACAAACC  TTCCCATCAA
3661  TTTCAGGGCT  GGAAATTTTC  ACAGCATTGG  CAAACTGAAC  GATGTCTTTC  CCAGAGGTTT
3721  TGGCAAGAGC  AGCGGCAAGG  TTATCAGTCT  GCCCAGTAAC  AACATCATAA  GCTAACTCCT
3781  TAGCTAGTAG  ATATACTGTA  TCAGCTTCAT  CTTCCTTACT  AACACTATCT  CTAATACCCT
3841  TGGTCTTCCT  TTTAATAATA  AGAGTTATTG  CATAGGATAT  TGATATACCT  ATCGATTTAT
3901  AGGCAGTTGA  GCCGGAAGAT  CATCTTAAAC  ACCATCTCCC  ACAACACGAT  GGTAAAAGCC
3961  ACCCGCAGGA  ATTCCGGAAT  TCCGGAATTC                (SEQ ID NO:5)
```

FIG. 8C

```
  1  MYGIDIELSD  YRIGSETISS  GDDGYYEGCA  CDKDASTNAY  SYDKCRVVRG  TWRPSELVLY
 61  VGDEHVACRD  VASGMHHGNL  PGKVYFIEAE  AGRAATAEGG  VYTTVVEALS  LVQEEEGTGM
121  YLINAPEKAV  VRFFKIEKSA  AEEPQTVDPS  VVESATGSGV  DTQEEQEIDQ  EAPAIEEVET
181  EEQEVILEEG  TLIDLEQPVA  QVPVVAEAEL  PGVEAAEAIV  PSLEENKLQE  VVVAPEAQQL
241  ESAPEVSAPA  QPESTVLGVA  EGDLKSEVSV  EANADVPQKE  VISGQQEQEI  AEALEGTEAP
301  VEVKEETEVL  LKEDTLIDLE  QPVAQVPVVA  EAELPGVEAA  EAIVPSLEEN  KLQEVVAPE
361  AQQLESAPEV  SAPAQPESTV  LGVTEGDLKS  EVSVEADAGM  QQEAGISDQE  TQATEEVEKV
421  EVSVETKTEE  PEVILEEGTL  IDLEQPVAQV  PVVAEAELPG  VEAAEAIVPS  LEENKLQEVV
481  VAPEAQQLES  APEVSAPVQP  ESTVLGVTEG  DLKSEVSVEA  DAGMQQEAGI  SDQETQATEE
541  VEKVEVSVEA  DAGMQQELVD  VPTALPLKDP  DDEDVLSY   (SEQ ID NO:6)
```

FIG. 9A

```
  1  ATCGTGTAGCACTTAAACAAATGCTGGTGAACGTAGAGGATTAAAGGAGGATTTGCGTA
 61  TATGTATGGTATAGATATAGAGCTAAGCTGATTACAGAATTGGTAGTGAAACCATTTCCAG
      M  Y  G  I  D  I  E  L  S  D  Y  R  I  G  S  E  T  I  S  S
121  TGGAGATGATGGCTACTACGAAGGATGTGCTTGTGACAAAGATGCCAGCACTAATGCGTA
      G  D  D  G  Y  Y  E  G  C  A  C  D  K  D  A  S  T  N  A  Y
181  CTCGTATGACAAGTGTAGGGTAGTAGTGGCAACCGTGAGCGAGCGAACTGGTTTTATA
      S  Y  D  K  C  R  V  V  R  G  T  W  R  P  S  E  L  V  L  Y
241  TGTTGGTGATGAGCATGGCATGTAGAGATGTTGCTTCGGTATGCATCATGTAATTT
      V  G  D  E  H  V  A  C  R  D  V  A  S  G  M  H  H  G  N  L
301  GCCAGGGAAGGTGTATTTTATAGAGCCAGAAGCAGAGCTGCTACTGCTGAAGGTGG
      P  G  K  V  Y  F  I  E  A  E  G  R  A  A  T  A  E  G  G
361  TGTTTATACTACCGTTGTGGAGCCATTATGCCTGTCCAAGAAGAGGTACAGGTAT
      V  Y  T  T  V  V  E  A  L  S  L  V  Q  E  E  E  G  T  G  M
421  GTACTTGATAAACGCACCCAGAAAAGCGGGTCGTAAGTTTTTCAAGATAGAAAAGAGTGC
      Y  L  I  N  A  P  E  K  A  V  V  R  F  F  K  I  E  K  S  A
481  AGCAGAGGAACCTCAAACAGTAGATCCTAGTGTAGTTGAGTCAGCAACAGGGTCGGGTGT
      A  E  P  Q  T  V  D  P  S  V  V  E  S  A  T  G  S  G  V
541  AGATACGCAAGAAGAACAAATAGATCAAGAAGCACCAGCAATTGAAGAAGTTGAGAC
      D  T  Q  E  E  Q  E  I  D  Q  E  A  P  A  I  E  E  V  E  T
601  AGAAGAGCAAGAAGTTATTCTGGAAGAAGTACTTTGATAGATCTTGAGCAACCTGTAGC
      E  E  Q  E  V  I  L  E  E  G  T  L  I  D  L  E  Q  P  V  A
661  GCAAGTACCTGTAGTAGCTGAAGCAGAATTACCTGGTGTTGAAGCTGCAGAAGCGATTGT
      Q  V  P  V  V  A  E  A  E  L  P  G  V  E  A  E  A  I  V
721  ACCATCACTACTAGAAGAAAATAAGCTTCAAGAAGTGTAGTTGCTCCAGAAGCGCAACAACT
      P  S  L  E  E  N  K  L  Q  E  V  V  V  A  P  E  A  Q  Q  L
781  AGAATCAGCTCCTGAAGTTCTGGCGCCACCACCTGAGTCTACAGTTCTTGGTGTTGC
      E  S  A  P  E  V  S  A  P  A  Q  P  P  E  S  T  V  L  G  V  A
```

FIG. 9B-1

```
841   TGAAGGTGATCTAAAGTCTGAAGTATCTGAAGTAGTAATGCTGATGTACCGCAAAAGA
        E  G  D  L  K  S  E  V  S  E  A  N  A  D  V  P  Q  K  E
901   AGTAATCTCTGGTCACAAGAGCCAAGAAATTGCAGAGGACACTAGAACTGAAGCTCC
        V  I  S  G  Q  Q  E  Q  I  A  E  A  L  E  G  T  E  A  P
961   TGTAGAAGTAAAAGAAGAAACAGAAGTTCTTCTAAAGGAAGATACTTTGATAGATCTTGA
        V  E  V  K  E  E  T  E  V  L  L  K  E  D  T  L  I  D  L
1021  GCAACCTGTAGCACAAGTACCTGTGAAGCTAGTAGCAGAATTACCTGGTGTTGAAGCTGC
        Q  P  V  A  Q  V  P  V  A  E  L  P  G  V  E  A  A
1081  AGAAGCCGATTGTACCATCACTAGAAGAAATAAGCTTCAAGAAGTGGTAGTTGCTCCAGA
        E  A  I  V  P  S  L  E  E  N  K  L  Q  E  V  V  A  P  E
1141  AGCGCAACAACTAGAATCAGCTCCTGAAGTTTCTGCGCCAGCACAACCTGAGTCTACAGT
        A  Q  Q  L  E  S  A  P  E  V  S  A  P  A  Q  P  E  S  T  V
1201  TCTTGGTGTTACTGAAGGTGATCTGAAGTCTGAAGTATCTGAAGCTGATGCTGGTAT
        L  G  V  T  E  G  D  L  K  S  E  V  S  E  A  D  A  G  M
1261  GCAGCAAGAGCAGGAATCTCTGATCAAGAACAAAACGGAAGAGCCAGAAGTTATTCTAGAAGAAGGTACTTT
        Q  Q  E  A  G  I  S  D  Q  E  T  Q  A  T  E  E  V  I  L  E  E  G  T  L
1321  TGAAGTATCTGTAGAAACAAAAACGGAAGAGCCAGTAGCCAGAATTACCTGG
        E  V  S  V  E  T  K  T  E  E  P  E  V  I  L  E  G  T  L
1381  GATAGATCTTGAGCAACCTGTAGCACAAGTACCTGTGGCAGAAGCTTCAAGAAGTGGT
        I  D  L  E  Q  P  V  A  Q  V  P  V  V  A  E  A  E  L  P  G
1441  TGTTGAAGCTGCAGAAGCCGATTGTACCATCACTAGAAGAAATAAGCTTCAAGAAGTTGT
        V  E  A  A  E  A  I  V  P  S  L  E  E  N  K  L  Q  E  V  V
1501  AGTTGCTCCAGAAGCCAACAACTAGAATCAGCTCCTGAAGTTTCTGCGCCAGTACAACC
        V  A  P  E  A  Q  Q  L  E  S  A  P  E  V  S  A  P  V  Q  P
1561  TGAGTCTACAGTTCTTGGTGTTACTGAAGGTGATCTGAAGTCTGAAGTATCTGTAGAAGC
        E  S  T  V  L  G  V  T  E  G  D  L  K  S  E  V  S  V  E  A
```

FIG. 9B-2

1621  TGATGCTGGTATGCAGCAAGAAGCAGGAATCTCTGATCAAGAGACACAAGCAACTGAAGA
      D   A   G   M   Q   Q   E   A   G   I   S   D   Q   E   T   Q   A   T   E   E

1681  AGTTGAGAAGGTTGAAGTATCTGTAGAAGCTGATGCTGGTATGCAGCAAGAGTTAGTAGA
      V   E   K   V   E   V   S   V   E   A   D   A   G   M   Q   Q   E   L   V   D

1741  TGTTCCGACTGCTTTGCCGTTAAAGGATCCTGACGATGAAGATGTTCTAAGTTATTAGGA
      V   P   T   A   L   P   L   K   D   P   D   D   E   D   V   L   S   Y

1801  TATCTTTCTCGTGAAAAGTATGGGGAAGGT

FIG. 9B-3

```
   1 GAATTCCCTG TGGTTATTAG GCGTGGTTTC GCCTGATAAT AAAGATACTT TAGAGGGTAT
  61 AAACTTGGAA AAAATAATGA AAAACCCTCC TTAGTGCCTC CCCGTTTTTG ACAACATACT
 121 CTTATGGAAA AGCGTTAGGG AGTTGCTTCG CTTGTCACGC GTGCGTTAGG TTTTACGTAT
 181 ACGTGTCTGG GACTTCACGA AAACTCGACG CAGGCGGATT TTGTACTATG TTTCACTTAA
 241 CAAGTATTA TAAATGTTTG AACACAATAT TCCTGATACA TACACAGGAA CAACTGCAGA
 301 AGTTCTCCT GGCTTAGCAG GCGGGGATTT TAGCTTAAGT TCTATTGACT TTACAAGGA
 361 CTTTACAATT GAATCACATA GAGGAAGCTC AGCTGATGAC CCAGGTTACA TCAGCTTTAG
 421 GGATCAAGAC GGAAACGTCA TGTCACGTTT TCTTGATGTG TACGTAGCTA ATTTCAGCTT
 481 GCGATGCAAG CATTCTCCCT ATAAACAACGA CAGAATCA ACAGCTGCGT TCTCTCTAAC
 541 TCCCGACATA ATAGAGCCTT CTGCTTTATT GCAAGAATCA CATAGTACAC AAAACAATGT
 601 AGAAGAGGCA GTACAAGTTA CAGCTCTTGA GTGCCCTCCA TGTAATCCAG TCCCTGCCGA
 661 GGAAGTAGCT CCTCAACCGT CTTTTCTAAG CAGAATAATT CAGGCGTTCT TGTGGTTATT
 721 CACGCCCTTCT TCTACTACCG ACACTGCTGA TGTAATAGTA GCGATACTTC
 781 AAAAATGTACC TCTGCTAGCA GTGAGTCATT AGAGCAGCAG TGGAAGTGCA
 841 ACCATCTGTA CTTATGTCTA CTGCCCCTAT AGCAACAGAG CGGTTGTTAA
 901 CCAAGTAAAC ATAGCTGCAG TACAAGTAGA ATCATCCATT ATTGTGCCAG AATCGCAACA
 961 CACTGACGTT ACCGTGCTCG AAGATACTAC TGAGACGATA ACTGTTGATG GGGAATATGG
1021 ACATTTTAGT GACATTGCTT CAGGTGAACA CAATAACGAT CTGCCCTGCCA TGTTGTTAGA
1081 TGAAGCAGAC TTCACTATGT TATTAGCGAA CGAGGAGTCA AAGACCCTGG AGTCTATGCC
1141 TTCTGATAGC CTAGAAGACA ATGTTCAGGA ACTAGGTACA TTGCCTTTAC AAGAAGGTGA
1201 AACAGTTTCT GAGGGCAACA CACGGAGTC ACTACCCACT GACGTTCAC AAGACTCAGT
1261 TGGTGTAAGT ACAGATCTTG AAGCTCATTC TCAAGAAGTT GAAACAGTTT CTGAGGTCAG
1321 CACACAAGAT TCACTATCCA CTAACATTTC AAGCTTGTGTAA GTTGGTGTAA GTACAGATCT
1381 TGAAGTTCAT TCTCAAGAAG TTGAAATAGT TTCTGAGGGC GGCACACAAG ATTCACTATC
1441 CACTAACATT TCACAAGACT CAGTTGGTGT CAGTTGGTGT CTTGAAGCTC ATTCTAAAGG
```

FIG. 10A

| | | | | | |
|---|---|---|---|---|---|
| 1501 | AGTTGAAATA | GTTTCTGAGG | GCGGCACACA | AGATTCACTA | TCCGCTGATT | TTCCAATAAA |
| 1561 | CACAGTTGAA | AGTGAAAGTA | CAGATCTTGA | AGCTCATTCC | CCAGAAGGTG | AAATAGTTTC |
| 1621 | TGAGGTCAGC | ACACAAGATG | CGCCATCCAC | TGGAGTAGAG | ATCAGATTTA | TGGATCGTGA |
| 1681 | TTCTGATGAT | GACGTGCTCG | CGTTGTGAAG | TGATCATGGT | AGGGAAAACA | GTTATGGCGT |
| 1741 | AAAGACATCT | TTGATGACTT | GTCTTGCGTG | AATAAGTAGT | GCAAGTTTTT | TATGCATTGA |
| 1801 | TGTGCATGAT | CATTGCCCCT | AAGGAAAGCA | GTACTAATGG | TAGTCTAAGA | TCTTATACAG |
| 1861 | GGTTTCGGAC | TACCACTTTT | GGTGTTTTAA | AACGTCTTAT | TCGCGTTGGG | TGCTTGCTTA |
| 1921 | CAATGTACCT | GTACGTGCCC | AACACTAAAA | ATGGTCAGTA | TTACTTAGGG | GAGTTCGTAG |
| 1981 | ACGAGGCATC | TCGATTTACT | CTAAGTAAGC | TACAAATAAC | TCAGTCATAT | CAAGGTAGTT |
| 2041 | CAAGATGAAA | GCAGTGCTAT | GCTTATCATG | GAGAATTCCT | GCGGTTCTCT | TCAAAATTCT |
| 2101 | CTTTTCCCGC | AAGGGCAGAC | TCTTTATTGT | TAAAAATAACA | AAATTTCTCT | ACAGGAAGCG |
| 2161 | ACATTTCATA | TCAAAGCTGA | TTGTGAAATA | ATGGCATTGA | GTATTTTTCT | CGCCCTAGAA |
| 2221 | GATAATCATT | TCGGCACTAT | CAAAGCATTT | ACGATATTCT | CCATTATCTT | GTAATCAGAT |
| 2281 | GGCTATCTTG | AAAGCAACCA | AGGATATCCG | TACATGGTAG | CTTACATACT | GCTATCAATC |
| 2341 | TCCTATACGA | CCTTAGATAT | AACGGTAACT | GTTGCTGACA | GCTTGCACAT | GCTGTGATTC |
| 2401 | AATTCCTGGT | TCCTAGATGT | TCTACTACGT | TTATCCGGTA | CTAATATTAT | TCTTTGGCGC |
| 2461 | TCTATTATCT | AGCAACTCAG | AGTCCATTAT | TGGATCTCTA | ATACCAAGGG | TATAAGGGAA |
| 2521 | AGTGGAAGAG | TATTATTAGA | GAGAAGAAGC | AAATACAGTA | TATCTACTAG | CTAAGGAGTT |
| 2581 | AGCTTATGAT | GTTGTTACTG | GACAGACTGA | TAAGCTTGCT | GCTGCTCTTG | CCAAGACCTC |
| 2641 | CGGGAAAGAT | ATCGTTCAGT | TTGCTAAGGC | AGTTGAGATT | TCGGCTCCTA | AGATCGATAA |
| 2701 | GCAAGTTTGT | GTGACTAATA | AGAATGGGGA | TAGCGGAAACA | AGATATGCTA | AGTACCTCGA |
| 2761 | AGAAGCTGGA | ACGTCTAGCA | ATGCTGGCAC | GTCGTTGTGT | TAGCGGTAAAA | ACCTAAAGAC |
| 2821 | GACTGACTCC | AACACAGGAG | TAGAGAAAGG | ACAGGTGTTA | CATGACTTTG | TTTCTGGAAC |
| 2881 | GTTGAGTGGG | GGTACTAAGA | ACTGGCCGAC | ATCTAGTGAA | AGTACTAGAA | AAAATAACGA |
| 2941 | CAACGCCAGG | AAGGTAGCTA | AAGACCTGAC | AAAACTAACC | CCTGAAGAAA | AAACCATAGT |

FIG. 10B

```
3001  AGCAGGGTTA CTAGCTAAGA CTATTGAAGG GGGTGAAGTT GTTGAGATCA GGCGGGTTTC
3061  TTCTACTTCT GTGATGGTTA ATGCTTGTTA TGATCTTCTT AGTGAAGGTT TAGGTGTCGT
3121  TCCTTACGCT TGTGTTGGTC TTGGGGGTAA CTTCGTGGGG GGTTGTTGAT GGCACGGCGC
3181  AGCGTTACAC AATCCGTCCT TGACCTGAAT ACTCTAGTTA AGCACTAGGC AAAATTAGTG
3241  CTGGATCACT TACGCAACAT ACTACGGTCA GCGATTTTCC ATACTGAGCA GGTACGTACA
3301  GTGGCTTTAT ACTCTTACCC AGCATGAAAT TACTTGTTAT CTAAGAATCT CCACAGCTGA
3361  CCTTAGAAAG GTTATCTGTC C-TTCGAGAG AAAGCTAATC TGTGTCTTAT GCGGATGGCG
3421  TTGAACGTAT TACAGGTCCC AAGCTGTCTT GCAAGTTTCT AAGGATATTA TAAGGGCACA
3481  CCTATAAAAC TGCGCAATAT ATCACCTGCA ATACGGTCCC GATTCGAAAG CACTGGGAAG
3541  TGCGCTCATT ATCTATGAAT CGCTAGCTAG GCATAAATAA GAGTATACGC AATAACGCTT
3601  ATTATTAAAA ACAAGACCAA GGGTATTAGA GATAGTGGTA GTAAGGAAGA TGAAGCTGAT
3661  ACAGTATATC TACTAGCTAA GGAGTTAGCT TATGATGTTG TTACTGGGCA GACTGATAAC
3721  CTTGCTGCTG CTCTTGCCAA GACTTCTGGT AAAGATATTG TTCAGTTTGC TAAGACTCTT
3781  AATATTTCTC ACTCTAATAT CGATGGGAAG GTTTGTAGGA GGGAAAAGCA TGGGAGTCAA
3841  GGTTTGACTG GAACCAAAGC AGTTTCGTGT GATAGTCAGC CACAAACGGC GGGTTTCGAT
3901  TCCATGAAAC AAGGTTTGAT GGCAGCTTTA AACAATTTAT AGCGAACAAG GCGCTGAAAA GTGGCCCAAA
3961  ATTAACAATG GTGGCCACGC AACAATTTAT AGTAGTAGCG CAGGTCCAGG AAATGCGTAT
4021  GCTAGAGATG CATCTACTAC GGTAGCTACA GACCTAACAA AGCTCACTAC TGAAGAAAAA
4081  ACCATAGTAG CAGGGTTACT AGCTAGAACT ATTGAAGGGG GTGAAGTTGT TGAGATTAGG
4141  GCAGTTTCTT CTACTTCTGT GATGGTTAAT GCTTGTTATG ATCTTCTGAA GGGAAACCCA
4201  TCACATTATT TATCTGGTTG CTGTAATCTG ATCTTCCCGT TGCTATGATC GCATCTCCCC
4261  CTCACTTCTC TCGCAAACTC TGGATTAACC TCTGGATGCG AATAATGTTT ATCAGCTTTG
4321  AGAAAAACAT ATTAGAGTTT TATACAGCAC CAATGATAAG CGTGGGCACT TAAATAAAGG
4381  TTCATATCCC TAGAAATTTA TCCCACTAGC TAAAACTATT GAAGGGGGTG AGTCGTTGA
4441  GATAAGGGCA GTTTCTTCTA CTTCTGTGAT GGTTAATGCT TGTTATGATC TTCTTAGTGA
4501  AGGTTTAGGC GTTGTTCCTT ATGCTTGGT GGGTCTTGGT GGGAACTTCG TGGGCGTGGT
```

FIG. 10C

| | | | | | |
|---|---|---|---|---|---|
| 4561 | TGATGGGCAT | ATCACAAACC | ACTCCATCTC | TGACCCTGTA | TGCACTAGCA | AGTAACTAGG |
| 4621 | CAAAATTATT | GCTGCATCAC | TTTGAAACAA | ACTACGATCA | GCAATGTTCA | ATACTTAGCA |
| 4681 | GGTCTGTACA | GTGGCTTTAC | ACTCTTACCC | AGCATGAAAT | ACTTGCTATC | TAAGAATCTC |
| 4741 | CTCTAAAACT | TTCCAGAGGT | TATCTGTACT | TTGAGGGAAG | CTAAATCTGTG | GCTAATGAGG |
| 4801 | ATGGTGTCTA | GAATATCACT | CCTAAGCTTG | CTTATAGGTT | AAAGGCTGGG | TTGAGTTATC |
| 4861 | AGCTTTCTCC | TGAAATCTCT | GCTTTTGTAT | GTGGTTTCTA | TCATTGGTTT | GTTGGTTATG |
| 4921 | GTGTTTATGA | TGATCTTCCG | GCTCAACGTC | TTGTAGATGA | TACTAGTCCG | GCGGGTCGTA |
| 4981 | CTAAGGATAC | TGCTATTGCT | AACTTCTCCA | TGGCCTATGT | TGGTGCATCA | TTTCAGCCAT |
| 5041 | ATTACGCAGT | TCTTCTAGTA | GAACTGTATG | AGTATCGATA | AAAAGATATA | CGACGCAGCA |
| 5101 | TGCTCTGAAA | AAGTGACAGG | GTGAACAGCA | ATTCTTTTAA | CATTAGCCTG | TCTGTATCAG |
| 5161 | TGTGCAATCT | GTTACAAAAC | TACTAGGATC | AAAACGCTAA | CACCTATCGG | GTTCATCAAG |
| 5221 | AAAATGAGTG | CATACGTGAC | GTTAGACCCTT | GGCAAGCGCT | AAACGCTAA | AGCTGATGCA | TCACATTAAA |
| 5281 | ATGTGTTGAC | GTTAGACCCTT | CCAAGCACTG | TAAAGTGTGG | CGATTCCCCC | GCATACGTTC |
| 5341 | TTATGCTGTGA | TTTTGAAAAA | CCCGGCGTCT | GCAACTTCGG | AAGAGAATTG | TTTTTGTGTG |
| 5401 | GGAAAAGCTC | TTATGCTTTC | AACTAAGTAG | GAATATGCAT | CAATATCCCC | GGCTACTATT |
| 5461 | TTGCCAATTT | TCGGTATAAC | AAAGAAAAGA | TACAGGTCAT | AAGCTGTTTT | GAATGCACTG |
| 5521 | TCTTCGAGTA | TAGGAGAAAA | CTCCAAGCAT | AAAAACCTAC | CACATGGTTT | CAGGAATTC |

(SEQ ID NO:7)

FIG. 10D

```
  1 MFEHNIPDTY TGTTAEGSPG LAGGDFSLSS IDFTRDFTIE SHRGSSADDP GYISFRDQDG
 61 NVMSRFLDVY VANFSLRCKH SPYNNDRMET AAFSLTPDII EPSALLQESH STQNNVEEAV
121 QVTALECPPC NPVPAEEVAP QPSFLSRIIQ AFLWLFTPSS TTDTAEDSKC NSSDTSKCTS
181 ASSESLEQQQ ESVEVQPSVL MSTAPIATEP QNAVVNQVNT TAVQVESSII VPESQHTDVT
241 VLEDTTETIT VDGEYGHFSD IASGEHNNDL PAMLLDEADF TMLLANEESK TLESMPSDSL
301 EDNVQELGTL PLQEGETVSE GNTRESLPTD VSQDSVGVST DLEAHSQEVE TVSEVSTQDS
361 LSTNISQDSV GVSTDLEVHS QEVEIVSEGG TQDSLSTNIS QDSVGVSTDL EAHSKGVEIV
421 SEGGTQDSLS ADFPINTVES ESTDLEAHSP EGEIVSEVST QDAPSTGVEI RFMDRDSDDD
481 VLAL   (SEQ ID NO:8)
```

FIG. 11

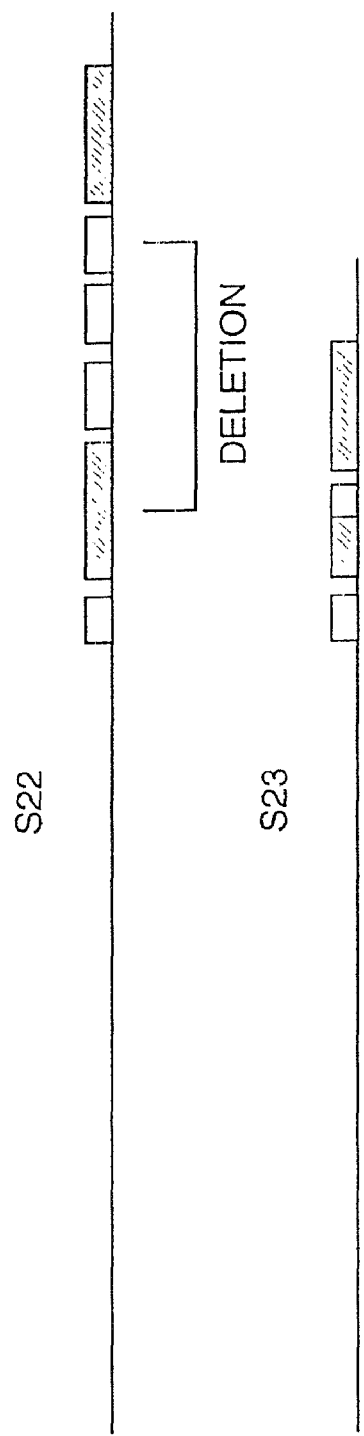

S2
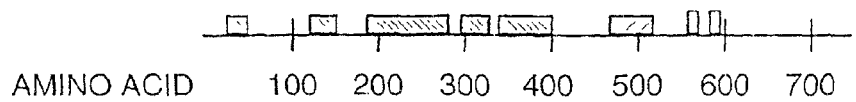
AMINO ACID  100  200  300  400  500  600  700
▨  1ST SET REPEATS: 27 AMINO ACIDS
☐  2ND SET REPEATS: 11 AMINO ACIDS
▧  ANKYRIN-LIKE REPEAT UNITS (8)
HOMOLOGY TO PROTEINS CONTAINING
ANKYRIN REPEATS
S7
AMINO ACID  100    200    300    400    500
▨▨▨  REPEATS 93, 111, 122 AMINO ACIDS
———————  93
————————  111
—————————  122
FIG. 13

1   MGDAVEVRAE NLGGESILEA PIRVMKKVGD TVSAEDVLFI VETDKTSLEI SAPVAGVLTE
61  LRVADEEVIT KGQVLAIIRP QGEATAEGVN KEPESKEEVP AQPVVAQAVS TQKPQEKTII
121 EGKGLVTPTV EDFVAGINTT PTSRALGMSA KSEQDKKIVA SQPSKDLMSC HGDVVGERRV
181 KMSKIRQVIA ARLKESQNTS ATLSTFNEVD MSKVMELRAK YKDAFVKRYD VKLGFMSFFI
241 RAVVLVLSEI PVLNAEISGD DIVYRDYCNI GVAVGTDKGL VVPVIRRAET MSLAEMEQAL
301 VDLSTKARSG KLSVSDMSGA TETITNGGVY GSLLSTPIIN PPQSGILGMH AIQQRPVAVD
361 GKVEIRPMMY LALSYDHRIV DGQGAVTFLV RVKQYIEDPN RLALGI
                                              (SEQ ID NO:21)

FIG. 21

1   MGRGTITIHS KEDFACMRRA GMLAAKVLDF ITPHVVPGVT TNALNDLCHD FIISAGAIPA
61  PLGYRGYPKS ICTSKNFVVC HGIPDDIALK NGDIVNIDVT VILDGWHGDT SRMYWVGDNV
121 SIKAKRICEA SYKALMAAIG VIQPGKKLNS IGLAIEEEIR GYGYSIVRDY CGHGIGREFH
181 AAPNIVHYYD EEDDVTIQEG MFFTVEPMIN AGKYHTVLDK KDGWTVTTRD FSLSAQFEHT
241 LGVTETGVEI FTMSPKNWHC PPYL (SEQ ID NO:22)

FIG. 22

```
   1 GAATTCCGGA ATTCCGGAAT TCCTATGGAT CGTGCAGTGA TGGAAGAGGG CAGCATGTTA
  61 GCTGCAGGTT CACTGCTCAC TAGGGTAAG  TATGATGACT ATTGTAAAAT CTGGAGAGTT ATGGGCAGGT
 121 AGGCCTGCAA AATTTCTACG TATGATGACT GAAGAGAGA  TTTTATACCT ACAAAAATCT
 181 GCTGAAAATT ACATAGCGTT ATCGCGTGGA TACTTATAAC AAGTATTCA  TCTATGGTTT
 241 GACATTAGTG TCTTTTGGTG ATTACACTGC CTTTCAATCT GTGTTTTTTG TTTTAGTTCT
 301 GGTTTGTATT TATGGGTGAT GCTGTAGAAG TTAGGCTGA  GAATCTTGGT GGCGAATCCA
 361 TTCTAGAAGC TCCGATTCGG GTAATGAAAA AGGTGGGAGA TACTGTATCT GCAGAAGATG
 421 TGCTCTTCAT TGTTGAAACA GACAAGACTT CTCTTGAAAT ATCAGCCCCT GTTGCTGGTG
 481 TTCTCACAGA GTTGAGAGTT GCAGATGAAG AAGTGATTAC CAAGGGGCAG GTCTTGGCTA
 541 TCATACGGCC ACAGGGTGAG GCTACTGCAG AAGTGTTAA  TAAGGAGCCA GAGAGCAAGG
 601 AGGAGGTGCC TGCTCAACCC GTTGTTGCAC AGGCAGTGAG CACTCAAAAA CCGCAGGAAA
 661 AGACAATTAT TGAAGGCAAA GGTCTAGTAA CTCCTACTGT AGAAGATTTT GTTGCAGGAA
 721 TCAACACAAC TCCTACTTCT AGAGCTTTGG GTATGAGTGC TAAGAGTGAA CAAGACAAGA
 781 AGATAGTTGC TAGCCAGCCG TCTAAGGATC TGATGAGTTG CCATGGCGAC GTGGTGGGTG
 841 AAAGACGCGT GAAGATGAGC AAAATCCGCC AAGTTATAGC TGCTAGGCTT AAGGAGTCAC
 901 AAAATACCTC TGCTACACTC AGCACCTTTA ATGAAGTTGA TATGAGCAAA GTGATGGAGC
 961 TCAGAGCTAA GTACAAAGAT GCCTTTGTGA AGAGGTATGA TGTTAAGCTT GGGTTTATGT
1021 CCTTCTTTAT CAGAGCGGTT GTGCTAGTCC TTTCCGAAAT TCCTGTGCTG AATGCGGAGA
1081 TTTCAGGCGA TGATATAGTC TACAGGGACT ATTGTAACAT TGGAGTCGCG GTAGGTACCG
1141 ATAAGGGGTT AGTGGTGCCT GTTATCAGAA GAGCGGAAAC TATGTCACTT GCTGAAATGG
1201 AGCAAGCACT TGTTGACTTA AGTACAAGTG CAAGCTCTCT GTTTCTGATA
1261 TGTCTGGTGC AACCTTTACT ATTACCAATG GTGGTGTGTA TGGGTCGCTA TTGTCTACCC
1321 CTATAATCAA CCCCTCCTCAA TCTGGAATCT TGGTTATGCA TGCTATACAG CAGCGTCCTG
1381 TGGCAGTAGA TGGTAAGGTA GAGATAAGGC CTATGATGTA TTTGGCGCTA TCATATGATC
1441 ATAGAATAGT TGACGGGCAA GGTGCTGTGA CGTTTTTTGGT AAGAGTGAAG CAGTACATAG
1501 AAGATCCTAA CAGATTGGCT CTAGGAATTT AGGGGGTTTT TATGGGGCGG GGTACAATAA
```

FIG. 23A

```
1561  CCATCCACTC  CAAAGAGGAT  TTTGCCTGTA  TGAGAAGGGC  TGGGATGCTT  GCAGCTAAGG
1621  TGCTTGATTT  TATAACGCCG  CATGTTGTTC  CTGGTGTGAC  TACTAATGCT  CTGAATGATC
1681  TATGTCACGA  TTTCATCATT  TCTGCCGGGG  CTATTCCAGC  GCCTTTGGGC  TATAGAGGGT
1741  ATCCTAAGTC  TATTTGTACT  TCGAAGAATT  TTGTGGTTTG  CCATGGCATT  CCAGATGATA
1801  TTGCATTAAA  AAACGGCGAT  ATAGTTAACA  TAGACGTTAC  TGTGATCCTC  GATGGTTGGC
1861  ACGGGATAC  TAGTAGGATG  TATTGGGTTG  GTGATAACGT  CTCTATTAAG  GCTAAGCGCA
1921  TTTGTGAGGC  AAGTTATAAG  GCATTGATGG  CGGCGATTGG  TGTAATACAG  CCAGGTAAGA
1981  AGCTCAATAG  CATAGGGTTA  GCTATAGAGG  AAGAAATCAG  AGGTTATGGA  TACTCCATTG
2041  TTAGAGATTA  CTGCGGACAT  GGGATAGGTC  GCGAATTTCA  TGCTGCTCCT  AACATAGTTC
2101  ACTACTATGA  CGAAGAGGAT  GATGTTACGA  TTCAGGAGGG  AATGTTTTTC  ACTGTTGAGC
2161  CAATGATCAA  TGCTGGAAAG  TATCATACTG  TGCTAGATAA  GAAAGACGGA  TGGACAGTTA
2221  CAACGAGAGA  CTTTTCCCTT  TCAGCGCAGT  TTGAACATAC  CTTGGGTGTA  ACTGAAACTG
2281  GCGTTGAGAT  TTTTACTATG  TCGCCAAAAA  ATTGGCATTG  TCCGCCATAC  CTTTAAGTAG
2341  GATATTTTTG  TTATGTGTAA  AGCGTGTGGC  AGGGTAATGT  TAGGTGCATG  TTCTGTTGAC
2401  GATGTGTGCT  GATAAGAAAT  TGTACAATCA  TACTGCGTTG  GAAGTTAGGA  ATATGTACTT
2461  ATGAGTGCTA  ATAAGCTTGC  TGTGTTATTA  AGCGAAGCCG  CTTCAGTTTT  GAAAAGAGTA
2521  GGAATAGATA  CACCGGGGTT  AGACGCTCGA  CTAATTGCGG  GACATGTTTT  GGGTTTAAGT
2581  GAGCATGAGG  TGCTAATAAA  TCCAGATTTA  GTTGTTACTG  CTGCTAAAAC  AAAAGAATTT
2641  TTTGAAGTTA  TTGCAAGACG  TTTAGCCCGGG  GTACCAGTTT  CGCATATTTT  ACGCAGACGA
2701  GAATTC
```
(SEQ ID NO:23)

FIG. 23B

```
                        10              20
PCR prod   tg GAG y FY V GLDYSPAF sk I RD F s I    (SEQ ID NO:24)
AM MSP-2   ga GAG s FY I GLDYSPAF gs I KD F k V    (SEQ ID NO:25)

30              40           50
PCR prod   R E S N G a T K a V V P Y l K D g k - s V k l e s
AM MSP-2   Q E A G G i T R g V F P Y k R D a a g r V d f k v 60              70
PCR prod   H k F D W a T P D P R I g F K D a M L v A M E G S
AM MSP-2   H a F D W s A P E P K I s F K D s M L t A L E G S 80              90          100
PCR prod   V G Y g I G G A R V E L E I G Y E R F k t K G i R
AM MSP-2   I G Y s I G G A R V E V E V G Y E R F v i K G g K 110             120
PCR prod   d S G s k E D e A d T V Y L L a K E L A Y d v v t
AM MSP-2   k S N - - E D - T a S V F L L g K E L A Y h t a r 130             140         150
PCR prod   G Q t D a L A A A L a K t S g k D i v Q f a k A V
AM MSP-2   G Q v D f L A T A L g K m T k s E a k K w g a A I 160             170
PCR prod   g - - - - - v S h p g I d K K V C d g G h A r G k
AM MSP-2   e s a t g t t S g d e L s K K V C g k G t T s G s 180
PCR prod   k - - S G d N q S
AM MSP-2   t a q C G t T d S
```

```
Sequence Range: 1 to 3435
               10         20         30         40         50         60
                *          *          *          *          *          *
       TTTTTATATC TGGAGCTCTT GTACTGTGTT TACCACGGGA TTTATTATTG GGTAGGCTTG
               70         80         90        100        110        120
                *          *          *          *          *          *
       ATATTCAGGC TCTATCAACG CAGCTATTCA TGGCATTATT ACAGATAAAT TTGGCATTTT
              130        140        150        160        170        180
                *          *          *          *          *          *
       GGAGATAGGC GATCTAGGGT TCTATTATTA GGAATCTATT ATTTAGATAT ATAGGGATAT
              190        200        210        220        230        240
                *          *          *          *          *          *
       AAGGGAGAGT AACGGAGAGA CTAAGGCAGT ATATCCATAC TTAAAGGATG GAAAGAGTGT
              250        260        270        280        290        300
                *          *          *          *          *          *
       AAAGCTAGAG TCACACAAGT TTGACTGGAA CACTCCCTGAT CCTCGGATTG GGTTTAAGGA
```

FIG. 30A

```
                              310            320            330            340
                               *              *              *              *
                        CAAC ATG CTT GTA GCT ATG GAA GGC AGT GTT GGT TAT GGT ATT GGT GGT
                             Met Leu Val Ala Met Glu Gly Ser Val Gly Tyr Gly Ile Gly Gly>
                              a   a   a   a   a   a ORF 1 a   a   a   a   a   a   a   a 350            360            370            380            390
              *              *              *              *              *
        GCC AGG GTT GAG CTT GAG ATT GGT TAC GAG CGC TTC AAG ACC AAG GGT
        Ala Arg Val Glu Leu Glu Ile Gly Tyr Glu Arg Phe Lys Thr Lys Gly>
         a   a   a   a   a   a ORF 1 a   a   a   a   a   a   a   a   a 400            410            420            430            440
              *              *              *              *              *
        ATT AGA GAT AGT GGT AGT AAG GAA GAT GAA GCA GAT ACA GTA TAT CTA
        Ile Arg Asp Ser Gly Ser Lys Glu Asp Glu Ala Asp Thr Val Tyr Leu>
         a   a   a   a   a   a ORF 1 a   a   a   a   a   a   a   a   a 450            460            470            480            490
              *              *              *              *              *
        CTA GCT AAG GAG TTA GCT TAT GAT GTT GTT ACT GGA CAG ACT GAT AAC
        Leu Ala Lys Glu Leu Ala Tyr Asp Val Val Thr Gly Gln Thr Asp Asn>
         a   a   a   a   a   a ORF 1 a   a   a   a   a   a   a   a   a
```

FIG. 30B

```
       500            510            520            530            540
        *              *              *              *              *
CTT GCC GCT GCT CTT GCC AAA ACC TCG GGG AAG GAC ATC GTT CAG TTT
Leu Ala Ala Ala Leu Ala Lys Thr Ser Gly Lys Asp Ile Val Gln Phe>
 a   a   a   a   a   a   a   a  ORF 1  a   a   a   a   a   a   a  >

550            560            570            580
        *              *              *              *
GCC AAT GCT GTG AAA ATT TCT TAC CCT AAA ATT GAT GAG CAG GTT TGT
Ala Asn Ala Val Lys Ile Ser Tyr-Pro Lys Ile Asp Glu Gln Val Cys>
 a   a   a   a   a   a   a   a  ORF 1  a   a   a   a   a   a   a  >

590            600            610            620            630
  *              *              *              *              *
AAT AAA AAT CAT ACA GTG TTG AAT ACG GGG AAA GGG ACA ACC TTT AAT
Asn Lys Asn His Thr Val Leu Asn Thr Gly Lys Gly Thr Thr Phe Asn>
```

FIG. 30C

```
         a    a    a    a    a    a  ORF 1   a    G    a    a    a    a    a    >
640                      650                      660                      670                      680
 *                        *                        *                        *                        *
CCA GAT CCC AAG ACA ACC GAA GAT AAT ACA GCG CAG TGC AGT GGG TTG
Pro Asp Pro Lys Thr Thr Glu Asp Asn Thr Ala Gln Cys Ser Gly Leu>
         a    a    a    a    a    a  ORF 1   a    a    a    a    a    a    a    >
690                      700                      710                      720                      730
 *                        *                        *                        *                        *
AAC ACG AAG GGA ACG AAT AAG TTT AGC GAT TTT GCT GAA GGT GTA GGT
Asn Thr Lys Gly Thr Asn Lys Phe Ser Asp Phe Ala Glu Gly Val Gly>
         a    a    a    a    a    a  ORF 1   a    a    a    a    a    a    a    >
740                      750                      760                      770                      780
 *                        *                        *                        *                        *
TTG AAA GAT AAT AAG TGG CCT ACT GGT CAG GCT GGG AAG AGC AGT
Leu Lys Asp Asn Lys Asn Trp Pro Thr Gly Gln Ala Gly Lys Ser Ser>
         a    a    a    a    a    a  ORF 1   a    a    a    a    a    a    a    >
790                      800                      810                      820
 *                        *                        *                        *
GGT GGT CCT GTG GTG GGT GCA TCT AAT AGT AAT GCC AAC GCT ATG GCT
Gly Gly Pro Val Val Gly Ala Ser Asn Ser Asn Ala Asn Ala Met Ala>
         a    a    a    a    a    a    a    a    a    a    a    a    a    a    >

FIG. 30D
```

```
                830         840         850         860         870
                 *           *           *           *           *
         AGA GAC CTA GTA GAT CTT AAT CGA GAC GAA AAA ACC ATA GTA GCA GGG
         Arg Asp Leu Val Asp Leu Asn Arg Asp Glu Lys Thr Ile Val Ala Gly>
           a   a   a   a   a   a   a   a ORF 1 a   a   a   a   a   a   a >

880         890         900         910         920
                 *           *           *           *           *
         TTA CTA GCT AAA ACT ATT GAA GGT GGT GAG GTT GTT GAG ATT AGG GCG
         Leu Leu Ala Lys Thr Ile Glu Gly Gly Glu Val Val Glu Ile Arg Ala>
           a   a   a   a   a   a   a   a ORF 1 a   a   a   a   a   a   a >

930         940         950         960         970
                 *           *           *           *           *
         GTT TCT TCT ACT TCT GTA ATG GTC AAT GCT TGT TAT GAT CTT CTT AGT
         Val Ser Ser Thr Ser Val Met Val Asn Ala Cys Tyr Asp Leu Leu Ser>
           a   a   a   a   a   a   a   a ORF 1 a   a   a   a   a   a   a >

980         990        1000        1010        1020
                 *           *           *           *           *
         GAA GGT CTA GGC GTT GTT CCT TAC GCT TGT GTC GGT CTT GGA GGT AAC
         Glu Gly Leu Gly Val Val Pro Tyr Ala Cys Val Gly Leu Gly Gly Asn>
           a   a   a   a   a   a   a   a ORF 1 a   a   a   a   a   a   a >
```

FIG. 30E

```
                    1030                1040                1050                1060
                     *                   *                   *                   *
            TTC GTG GGC GTT GTT GAT GGG CAT ATC ACT CCT AAG CTT GCT TAT AGA
            Phe Val Gly Val Val Asp Gly His Ile Thr Pro Lys Leu Ala Tyr Arg>
             a   a   a   a   a   a   a   a   a   a   a   a   a   a   a   a
                                        ORF 1

1070                1080                1090                1100                1110
              *                   *                   *                   *                   *
            TTA AAG GCT GGG TTG AGT TAT CAG CTC TCT CCT GAA ATC TCC GCT TTT
            Leu Lys Ala Gly Leu Ser Tyr Gln Leu Ser Pro Glu Ile Ser Ala Phe>
             a   a   a   a   a   a   a   a   a   a   a   a   a   a   a   a
                                        ORF 1
```

FIG. 30F

```
1120      1130      1140      1150      1160
  *         *         *         *         *
GCT GGG GGA TTC TAT CAT CGC GTT GTG GGA GAT GGT GTC TAT GAT GAT
Ala Gly Gly Phe Tyr His Arg Val Val Gly Asp Gly Val Tyr Asp Asp >
 a   a   a   a   a   a   a   a   a   a   a   a   a   a   a   a   ORF 1

1170      1180      1190      1200      1210
  *         *         *         *         *
CTT CCA GCT CAA CGT CTT GTA GAT ACT AGT CCG GCG GGT CGT ACT
Leu Pro Ala Gln Arg Leu Val Asp Asp Thr Ser Pro Ala Gly Arg Thr >
 a   a   a   a   a   a   a   a   a   a   a   a   a   a   a   ORF 1

1220      1230      1240      1250      1260
  *         *         *         *         *
AAG GAT ACT GCT ATT GCT AAC TTC TCC ATG GCT TAT GTC GGT GGG GAA
Lys Asp Thr Ala Ile Ala Asn Phe Ser Met Ala Tyr Val Gly Gly Glu >
 a   a   a   a   a   a   a   a   a   a   a   a   a   a   a   a   ORF 1

1270      1280      1290      1300      1310
  *         *         *         *         *
TTT GGT GTT AGG TTT GCT TTT TAAGTGG TTTGTTGGAA GCGGGTAAG
Phe Gly Val Arg Phe Ala Phe *   ORF 1 >
 a   a   a   a   a   a   a 1320      1330      1340      1350      1360
  *         *         *         *         *
TCAAACTTAC CCCGCTTCTA TTAGGGAGTT AGTAT ATG AGA AGT AGA AGT AAG CTA
                                        Met Arg Ser Arg Ser Lys Leu >
                                         b   b  ORF 2  b   b   b   b
                                          (SEQ ID NO:29)
```

FIG. 30G

```
1370         1380         1390         1400         1410
  *            *            *            *            *
TTT TTA GGA AGC GTA ATG ATG TCG TTG GCT ATA GTC ATG GCT GGG AAT
Phe Leu Gly Ser Val Met Met Ser Leu Ala Ile Val Met Ala Gly Asn>
 b   b   b   b   b   b  ORF 2  b   b   b   b   b   b   b   b   b >

1420         1430         1440         1450         1460
         *            *            *            *            *
GAT GTC AGG GCT CAT GAT GAC GTT GAT AGC GCT TTG GAT ACT GGT GCG
Asp Val Arg Ala His Asp Asp Val Asp Ser Ala Leu Asp Thr Gly Ala>
 b   b   b   b   b   b  ORF 2  b   b   b   b   b   b   b   b   b >

1470         1480         1490         1500         1510
         *            *            *            *            *
GGA TAT TTC TAT GTT GGT TTG GAT TAC AGT CCA GCG TTT AGC AAG ATA
Gly Tyr Phe Tyr Val Gly Leu Asp Tyr Ser Pro Ala Phe Ser Lys Ile>
 b   b   b   b   b   b  ORF 2  b   b   b   b   b   b   b   b   b >

1520         1530         1540         1550
         *            *            *            *
AGA GAT TTT AGT ATA AGG GAG AGT AAC GGA GAG ACT AAG GCA GTA TAT
Arg Asp Phe Ser Ile Arg Glu Ser Asn Gly Glu Thr Lys Ala Val Tyr>
 b   b   b   b   b   b  ORF 2  b   b   b   b   b   b   b   b   b >

1560         1570         1580         1590         1600
  *            *            *            *            *
CCA TAC TTA AAG GAT GGA AAG AGT GTA AAG CTA GAG TCA CAC AAG TTT
Pro Tyr Leu Lys Asp Gly Lys Ser Val Lys Leu Glu Ser His Lys Phe>
 b   b   b   b   b   b  ORF 2  b   b   b   b   b   b   b   b   b >
```

FIG. 30H

```
                                 1610      1620      1630      1640      1650
                                   *         *         *         *         *
                                 GAC TGG AAC ACT CCT GAT CCT CGG ATT GGG TTT AAG GAC AAC ATG CTT
                                 Asp Trp Asn Thr Pro Asp Pro Arg Ile Gly Phe Lys Asp Asn Met Leu>
                                  b   b   b   b   b   b   b   b   b   b   b   b   b   b   b   b  >

1660      1670      1680      1690      1700
                                   *         *         *         *         *
                                 GTA GCT ATG GAA GGT AGT GTT GGT TAT GGT ATT GGT GGT GCC AGG GTT
                                 Val Ala Met Glu Gly Ser Val Gly Tyr Gly Ile Gly Gly Ala Arg Val>
                                  b   b   b   b   b   b   b  ORF 2 b   b   b   b   b   b   b   b  >

1710      1720      1730      1740      1750
                                   *         *         *         *         *
                                 GAG CTT GAG ATT GGT TAC GAG CGC TTC AAG ACC AAG GGT ATT AGA GAT
                                 Glu Leu Glu Ile Gly Tyr Glu Arg Phe Lys Thr Lys Gly Ile Arg Asp>
                                  b   b   b   b   b   b   b  ORF 2 b   b   b   b   b   b   b   b  >

1760      1770      1780      1790
                                   *         *         *         *
                                 AGT GGT AGT AAG GAA GAT GAA GCT GAT ACA GTA TAT CTA GCT AAG
                                 Ser Gly Ser Lys Glu Asp Glu Ala Asp Thr Val Tyr Leu Ala Lys>
                                  b   b   b   b   b   b   b  ORF 2 b   b   b   b   b   b   b  >

1800      1810      1820      1830      1840
                                   *         *         *         *         *
                                 GAG TTA GCT TAT GAT GTT GTT ACT GGG CAG ACT GAT AAC CTT GCC GCT
                                 Glu Leu Ala Tyr Asp Val Val Thr Gly Gln Thr Asp Asn Leu Ala Ala>
                                  b   b   b   b   b   b   b  ORF 2 b   b   b   b   b   b   b   b  >

FIG. 30I
```

```
      1850        1860        1870        1880        1890
        *           *           *           *           *
     GCT CTG GCC AAA ACC TCC GGT AAA GAC TTT GTC CAG TTT GCT AAG GCG
     Ala Leu Ala Lys Thr Ser Gly Lys Asp Phe Val Gln Phe Ala Lys Ala>
      b   b   b   b   b   b   b   b   b   b   b   b   b   b   b   b >

1900        1910        1920        1930        1940
        *           *           *           *           *
     GTT GGG GTT TCT CAT CCT AGT ATT GAT GGG AAG GTT TGT AAG ACG AAG
     Val Gly Val Ser His Pro Ser Ile Asp Gly Lys Val Cys Lys Thr Lys>
      b   b   b   b   b   b   b   b   b   b   b   b   b   b   b   b >
                                      <Gly Leu Ile Ser Pro Phe Thr Gln Leu Val Phe
                                       d   d   d   d ORF 4 d   d   d   d   d   d 1950        1960        1970        1980        1990
        *           *           *           *           *
     GCG GAT AGC TCG AAG AAA TTT CCG TTA TAT AGT GAC GAA ACG CAC ACG
     Ala Asp Ser Lys Ser Lys Phe Pro Leu Tyr Ser Asp Glu Thr His Thr>
      b   b   b   b   b   b   b   b   b   b   b   b   b   b   b   b >
     <Ala Ser Leu Glu Phe Phe Asn Gly Asn Tyr Leu Ser Ser Val Cys Val
      v   d   d   d   d   d   d   d   d   d   d   d   d   d   d   d 2000        2010        2020        2030
        *           *           *           *
     AAG GGG GCA AGT GAG GGG AGA ACG TCT TTG TGC GGT GAC AAT GGT AGT
     Lys Gly Ala Ser Glu Gly Arg Thr Ser Leu Cys Gly Asp Asn Gly Ser>
      b   b   b   b   b   b   b   b   b   b   b   b   b   b   b   b >
     <Phe Pro Ala Leu Ser Pro Leu Val Asp Lys His Pro Ser Leu Pro Leu
      v   d   d   d   d   d   d   d   d   d   d   d   d   d   d   d
```

FIG. 30J

```
2040        2050         2060         2070         2080
 *           *            *            *            *
TCT ACG ATA ACA AAC AGT GGT GCG AAT GTA AGT GAA ACT GGG CAG GTT
Ser Thr Ile Thr Asn Ser Gly Ala Asn Val Ser Glu Thr Gly Gln Val>
 b   b   b   b   b   b   b   b   ORF 2   b   b   b   b   b   b    ^
<Glu Val Ile Val Phe Leu Pro Ala Phe Thr Leu Ser Val Pro Cys Thr
  d   d   d   d   d   d   d   d   ORF 4   d   d   d   d   d   d
 v 2090        2100         2110         2120         2130
 *           *            *            *            *
TTT AGG GAT TTT ATC AGG GCA ACG CTG AAA GAG GAT GGT AGT AAA AAC
Phe Arg Asp Phe Ile Arg Ala Thr Leu Lys Glu Asp Gly Ser Lys Asn>
 b   b   b   b   b   b   b   b   ORF 2   b   b   b   b   b   b    ^
<Lys Leu Ser Lys Ile Leu Ala Val Ser Phe Ser Ser Pro Leu Leu Phe
  d   d   d   d   d   d   d   d   ORF 4   d   d   d   d   d   d
 v 2140        2150         2160         2170         2180
 *           *            *            *            *
TGG CCA ACT TCA AGC GGC ACG GGA ACT CCA AAA CCT GTC ACG AAC GAC
Trp Pro Thr Ser Ser Gly Thr Gly Thr Pro Lys Pro Val Thr Asn Asp>
 b   b   b   b   b   b   b   b   ORF 2   b   b   b   b   b   b    ^
<Gln Gly Val Glu Leu Pro Val Gly Phe Gly Thr Val Phe Ser
  d   d   d   d   d   d   d   d   ORF 4   d   d   d   d   d   d
 v 2190        2200         2210         2220         2230
 *           *            *            *            *
AAC GCC AAA GCC GTA GCT AAA GAC CTA GTA CAG GAG CTA ACC CCT GAA
Asn Ala Lys Ala Val Ala Lys Asp Leu Val Gln Glu Leu Thr Pro Glu>
 b   b   b   b   b   b   b   b   ORF 2   b   b   b   b   b   b    ^
<Leu Ala Leu Ala Thr Ala Leu Ser Arg Thr Cys Ser Ser Val Gly Ser
  d   d   d   d   d   d   d   d   ORF 4   d   d   d   d   d   d
 v
```

FIG. 30K

```
                            2240      2250      2260      2270
                              *         *         *         *
                  GAA AAA ACC ATA GTA GCA GGG TTA CTA GCT AAA ACT ATT GAA GGT GGT
                  Glu Lys Thr Ile Val Ala Gly Leu Leu Ala Lys Thr Ile Glu Gly Gly>
                   b   b   b   b   b   b   b  ORF 2  b   b   b   b   b   b   b   b  >
<Ser Phe Val Met
 <  d   d   d 2280      2290      2300      2310      2320
         *         *         *         *         *
GAG GTT ATT GAA ATC AGG GCG GTT TCT CTT AGT GAA GGT GTT TCT ACT TCT GTG ATG GTC AAT
Glu Val Ile Glu Ile Arg Ala Val Ser Leu Ser Glu Gly Val Ser Thr Ser Val Met Val Asn>
 b   b   b   b   b   b   b   b   b   b   b  ORF 2  b   b   b   b   b   b   b   b  >

2330      2340      2350      2360      2370
      *         *         *         *         *
GCT TGT TAT GAT CTT CTT AGT GAA GGT GTT GTC CCT TAT GCT
Ala Cys Tyr Asp Leu Leu Ser Glu Gly Val Val Pro Tyr Ala>
 b   b   b   b   b   b   b  ORF 2  b   b   b   b   b   b  >

2380      2390      2400      2410      2420
         *         *         *         *         *
TGT GTT GGT CTC GGT GGT AAC TTC GTG GGC GTG GTT GAT GGA ATT CAT
Cys Val Gly Leu Gly Gly Asn Phe Val Gly Val Val Asp Gly Ile His>
 b   b   b   b   b   b   b  ORF 2  b   b   b   b   b   b   b   b  >

2430      2440      2450      2460      2470
      *         *         *         *         *
TAC ACA AAC CAT CTT TAA CTCTGAATAC CCTAGTTAAG GTAAGTGAAG
Tyr Thr Asn His Leu>                          (SEQ ID NO:30)
 b  ORF 2   b    b  >
```

FIG. 30L

```
       2480       2490       2500       2510       2520       2530
         *          *          *          *          *          *
TAACTAGGCA AATTAGTGCT GCACCACTCG TGAAACAAAC TACGATCAGC GATTCACCAT 2540       2550       2560       2570       2580       2590
         *          *          *          *          *          *
ACTTAGTAAG TCCGTACAGT GGCTTTACGC TCTTACCCAT CATGAAAAAT ACTTGCTATC 2600       2610       2620       2630       2640       2650
         *          *          *          *          *          *
TAGGAATCTC CTCTAAAACT TTACAGAGGT TATCTGTACT TCGAGAGGAA GCTAATCTGT 2660       2670       2680       2690       2700       2710
         *          *          *          *          *          *
GGCTCATGAG GATGGTATTT AGCGTATCAC AGGTTCCAGC TGTCTTACAG TCTCTGGAGA 2720       2730       2740       2750       2760       2770
         *          *          *          *          *          *
TGTTATAAGG GTGCACATAT AAAACTATGC AATATTTCGC TGCAATACGA TTCCGATTCG 2780       2790       2800       2810       2820       2830
         *          *          *          *          *          *
AAAACACTGA AAAGTATTCC CATTATCTAT GAAATCTCTG GTAGATATAA ATAAGGTAT 2840       2850       2860       2870       2880       2890
         *          *          *          *          *          *
ACGCAGTAAC TCTTACTTGT TAAAACAAG ACCAATGGTA TAAGGAAAAA GCCTCAGTGT 2900       2910       2920       2930       2940       2950
         *          *          *          *          *          *
TGTTCCTCAT GCTTGCAGCT TACCCGATGC ACTCTTATTT AATAAGGTTG AATGTTAATC 2960       2970       2980       2990       3000       3010
         *          *          *          *          *          *
AGTGTTTCTG GGAAGGGAAT ATCTTATTGC AAAAACCTCA GCAGCTGCTT AGATATTGAA
```

FIG. 30M

```
        3020       3030       3040       3050       3060       3070
          *          *          *          *          *          *
     ACAAATGCGA TCATGCCGTC AGCACAATTA TGACATCTCT TAAGGCTCTG TAGTGCGCTT 3080       3090       3100       3110       3120       3130
          *          *          *          *          *          *
     ATTTAGTCTA ACATGTGGTA AAGCTTTGCC AGTTCTTTAC CACATGTTCA CCATCAGTTA 3140       3150       3160       3170
                *          *          *          *
     ATT GAA AGC AAA TCT TGC TCC TAT GTT GAA GCC GTA ACT AGC TAT ATT
    <Asn Phe Ala Phe Arg Ala Gly Ile Asn Phe Gly Tyr Ser Ala Ile Asn
     v   c   c   c   c   c   c   c  ORF 3  c   c   c   c   c   c   c 3180       3190       3200       3210       3220
       *          *          *          *          *
     TGC CTT TAC CTT GGC TGC AGC ACC TGC TAT GTT TAC ACG GTT ACT
    <Ala Lys Val Lys Ala Ala Ala Gly Ala Ile Asn Val Arg Asn Ser
     v   c   c   c   c   c   c   c  ORF 3  c   c   c   c   c   c 3230       3240       3250       3260       3270
          *          *          *          *          *
     AGC GGG AAT ACC TGC ATA CTG TTC ATC GAA AAT TCC GTG GTA AAA ACC
    <Ala Pro Ile Gly Ala Tyr Gln Glu Asp Phe Ile Gly His Tyr Phe Gly
     v   c   c   c   c   c   c   c  ORF 3  c   c   c   c   c   c   c

FIG. 30N
```

```
                    3280              3290              3300              3310              3320
                      *                 *                 *                 *                 *
              TCC AGC TAT TAA AGA TAT TTC AGG AGT AAG CTT GTA ACT TAC GCC TAC
             <Gly Ala Ile Leu Ser Ile Glu Pro Thr Leu Lys Tyr Ser Val Gly Val
              v   c   c   c   c   c   c  ORF 3 c   c   c   c   c   c   c   c 3330              3340              3350              3360              3370
                      *                 *                 *                 *                 *
              CTT TCC TCT ATA AGC CAA CTT ACT TGT AAC GTG ATC GGC GAT ATT AAT
             <Lys Gly Arg Tyr Ala Leu Lys Ser Thr Val His Asp Ala Ile Asn Ile
              v   c   c   c   c   c   c  ORF 3 c   c   c   c   c   c   c   c 3380              3390              3400              3410
                      *                 *                 *                 *
              AAA GCT CGC CCC TAA CCC AGC ACA CAT GTA AGG AGG GAA TTC GAT ATC
             <Phe Ser Ala Gly Leu Gly Ala Cys Met Tyr Pro Pro Phe Glu Ile Asp
              v   c   c   c   c   c   c  ORF 3 c   c   c   c   c   c   c   c 3420        3430
                *           *
              AAG CTT ATC GAT ACC GT    (SEQ ID NO:28)
             <Leu Lys Asp Ile Gly
              v   c  ORF 3 c

FIG. 30O
```

```
GE MSP-2A     mr.kgKIiLGsVMMSMAivMAgndvrahddvSaleTGG..........AGyFYVGLDYSP   (SEQ ID NO:27)
GE MSP-2B                                                                    (SEQ ID NO:30)
GE MSP-2C     mrsrsKLfLGsVMMSLAivMAgndvrahddvSaldTGG..........AGyFYVGLDYSP
AM msp2       msavsnrKLpLGgVLMALAaaVApihsllaapaAGGeglfsgagAGsFYIGLDYSP        (SEQ ID NO:31)

GE MSP-2A     AFskIRDFsIRESNGeTKaVYPYlKDgk.sVklesHkFDWnTPDPRIgFKDnMLVAMEGS
GE MSP-2B                                         MLVAMEGS                   (SEQ ID NO:29)
GE MSP-2C     AFskIRDFsIRESNGeTKaVYPYlKDgk.sVklesHkFDWnTPDPRIsFKDnMLVAMEGS
AM msp2       AFgsIKDFkVQEAGgtIRgVFPYkRDaagrivHnFDWsAPEPKIsFKDsMLtALEGS GE MSP-2A     VGYGIGGARVELEIGYERFKTKGIRDSGSKEDEADTVYLLAKELAYDVVTGQTDNLAAAL
GE MSP-2B     VGYGIGGARVELEIGYERFKTKGIRDSGSKEDEADTVYLLAKELAYDVVTGQTDNLAAAL
GE MSP-2C     VGYGIGGARVELEIGYERFKTKGIRDSGSKEDEADTVYLLAKELAYDVVTGQTDNLAAAL
AM msp2       IGYsIGGARVEVEVGYERFviKGgkkS..nED.TaSVFLLgKELAYhtarGQvDFLATAL
```

FIG. 31A

```
GE MSP-2A           AKTSGKDiVQFAkAVsVShPgIDkKVCdgghargkksgdngslAdyTdggaSqtNkTAQC
GE MSP-2B           AKTSGKDiVQFAnAVklSyVShPkIDeQVCnknhtvlnt...gkgTtfNpdpkTTednTAQC
GE MSP-2C           AKTSGKDfVQFAkAVgVShPsIDgKVCktkadsskk...fplysdeThtkgASeGrTSlC
AM msp2             gKmTksEakKwgnAIesAtgttsg.........delskkvcgkgTTsGsTnQC GE MSP-2A           sgmG........tgkAgkriglgITKFvnkTkvgEG.KNWPTgyvndgdnvNVlGdTNgNAe
GE MSP-2B           sglN.........TkgT.nkfSDFaegvglkDN.KNWPTgqagkssggPVvGaSNsNAn
GE MSP-2C           gdnGsstitnsgnnvseTggvfrDFirnTlkeDGsKNWPTssglg....TpkpvTNdNAk
AM msp2             gttd.............StaTtkisAvFtedAaaqls.......TMdNTTin.Tt GE MSP-2A           AVAKDLVqeltpEEKTIVAGLLAKTIEGGEVVEIRAVSSTSVMVNACYDLLSEGLGVVPY
GE MSP-2B           AMARDLVdlnr.DEKTIVAGLLAKTIEGGEVVEIRAVSSTSVMVNACYDLLSEGLGVVPY
GE MSP-2C           AVAKDLVqeltpEEKTIVAGLLAKTIEGGEVIEIRAVSSTSVMVNACYDLLSEGLGVVPY
AM msp2             gMAhnInsltk.DEKAlVAGafARAVEGaEVIEVRAIgSTSVMlNACYDLLTDgIGVVPY GE MSP-2A           ACVGLGGNFVGVVDGHITPKlAYRLKAGLSYqlSPviSAFAGGFYHRVVGDGvYDDLPaq
GE MSP-2B           ACVGLGGNFVGVVDGHITPKlAYRlKAGLSYqlSPelSAFAGGFYHRVVGDGvYDDLPaq
GE MSP-2C           ACVGLGGNFVsVVDGHINPKfAYRVKAGLSYalTPeISAFAGaFYHKVLGDGdYDELPls
AM msp2             ACaGIGGGNFVsVVDGHINPKfAYRVKAGLSYalTPeISAFAGaFYHKVLGDGdYDELPls GE MSP-2A           RLvDdTspAGRTKDTalAnFsmAYvGGKfGVRFAF
GE MSP-2B           RLvDdTspAGRTKDTalAnFsmAYvGGKfGVRFAF
GE MSP-2C           HlSDyTgtAGKNKDTgIASEnfAYfGGElGVRFAF
AM msp2
```

FIG. 31B

PEPTIDE #23

\*-E-L-\*-\*-V-V-\*-G-E-N-T-L
(SEQ ID NO:36)

PEPTIDE #24

\*-\*-P-F-H-M-Y-P-G-L-Y-S-E-N-L-F-R-S-T-R-D-L-R-G-V-S-G-V (SEQ ID NO:34)

PRIMER 5F: CCNTTYCAYATGTAYCCNGG (SEQ ID NO:32)

PEPTIDE #26

\*-\*-E-D-T-V-R-D-G-I-A-G-F-D-S-L (SEQ ID NO:37)

PEPTIDE #25

F-R-L-S-L-A-G-E-Y-A-R-P-K (SEQ ID NO:35)

PRIMER 6R: GGNCKNGCRTAYTCNCCNGC (SEQ ID NO:33)

FIG. 34

```
    1 GAATTCCTAGCAACAAGGGTGGATATTTCACGCTTGCTAGCTGAGTGATTTAGGACTGA
   61 GGGTGAGCTATGAGATGTATAGGGGGAGAGTATGCGCTGCTGCTTTTTACTCAGCTTC
  121 ATAAGATAGCGGCGAGCTACAGCTTTGCTACGGGTTCGTTATCATCATCAGCTTATTGTCGT
  181 ATAACACTCGTGATGTATATCATCGTGATGTCGTTGGCTTGATGTCGGTTATAAGGATCATGGATGTGCTATGG
  241 TTAAGCCTTTGAAGTATGACTTTGGCTTGATGGCTTGATTTTGTGGATTTTGTGAAGTTTGTGATGGTTCTAAG
  301 AAGAGTGTGGGTGTGTTGTGGATTTTTGAAGTTTTGTATGAAGGTTCTCTGGTAGTTGT
                                              M  R  G  S  L  V  V  V
  421 GAGTATGGCCGATGCTCTTCCTCGGGTCCTCTGGTGTGTAGTTGCTGCATCTTCTGGAGG
        S  M  A  M  L  L  L  G  S  S  G  G  V  V  A  A  S  G  G
  481 GGGGTTTGAAGGAGAGCGTGCGTCGGTAACGGGTAAGGTGTTATCTTATGCCTGGTTGTT
        G  F  E  G  E  R  A  S  V  T  G  K  V  L  S  Y  A  W  L  L
  541 GAGTGATCGGGCTGTAAAAGGGCAAGGTAACAGTGAAGGTCAGAAGCTCGCGTGAAAT
        S  D  R  A  V  K  G  Q  G  N  S  E  G  Q  K  L  A  L  E  M
  601 GTATGGCGCAAAGTTGGGCTATAAGGCTTATGGTTATCCAGGAGTTGGAGATGTCTTTTC
        Y  G  A  K  L  G  Y  K  G  Y  G  Y  P  G  V  G  D  V  F  S
  661 TTCGCCCGTTGGAGCATGGTCTTGATTCTTGGGGAGCTATGATGGGCAAATTTTCCCTTAT
        S  P  L  E  H  G  L  D  S  W  G  A  S  Y  D  A  M  L  S  L
  721 TGGATTGCGTACGGGCGTCGTGATGTGCTAGGTACCCAATATGGGCAAATTTTCCCTTAT
        G  L  R  T  G  R  D  V  L  G  T  Q  Y  G  A  N  F  S  L  M
  781 GGTTCCTCGCGGGTTCTGGTGGATTCATGTGTTTCATGGTGCGCCCTGGTATAGAGAGCAG
        V  P  A  G  S  G  G  S  M  V  F  H  G  A  P  G  I  E  S  R
  841 GGTTTTTGCTGATACTTCCTTGGGAAATTTTCTGTTGGTTACCAGGAAGGTGTCGAGTC
        V  F  A  D  T  S  L  G  N  F  S  V  G  Y  Q  E  G  V  E  S
  901 AAAAATGAAGGTCGATGTCTTCGGTGGCTTATCAGTGAAAATGGAAGCGCTTGGGGTCG
        K  M  K  V  D  V  F  G  G  L  S  G  E  N  G  S  A  W  G  R
  961 GTACTTGCGTGGCTTTTTAAAGTATGCGAAGGTGTACCTTTTCACATGTATCCAGGGCT
        Y  L  R  G  F  L  K  Y  A  K  G  V  P  F  H  M  Y  P  G  L
 1021 TTACAGTGAGAATTTATTCCGGTCTACAAGAGACTTACGGGGTGTTAGTGGTGTTTCTGC
        Y  S  E  N  L  F  R  S  T  R  D  L  R  G  V  S  G  V  S  A
```

FIG. 36A

```
1081  GAAGACAAAGGATGTCTTAAATTCTATGCCGCTGAGGTTTTCTTTTGAGTCTGCTAGGTT
       K  T  K  D  V  L  N  S  M  P  L  R  F  S  F  E  S  A  R  L
1141  GGGTGGCTTGTCTGTGTTGGTTTTAGTTACTCTCCAACGGATATCGGGATGATATGTACAA
       G  G  L  S  V  G  F  S  Y  S  P  T  G  Y  R  D  D  M  Y  K
1201  GGGTGGAGAGTTTACTGTACGGGATGGTTAAGTTGGCAAAATGATTGCCGTGGTGCCTCCTCGTTT
       G  G  E  F  T  V  R  D  G  I  A  G  E  D  S  L  G  T  V  N
1261  TTTATTCGCGAAGACGGGGTTAAGTTTGGCAAAATGATTGCCGTGGTGCCTCCTCGTTT
       L  F  A  K  T  G  V  K  F  G  K  M  I  A  V  V  P  P  R  F
1321  TGATTCTGGTCCGGTATATAAAAACATAGTAAGCGGTGCTGCGAATTACGAGTACGAGTT
       D  S  G  P  V  Y  K  N  I  V  S  G  A  A  N  Y  E  Y  E  L
1381  AGCCGATATTGCTAAGTTTAGGTTATCGCTTGCTGGTGAGTATGCAAGACCGAAGAAGGC
       A  D  I  A  K  F  R  L  S  L  A  G  E  Y  A  R  P  K  K  A
1441  TAGGGATATAGTGCCAGAAGGAAGAAGAAAATTATGTAGCTGATTACAATGA
       R  D  I  V  P  E  G  R  R  K  E  E  I  Y  V  A  D  Y  N  D
1501  TTTGTCCGCGTTTTCCAGTGGCTTAGAAATAGACTTGGGTAGGTTGCGGTTTGCTGTTGG
       L  S  A  F  S  S  G  L  E  O  D  L  G  R  L  R  F  A  V  G
1561  CGGTGGATACCTTGGAAGTCTGGTAGTCCTAAAATGTACATATTAAAGGATGTAAGACA
       G  G  Y  L  G  K  S  G  S  P  K  M  Y  I  L  K  D  V  R  H
1621  TAAGGTACCTTATGTGAAAAAGAAGGGTTTGCCGTCTCATTATGTGACTTCAGCGGTTTC
       K  V  P  Y  V  K  K  K  G  L  P  S  H  Y  V  T  S  A  V  S
1681  CTATACGATTGGTTCTTTTCTGCTACAGTTGCTTACTTTATGAGTAGGTTAACGCACAT
       Y  T  I  G  S  F  S  A  T  V  A  Y  F  M  S  R  L  T  H  I
1741  TCCGCCTGCTACGGTATCTCATAAGATCCCAGGAAGTATGGATTCCGTTGTGA
       P  P  A  T  V  S  H  K  I  P  G  K  Y  E  L  D  S  V  V  D
1801  TGGGGAGAATACGTTGAAGGATTGGTTGTAGGAGTCGGTTATAACCTTTTTAGTAAGG
       G  E  N  T  L  K  D  L  V  V  G  V  G  Y  N  L  F  S  K  G
```

FIG. 36B

```
1861  AAGTACGAGCTTAGAAGTATTTCTAAATTGTCACATGTTCTCTGTGCAACATAAATTCAA
        S   T   S   L   E   V   F   L   N   C   H   M   F   S   V   Q   H   K   F   N
1921  CATCCATGAGTACAAATCTACTGAGAGTAGTGGGTTTGTATTGAAAGAAGGTGGAGAGCG
        I   H   E   Y   K   S   T   E   S   S   G   F   V   L   K   E   G   G   E   R
1981  TGCAAATACTAATAATGGCGTTGCTGGCGTTATTAGGAATGAAGTTTGCGTTTAATAACA
        A   N   T   N   N   G   A   V   A   L   L   G   M   K   F   A   F     (SEQ ID NO:39)
2041  AGGGGTTGTTGCAAGAATACTCTTGTGGTTTATTAGCCAAGTCTTCTTATTGGGGCGTG
2101  TACTGAGGTACGGCGCCCCTTTTTTGTGGAGAGTCTAAGGTTTGTTATGTTTGTAGA (SEQ ID NO:38)
```

CHARACTERIZATION OF GRANULOCYTIC EHRLICHIA AND METHODS OF USE

This application is a divisional of U.S. patent application Ser. No. 09/792,957, filed Feb. 26, 2001, now U.S. Pat. No. 7,863,434, which is a divisional of U.S. patent application Ser. No. 09/066,046, filed Apr. 24, 1998, now U.S. Pat. No. 6,204,252 B1, which claims benefit of U.S. Provisional Application No. 60/044,933, filed Apr. 25, 1997, each of which is hereby incorporated by reference herein in its entirety.

BACKGROUND OF THE INVENTION

1. Field of the Invention

The present invention relates, in general, to granulocytic Ehrlichia (GE) proteins. In particular, the present invention relates to nucleic acid molecules coding for GE S2, S7, S22, S23, C6.1, C6.2, S11, E8, E46#1, and E46#2 proteins; purified GE S2, S7, S22, S23, C6.1, C6.2, S11, E8, E46#1, and E46#2 proteins and polypeptides; recombinant nucleic acid molecules; cells containing the recombinant nucleic acid molecules; antibodies having binding affinity specifically to GE S2, S7, S22, S23, C6.1, C6.2, S11, E8, E46#1, and E46#2 proteins and polypeptides; hybridomas containing the antibodies; nucleic acid probes for the detection of nucleic acids encoding GE S2, S7, S22, S23, C6.1, C6.2, S11, E8, E46#1, and E46#2 proteins; a method of detecting nucleic acids encoding GE S2, S7, S22, S23, C6.1, C6.2, S11, E8, E46#1, and E46#2 proteins or polypeptides in a sample; kits containing nucleic acid probes or antibodies; bioassays using the nucleic acid sequence, protein or antibodies of this invention to diagnose, assess, or prognose a mammal afflicted with ehrlichiosis; therapeutic uses, specifically vaccines comprising GE S2, S7, S22, S23, C6.1, C6.2, S11, E8, E46#1, and E46#2 proteins or polypeptides; and methods of preventing ehrlichiosis in an animal.

2. Related Art

Granulocytic ehrlichiosis is an acute, potentially fatal tick-borne infection. The causative agent, granulocytic Ehrlichia (GE), has been identified by the polymerase chain reaction (PCR) using universal primers for eubacterial 16S ribosomal RNA (rRNA) to amplify the DNA of infected patients' blood (Chen et al., *J. Clin. Micro.* 32:589-595 (1994)). Comparison of the 16S rRNA gene sequence of GE to other known 16S rDNA sequences revealed a nearly identical match to the 16S genes of *Ehrlichia phagocytophila* and *Ehrlichia equi* (Chen et al., 1994). Two other groups of *Ehrlichia* species have also been categorized according to their 16S rRNA gene sequences, the *Ehrlichia canis* and *Ehrlichia sennetsu* groups. The *E. canis* and *E. sennetsu* species predominantly infect mononuclear phagocytes (Dumler et al, *N. Eng. J. Med.* 325:1109-1110 (1991)), whereas members of the *E. phagocytophila* group including GE are tropic for granulocytes (Ristic et al., in *Bergey's Manual of Systemic Bacteriology*, Kreig et al., eds., (1984), pp. 704-709). The near identity of the 16S rRNA gene sequences and the sharing of significant antigenicity by IFA and immunoblot (Dumler et al., *J. Clin. Micro.* 33:1098-1103 (1995)) indicate that *E. phagocytophila*, *E. equi*, and GE are closely related.

Full classification of the *E. phagocytophila* species including antigenic relationships among the individual isolates has been impeded by the inability to cultivate these organisms in cell culture. It has been shown that GE can be successfully cultivated in HL60 cells, a human promyelocytic leukemia cell line (Coughlin et al., PCT Application No. PCT/US96/10117; Goodman et al., *N. Eng. J. Med.* 334:209-215 (1996)). Walker et al., PCT Application No. PCT/US97/09147 teaches an isolated gene encoding a 120 kDa immunodominant antigen of *E. chaffeensis* that stimulates production of specific antibodies in infected humans.

The present invention describes GE specific genes encoding ten proteins (S2, S7, S22, S23, C6.1, C6.2, S11, E8, E46#1, and E46#2) which can be used as diagnostic reagents and vaccines.

SUMMARY OF THE INVENTION

The invention provides isolated nucleic acid molecules coding for polypeptides comprising amino acid sequences corresponding to GE S2, S7, S22, S23, C6.1, C6.2, S11, E8, E46#1, and E46#2 proteins.

The invention further provides purified polypeptides comprising amino acid sequences corresponding to GE S2, S7, S22, S23, C6.1, C6.2, S11, E8, E46#1, and E46#2 proteins.

The invention also provides nucleic acid probes for the specific detection of the presence of GE S2, S7, S22, S23, C6.1, C6.2, S11, E8, E46#1, and E46#2 proteins or polypeptides in a sample.

The invention further provides a method of detecting nucleic acid encoding GE S2, S7, S22, S23, C6.1, C6.2, S11, E8, E46#1, or E46#2 protein in a sample.

The invention also provides a kit for detecting the presence of nucleic acid encoding GE S2, S7, S22, S23, C6.1, C6.2, S11, E8, E46#1, or E46#2 protein in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides a recombinant nucleic acid molecule comprising a sequence complimentary to an RNA sequence encoding an amino acid sequence corresponding to the above-described polypeptide.

The invention also provides a cell that contains the above-described recombinant nucleic acid molecule.

The invention further provides a non-human organism that contains the above-described recombinant nucleic acid molecule.

The invention also provides an antibody having binding affinity specifically to a GE S2, S7, S22, S23, C6.1, C6.2, S11, E8, E46#1, or E46#2 protein or polypeptide.

The invention further provides a method of detecting GE S2, S7, S22, S23, C6.1, C6.2, S11, E8, E46#1, or E46#2 protein or polypeptide in a sample.

The invention also provides a method of measuring the amount of GE S2, S7, S22, S23, C6.1, C6.2, S11, E8, E46#1, or E46#2 protein or polypeptide in a sample.

The invention further provides a method of detecting antibodies having binding affinity specifically to a GE S2, S7, S22, S23, C6.1, C6.2, S11, E8, E46#1, or E46#2 protein or polypeptide.

The invention further provides a diagnostic kit comprising a first container means containing the above-described antibody, and a second container means containing a conjugate comprising a binding partner of the monoclonal antibody and a label.

The invention also provides a hybridoma which produces the above-described monoclonal antibody.

The invention further provides diagnostic methods for ehrlichiosis. More specifically, the invention further provides a method for identifying granulocytic Ehrlichia in an animal comprising analyzing tissue or body fluid from the animal for an S2, S7, S22, S23, C6.1, C6.2, S 11, E8, E46#1, or E46#2 nucleic acid, protein, polysaccharide, or antibody.

The invention also provides methods for therapeutic uses involving all or part of the GE S2, S7, S22, S23, C6.1, C6.2, S11, E46#1, or E46#2 nucleic acid or protein. More specifically, the invention further provides a vaccine comprising a GE S2, S7, S22, S23, C6.1, C6.2, S11, E46#1, or E46#2 protein or nucleic acid together with a pharmaceutically acceptable diluent, carrier, or excipient, wherein the protein or nucleic acid is present in an amount effective to elicit a beneficial immune response in an animal to the protein.

The invention also provides a method of preventing or inhibiting ehrlichiosis in an animal comprising administering to the animal the above-described vaccine.

Further objects and advantages of the present invention will be clear from the description that follows.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA.

Recombinant DNA. Any DNA molecule formed by joining DNA segments from different sources and produced using recombinant DNA technology (i.e., molecular genetic engineering).

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Open Reading Frame ("orf"). The property of some nucleic acid sequences to encode for more than one peptide within the same sequence, which is possible because these sequences contain a series of triplets coding for amino acids without any termination codons interrupting the relevant reading frames.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome can be digested by a particular restriction endonuclease into a discrete set of restriction fragments.

Agarose Gel Electrophoresis. To determine the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoR1. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action or electrophonetic transfer.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter as by the Southern hybridization transfer procedures. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe. Examples of hybridization conditions can be found in Ausubel, F. M. et al., *Current Protocols in Molecular Biology*, John Wily & Sons, Inc., New York, NY (1989). For examples, a nitrocellulose filter is incubated overnight at 68° C. with labeled probe in a solution containing 50% formamide, high salt (either 5×SSC [20×: 3M NaCl/0.3M trisodium citrate] or 5×SSPE [20×: 3.6M NaCl/0.2M $NaH_2PO_4$/0.02M EDTA, pH 7.7]), 5×Denhardt's solution, 1% SDS, and 100 µg/ml denatured salmon sperm DNA. This is followed by several washes in 0.2×SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens. A mutant variation of a nucleic acid molecule results from a mutation. A mutant polypeptide can result from a mutant nucleic acid molecule.

Species. A "species" is a group of actually or potentially interbreeding natural populations. A species variation within a nucleic acid molecule or protein is a change in the nucleic acid or amino acid sequence that occurs among species and can be determined by DNA sequencing of the molecule in question.

Purified. A "purified" protein or nucleic acid is a protein or nucleic acid that has been separated from a cellular component. "Purified" proteins or nucleic acids have been purified to a level of purity not found in nature.

BRIEF DESCRIPTION OF THE FIGURES

FIG. 4. DNA sequence of S22 (SEQ ID NO: 1). The complete DNA sequence of the S22 insert in Lambda Zap II is shown. The nucleotide number is indicated in the left margin.

FIG. 5. FIG. 5A shows the amino acid sequence of S22 (SEQ ID NO:2). This sequence constitutes the translated amino acid sequence for the open reading frame of S22 beginning at nucleotide 500 and ending with the stop codon at nucleotide 2539 of SEQ ID NO:1 (See, FIG. 4). FIG. 5B shows the nucleic acid sequence of the 130 kDa protein gene, corresponding to nucleotides 451-2379 of SEQ ID NO:1. Nucleotide numbers are indicated at the left. The ATG start codon and TAA stop codon are shown in bold type. The translated amino acid sequence for the open reading frame is displayed underneath the DNA sequence using the single-letter amino acid code (SEQ ID NO:2).

FIG. 6. DNA sequence of S2 (SEQ ID NO:3). The complete DNA sequence of the S2 insert in Lambda Zap II is shown in FIG. 6A and continued in FIGS. 6B and 6C. The nucleotide number is indicated in the left margin.

FIG. 7. FIG. 7A shows the amino acid sequence of S2 (SEQ ID NO NO:4) for the open reading frame beginning at nucleotide 1576 and ending with the stop codon at nucleotide 3801 (See, FIG. 6). FIG. 7B shows the nucleic acid sequence of the 160 kDa protein gene (nucleotides 1501-3850 of SEQ ID NO:3). Nucleotide numbers are indicated at the left. The ATG start codon and TAA stop codon are shown in bold type. The translated amino acid sequence for the open reading frame is displayed underneath the DNA sequence using the single-letter amino acid code (SEQ ID NO:4).

FIG. 8. DNA sequence of S7 (SEQ ID NO:5). The complete DNA sequence of the S7 insert in Lambda Zap II is shown in FIG. 8A and continued in FIGS. 8B and 8C. The nucleotide number is indicated in the left margin.

FIG. 9. FIG. 9A shows the amino acid sequence of S7 (SEQ ID NO:6) for the open reading frame beginning at nucleotide 233 and ending with the stop codon at nucleotide 1969 (See, FIG. 8). FIG. 9B shows the nucleic acid sequence of the 100 kDa protein gene (nucleotides 172-2001 of SEQ ID NO:5). Nucleotide numbers are indicated at the left. The ATG start codon and TAA stop codon are shown in bold type. The translated amino acid sequence for the open reading frame is displayed underneath the DNA sequence using the single-letter amino acid code (SEQ ID NO:6).

FIG. 10. DNA sequence of S23 (SEQ ID NO:7). The complete DNA sequence of the S23 insert in Lambda Zap II is shown in FIG. 10A and continued in FIGS. 10B, 10C and 10D. The nucleotide number is indicated in the left margin.

FIG. 11. Amino acid sequence of S23 for the open reading frame which begins at nucleotide 254 and ends at nucleotide 1708 of SEQ ID NO:7 (See, FIG. 10) is shown (SEQ ID NO:8). Two smaller open reading frames are found at nucleotides 2656-2997 (complementary strand) and nucleotides 3904-4248 (See, FIG. 10).

FIG. 12. Schematic diagram of S22 and S23 proteins. The boxes represent amino acid repeat regions. Lighter boxes: 28 amino acid repeats; Darker boxes: 59 amino acid repeats. Note: the 28 amino acid repeats are also contained within the 59 amino acid repeat regions. The approximate size and location of the S22 deletion which results in S23 is indicated.

FIG. 13. Schematic diagrams of S2 (top) and S7 (bottom) proteins. Repeat regions are indicated by the boxes.

FIG. 15. Amino acid sequence alignments of selected regions of GE 130 kDa and *E. chaffeensis* 120 kDa proteins (A) (SEQ ID NOS:73-77) and GE 100 kDa (SEQ ID NOS: 78-81) and *E. chaffeensis* 120 kDa proteins (SEQ ID NOS: 82-83) (B). Each protein is shown as a linear amino acid sequence and amino acids are numbered in hundreds. Boxed regions on the linear sequence represent repeated amino acids.

FIG. 21. Amino acid sequence (SEQ ID NO:21) which is the translated amino acid sequence for the open reading frame of the C6.1 gene, which begins at nucleotide 312 and ends at nucleotide 1532 of SEQ ID NO:23 (See, FIG. 23).

FIG. 22. Amino acid sequence (SEQ ID NO:22) which is the translated amino acid sequence for the open reading frame of the C6.2 gene, which begins at nucleotide 1542 and ends at nucleotide 2336 of SEQ ID NO:23 (See, FIG. 23).

FIG. 23. DNA sequence of C6 (SEQ ID NO:23). The complete double strand DNA sequence of the C6 insert in Lambda Zap II is shown.

Figure 24:
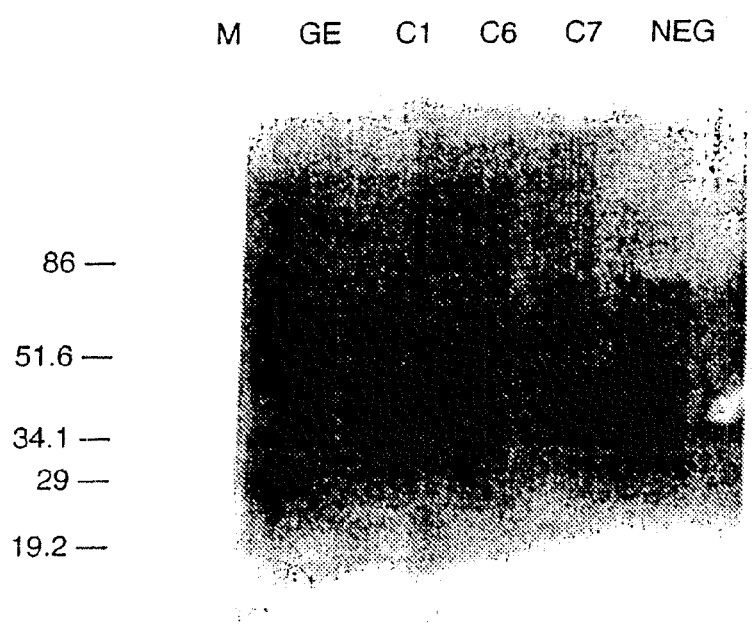

FIG. 24. Western blot analysis of three C clones. Individual recombinant clones of C1, C6, and C7 were grown and induced by IPTG to induce protein expression according to Materials and Methods. Samples of each were electrophoresed on SDS-PAGE gels and transferred to nitrocellulose for Western blotting. SDS-disrupted GE was used as a positive control The blot was probed with vaccinated mouse "C" sera. Samples are indicated at the top of the gel. Molecular weight markers (in kilodaltons) are shown to the left of the figure.

Figure 25:
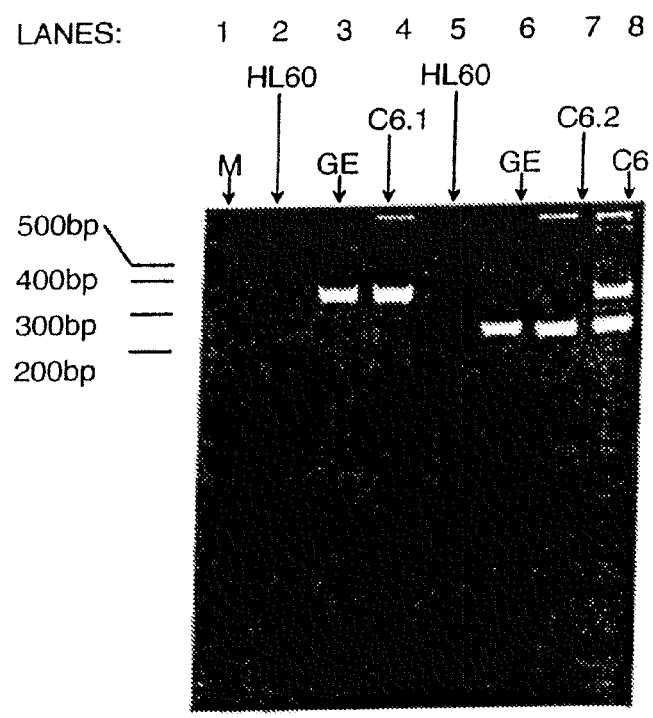

FIG. 25. PCR analysis of C6. PCR reactions were performed and the products analyzed using 4% Nusieve gels. Primer sequences are listed in Table 5. C6.1 primers (from the first open reading frame, lanes 2, 3, 4) were used to amplify a 500bp region of C6 DNA using as templates: C6 plasmid DNA (lane 4), HL60 DNA (lane 2) and GE DNA (lane 3). C6.2 primers (from the second open reading frame, lanes 5, 6, 7) were used to amplify a 300 bp region of C6 DNA using as templates: C6 plasmid DNA (lane 7), HL60 DNA (lane 5) and GE DNA (lane 6). Both primer sets were also used together in the same PCR reaction using C6 plasmid DNA as template (lane 8). DNA molecular weight markers (50-1000 bp, FMC) are present in lane 1.

FIG. 26. ClustalW alignment of amino acids encoded by the 550 by PCR product (SEQ ID NO:24) and the MSP-2 protein of *A. marginale* (GenBank accession number U07862) (SEQ ID NO:25). Identical amino acids are enclosed by boxes. Amino acids which represent conservative codon changes are shown in capital letters.

Figures 27A, 27B:
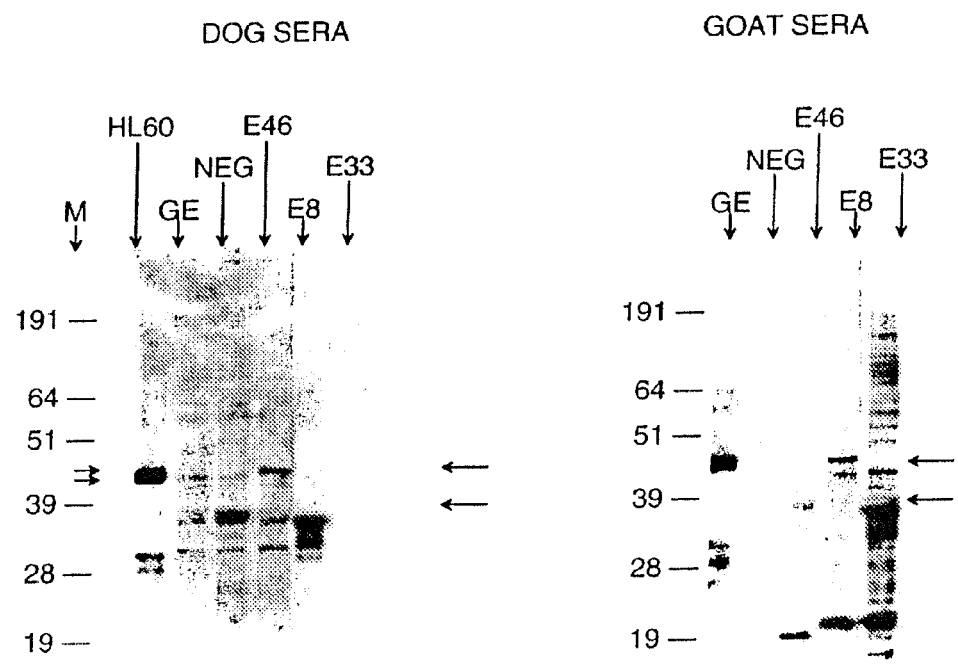

FIG. 27. Western blot of GE proteins. Samples containing purified USG3 antigen (GE lanes), uninfected HL60 cell proteins (HL60), a pBluescript library clone with no insert (NEG),E46, E8, or E33 were analyzed by SDS-PAGE and transferred to nitrocellulose blots. Blots were probed with either dog (FIG. 27A) or goat (FIG. 27B) sera. Molecular size markers are indicated on the left of each blot. Positions of expressed proteins are indicated by arrows at the right side of each blot. The double arrow on the left indicates the proteins that were excised for peptide sequencing.

Figure 28:
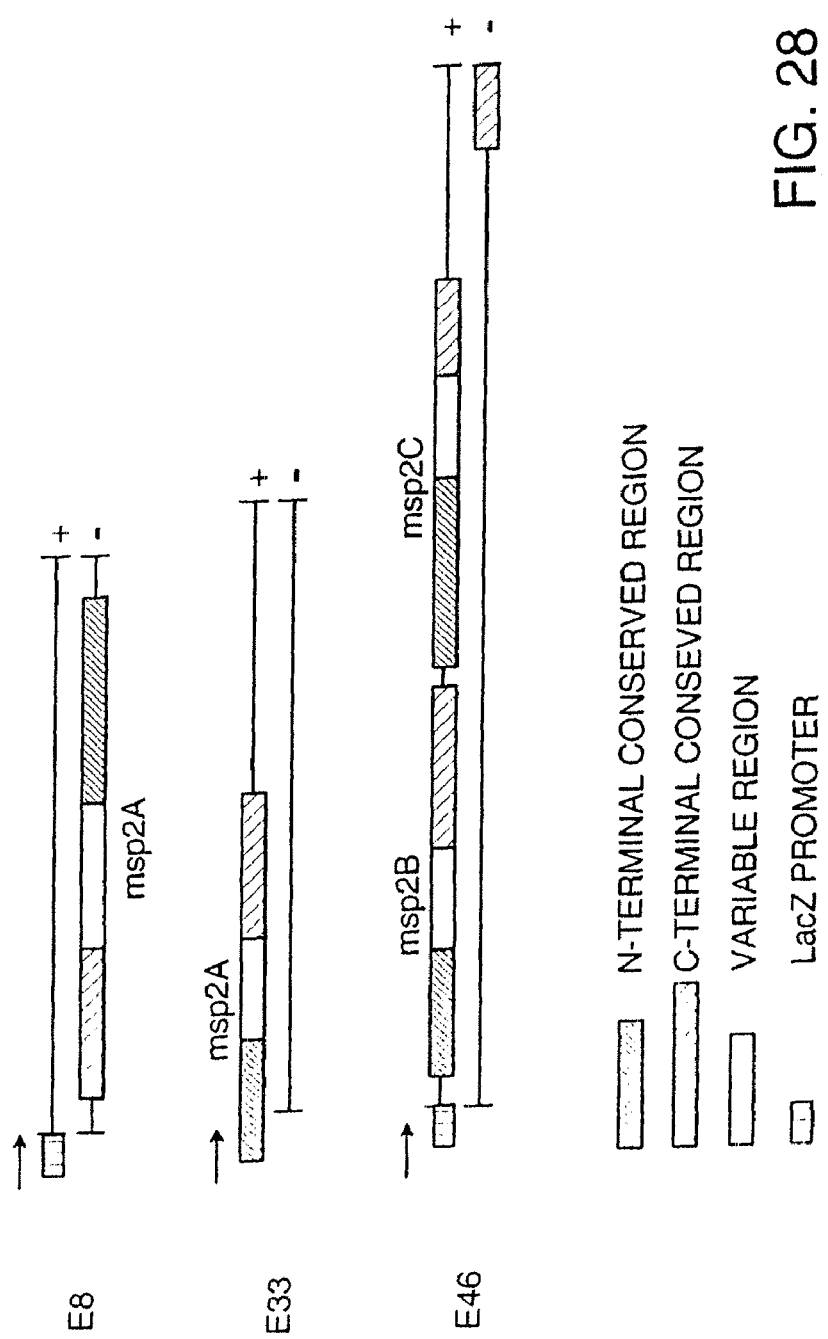

FIG. 28. Schematic diagram of E8, E33 and E46 pBluescript inserts. Each strand of the DNA insert is shown as a line; +) plus strand of DNA; -) minus strand of DNA. Boxed regions indicate related open reading frames. The position and orientation (arrows) of the lacZ promoter is indicated.

Figure 29:
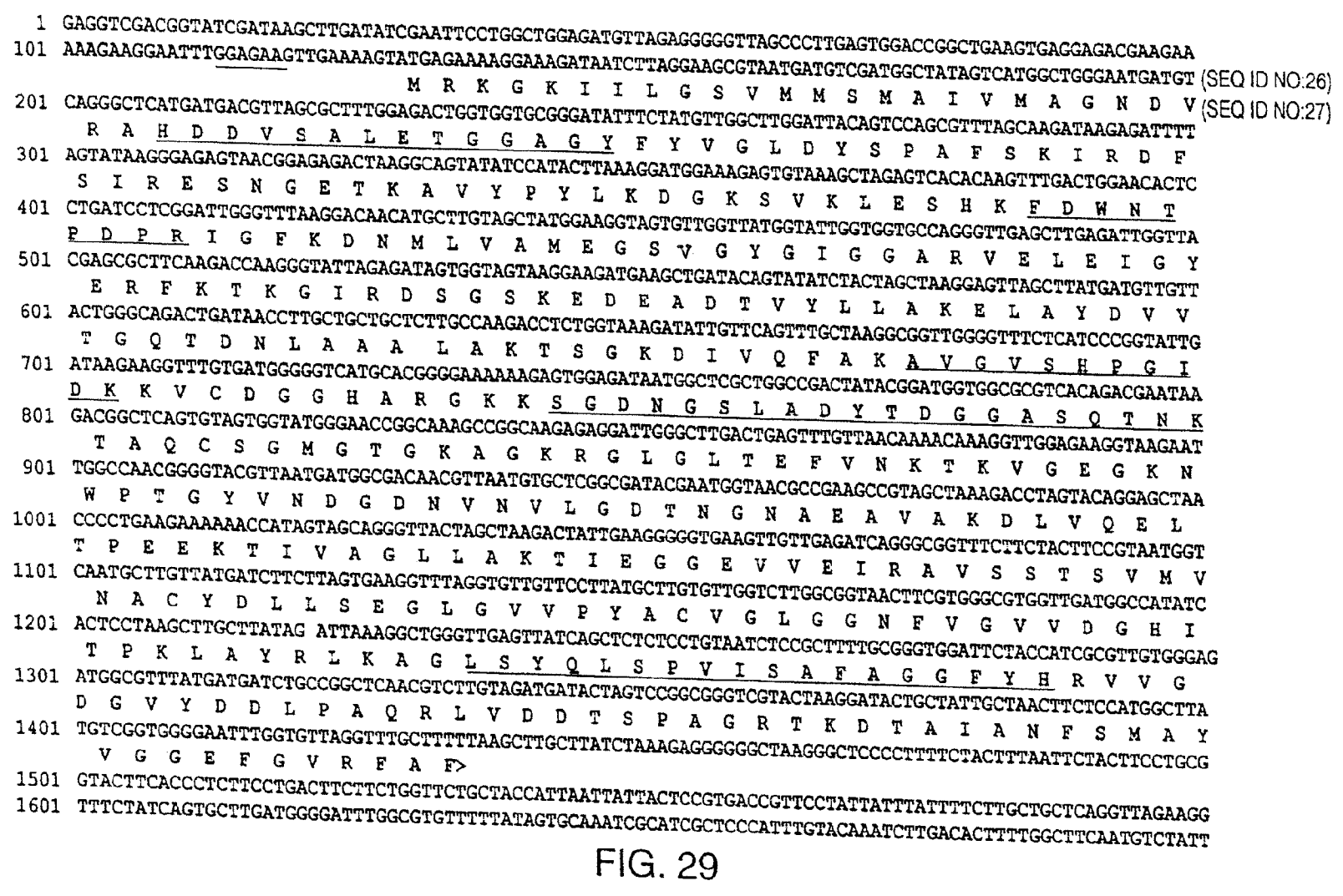

FIG. 29. Sequence of the GE E8 msp2 gene (SEQ ID NO:26). Nucleotide numbers are indicated at the left. The ATG start codon and TAA stop codon are shown in bold type. The translated amino acid sequence for the open reading frame is displayed underneath the DNA sequence using the single letter amino acid code (SEQ ID NO:27). A possible ribosome binding site upstream of the ATG codon is also underlined.

FIG. 30. Complete sequence of E46. The nucleotide number is indicated above the sequences. The complete DNA sequence of the E46 insert in Lambda Zap II is shown (SEQ ID NO:28). The translated amino acid sequences for the open reading frames are displayed underneath the DNA sequences. The amino acid sequence of E46#1 which begins at nucleotide 305 and ends at nucleotide 1282, is shown (SEQ ID NO:29). The amino acid sequence of E46#2 which begins at nucleotide 1346 and ends at nucleotide 2437, is show (SEQ ID NO:30).

FIG. 31. ClustalW alignment of GE MSP-2 and *A. marginale* MSP-2 (U07862) protein sequences (SEQ ID NOS:27, 29-31). Identical amino acids are enclosed by boxes. Amino acids which represent conservative codon changes are indicated by capital letters. The symbol—denotes a gap used to achieve optimal alignment between the sequences.

Figures 32A, 32B:
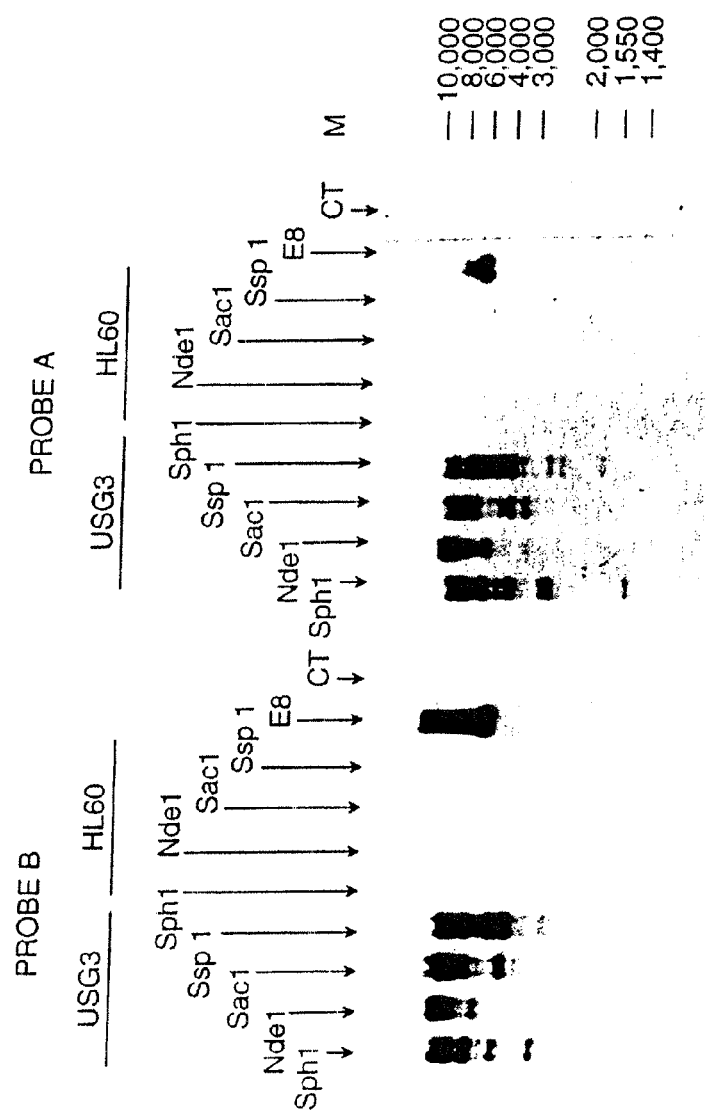

FIG. 32. Southern blot analysis of USG3 genomic DNA. Genomic DNA from USG3 or HL60 cells was digested with the restriction enzymes indicated above the lanes and Southern blotted. Eco RI-digested E8 plasmid DNA was used as a positive control for probe hybridization and calf thymus DNA (CT) as a negative control. The blots were hybridized with digoxigenin-labeled probe A (5'end of E8 msp-2A) (FIG. 32B) or probe B (3' end of E8 msp-2A) (FIG. 32A).

Figures 33A, 33B:
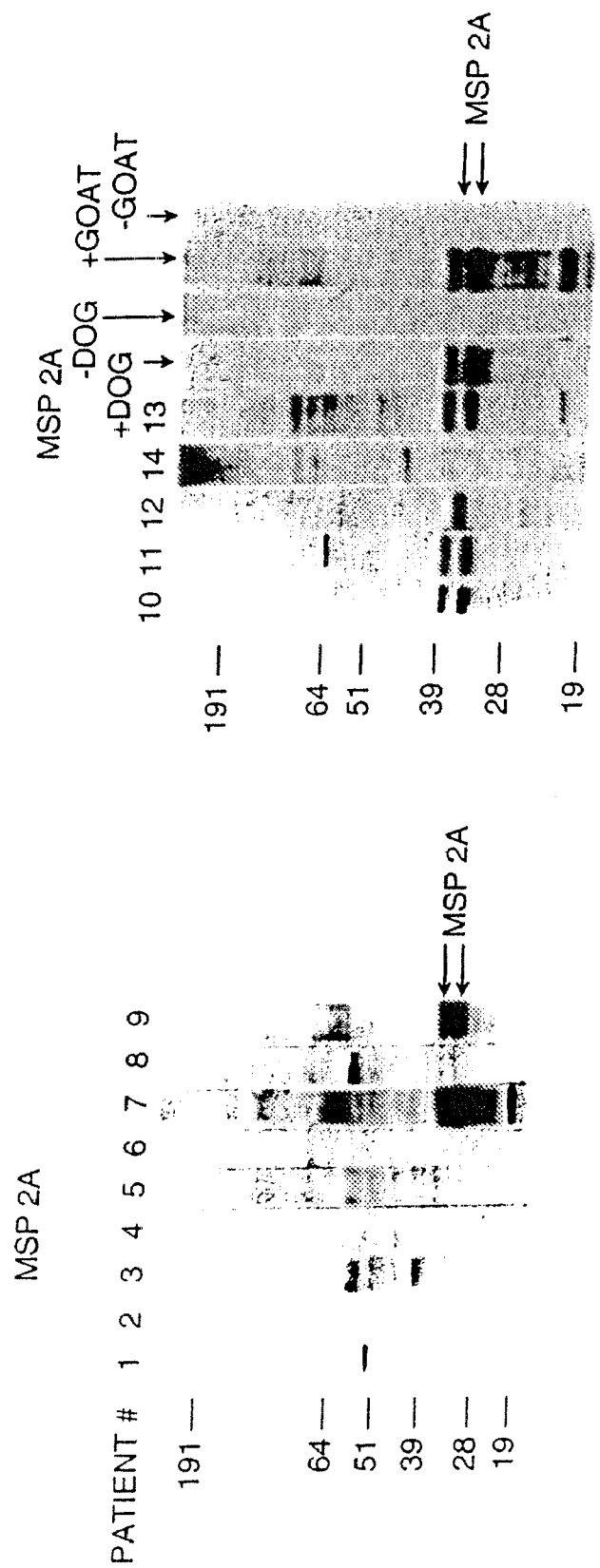
Figures 33C, 33D:
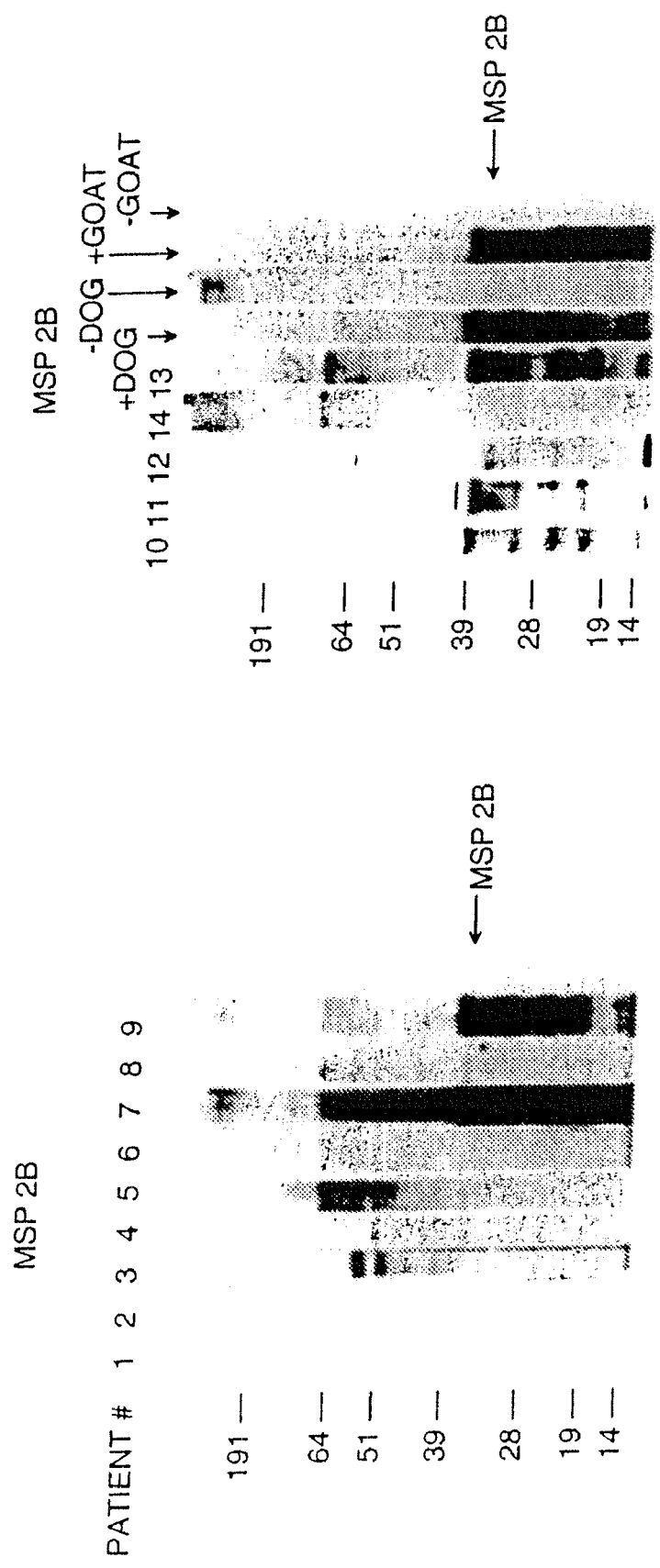

FIG. 33. Western blot analysis of E33 bacterial cultures expressing MSP-2A and MSP-2B probed with HGE patient sera. Bacterial cultures of E33 MSP-2A (top) and MSP-2B (bottom) were analyzed by SDS-PAGE and the proteins transferred to nitrocellulose blots. The blots were cut into strips and probed with patient sera #1-14 as indicated above the lanes. These numbers correspond to the patient numbers shown in Table 7. Immune(+) and preimmune(−) dog and goat sera were also used as positive and negative controls. Molecular size markers are indicated on the left side of each blot. The arrows show the positions of the MSP-2 proteins.

FIG. 34. Ammo acid sequence of 64 kDa protein degenerate primer sequences derived therefrom (SEQ ID NOS:32-33) are listed for SEQ ID NOS:34 and 35 (peptides 24 and 25, respectively). Amino Acids from which the primer sequences were generated are underlined. Two other peptides are listed: peptide #23 (SEQ ID NO:36) and peptide #26 (SEQ ID NO:37). Undetermined positions of the peptide sequences are designated with an asterisk (*).

Figure 35:

FIG. 35. Linear map of pBluescript S11. Boxes on either end represent vector sequences and the solid center line denotes the insert. The T3 and T7 promoter sequences are positioned as indicated and the S11 gene is shown as a bold line.

FIG. 36. Nucleic acid sequence (SEQ ID NO:38) and amino acid sequence (SEQ ID NO:39) of S11/GE 59 kDa. Start and stop codons are in bold type. Sequenced peptides are underlined in FIG. 36.

DETAILED DESCRIPTION OF THE PREFERRED EMBODIMENTS

The sequencing and protein analysis of nine recombinant clones (S2, S7, S22, S23, C6, S11, E8, E46# 1, and E46#2) identified by immunological screening of a GE genomic library is described. Two of these clones, S22 and S23, encode identical proteins which differ only by the loss of a repeated region in S23. One clone, C6, contains two open reading frames encoding polypeptides C6.1, C6.2. Clones E8, E46#1, and E46#2 contain conserved amino- and carboxy-terminus regions. These genomic DNA isolates were proven to be specific to GE based on PCR analysis of GE DNA and HL60 DNA.

Of the hundreds of phage plaques that came up positive using either convalescent dog sera or vaccinated mouse sera, the vast majority were identified as either group I (e.g., S22 or S23), group II (e.g., S2), group III (e.g., S7). The genes described herein most likely encode immunodominant GE antigens which may also be present in more than one copy in the GE genome. Other immunodominant rickettsial antigens have been shown to be important diagnostic reagents and vaccine targets including the outer membrane polypeptides of Anaplasma marginate (Tebele et al., *Infect. Immun.* 59:3199-3204 (1991)), immunogenic proteins of *Cowdria rumantiun* (Mahan et al., *Microbiology* 140:2135-2142 (1994); van Vliet et al., *Infect. Immun.* 62:1451-1456 (1994)), the 120 kDa immunodominant protein of *E. chaffeensis* (Yu et al., *J. Clin. Micro.* 34:2853-2855 (1996)), the immuno-dominant surface protein antigen of *Rickettsia prowazekii* (Dasch et al., in *Microbiology*, D. Schlessinger (ed.), American Society for Microbiology, Washington, D. G, (1984), pp. 251-256,) and two *Rickettsia rickettsii* surface proteins (Anacker et al., *Infect. Immun.* 55:825-827 (1987); Sumner et al., *Vaccine* 13:29-35 (1995)). Many of these proteins contain highly repeated regions similar to those found for GE proteins. Repetitive protein domains have been shown to function in ligand binding—(Wren, *Mol. Microbiol.* 5:797-803 (1991)) and may function to facilitate rickettsial uptake by host cell membranes.

For purposes of clarity of disclosure, and not by way of limitation, the detailed description of the invention is divided into the following subsections:

I. Isolated Nucleic Acid Molecules Coding for S2, S7, S22, S23, C6.1, C6.2, S11, E8, E46#1, and E46#2 Polypeptides;

II. Recombinantly Produced S2, S7, S22, S23, C6.1, C6.2, S11, E8, E46#1, and E46#2 Polypeptides;

III. A Nucleic Acid Probe for the Specific Detection of S2, S7, S22, S23, C6.1, C6.2, S11, E8, E46#1, and E46#2;

IV. A Method of Detecting The Presence of S2, S7, S22, S23, C6.1, C6.2, S11, E8, E46#1, or E46#2 in a Sample;

V. A Kit for Detecting the Presence of S2, S7, S22, S23, C6.1, C6.2, S11, E8, E46#1, or E46#2 in a Sample;

VI. DNA Constructs Comprising S2, S7, S22, S23, C6.1, C6.2, S11, E8, E46#1, and E46#2 Nucleic Acid Molecule and Cells Containing These Constructs;

VII. An Antibody Having Binding Affinity to S2, S7, S22, S23, C6.1, C6.2, S11, E8, E46#1, or E46#2 Polypeptide and a Hybridoma Containing the Antibody;

VIII. A Method of Detecting an S2, S7, S22, S23, C6.1, C6.2, S11, E8, E46#1, or E46#2 Polypeptide or Antibody in a Sample;

IX. A Diagnostic Kit Comprising S2, S7, S22, S23, C6.1, C6.2, S11, E8, E46#1, or E46#2 Protein or Antibody;

X. Diagnostic Screening; and

XI. Vaccines

I. Isolated Nucleic Acid Molecules Coding for S2, S7, S22, S23, C6.1, C6.2, S11, E8, E46#1, and E46#2 Polypeptides In one embodiment, the present invention relates to isolated nucleic acid molecules comprising a polynucleotide sequence at least 90% identical (more preferably, 95%, 96%, 97%, 98%, 99%, or 100% identical) to a sequence selected from:

(a) a nucleotide sequence encoding the S2, S7, S22, S23, C6.1, C6.2, S11, E8, or E46#1, E46#2 polypeptide comprising the complete amino acid sequence in SEQ ID NOS:4, 6, 2, 8, 21, 22, 39, 27, 29, and 30, respectively;

(b) a nucleotide sequence encoding the S2, S7, S22, S23, C6.1, C6.2, S11, E8, E46#1, or E46#2 polypeptide comprising the complete amino acid sequence encoded by the polynucleotide clone contained in ATCC Deposit Nos. 97844, 97840, 97842, 97843, 97841, 97841, 209740, 209736, 209743, and 209743 respectively (note, C6.1 and C6.2, are encoded by the polynucleotide clone contained in ATCC Deposit No. 97841 and that E46#1 and E46#2 are encoded by the polynucleotide clone contained in ATCC Deposit No. 209743); and (c) a nucleotide sequence complementary to any of the nucleotide sequences in (a) or (b).

The S2, S7, S22, S23, and C6 (encoding C6.1 and C6.2) nucleic acids were deposited at the American Type Culture Collection (ATCC), 12301 Parklawn Drive, Rockville, Md. 20852, USA on Dec. 31, 1996 as ATCC Deposit Nos. 97844, 97840, 97842, 97843, and 97841, respectively. The S11, E8, and E46 (encoding E46# 1 and E46#2) nucleic acids were deposited at the ATCC on Mar. 31, 1998 as ATCC Deposit Nos. 209740, 209736 and 209743, respectively.

In one preferred embodiment, the isolated nucleic acid molecule comprises a GE S2, S7, S22, S23, C6.1, C6.2, S11, E8, E46#1, or E46#2 nucleotide sequence with greater than 90% identity or similarity to the nucleotide sequence present in SEQ ID NOS:3, 5, 1, 7, 23, 23, 38, 26, 28 or 28 (preferably greater than 95%, 96%, 97%, 98%, 99% or 100%), respectively. In another preferred embodiment, the isolated nucleic acid molecule comprises the S2, S7, S22, S23, C6.1, C6.2 S11, E8, E46#1, or E46#2 nucleotide sequence present in SEQ ID NOS:3, 5, 1, 7, 23, 23, 38, 26, 28, or 28, respectively. In another embodiment, the isolated nucleic acid molecule encodes the S2, S7, S22, S23, C6.1, C6.2, S11, E8, E46#1, and E46#2 amino acid sequence present in SEQ ID NOS:4, 6, 2, 8, 21, 22, 39, 27, 29, or 30, respectively.

Also included within the scope of this invention are the functional equivalents of the herein-described isolated nucleic acid molecules and derivatives thereof. For example, the nucleic acid sequences depicted in SEQ ID NOS:3, 5, 1, 7, 23, 23, 38, 26, 28, or 28 can be altered by substitutions, additions or deletions that provide for functionally equivalent molecules. Due to the degeneracy of nucleotide coding sequences, other DNA sequences which encode substantially the same amino acid sequence as depicted in SEQ ID NOS:4, 6, 2, 8, 21, 22, 39, 27, 29, or 30 can be used in the practice of the present invention. These include but are not limited to nucleotide sequences comprising all or portions of S2, S7, S22, S23, C6.1, C6.2, S11, E8, E46#1, and E46#2 nucleic acid depicted in SEQ ID NOS:3, 5, 1, 7, 23, 23, 38, 26, or 28, respectively which are altered by the substitution of different codons that encode a functionally equivalent amino acid residue within the sequence.

In addition, the nucleic acid sequence can comprise a nucleotide sequence which results from the addition, deletion or substitution of at least one nucleotide to the 5'-end and/or the 3'-end of the nucleic acid formula shown in SEQ ID NOS:3, 5, 1, 7, 23, 23, 38, 26, 28, or 28 or a derivative thereof. Any nucleotide or polynucleotide can be used in this regard, provided that its addition, deletion or substitution does not substantially alter the amino acid sequence of SEQ ID NOS: 4, 6, 2, 8, 21, 22, 39, 27, 29, or 30 which is encoded by the nucleotide sequence. Moreover, the nucleic acid molecule of the present invention can, as necessary, have restriction endonuclease recognition sites added to its 5'-end and/or 3'-end. All variations of the nucleotide sequence of the S2, S7, S22, S23, C6.1, C6.2, S11, E8, E46#1, and E46#2 gene and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid

In one aspect of the present invention, isolated nucleic acid molecules coding for polypeptides having amino acid sequences corresponding to S2, S7, S22, S23, C6.1, C6.2, S11, E8, E46#1, and E46#2 are provided. In particular, the nucleic acid molecule can be isolated from a biological sample (preferably of mammalian or tick origin) containing GE RNA or DNA.

The nucleic acid molecule can be isolated from a biological sample containing GE RNA using the techniques of cDNA cloning and subtractive hybridization. The nucleic acid molecule can also be isolated from a cDNA library using a homologous probe.

The nucleic acid molecule can be isolated from a biological sample containing genomic DNA or from a genomic library. Suitable biological samples include, but are not limited to, whole organisms, organs, tissues, blood and cells. The method of obtaining the biological sample will vary depending upon the nature of the sample.

One skilled in the art will realize that genomes can be subject to slight allelic variations between individuals. Therefore, the isolated nucleic acid molecule is also intended to include allelic variations, so long as the sequence is a functional derivative of the S2, S7, S22, S23, C6.1, C6.2, S11, E8, E46#1, and E46#2 coding sequence. When an S2, S7, S22, S23, C6.1, C6.2, S11, E8, E46#1, or E46#2, allele does not encode the identical sequence to that found in SEQ ID NOS: 3, 5, 1, 7, 23, 23, 38, 26, 28 or 28 it can be isolated and identified as S2, S7, S22, S23, C6.1, C6.2, S11, E8, E46#2, or E46#2 using the same techniques used herein, and especially PCR techniques to amplify the appropriate gene with primers based on the sequences disclosed herein.

One skilled in the art will realize that organisms other than GE will also contain S2, S7, S22, S23, C6.1, C6.2, 511, E8, E46#1, and E46#2 genes. The invention is intended to include, but not be limited to, S2, S7, S22, S23, C6.1, C6.2, S11, E8, E46#1, and E46#2 nucleic acid molecules isolated from the above-described organisms. Also, infected eukaryotes (for example, mammals, birds, fish and humans) may contain the S2, S7, S22, S23, C6.1, C6.2, S11, E8, E46#1, and E46#2 genes.

B. Synthesis of Nucleic Acid

Isolated nucleic acid molecules of the present invention are also meant to include those chemically synthesized. For example, a nucleic acid molecule with the nucleotide sequence which codes for the expression product of S2, S7, S22, S23, C6.1, C6.2, S11, E8, E46#1, or E46#2 gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 105:3185-3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

II. Recombinantly Produced S2, S7, S22, S23, C61, C6.2, S11, E8, E46#1, and E46#2 Polypeptides In another embodiment, the present invention relates to a purified polypeptide (preferably, substantially pure) having an amino acid sequence corresponding to S2, S7, S22, S23, C6.1, C6.2 S11, E8, E46#1, or E46#2 or a functional derivative thereof. In a preferred embodiment, the polypeptide has the amino acid sequence set forth in SEQ ID NOS:4, 6, 2, 8, 21, 22, 39, 27, 29, or 30, respectively, or mutant or species variation thereof, or at least 60% identity or at least 70% similarity thereof (preferably, at least 85%, 90%, 95%, 96%, 97%, 98%, or 99% identity or at least 95%, 96%, 97%, 98%, or 99% similarity thereof), or at least 6 contiguous amino acids thereof (preferably, at least 10, 15, 20, 25, or 50 contiguous amino acids thereof).

In a preferred embodiment, the invention relates to S2, S7, S22, S23, C6.1, C6.2, S11, E8, E46#1, or E46#2 epitopes. The epitope of these polypeptides is an immunogenic or antigenic epitope. An immunogenic epitope is that part of the protein which elicits an antibody response when the whole protein is the immunogen. An antigenic epitope is a fragment of the protein which can elicit an antibody response. Methods of selecting antigenic epitope fragments are well known in the art. (Sutcliffe et al., *Science* 219:660-666 (1983)). Antigenic epitope-bearing peptides and polypeptides of the invention are useful to raise an immune response that specifically recognizes the polypeptides. Antigenic epitope-bearing peptides and polypeptides of the invention comprise at least 7 amino acids (preferably, 9, 10, 12, 15, or 20 amino acids) of the proteins of the invention. Non-limiting examples of antigenic polypeptides or peptides include those listed in Table 1, below.

TABLE 1

| Antigenic Epitopes | | |
|---|---|---|
| | Size[1] | Amino Acids[2] |
| S2 | 10 | 181-190 |
| | 22 | 411-432 |
| | 15 | 636-650 |
| S7 | 16 | 13-28 |
| | 10 | 73-82 |
| | 11 | 496-506 |
| S22 | 13 | 41-53 |
| | 17 | 168-184 |
| | 19 | 317-335 |
| S23 | 15 | 6-20 |
| | 11 | 78-88 |
| | 18 | 387-404 |
| C6.1 | 9 | 110-118 |
| | 9 | 338-346 |
| | 11 | 353-363 |
| C6.2 | 12 | 65-76 |
| | 9 | 104-112 |
| | 9 | 170-178 |
| S11 | 12 | 90-101 |
| | 17 | 144-160 |
| | 9 | 334-342 |
| E8 | 10 | 40-49 |
| | 12 | 132-143 |
| | 15 | 261-275 |
| E46.#1 | 9 | 32-41 |
| | 12 | 125-136 |
| | 20 | 222-241 |

TABLE 1-continued

Antigenic Epitopes

| | Size[1] | Amino Acids[2] |
|---|---|---|
| E46.#2 | 12 | 55-66 |
| | 14 | 177-190 |
| | 10 | 291-300 |

[1]Number of amino acids.
[2]See FIGS. 7, (S2), 9 (S7), 5 (S22), 11 (S23), 17 (C6.1), 18 (C6.2) and 23 (S11) for amino acid numbering.

Amino acid sequence variants of S2, S7, S22, S23, C6.1, C6.2, S11, E8, E46#1, and E46#2 can be prepared by mutations in the DNA. Such variants include, for example, deletions from, or insertions or substitutions of, residues within the amino acid sequence shown in SEQ ID NOS:4, 6, 2, 8, 21, 22, 39, 27, 29, or 30. Any combination of deletion, insertion, and substitution can also be made to arrive at the final construct, provided that the final construct possesses the desired activity.

While the site for introducing an amino acid sequence variation is predetermined, the mutation per se need not be predetermined. For example, to optimize the performance of a mutation at a given site, random mutagenesis can be conducted at the target codon or region and the expressed S2, S7, S22, S23, C6.1, C6.2, S11, E8, E46#1, and E46#2 variants screened for the optimal combination of desired activity. Techniques for making substitution mutations at predetermined sites in DNA having a known sequence are well known, for example, site-specific mutagenesis.

Preparation of an S2, S7, S22, S23, C6.1, C6.2, S11, E8, E46#1, or E46#2 variant in accordance herewith is preferably achieved by site-specific mutagenesis of DNA that encodes an earlier prepared variant or a nonvariant version of the protein. Site-specific mutagenesis allows the production of S2, S7, S22, S23, C6.1, C6.2, S11, E8, E46#1, and E46#2 variants through the use of specific oligonucleotide sequences that encode the DNA sequence of the desired mutation. In general, the technique of site-specific mutagenesis is well known in the art, as exemplified by publications such as Adelman et al., *DNA* 2:183 (1983) and Ausubel et al., "Current Protocols in Molecular Biology", J. Wiley & Sons, New York, N.Y., 1996.

As will be appreciated, the site-specific mutagenesis technique can employ a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton (ed.), Elsevier, Amsterdam (1981). These phage are readily commercially available and their use is generally well known to those skilled in the art. Alternatively, plasmid vectors that contain a single-stranded phage origin of replication (Vieira et al., *Meth. Enzymol.* 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement.

After such a clone is selected, the mutated protein region can be removed and placed in an appropriate vector for protein production, generally an expression vector of the type that can be employed for transformation of an appropriate host.

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the complete S2, S7, S22, S23, C6.1, C6.2, S11, E8, E46#1, or E46#2 sequence) can range generally from about 1 to 10 residues, more preferably 1 to 5.

The third group of variants are those in which at least one amino acid residue in the S2, S7, S22, S23, C6.1, C6.2, S11, E8, E46#1, or E46#2 molecule, and preferably, only one, has been removed and a different residue inserted in its place. Such substitutions preferably are made in accordance with the following Table 2 when it is desired to modulate finely the characteristics of S2, S7, S22, S23, C6.1, C6.2, S11, E8, E46#1, or E46#2.

TABLE 2

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 2, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of S2, S7, S22, S23, C6.1, C6.2, S11, E8, E46#1, or E46#2. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native S2, S7, S22, S23, C6.1, C6.2, 511, E8, E46#1, or E46#2, encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified S2, S7, S22, S23, C6.1, C6.2, S11, E8, E46#1, or E46#2 molecule variant is then screened in a suitable screening assay for the desired characteristic. For example, a change in the immunological character of the S2, S7, S22, 523, C6.1, C6.2, S11, E8, E46#1, or E46#2 molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the above-described isolated nucleic acid fragments can be used to express the S2, S7, S22, S23, C6.1, C6.2, S11, E8, E46#1, or E46#2 protein in any organism. The samples of the present invention include cells, protein extracts or membrane extracts of cells, or biological fluids. The sample will vary based on the assay format, the detection method and the nature of the tissues, cells or extracts used as the sample.

Any prokaryotic (preferably, a granulocytic ehrlichia) organism can be used as a source for the peptide of the invention, as long as the source organism naturally contains such a peptide. A eukaryotic organism infected with granulocytic ehrlichia can also be used as the source organism. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromotography, size-exclusion chromatography, HPLC, ion-exchange chromatography, and immuno-affinity chromatography.

III. A Nucleic Acid Probe for the Specific Detection of S2, S7, S22, S23, C6.1, C6.2, S11, E8, E46#1 and E46#2

In another embodiment, the present invention relates to a nucleic acid probe for the specific detection of the presence of S2, S7, S22, S23, C6.1, C6.2, S11, E8, E46#1, or E46#2 nucleic acid in a sample comprising the above-described nucleic acid molecules or at least a fragment thereof which binds under stringent conditions to S2, S7, S22, S23, C6.1, C6.2, S11, E8, E46#1, or E46#2 nucleic acid.

In one preferred embodiment, the present invention relates to an isolated nucleic acid probe consisting of 10 to 1000 nucleotides (preferably, 10 to 500, 10 to 100, 10 to 50, 10 to 35, 20 to 1000, 20 to 500, 20 to 100, 20 to 50, or 20 to 35) which hybridizes preferentially to RNA or DNA of granulocytic ehrlichia but not to RNA or DNA of non-granulocytic ehrlichia organisms (example, humans), wherein said nucleic acid probe is or is complementary to a nucleotide sequence consisting of at least 10 consecutive nucleotides (preferably, 15, 20, 25, or 30) from the nucleic acid molecule comprising a polynucleotide sequence at least 90% identical to a sequence selected from:

(a) a nucleotide sequence encoding the S2, S7, S22, S23, C6.1, C6.2, S11, E8, E46#1, or E46#2 polypeptide comprising the complete amino acid sequence in SEQ ID NOS:4, 6, 2, 8, 21, 22, 39, 27, 29, or 30, respectively;

(b) a nucleotide sequence encoding the S2, S7, S22, S23, C6.1, C6.2, S11, E8, E46#1, E46#2 polypeptide comprising the complete amino acid sequence encoded by the polynucleotide clone contained in ATCC Deposit Nos. 97844, 97840, 97842, 97843, 97841, 97841, 209740, 209736, 209743 or 209743 respectively (note, C6.1 and C6.2 are encoded by the polynucleotide clone contained in ATCC Deposit No. 97841 and E46#1 and E46#2 are encoded by the polynucleotide clone contained in ATCC Deposit No. 209743);

(c) a nucleotide sequence complementary to any of the nucleotide sequences in (a) or (b); and (d) a nucleotide sequence as previously described above.

Examples of specific nucleic acid probes which can be used in the present invention are set forth in Table 3, below.

TABLE 3

| Nucleic Acid Probes | | |
|---|---|---|
| | Size[1] | Nucleotides[2] |
| S2 | 20 | 2660-2679 |
| | 37 | 2643-2679 |
| | 75 | 1820-1894 |
| | 450 | 2150-2599 |
| S7 | 20 | 489-508 |
| | 35 | 321-355 |
| | 75 | 420-494 |
| | 450 | 300-749 |
| S22 | 23 | 1220-1242 |
| | 36 | 1187-1222 |
| | 75 | 1220-1294 |
| | 450 | 570-1019 |
| S23 | 23 | 974-996 |
| | 35 | 962-996 |
| | 75 | 720-794 |
| | 450 | 600-1049 |
| C6 | 19 | 530-548 |
| | 35 | 1097-1131 |
| | 75 | 1710-1784 |
| | 450 | 1850-2299 |
| S11 | 20 | 570-589 |
| | 35 | 1045-1079 |
| | 75 | 1600-1674 |
| | 450 | 500-949 |
| E8 | 20 | 520-539 |
| | 35 | 650-684 |
| | 75 | 900-974 |
| | 450 | 700-1149 |
| E46 | 20 | 1450-1469 |
| | 35 | 1800-1834 |
| | 75 | 1030-1104 |
| | 450 | 400-849 |

[1]Number of bases.

[2]See FIGS. 6 (S2), 8 (S7), 4 (S22), 10 (S23), 16 (C6) and 23 (S11) for nucleotide numbering.

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (cf. *Molecular Cloning: A Laboratory Manual, 2nd edition*, edited by Sambrook, Fritsch, & Maniatis, Cold Spring Harbor Laboratory, 1989).

In the alternative, chemical synthesis is carried out in order to obtain nucleic acid probes having nucleotide sequences which correspond to amino-terminal and carboxy-terminal portions of the S2, S7, S22, S23, C6.1, C6.2, S11 amino acid sequence (See, Table 3) or E8, E46#1, or E46#2 amino acid sequence. Thus, the synthesized nucleic acid probes can be used as primers in a polymerase chain reaction (PCR) carried out in accordance with recognized PCR techniques, essentially according to *PCR Protocols, A Guide to Methods and Applications,* edited by Michael et al., Academic Press, 1990, utilizing the appropriate chromosomal, cDNA or cell line library to obtain the fragment of the present invention.

One skilled in the art can readily design such probes based on the sequence disclosed herein using methods of computer alignment and sequence analysis known in the art (cf. *Molecular Cloning: A Laboratory Manual,* 2nd edition, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting The Presence of S2, S7, S22, S23, C6.1, C6.2, S11, E8, E46#1, or E46#2 in a Sample In another embodiment, the present invention relates to a method of detecting the presence of S2, S7, S22, S23, C6.1, C6.2, S11, E8, E46#1, or E46#2 nucleic acid in a sample comprising a) contacting the sample with the above-described nucleic acid probe, under specific hybridization conditions such that hybridization occurs, and b) detecting the presence of the probe bound to the nucleic acid molecule. Alternatively, in another preferred embodiment, the method of detecting the presence of S2, S7, S22, S23, C6.1, C6.2, S11, E8, E46#1, or E46#2 nucleic acid in a sample may comprise a) amplifying the nucleic acid in the sample with the nucleic acid probe wherein the amplification uses PCR techniques and b) detecting the presence of the amplified nucleic acid molecules. One skilled in the art would select the nucleic acid probe according to techniques known in the art as described above. Samples to be tested include but should not be limited to RNA samples from human tissue.

V. A Kit for Detecting the Presence of S2, S7, S22, S23, C6J, C6.2, S11, E8, E46#1, or E46#2 in a Sample In another embodiment, the present invention relates to a kit for detecting the presence of S2, S7, S22, S23, C6.1, C6.2, S11, E8, E46#1, or E46#2 nucleic acid in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising an S2, S7, S22, S23, C6.1, C6.2, S11, E8, E46#1, or E46#2 Nucleic Acid Molecule and Cells Containing These Constructs In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the S2, S7, S22, S23, C6.1, C6.2, S11, E8, E46#1, or E46#2 coding sequence can be obtained by the above-described methods. This region can be retained for its transcriptional termination regulatory sequences, such as termination and polyadenylation. Thus, by retaining the 3'-region naturally contiguous to the DNA sequence encoding an S2, S7, S22, S23, C6.1, C6.2, S11, E8, E46#1, or E46#2 gene, the transcriptional termination signals can be provided. Where the transcriptional termination signals are not satisfactorily functional in the expression host cell, then a 3' region functional in the host cell can be substituted. Two DNA sequences (such as a promoter region sequence and an S2, S7, S22, S23, C6.1, C6.2, S11, E8, E46#1, or E46#2 coding sequence) are said to be operably linked if the nature of the linkage between the two DNA sequences does not (1) result in the introduction of a frameshift mutation, (2) interfere with the ability of the promoter region sequence to direct the transcription of an S2, S7, S22, S23, C6.1, C6.2, S11, E8, E46#1, or E46#2 coding sequence, or (3) interfere with the ability of the S2, S7, S22, S23, C6.1, C6.2, S11, E8, E46#1, or E46#2 coding sequence to be transcribed by the promoter region sequence. Thus, a promoter region would be operably linked to a DNA sequence if the promoter were capable of effecting transcription of that DNA sequence.

The present invention encompasses the expression of the S2, S7, S22, S23, C6.1, C6.2, S11, E8, E46#1, or E46#2 coding sequence (or a functional derivative thereof) in either prokaryotic or eukaryotic cells. Prokaryotic hosts are, generally, the most efficient and convenient for the production of recombinant proteins and, therefore, are preferred for the expression of the S2, S7, S22, S23, C6.1, C6.2, S11, E8, E46#1, or E46#2 coding sequence.

Prokaryotes most frequently are represented by various strains of $E.\ coli$. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC18, pUC19, pUC118, pUC119 and the like; suitable phage or bacteriophage vectors include $\lambda$gt10, $\lambda$gt11 and the like; and suitable virus vectors include pMAMneo, pKRC and the like. Preferably, the selected vector of the present invention has the capacity to replicate in the selected host cell.

Recognized prokaryotic hosts include bacteria such as $E.\ coli,\ Bacillus,\ Streptomyces,\ Pseudomonas,\ Salmonella,\ Serratia$, and the like. However, under such conditions, the peptide will not be glycosylated. The prokaryotic host must be compatible with the replicon and control sequences in the expression plasmid.

To express S2, S7, S22, S23, C6.1, C6.2, S11, E8, E46#1, or E46#2 in a prokaryotic cell, it is necessary to operably link the S2, S7, S22, S23, C6.1, C6.2, S11, E8, E46#1, or E46#2 coding sequence to a functional prokaryotic promoter. Such promoters can be either constitutive or, more preferably, regulatable (i.e., inducible or derepressible). Examples of constitutive promoters include the int promoter of bacteriophage $\lambda$, the bla promoter of the $\beta$-lactamase gene sequence of pBR322, and the CAT promoter of the chloramphenicol acetyl transferase gene sequence of pBR325, and the like. Examples of inducible prokaryotic promoters include the major right and left promoters of bacteriophage $\lambda$ ($P_L$ and $P_R$), the trp, recA, lacZ, lacI, and gal promoters of $E.\ coli$, the $\alpha$-amylase (Ulmanen et al., $J.\ Bacteriol.$ 162:176-182 (1985)) and the $\varsigma$-28-specific promoters of $B.\ subtilis$ (Gilman et al., Gene sequence 32:11-20 (1984)), the promoters of the bacteriophages of $Bacillus$ (Gryczan, In: $The\ Molecular\ Biology\ of\ the\ Bacilli,$ Academic Press, Inc., NY (1982)), and Streptomyces promoters (Ward et al., $Mol.\ Gen.\ Genet$ 203:468-478 (1986)). Prokaryotic promoters are reviewed by Click ($J.\ Ind.\ Microbiol.$ 1:277-282 (1987)); Cenatiempo ($Biochimie$ 68:505-516 (1986)); and Gottesman ($Ann.\ Rev.\ Genet$ 18:415-442 (1984)).

Proper expression in a prokaryotic cell also requires the presence of a ribosome binding site upstream of the gene sequence-encoding sequence. Such ribosome binding sites are disclosed, for example, by Gold et al., ($Ann.\ Rev.\ Microbiol.$ 35:365-404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell. Host cells which can be used in the expression systems of the present invention are not strictly limited, provided that they are suitable for use in the expression of the S2, S7, S22, S23, C6.1, C6.2, S11, E8, E46#1, or E46#2 peptide of interest. Suitable hosts include eukaryotic cells.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example $Drosophila$ larvae. Using insect cells as hosts, the $Drosophila$ alcohol dehydrogenase promoter can be used, (Rubin, $Science$ 240:1453-1459 (1988)). Alternatively, baculovirus vectors can be engineered to express large amounts of S2, S7, S22, S23, C6.1, C6.2, S11, E8, E46#1, or E46#2 in insect cells (Jasny, $Science$ 238:1653 (1987); Miller et al., In: $Genetic\ Engineering$ (1986), Setlow, J. K., et al., eds., $Plenum,\ Vol.$ 8, pp. 277-297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed.

Any of a series of yeast gene sequence expression systems can be utilized which incorporate promoter and termination elements from the actively expressed gene sequences coding for glycolytic enzymes. These enzymes are produced in large quantities when yeasts are grown in mediums rich in glucose.

Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of S2, S7, S22, S23, C6.1, C6.2, S11, E8, E46#1, or E46#2.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of S2, S7, S22, S23, C6.1, C6.2, S11, E8, E46#1, or E46#2 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273-288 (1982)); the TK promoter of Herpes virus (McKnight, *Cell* 31:355-365 (1982)); the SV40 early promoter (Benoist et al., *Nature (London)* 290:304-310 (1981)); the yeast gal4 gene sequence promoter (Johnston et al., *Proc. Natl. Acad. Sci. (USA)* 79:6971-6975 (1982); Silver et al., *Proc. Natl. Acad. Sci. (USA)* 81:5951-5955 (1984)) and the CMV immediate-early gene promoter (Thomsen et al., *Proc. Natl. Acad. Sci. (USA)* 81:659-663 (1984).

As is widely known, translation of eukaryotic mRNA is initiated at the codon which encodes the first methionine. For this reason, it is preferable to ensure that the linkage between a eukaryotic promoter and an S2, S7, S22, S23, C6.1, C6.2, S11, E8, E46#1, or E46#2 coding sequence does not contain any intervening codons which are capable of encoding a methionine (i.e., AUG). The presence of such codons results either in a formation of a fusion protein (if the AUG codon is in the same reading frame as the S2, S7, S22, S23, C6.1, C6.2, S11, E8, E46#1, or E46#2 coding sequence) or a frame-shift mutation (if the AUG codon is not in the same reading frame as the S2, S7, S22, S23, C6.1, C6.2, S11, E8, E46#1, or E46#2 coding sequence).

An S2, S7, S22, S23, C6.1, C6.2, S11, E8, E46#1, or E46#2 nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancer signal sequences, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX). Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). *Bacillus* plasmids include pC194, pC221, pT127, and the like. Such plasmids are disclosed by Gryczan (In: *The Molecular Biology of the Bacilli*, Academic Press, NY (1982), pp. 307-329). Suitable Streptomyces plasmids include pIJ101 (Kendall et al., *J. Bacteriol.* 169:4177-4183 (1987)), and streptomyces bacteriophages such as ΦC31 (Chater et al., In: *Sixth International Symposium on Actinomycetales Biology*, Akademiai Kaido, Budapest, Hungary (1986), pp. 45-54). Pseudomonas plasmids are reviewed by John et al., (*Rev. Infect. Dis.* 8:693-704 (1986)), and Izaki (*Jpn. J. Bacteriol.* 33:729-742 (1978)).

Preferred eukaryotic plasmids include, for example, BPV, vaccinia, SV40, 2-micron circle, and the like, or their derivatives. Such plasmids are well known in the art (Botstein et al, *Miami Wntr. Symp.* 19:265-274 (1982); Broach, In: *The Molecular Biology of the Yeast Saccharomyces: Life Cycle and Inheritance*, Cold Spring Harbor Laboratory, Cold Spring Harbor, N.Y., p. 445-470 (1981); Broach, *Cell* 25:203-204 (1982); Bollon et al., *J. Clin. Hematol. Oncol.* 70:39-48 (1980); Maniatis, In: *Cell Biology: A Comprehensive Treatise*, Vol, 3, Gene Sequence Expression, Academic Press, NY, pp. 563-608 (1980)).

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of S2, S7, S22, S23, C6.1, C6.2, S11, E8, E46#1, or E46#2. This can take place in the transformed cells as such, or following the induction of these cells to differentiate (for example, by administration of bromodeoxyuracil to neuroblastoma cells or the like).

VII. An Antibody Having Binding Affinity to an S2, S7, S22, S23, C6.1, C6.2, S11, E8, E46#1, or E46#2 Polypeptide and a Hybridoma Containing the Antibody In another embodiment, the present invention relates to an antibody having binding affinity specifically to an S2, S7, S22, S23, C6.1, C6.2, S11, E8, E46#1, or E46#2 polypeptide as described above or specifically to an S2, S7, S22, S23, C6.1, C6.2, 511, E8, E46#1, or E46#2 polypeptide binding fragment thereof. An antibody binds specifically to an S2, S7, S22, S23, C6.1, C6.2, S11, E8, E46#1, or E46#2 polypeptide or to consensus sequences described herein corresponding to the amino- and/or carboxy-terminus regions shared by E8, E46#1, and E46#2, or binding fragment thereof if it does not bind to non-S2, S7, S22, S23, C6.1, C6.2, S11, E8, E46#1, or E46#2 polypeptides. Those which bind selectively to S2, S7, S22, S23, C6.1, C6.2, S11, E8, E46#1, or E46#2 or to consensus sequences described herein corresponding to the amino- and/or carboxy-terminus regions shared by E8, E46#1, and E46#2, would be chosen for use in methods which could include, but should not be limited to, the analysis of altered S2, S7, S22, S23, C6.1, C6.2, S11, E8, E46#1, or E46#2 expression in tissue containing S2, S7, S22, S23, C6.1, C6.2, S11, E8, E46#1, or E46#2.

The S2, S7, S22, S23, C6.1, C6.2, S11, E8, E46#1, or E46#2 proteins, or proteins including the consensus sequences corresponding to the amino- and/or carboxy-terminus regions shared by E8, E46#1, and E46#2 of the present invention can be used in a variety of procedures and methods, such as for the generation of antibodies, for use in identifying pharmaceutical compositions, and for studying DNA/protein interaction.

The S2, S7, S22, S23, C6.1, C6.2, S11, E8, E46#1, or E46#2 proteins, or proteins including the consensus sequences corresponding to the amino and/or carboxy terminus regions shared by E8, E46#1, and E46#2 of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to S2, S7, S22, S23, C6.1, C6.2, S11, E8, E46#1, E46#2 or to proteins, or proteins including the consensus sequences corresponding to the amino- and/or carboxy-terminus regions shared by E8, E46#1, and E46#2 which are produced in humans, or are "humanized" (i.e.; non-immunogenic in a human) by recombinant or other technology. Humanized antibodies can be produced, for example by replacing an immunogenic portion of an antibody with a corresponding, but non-immunogenic portion (i.e., chimeric antibodies) (Robinson et al., PCT Application No. PCT/US86/02269; Akira et al., European Patent No. 184,187; Taniguchi, European Patent No. 171,496; Morrison et al., European Patent No. 173,494; Neuberger et al., PCT Application WO 86/01533; Cabilly et al., European Patent No. 125,023; Better, et al., *Science* 240:1041-1043 (1988); Liu et al., *Proc. Natl. Acad. Sci. USA* 84:3439-3443 (1987); Liu et al., *J. Immunol.* 139:3521-3526 (1987); Sun, et al., *Proc. Natl. Acad. Sci. USA* 84:214-218 (1987); Nishimura et al., *Canc. Res.* 47:999-1005 (1987); Wood et al., *Nature* 314:446-449 (1985)); Shaw et al., *J. Natl. Cancer Inst.* 80:1553-1559 (1988). General reviews of "humanized" chimeric antibodies are provided by Morrison (*Science,* 229:1202-1207 (1985)) and by Oi et al., *BioTechniques* 4:214 (1986)). Suitable "humanized" antibodies can be alternatively produced by CDR or CEA substitution (Jones et al., *Nature* 321:552-525 (1986); Verhoeyan et al., *Science* 239:1534 (1988); Beidler et al., *J. Immunol.* 141:4053-4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1-21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109-124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horseradish peroxidase, alkaline phosphatase, and the like), fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Coding, *J. Immunol. Meth.* 13:215 (1976)). The labeled antibodies of the present invention can be used for in vitro, in vivo, and in situ assays to identify cells or tissues which express a specific peptide.

In another embodiment of the present invention, the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immuno-chromatography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, NY, pp. 289-307 (1992), and Kaspczak et al., *Biochemistry* 28:9230-8 (1989).

Anti-peptide peptides can be generated in one of two fashions. First, the anti-peptide peptides can be generated by replacing the basic amino acid residues found in the S2, S7, S22, S23, C6.1, C6.2, S11, E8, E46#1, and E46#2 peptide sequence or consensus sequences described herein with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting an S2, S7, S22, S23, C6.1, C6.2, S11, E8, E46#1, or E46#2 Polypeptide or Antibody in a Sample In another embodiment, the present invention relates to a method of detecting an S2, S7, S22, S23, C6.1, C6.2, S11, E8, E46#1, or E46#2 polypeptide including the consensus sequence corresponding to the amino- and/or carboxy-terminus regions shared by E8, E46#1, and E46#2 polypeptide in a sample, comprising: a) contacting the sample with an above-described antibody (or protein), under conditions such that immunocomplexes form, and b) detecting the presence of the antibody bound to the polypeptide. In detail, the methods comprise incubating a test sample with one or more of the antibodies of the present invention and assaying whether the antibody binds to the test sample. Altered levels of peptides S2, S7, S22, S23, C6.1, C6.2, S11, E8, E46#1, or E46#2, or in a sample as compared to normal levels can indicate a specific disease.

In a further embodiment, the present invention relates to a method of detecting an S2, S7, S22, S23, C6.1, C6.2, S11, E8, E46#1, or E46#2 antibody in a sample, comprising: a) contacting the sample with an above-described S2, S7, S22, S23, C6.1, C6.2, S11, E8, E46#1, or E46#2 polypeptide, including the consensus sequence corresponding to the amino- and/or carboxy-terminus regions shared by E8, E46#1, and E46#2 polypeptide under conditions such that immunocomplexes form, and b) detecting the presence of the protein bound to the antibody or antibody bound to the protein. In detail, the methods comprise incubating a test sample with one or more of the proteins of the present invention and assaying whether the antibody binds to the test sample. The presence of antibodies to S2, S7, S22, S23, C6.1, C6.2, S11, E8, E46#1, or E46#2 may indicate exposure to GE, the potential need for therapy of the affected individual, or GE contamination of a biological sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising S2, S7, S22, S23, C6.1, C6.2, S11, E8, E46#1, or E46#2 Protein or Antibody In another embodiment of the present invention, a kit is provided which contains all the necessary reagents to carry out the previously described methods of detection.

The kit can comprise: i) a first container means containing an above-described antibody, and ii) second container means containing a conjugate comprising a binding partner of the antibody and a label.

The kit can comprise: i) a first container means containing an above-described protein, and preferably, ii) second container means containing a conjugate comprising a binding partner of the protein and a label. More specifically, a diagnostic kit comprises S2, S7, S22, S23, C6.1, C6.2, S11, E8, E46#1, E46#2, or a peptide having consensus sequences corresponding to the amino and/or carboxy terminus regions shared by E8, E46#1, and E46#2 protein as described above, to detect antibodies in the serum of potentially infected animals or humans.

Provided is a diagnostic kit comprising a container means containing (i) a purified polypeptide comprising an amino acid sequence corresponding to S2, S7, S22, S23, C6.1, C6.2, S11, E8, E46#1, or E46#2, wherein the polypeptide comprises the amino acid sequence set forth in SEQ ID NOS: 4, 6, 2, 8, 21, 22, 39, 27, 29, or 30, respectively; or (ii) a purified polypeptide having an amino-terminus comprising the amino acid sequence set forth in SEQ ID NOS:27, 29, or 30 and/or having a carboxy-terminus comprising the amino acid sequence set forth in SEQ ID NOS:27, 29, or 30; or (iii) immunologically reactive fragments thereof In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

X. Diagnostic Screening

It is to be understood that although the following discussion is specifically directed to human patients, the teachings are also applicable to any animal which can be infected with GE.

The diagnostic and screening methods of the invention are especially useful for a patient suspected of being at risk for developing ehrlichiosis.

According to the invention, a pre- and post symptomatic screening of an individual in need of such screening is now possible using DNA encoding the S2, S7, S22, S23, C6.1, C6.2, S11, E8, E46#1, or E46#2 protein or fragment thereof, or a protein having consensus sequences corresponding to the amino and/or carboxy terminus regions shared by E8, E46#1, and E46#2 of the invention. The screening method of the invention allows a presymptomatic diagnosis of the presence of S2, S7, S22, S23, C6.1, C6.2, S11, E8, E46#1, or E46#2 protein or DNA in individuals, and thus an opinion concerning the likelihood that such individual would develop or has developed ehrlichiosis. Early diagnosis is desired to maximize appropriate timely intervention.

In one preferred embodiment of the method of screening, a tissue sample would be taken from an individual, and screened for (1) the presence of the S2, S7S S22, S23, C6.1, C6.2, S11, E8, E46#1, or E46#2 DNA coding sequence; (2) the presence of S2, S7, S22, S23, C6.1, C6.2, S11, E8, E46#1, or E46#2 rnRNA; (3) the presence of S2, S7, S22, S23, C6.1, C6.2, S11, E8, E46#1, or E46#2 protein; and/or (4) the presence of antibody to S2, S7, S22, S23, C6.1, C6,2, S11, E8, E46#1, or E46#2 protein.

A preferred method of detecting the presence of S2, S7, S22, S23, C6.1, C6.2, S11, E8, E46#1, or E46#2 protein and/or the presence of antibody to S2, S7, S22, S23, C6.1, C6.2, S11, E8, E46#1, or E46#2 protein comprises: a) contacting the sample with a polypeptide or antibody to a polypeptide having the amino acid sequence of S2, S7, S22, S23, C6.1, C6.2, S11, E8, E46#1, or E46#2, or a fragment thereof under conditions such that immunocomplexes form; and b) detecting the presence of the immunocomplexed antibody and polypeptide.

Individuals not infected with GE do not have GE S2, S7, S22, S23, C6.1, C6.2, S11, E8, E46#1, or E46#2 DNA, mRNA, or protein.

The screening and diagnostic methods of the invention do not require that the entire S2, S7, S22, S23, C6.1, C6.2, S11, E8, E46#1, or E46#2 coding sequence be used for the probe. Rather, it is only necessary to use a fragment or length of nucleic acid that is sufficient to detect the presence of the S2, S7, S22, S23, C6.1, C6.2, S11, E8, E46#1, or E46#2 nucleic acid in a DNA preparation from an individual.

Analysis of nucleic acid specific to GE can be by PCR techniques or hybridization techniques (cf. *Molecular Cloning: A Laboratory Manual*, 2nd edition, edited by Sambrook, Fritsch, & Maniatis, Cold Spring Harbor Laboratory, 1989; Eremeeva et al., *J. Clin. Microbiol.* 32:803-810 (1994) which describes differentiation among spotted fever group *Rickettsiae* species by analysis of restriction fragment length polymorphism of PCR-amplified DNA). Nucleic acid probes used to analyze GE genomic DNA via PCR analysis have been described in Chen et al., *J. Clin. Microbiol.* 32:589-595 (1994).

XI. Vaccines

In another embodiment, the present invention relates to a vaccine comprising a GE S2, S7, S22, S23, C6.1, C6.2, S11, E8, E46#1, or E46#2 protein or a fragment thereof, or a protein having consensus sequences corresponding to the amino and/or carboxy terminus regions shared by E8, E46#1, and E46#2 (preferably, an immunologically active fragment) together with a pharmaceutically acceptable diluent, carrier, or excipient, wherein the protein is present in an amount effective to elicit a beneficial immune response in an animal to GE. S2, S7, S22, S23, C6.1, C6.2, S11, E8, E46#1, or E46#2 protein, or a protein having consensus sequences corresponding to the amino- and/or carboxy-terminus regions shared by E8, E46#1, and E46#2 may be obtained as described above and using methods well known in the art. An immunologically active fragment comprises an epitope-bearing portion of the protein.

In a further preferred embodiment, the present invention relates to a composition comprising a GE S2, S7, S22, S23, C6.1, C6.2, S11, E8, E46#1, or E46#2 protein or fragment thereof, or a protein having consensus sequences corresponding to the amino-and/or carboxy-terminus regions shared by E8, E46#1, and E46#2 (preferably, an immunologically reactive fragment-antigenic epitope, examples are listed in Table 1) and a carrier.

In another embodiment, the present invention relates to a vaccine comprising a GE S2, S7, S22, S23, C6.1, C6.2, S11, E8, E46#1, or E46#2 nucleic acid (preferably, DNA) or a fragment thereof (preferably, a fragment encoding an immunologically active protein or peptide), or nucleic acid coding for a polypeptide, or a protein having consensus sequences corresponding to the amino and/or carboxy terminus regions shared by E8, E46#1, and E46#2 together with a pharmaceutically acceptable diluent, carrier, or excipient, wherein the nucleic acid is present in an amount effective to elicit a beneficial immune response in an animal to GE. S2, S7, S22, S23, C6.1, C6.2, S11, E8, E46#1, or E46#2 nucleic acid may be obtained as described above and using methods well known in the art. An immunologically active fragment comprises an epitope-bearing portion of the nucleic acid.

In a further preferred embodiment, the present invention relates to a composition comprising a GE S2, S7, S22, S23, C6.1, C6.2, S11, E8, E46#1, or E46#2 nucleic acid (preferably, DNA) or fragment thereof (preferably, encoding an immunologically reactive protein or fragment-antigenic epitope) and a carrier.

In a further preferred embodiment, the present invention relates to a method of producing an immune response which recognizes GE in a host comprising administering to the host the above-described composition.

In a preferred embodiment, the animal to be protected is selected from humans, horses, deer, cattle, pigs, sheep, dogs, and chickens. In a more preferred embodiment, the animal is a human or a dog.

In a further embodiment, the present invention relates to a method of preventing ehrlichiosis in an animal comprising administering to the animal the above-described vaccine, wherein the vaccine is administered in an amount effective to prevent or inhibit Ehrlichiosis. The vaccine of the invention is used in an amount effective depending on the route of administration. Although intranasal, subcutaneous or intramuscular routes of administration are preferred, the vaccine of the present invention can also be administered by an oral, intraperitoneal or intravenous route. One skilled in the art will appreciate that the amounts to be administered for any particular treatment protocol can be readily determined without undue experimentation. Suitable amounts are within the range of 2 μg of the S2, S7, S22, S23, C6.1, C6.2, S11, E8, E46#1, E46#2 protein, or a protein having consensus sequences corresponding to the amino and/or carboxy terminus regions shared by E8, E46#1, and E46#2 per kg body weight to 100 μg per kg body weight (preferably, 2 μg to 50 μg, 2 μg to 25 μg, 5 μg to 50 μg, or 5 μg to 10 μg).

Examples of vaccine formulations including antigen amounts, route of administration and addition of adjuvants can be found in Kensil, *Therapeutic Drug Carrier Systems* 13:1-55 (1996), Livingston et al., *Vaccine* 72:1275 (1994), and Powell et al., *AIDS RES, Human Retroviruses* 10:5105 (1994).

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the vaccine has suitable solubility properties. The vaccines may be in the form of single dose preparations or in multi-dose flasks which can be used for mass vaccination programs. Reference is made to Remington's *Pharmaceutical Sciences*, Mack Publishing Co., Easton, Pa., Osol (ed.) (1980); and *New Trends and Developments in Vaccines*, Voller et al. (eds.), University Park Press, Baltimore, Md. (1978), for methods of preparing and using vaccines.

The vaccines of the present invention may further comprise adjuvants which enhance production of antibodies and immune cells. Such adjuvants include, but are not limited to, various oil formulations such as Freund's complete adjuvant (CFA), the dipeptide known as MDP, saponins (e.g., QS-21, U.S. Pat. No. 5,047,540), aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes according to Fullerton, U.S. Pat. No. 4,235,877.

The present invention is described in further detail in the following non-limiting examples.

EXAMPLES

The following Protocols A-G and experimental details are referenced in the non-limiting examples, Examples 1-16.

Protocol A: Cultivation of GE in HL60 Cells

The GE-infected HL60 cell line, USG3, was obtained by co-culturing HL60 cells (ATCC CCL 240) with blood cells from dogs challenged with field collected *Ixodes scapularis* ticks. After degenerative cell morphology became noticeable, the infected cells were passed over fresh uninfected HL60 cells to maintain the culture. USG3 was grown in RPMI 1640 containing 10-20% heat-inactivated fetal bovine serum, 2 mM 1-glutamine, 1 mM sodium pyruvate, 0.1 mM MEM non-essential amino acids and was split into fresh HL60 cells two to three times per week. This procedure is also outlined in Coughlin et al., PCT Application No. PCT/US96/10117 and has also been demonstrated by Goodman et al., *N. Eng. J. Med.* 334:209-215 (1996).

Protocol B: DNA Isolation

USG3 cultures at approximately 80% cell lysis (monitored microscopically) were centrifuged at 840×g for 15 min at 4° C. to remove host HL60 cell debris. The supernatant was filtered through a Poretics (Livermore, CA) 5 μm polycarbonate membrane, 47 mm in diameter, followed by a Poretics 3 μm filter under negative pressure. The USG3 filtrate was centrifuged at 9460×g in a Sorvall centrifuge for 30 min at 4° C. Following centrifugation, the GE pellet was resuspended in 5 ml 25mM Tris, pH 8.0, 10 mM MgCl, and 0.9% NaCl. DNase I (Life Technologies, Gaithersburg, Md.) was added to a final concentration of 9 μg per ml and the solution was incubated for 15 min at 37° C. Following incubation, the DNase was inactivated by the addition of 0.5 ml of 0.5M EDTA and the GE was pelleted at 14,000×g in a Sorvall centrifuge for 30 min at 4° C.

Protocol C: Construction of the GE Genomic Library

Genomic DNA was isolated from purified GE using the QIAamp Genomic DNA kit (Qiagen, Chatsworth, Calif.) for library preparation (Stratagene, La Jolla, Calif.). The DNA was mechanically sheared to a 4-10kb size range and ligated to EcoRI linkers. Linkered fragments were ligated into the EcoRI site of Lambda Zap II and the library was amplified in *E. coli* strain XL1-Blue MFR' to a titer of $10^{10}$ Pfu/ml.

Protocol D: Preparation of the Screening Sera

Dog sera: Adult *Ixodes scapularis* ticks collected from regions of the eastern United States having a high incidence of human Lyme disease were applied to dogs as described (Coughlin et al., *J. Infect. Dis.* 171:1049-1052 (1995)). Sera from the dogs was tested for immunoreactivity to *E. equi* by an immunofluorescence assay. Positive sera from infected dogs was pooled and used for immuno screening of the GE genomic library.

Mouse sera: Proteins contained in SDS-disrupted whole GE were separated by SDS-PAGE and forty-six individual bands were excised from each of two gels, 10% and 15% acrylamide. Each gel fragment was mashed, added to buffer and Ribi adjuvant and used to immunize two mice. Sera with similar immuno reactivity patterns against GE antigen as determined by Western blot were pooled into 4 groups: A, B, C, and D.

Goat sera: Mixtures of 100 μg of purified heat-inactivated USG3 antigen were used to immunize goats. Goats received three subcutaneous doses of antigen at bi-weekly intervals. Serum was collected two weeks following the third immunization and used for immunoscreening of the GE genomic DNA library.

Protocol E: Screening of the GE Genomic DNA Library

Bacteriophage were diluted and plated with XL1-Blue MRF' cells on NZY agar plates. Plates were prepared giving approximately 50,000 plaques per plate. Phages were induced to express cloned protein with 10 mM IPTG (Sigma, St. Louis, Mo.) and transferred to nitrocellulose filters. For immuno screening, filters were blocked in TBS (25 mM Tris HCl, pH 7.5,0.5 M NaCl) containing 0.1% polyoxyethylene 20 cetyl ether (Brij 58) and incubated with pooled dog sera, pooled mouse sera, or pooled goat sera. The filters were washed and then reacted with anti-dog HRP conjugated antibody, anti-mouse HRP conjugated antibody, or anti-goat HRP conjugated antibody. The filters were washed again and developed with 4-chloronapthol (Bio-Rad).

Positive plaques were isolated, replated and rescreened twice to achieve purity. Plasmid DNA containing the putative recombinant clones was obtained by plasmid rescue (Stratagene, La Jolla, Calif.).

Protocol F: DNA Analysis

Restriction enzyme analysis: Standard techniques were followed according to the protocols of Sambrook et al., *Molecular Cloning* (2nd ed.), Cold Spring Harbor Laboratory Press, New York (1989)).

DNA sequencing and sequencing analysis: DNA sequencing of recombinant clones was performed using the primer walking method and an ABI 373A DNA sequencer (ACGT, Northbrook, Ill.; Lark Technologies, Houston, Tex.; and Sequegen, Shrewsbury, Mass.). Sequences were analyzed by using the Mac Vector (Oxford Molecular Group) sequence analysis program, version 6.0. The BLAST algorithm, D version 1.4, was used to search for homologous nucleic acid and protein sequences available on the National Center for Biotechnology Information (NCBI) server.

PCR amplification of target sequences: DNA oligonucleotide primer sets were designed based on sequencing information from each individual clone. PCR primers were synthesized by Life Technologies, (Gaithersburg, Md.). Templates for PCR were either purified plasmid DNA, purified GE or HL60 genomic DNA, or phage lysates. All reactions were performed using a Gene Amp 9600 thermal cycler (Perkin-Elmer, CT), GenAmp reagents from Perkin-Elmer, and TaqStart antibody (Clontech, CA). The cycling program consisted of 30 cycles, each of 30 s at 94° C., 30s at 48° C. to 55° C., and 1 min at 72° C., and an additional cycle of 10 min at 72° C. PCR products were analyzed on 4% Nusieve 3:1 agarose gels (FMC Bioproducts, Rockland, Me.).

Protocol G: Protein Isolation and Analysis

Overnight cultures of individual clones were diluted 1:25 into TP broth (per liter: 20 g bactotryptone, 2 g $Na_2HPO_4$, 1 g $KH_2PO_4$, 8 g NaCl, 15 g yeast extract) and grown at 37° C. until an $OD_{600}$ of 0.5 to 1 was reached. A 1.5 ml aliquot of culture was harvested. IPTG was added to a concentration of 5 mM and growth was continued for 3 hours at 37° C. The $OD_{600}$ was read and each culture was pelleted. Pellets were resuspended in 5× Laemmli buffer (12% glycerol, 0.2M Tris-HCl, pH 6.8, 5% SDS, 5% β-mercaptoethanol) at 200 µl per 1 OD unit. In the alternative, harvested GE protein preparations were pelletted and resuspended in 0.4% SDS, 12.5 mM Tris, pH 6.8 and heated at 90-100° C. for 20 min. For cell lysis, 50 µl of a cocktail consisting of RNase (33 µg/ml) and aprotinin (0.2 mg/ml) and 9 µl of DNase (0.17 mg/ml) was added per 5 mg of GE. Twenty µl of 25× Boehringer/Mannheim protease inhibitor cocktail (Cat. #1697498) was added per 0.5 ml cell suspension and 2 µl of a PMSF solution (1M in DMSO) was added just prior to cell disruption. Cells were disrupted in 30 second intervals for a total of 3 min in a mini-beadbeater cell disrupter, Type BX-4(BioSpec), agitated at room temperature for 30 min and centrifuged at 15,000×g for 10 min. The pellet was suspended in Laemmli sample buffer and adjusted to 1.4 mg SDS/mg protein. Samples were boiled and 10 µl of each were electrophoresed on SDS-PAGE gels.

For Western blot analysis, gels were transferred to nitrocellulose filters, the filters were blocked in TBS/Brij 58 and the blots were probed with antisera. Blots were then washed and incubated with HRP conjugated secondary antibody. After a final washing step, blots were developed with 4-chloronapthol (Bio-Rad, Hercules, Calif.) or detected using enhanced chemiluminescence (Pierce, Rockford, Ill.).

Example 1

PCR Amplification and Cloning of GE 16S rDNA

GE was cultivated in HL60 cells as described in Protocol A (supra). Cell extracts were prepared by lysis protocols as described supra, PCR primers (specific for the 16S ribosomal DNA of the genogroup comprising *E. equi., E. phagocytophila*, and the HGE agent used to amplify DNA from the cell extracts) were modified to include restriction enzyme recognition sites as follows:

```
                                        (SEQ ID NO: 40)
forward primer,
5'-CTGCAGGTTTGATCCTGG-3' (PstI site);

(SEQ ID NO: 41)
reverse primer,
5'-GGATCCTACCTTGTTACGACTT-3' (BamHI site).
```

These primers (0.5 µM) were added to a 100 µl reaction mixture containing IX PCR buffer II (Perkin-Elmer Corp), 1.5mM $MgCl_2$ (Perkin-Elmer Corp.), 200 µM each dATP, dGTP, dCTP and dTTP, 2.5 U of Amplitaq DNA polymerase and 20 µl of USG3 DNA. Amplification was performed as described in Protocol F. The amplified 1500 bp fragment was digested with Pst I and Bam HI and ligated to pUC 19 linearized with the same enzymes. The resulting clone, pUCHGE16S, was sequenced.

Example 2

Isolation of Clones Using Canine Sera

Figure 1:
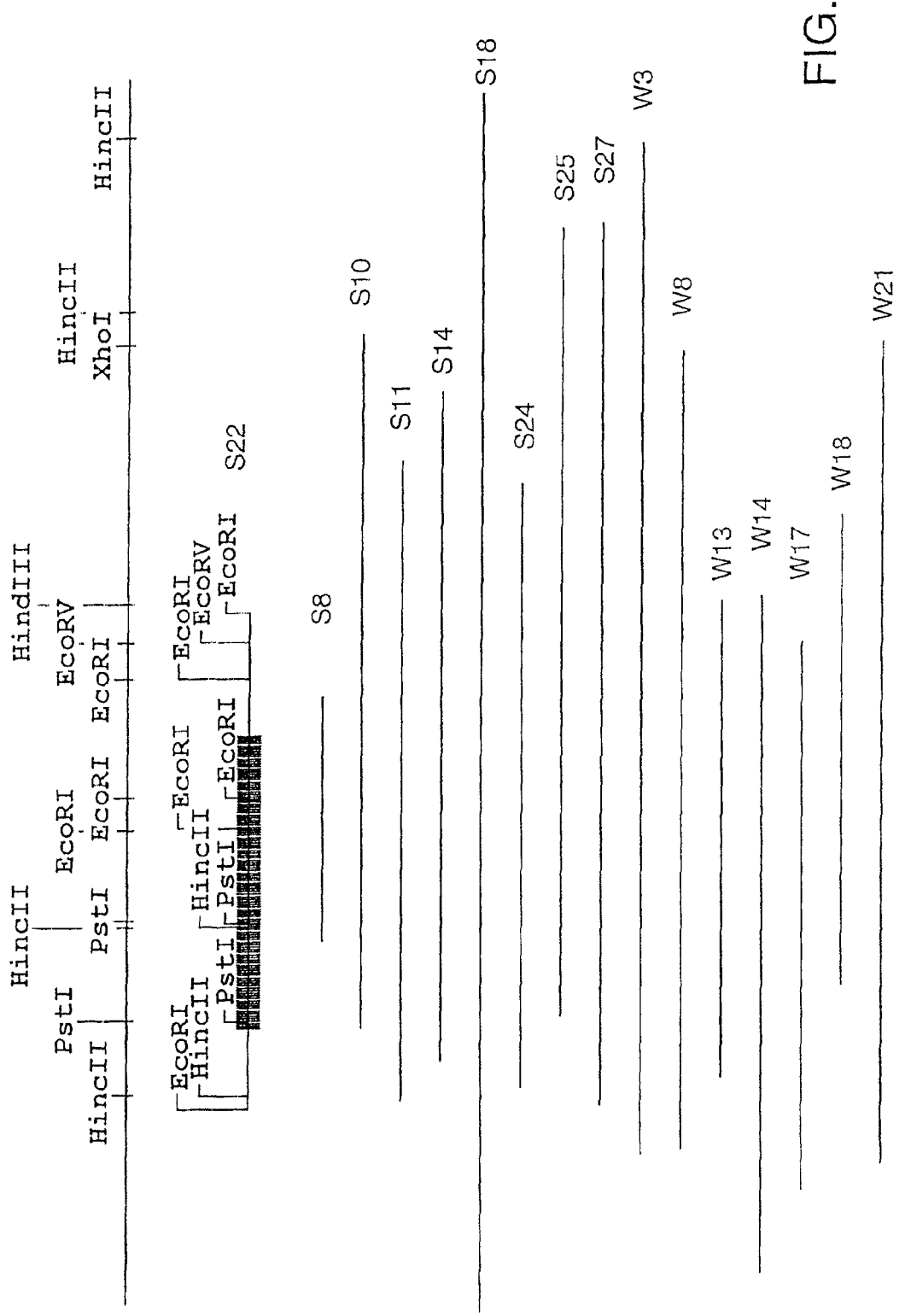
FIG. 1. Restriction enzyme map of group I clones. The top line represents a composite map of all the group I clones and contains the recognition sites for selected enzymes. Each group I clone is listed individually below this map and the relative length of the DNA insert is indicated by the line next to the clone name. A more detailed map of S22 is shown with the open reading frame indicated by the black box.
Figure 2:
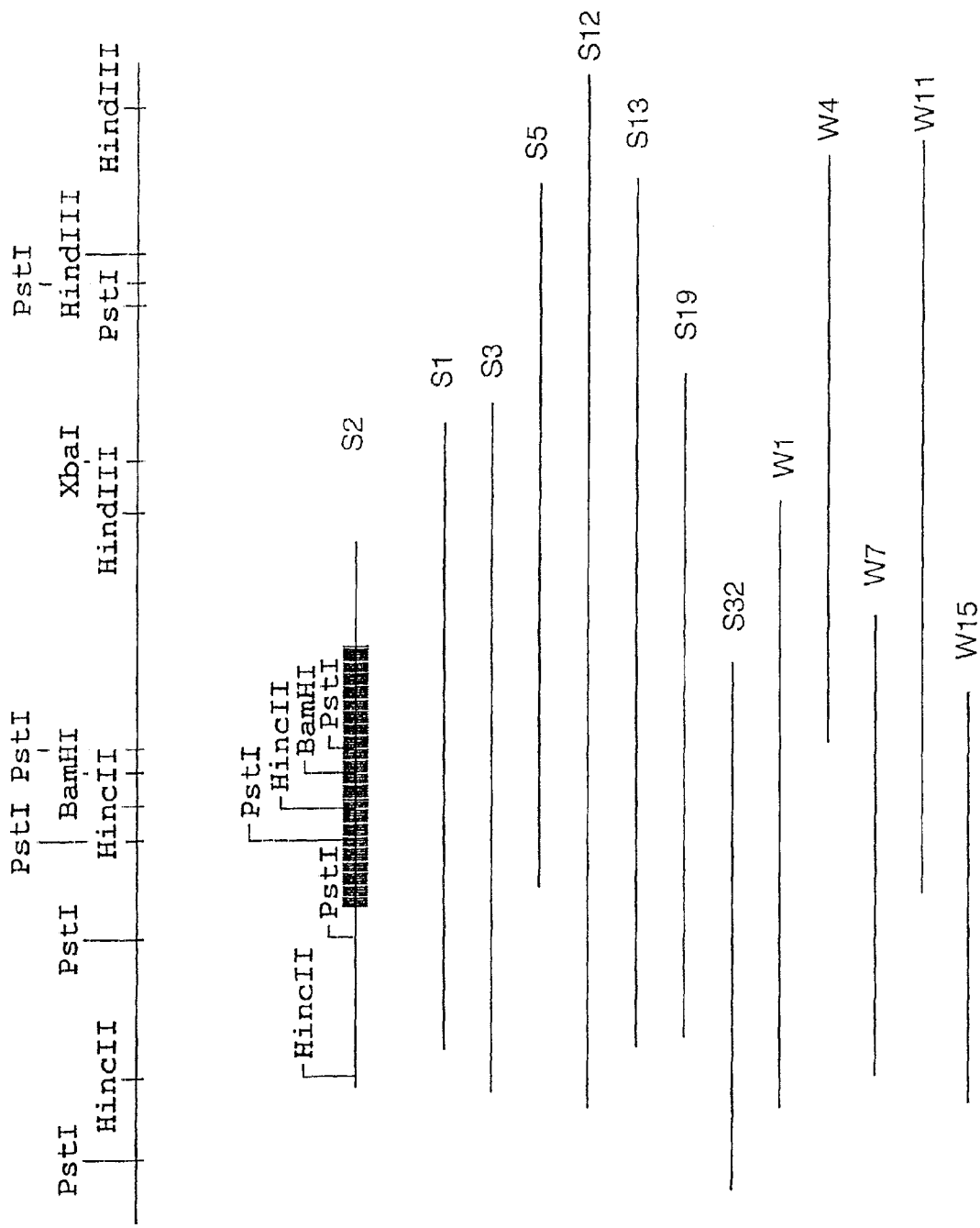
FIG. 2. Restriction enzyme map of group II clones. Individual group II clones are depicted as described in the legend for FIG. 1. S2 is the representative clone for this group and the open reading frame is indicated by the black box, FIG. 3. Restriction enzyme map of group III clones. Individual group III clones are depicted as described in the legend for FIG. 1. S7 is the representative clone for this group and the open reading frame is indicated by the black box.
Figure 3:
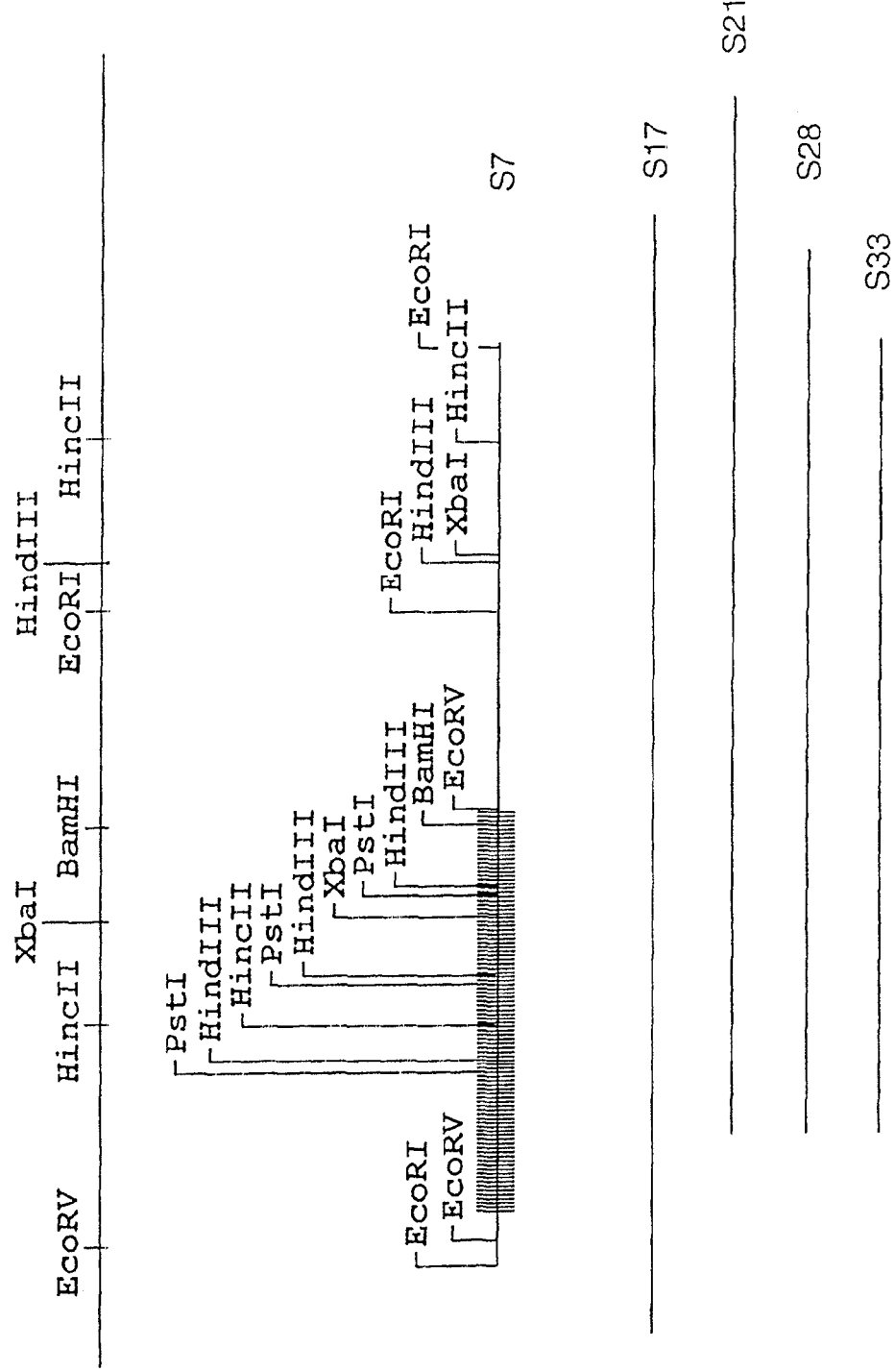

Western blot analysis of the individual recombinant plasmid was performed as described in Protocol G using canine sera prepared as described in Protocol D or a 1:1000 dilution of human sera prepared from two convalescent-phase sera from patients (No. 2 and 3, New York, kindly provided by Dr. Aguero-Rosenfeld) and from an individual in Wisconsin who was part of a seroprevalence study (No. 1, kindly provided by Dr. Bakken). Blots were washed and incubated with biotin-labeled goat anti-dog IgG (Kirkegaard & Perry Laboratories, Inc., Gaithersburg, MD) followed by peroxidase labeled streptavidin (Kirkegaard & Perry Laboratories, Inc., Gaithersburg, Md.) or HRP conjugated anti-human IgG (Bio-Rad, Hercules, Calif.). After several additional washes, the dog sera blots were developed with 4-chloronapthol (Bio-Rad, Hercules, Calif.). Over 1000 positive clones were identified. Three hundred of these clones (both strong (S) and weak (W) immunoreactivity) were further purified by a secondary screen of the library. From this group, 48 clones were purified as single plaques by a third immunoscreening. Plasmids were rescued according to the Stratagene protocol and DNA was purified using Qiagen plasmid purification kits. Of the original forty-eight clones, seven were not able to be analyzed due to lack of sufficient DNA. A number of restriction digests were performed on each clone to assess their relatedness. Single enzyme digests were performed with EcoRI, HindIII, BamHI, HincII, XbaI, PstI and Alw26I and in some cases a number of double digests were done. Based on these digests restriction maps were generated and most of the clones could be placed into one of three groups—designated groups I, II and III. FIGS. 1-3 show the structures of the three groups based on the restriction enzyme analysis. Another five clones had lost the insert during the plasmid rescue and were not grouped.

Example 3

Characterization of Representative Clones S2, S7, S22, and S23

A representative clone was chosen for further characterization from each of the three groups (see Example 2, supra).

Figure 5B-2:
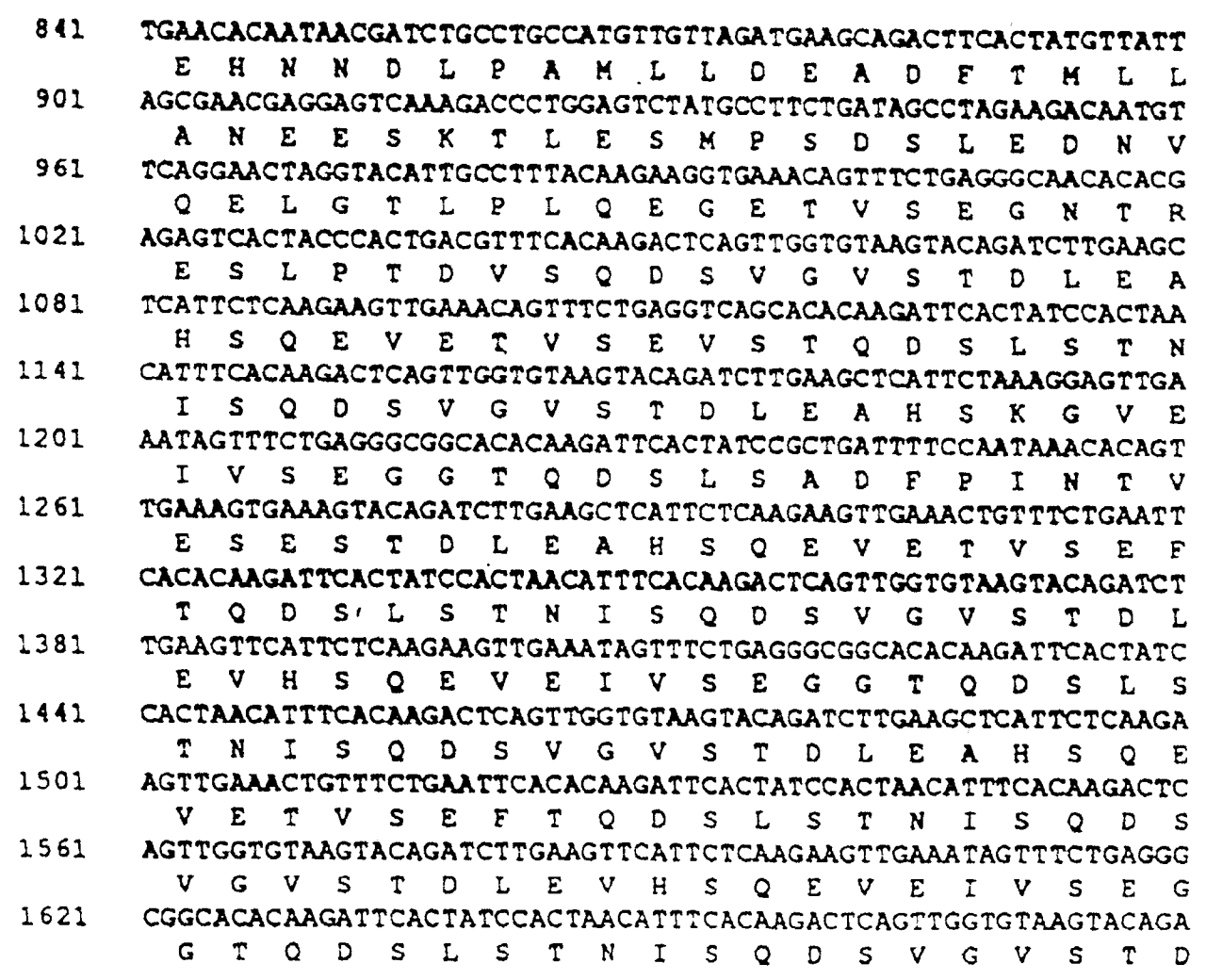

These clones, S2, S7, and S22, were sequenced according to Protocol F. S23 was also sequenced since it did not appear to fall into one of these groups. The complete nucleic acid sequence of each of these clones is shown as follows: FIG. 4, group I (S22); FIG. 6, group II (S2); FIG. 8, group III (S7); FIG. 10, (S23). Sequence analysis (MacVector, Oxford Molecular Group) showed that each clone contained a single large open reading frame encoded by the plus strand of the insert and each one appeared to be a complete gene. The amino acid sequences encoded by each clone are shown in FIG. 5 (S22), FIG. 7, (S2), and FIG. 9 (S7), and FIG. 11 (S23). There are also two additional small open reading frames in the S23 DNA insert, one on the negative strand and the other on the positive strand. A comparison of the DNA sequences of the 4 clones revealed that S23 is a group I clone which is missing a stretch of nucleotides in S22 containing two EcoRI sites. The nucleotide sequences of the genes described here have been assigned the following GenBank accession numbers: GE ank (GE 160), AF020521; GE rea (GE 130), AF020522; GE gra (GE 100), AF020523. Further sequence analysis of the four clones showed that all of them contain regions of repeated amino acids.

Figure 14:
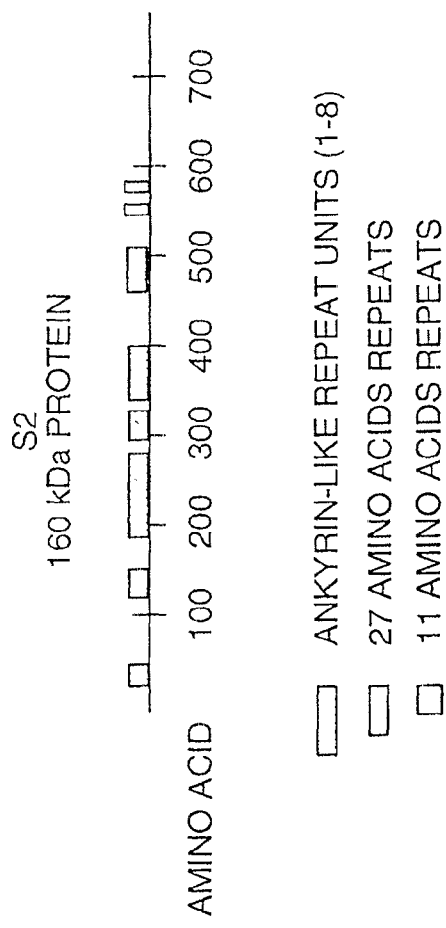
FIG. 14. Schematic diagram of GE 160 kDa protein. Repeat regions are indicated by the boxes. Sequences of proposed ankyrin repeats, numbered 1-8 (SEQ ID NOS:9-16), are aligned using the consensus sequence (SEQ ID NO:17) at the top: h, hydrophobic; t, turn-like or polar; S/T, serine or threonine; capitals, conserved amino acids.

FIG. 12 represents a schematic diagram of the S22 and S23 proteins and the repeat regions within those proteins. Similarly, FIG. 13 shows the repeat regions of the S2 and S7 proteins in a schematic diagram. Amino acid sequence analysis of the proteins encoded by the three gene clones S22, S2, and S7, showed that all contain regions of repeated amino acids. A schematic version of these repeat structures is shown in FIGS. 14 and 15. The S2 encoded protein (160 kDa) has three groups of repeats. The first set consists of a number of ankyrin-like repeat units of 33 amino acids, the second consists of repeat units of 27 amino acids, and the third consists of repeat units of 11 amino acids. The ankyrin repeats were revealed by a BLAST database search for protein homologies. Ankyrin repeats occur in at least four consecutive copies and are present in yeast, plants, bacteria, and mammals. FIG. 14 shows a multiple alignment of the S2 encoded protein (160 kDa) ankyrin repeats under a consensus sequence derived from the analysis of several hundred similar ankyrin-like motifs. The eighth repeat sequence holds to the consensus only through the first half of the repeat unit and may not represent a full ankyrin-like repeat.

Figure 15A:
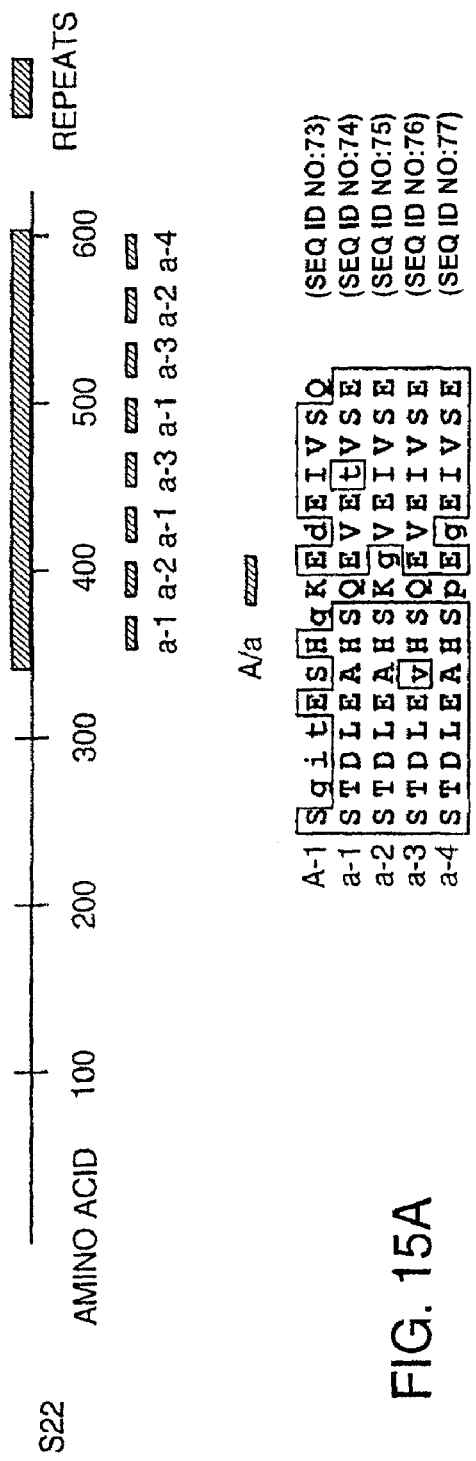
FIG. 15A shows the amino acid alignments of a sequence which occurs 4 times in the *E. chaffeensis* protein [(45)] (top line of alignment, A-I) and 8 times in the GE 130 kDa protein (a-1 to a-4). Sequence a-1 is repeated 3 times, related sequences a-2 and a-3 are each repeated twice, and related sequence a-4 is found once. The position of these sequences in the proteins is indicated by the small bold lines.

The S22 encoded protein (130 kDa) has a repeat unit of 26 to 34 amino acids which occurs eight times in the carboxy-terminal half of the protein (See FIG. 15). The sequence varies somewhat from repeat to repeat. A database homology search with the NCBI BLAST algorithm revealed that the S22 encoded protein has limited homology to the *E. chaffeensis* 120 kDa protein. An amino acid sequence alignment of a motif common to both proteins is shown in FIG. 15A. This motif is represented by a bold line and occurs four times in an identical fashion in the *E. chaffeensis* protein (designated A-1) and eight times with four variations in the 130 kDa protein (a-1, a-2, a-3, and a-4).

Figure 15B:
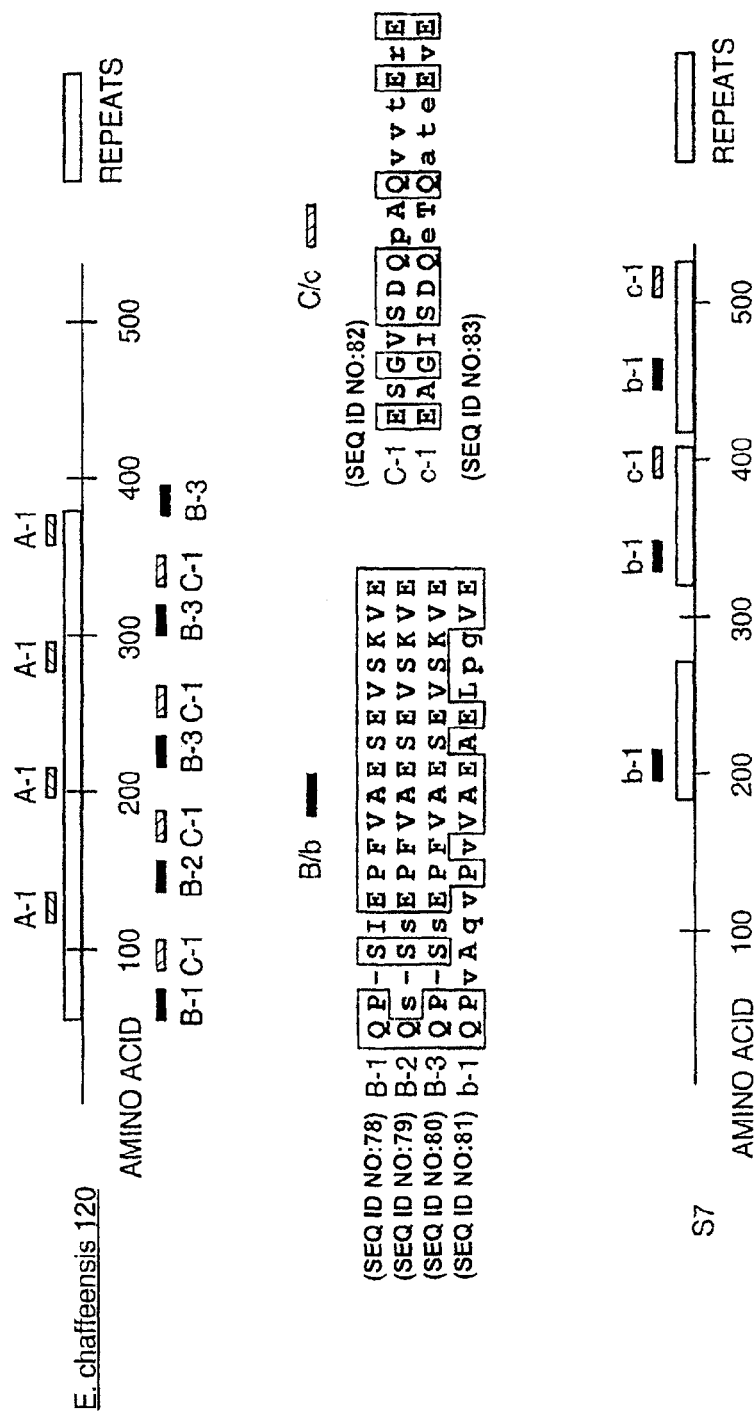
FIG. 15B shows the amino acid alignments of two different sequence motifs which occur in the *E. chaffeensis* 120 kDa protein (B-1 to B-3 and C-1) and the GE 100 kDa protein (b-1 and c-1). Bold and cross-hatched boxes indicate the position of these sequences in the proteins. Identical amino acids are surrounded by boxes and conserved amino acids are in capital letters.

The S7 encoded protein (100 kDa) has three large repeat units, which differ somewhat in length (See FIG. 15). A database search revealed that it is similar to the 120 kDa *E. chaffeensis* protein, which contains four repeats of 80 amino acids each. Both proteins contain large amounts of glutamic acid: 18% for the 100 kDa protein and 17% for the 120 kDa protein. When the two protein sequences are aligned, most of the homology occurs in the repeat regions. FIG. 15B shows alignments for two homologous groups of amino acid motifs from the two proteins (designated B/b and C/c) found with the BLAST algorithm. These are not the only possible alignments of the two proteins but do provide an example of their similarities. The locations of the homologous sequences are indicated by bold or hatched lines above (S7 encoded 100 kDa protein) or below (*E. chaffeensis* 120 kDa protein) the respective proteins. The B sequence represented by the bold line varies slightly in the *E. chaffeensis* protein (shown as B-1, B-2, and B-3) and occurs a total of five times. The S7 encoded protein equivalent, b-1, is invariant and occurs three times. The sequence represented by the hatched line occurs four times in *E. chaffeensis* 120 kDa (C-1) and two times in S7 (C-1).

Figure 16A:
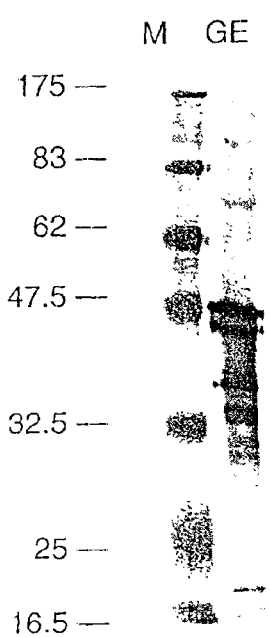
FIG. 16. Western blot analysis of: A) Purified USG3 disrupted in SDS (lane GE). B) Individual recombinant clones of GE 100 kDa (S7), GE 160 kDa (S2), GE 130 kDa (S22), and a negative control (NEG, no insert), were grown and incubated with IPTG to induce protein expression according to Materials and Methods. Samples of each were electrophoresed on SDS-PAGE gels and transferred to nitrocellulose for Western blotting. Blots were probed with convalescent dog sera. Molecular weight markers (in kilodaltons) are shown to the left of each figure.
Figure 16B:
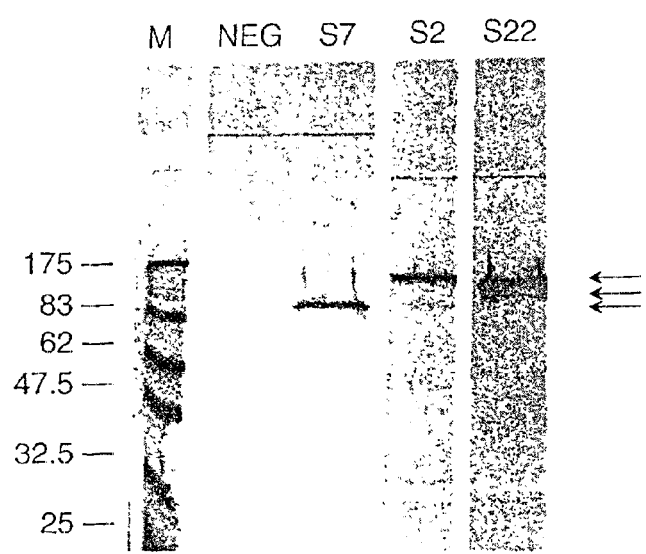
Figure 17:
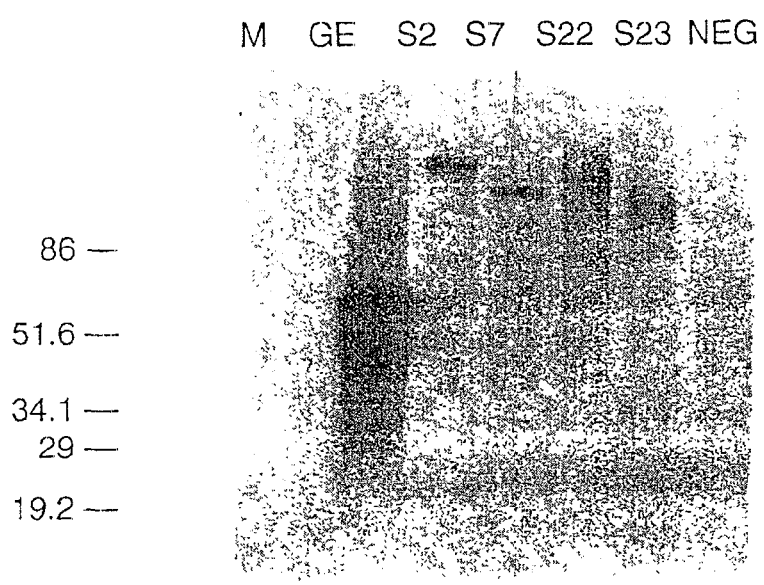
FIG. 17. Western blot analysis of S2, S7, S22, and S23 proteins. Individual recombinant clones of S2, S7, S22, S23, and a negative control were grown and induced by IPTG to induce protein expression. Samples of each were electrophoresed on a SDS-PAGE gel and transferred to nitrocellulose for Western blotting. SDS disrupted GE was used as a positive control. The blot probed with convalescent dog sera and samples are indicated at the top of the gel. Molecular weight markers (in kilodaltons) are shown to the left of each figure.
Figures 18A, 18B, 18C:
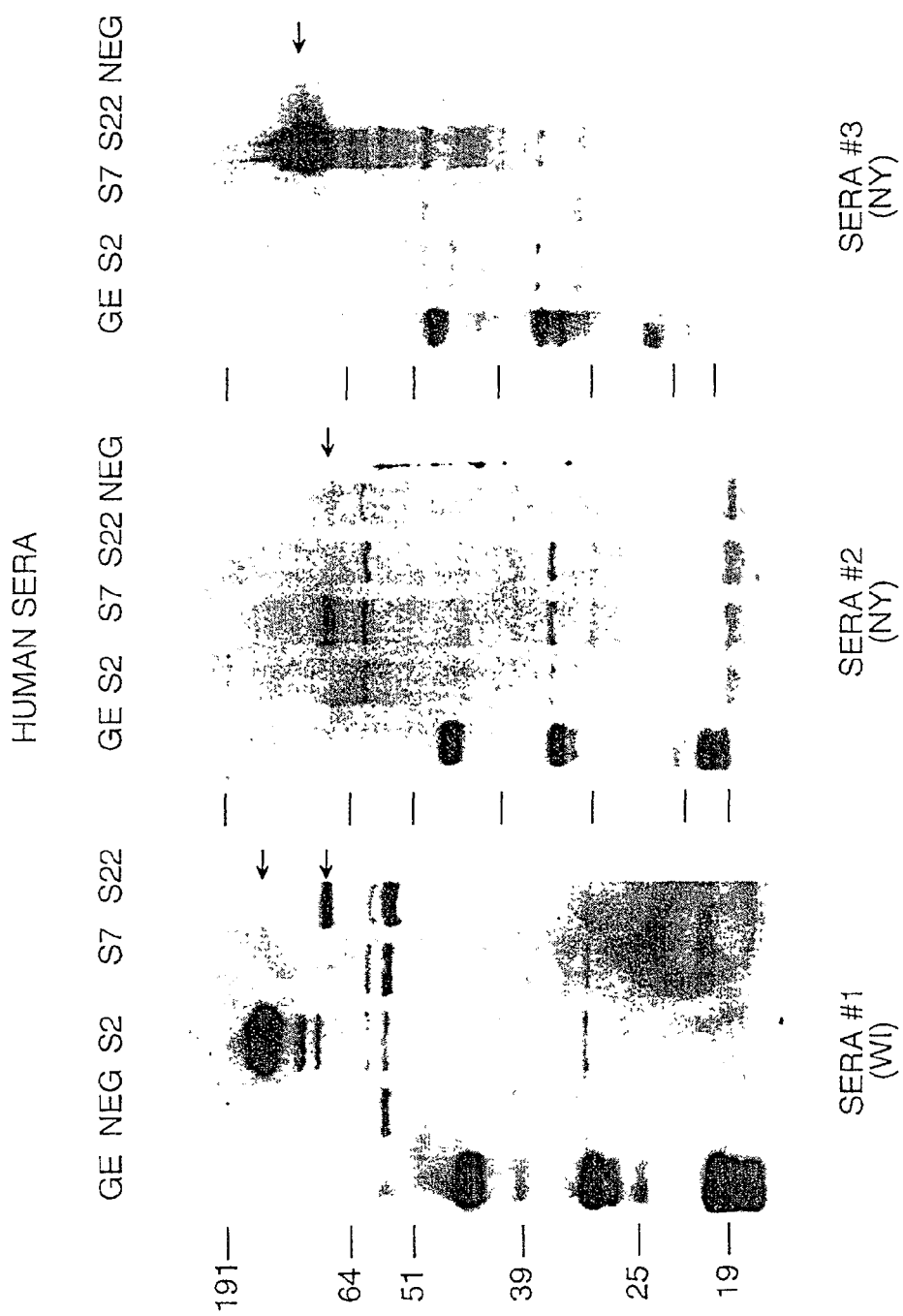
FIG. 18. Western blot analysis of GE proteins. Three different human serum samples were used to probe Western blots containing SDS-disrupted USG3 (GE lanes), GE160, GE100, and GE130. A pBluescript library clone containing no insert was used as a negative control (NEG). Origin of sera is indicated at the bottom of each panel (WI, Wisconsin; NY, New York). Molecular weight markers (in kilodaltons) are shown to the left of each panel.

Samples of recombinant clones were induced to express the encoded protein and bacterial extracts were prepared for SDS-PAGE as outlined in Protocol G. FIG. 16 shows a Western blot containing samples of S2, S7, S22, and FIG. 17 shows a western blot also containing a sample of S23. SDS-disrupted whole GE was used as a positive control and a non-protein expressing clone was run as a negative control. Immunoreactive proteins for all 4 clones were detected by the dog sera. The same proteins were also detected when the blots were probed with sera obtained from a human patient with GE, as evident in FIG. 18. The blots were probed with human antisera. Based on the amino acid sequences of these proteins, the calculated molecular weights are significantly lower than the apparent molecular weights by SDS-PAGE. The calculated (based on the amino acid sequence) and apparent (based on mobility in SDS-PAGE) molecular weights of each protein encoded by the open reading frames of the listed clones are compared in Table 4. This phenomenon has been observed in other proteins (see Barbet et al., *Infect. Immun.* 59:971-976 (1991); Hollingshead et al., *J. Biol. Chem.* 267:1677-1686 (1986); Yu et al., *Gene* 184:149:154 (1997)).

TABLE 4

| Clone | Calculated Molecular Weight | Apparent Molecular Weight |
| --- | --- | --- |
| S2 | 78 kDa | 160 kDa |
| S7 | 61 kDa | 100 kDa |
| S22 | 66 kDa | 130 kDa |
| S23 | 52 kDa | 90 kDa |

Example 4

Verification that Clones S2, S7, S22, and S23 are GE Derived by PCR Analysis

PCR primer sets were designed based on the sequences of each of the three GE clones and are as described in Table 5. The sequences of each primer set indicated in Table 5 were used to amplify regions of the listed clones (SEQ ID NOS: 47-52). Each oligonucleotide sequence is shown in the 5' to 3' orientation. Each 50 µl reaction contained 0.5 µM of each primer, IX PCR Supermix (Life Technologies, Gaithersburg, Md.) and either 100 ng USG3 DNA, 100 ng HL60 DNA or 200 ng plasmid DNA. PCR amplification was performed as described in Protocol F.

TABLE 5

| Clone | Forward Primer | Reverse Primer |
| --- | --- | --- |
| S22 | CACGCCTTCTTCTAC (SEQ ID NO: 42) | CTCTGTTGCTATAGGGGC (SEQ ID NO: 43) |
| S7 | GATGTTGCTTCGGGTATGC (SEQ ID NO: 44) | CAGAGATTACTTCTTTTTGCGG (SEQ ID NO: 45) |

TABLE 5-continued

| Clone | Forward Primer | Reverse Primer |
|---|---|---|
| S2 | GCGTCTCCAGAACCAG (SEQ ID NO: 46) | CCTATATAGCTTACCG (SEQ ID NO: 47) |

Figure 19A:
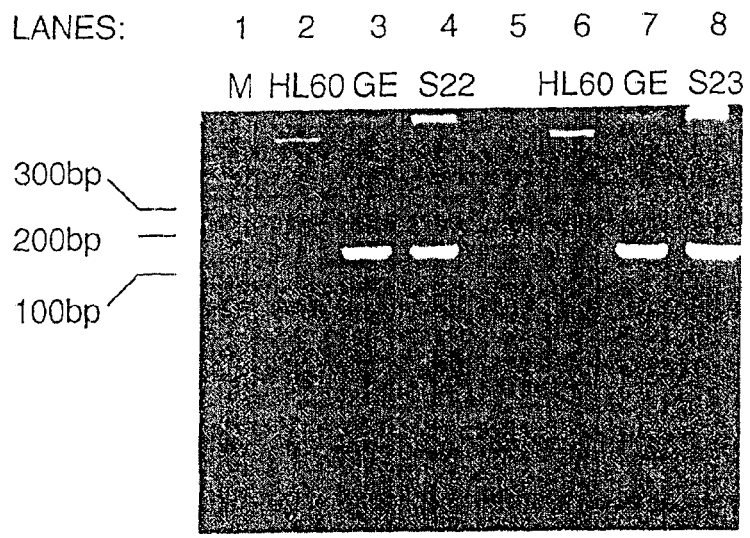
FIG. 19. PCR analysis of groups I, II and III. PCR reactions were performed and the products analyzed using 4% Nusieve gels. Primer sequences are listed in Table 5. A) S22 primers were used to amplify a 159bp region of S22 DNA using as templates: S22 plasmid DNA (lane 4), S23 plasmid DNA (lane 8), HL60 DNA (lanes 2 and 6) and GE DNA (lanes 3 and 7). B) S2 primers were used to amplify a 395 by region of S2 DNA using as templates: S2 plasmid DNA (lanes 4 and 5), HL60 DNA (lane 2) and GE DNA (lane 3). C) S7 primers were used to amplify a 643 by region of S7 DNA using as templates: S7 plasmid DNA (lane 3), HL60 DNA (lane 4) and GE DNA (lane 2). DNA molecular weight markers (50-1000 bp, FMC) are present in lane 1 of each figure.
Figure 19B:
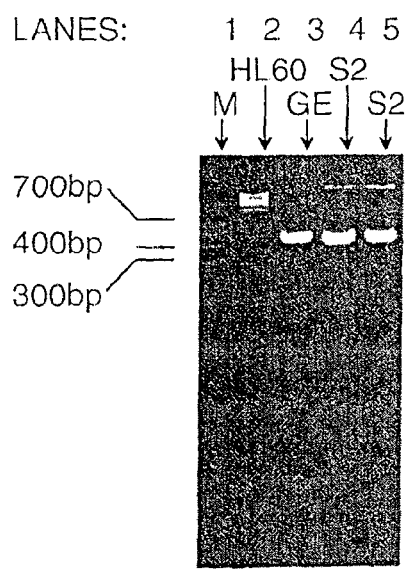
Figure 19C:
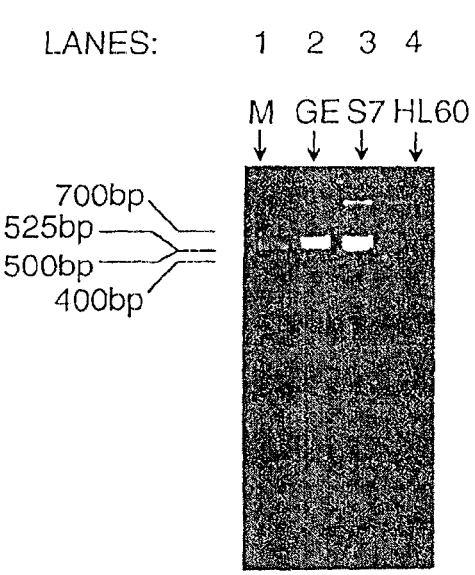
Figure 20:
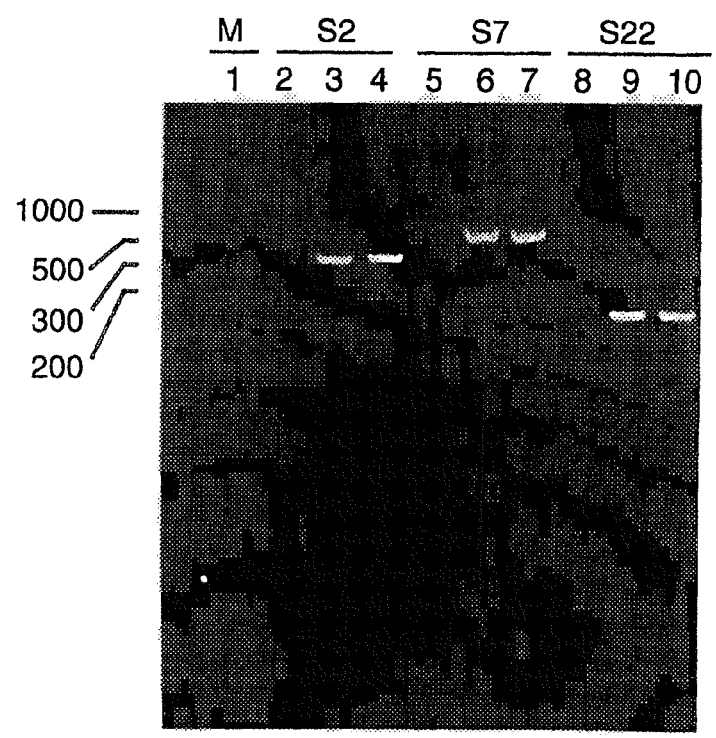
FIG. 20. PCR analysis of GE genes. PCR reactions were performed as described in Materials and Methods and the products analyzed using 4% Nusieve gels. S2 primers were used to amplify a 395 by region of S2 DNA using as templates: HL60 DNA (lane 2), S2 plasmid DNA (lane 3), and USG3 DNA (lane 4). S7 primers were used to amplify a 643 by region of S7 DNA using as templates: HL60 DNA (lane 5), S7 plasmid DNA (lane 6), and USG3 DNA (lane 7). S22 primers were used to amplify a 159bp region of S22 DNA using as templates: HL60 DNA (lane 8), S22 plasmid DNA (lane 9), and USG3 DNA (lane 10). DNA molecular weight markers (50-1000 bp, FMC, Rockland, ME.) are present in lane 1.

These experiments established that the sequenced genes were derived from GE DNA and not HL60 DNA, and allowed the elimination of duplicate clones prior to plasmid rescue and DNA isolation by using them in PCR of phage lysates. Primer pairs specific for S22/S23, S2 and S7 were used in separate PCR reactions to amplify three different templates: GE DNA, HL60 DNA, or the purified plasmid DNA of each clone. FIGS. 19 and 20 show the results obtained for primers of S22, S23, S2, and S7 using the PCR conditions outlined above. All three clones were specific to GE and were not present in HL60 DNA. In each case the size of the PCR product using genomic DNA as template was the same as that generated by purified plasmid DNA.

Example 5

Further Characterization of Isolated GE Clones

The same primer pairs (supra) were also used to confirm or establish the identity of each purified phage stock from all 48 clones derived from the library screening with the dog sera. Every isolate, with one exception (W20), was either a group I, II, or III clone, as evident in Table 6 below. Clones were isolated by immunoscreening with convalescent dog sera. Each clone is classified as a group I, II or III clone based on PCR with primers specific for the group I, II or III DNA sequences. Clone W20 was the only clone different from the other 3 groups.

TABLE 6

| Clone Name | Group |
|---|---|
| S1 | II |
| S2 | II |
| S3 | II |
| S5 | II |
| S6 | III |
| S7 | III |
| S8 | I |
| S9 | I |
| S10 | I |
| S11 | I |
| S12 | II |
| S13 | II |
| S14 | I |
| S19 | II |
| S22 | I |
| S23 | I |
| S24 | I |
| S25 | I |
| S27 | I |
| S32 | II |
| W1 | II |
| W2 | I |
| W3 | I |
| W4 | I |
| S16 | III |
| S17 | III |
| S18 | I |
| S20 | III |
| S21 | III |
| S28 | III |
| S30 | II |
| S33 | III |
| W5 | II |

TABLE 6-continued

| Clone Name | Group |
|---|---|
| W7 | II |
| W8 | I |
| W9 | III |
| W10 | III |
| W11 | I |
| W13 | I |
| W14 | I |
| W15 | II |
| W16 | III |
| W17 | I |
| W18 | I |
| W19 | III |
| W20 | — |
| W21 | I |
| W22 | III |

Example 6

Isolation of Clones Using Murine Sera

Four different pools of sera (designated A, B, C, and D) obtained from mice immunized with gel band samples of GE protein (Protocol D) were used to screen the GE genomic DNA library. Twenty-six clones were plaque purified and used for further analysis. These were designated A1, A2, A8, A11, A14, A16; B1, B3, B6, B8, B9, B12; C1, C3, C5, C6, C7, C10, C11; D1, D2, D7, D8, D9, D11, and D14. Plasmid DNA was rescued from each clone and restriction analyses were performed. Several of the clones (A14, B12, C3, C5, D1, D2, D9 and D11) had no insert. Of the remaining clones, nine could be placed into one of two groups due to similarities in their restriction enzyme patterns. The first group included all of the C clones and the second group consisted of all of the D clones plus B3. Some of the other clones were not grouped at this stage due to lack of sufficient DNA.

Example 7

Characterization of Representative Clone C6

One representative clone from the C group (C6) was selected for DNA sequencing. The insert of 2.7 kb contained two open reading frames (designated C6.1, C6.2, and whose amino acid sequences are given in FIGS. 21 and 22, respectively) on the plus strand which were separated by 9 nucleotides (FIG. 23), A search of the protein/nucleotide databases revealed that the first amino acid sequence (C6.1) has significant homology to dihydrolipoamide succinyltransferase, an enzyme involved in the oxidative decarboxylation of pyruvate and 2-oxoglutarate (Spencer et al., *Eur. J. Biochem.* 141:361-374 (1984)). The second amino acid sequence (C6.2) is homologous to a methionine aminopeptidase found in several types of bacterial species.

Clones, C1, C6, and C7, were induced to express the encoded protein and bacterial extracts were prepared for SDS-PAGE. FIG. 24 shows a Western blot of these samples electrophoresed next to SDS-disrupted whole GE. The immune mouse serum designated "C" was used to probe the blot. All three recombinant clones expressed a protein of the same molecular weight, about 50 kDa. The calculated molecular weights of C6.1, C6.2 are 44 kDa and 29 kDa, respectively. Thus, based on size, C6.1 is more likely to be the expressed recombinant protein detected by immunoscreening.

DNA sequencing also revealed that the group of clones consisting of all of the D clones and the B3 clone contained an open reading frame for a protein with homology to the heat shock protein hsp70.

Based on the DNA sequences of each clone, PCR primers were designed to amplify specific regions of each open reading frame contained in C6. The primers used were as follows:

```
                                           (SEQ ID NO: 48)
forward primer for C6.1:
5'-CAGGCAGTGAGCACTCAAAAACC-3';

(SEQ ID NO: 49)
reverse primer for C6.1:
5'-GCGACTCCAATGTTACAATAGTCCC-3';

(SEQ ID NO: 50)
forward primer for C6.2:
5'-TGTGATCCTCGATGGTTGGC-3';

(SEQ ID NO: 51)
reverse primer for C6.2:
5'-CCCTCCTGAATCGTAACATCATCC-3'.
```

FIG. 25 shows the results obtained with each primer pair using GE DNA, HL60 DNA or the C6 plasmid DNA as templates in a PCR reaction. Both primer sets amplified a region of the expected size using GE or plasmid templates but not the HL60 template. Thus both C6 genes are GE specific.

The C6 primers were also used to amplify phage lysates from each of the other twenty-five clones isolated using the immune mouse sera. In addition to all of the C clones, the C6.1 and C6.2 genes were also found in A1, A11, A14 and A 16.

The following examples (Examples 8-15) all relate to the characterization of the GE immunoreactive protein in the 42-45 kDa molecular mass range.

Example 8

SDS-PAGE and Peptide Sequencing of Immunoreactive Proteins

To characterize the GE proteins in the 42 to 45 kDa range, a 50 pl of a cocktail consisting of RNase (33 µg/ml) and aprotinin (0.2 xng/ml) and 9 µl of DNase (0.17 mg/ml) was added per 5 mg of USG3 pellet in 2 mM $MgCl_2$, 50 mM Tris-HCl, pH 7.5 buffer. Twenty µl of 25× Boehringer/Mannheim protease inhibitor cocktail was added per 0.5 ml cell suspension and 2 µl of a PMSF solution (1M in DMSO) was added just prior to USG3 disruption. Cells were disrupted in 30 second intervals for a total of 3 min. in a mini-beadbeater cell disrupter, Type BX-4 (BioSpec), agitated at room temperature for 30 min and centrifuged at 15,000×g for 10 min. The pellet was suspended in Laemmli sample buffer and adjusted to 1.4 mg SDS per mg protein, and heated at 90-100° C. for 5 min. The protein concentration was determined by BCA assay (Pierce Chemical Co., Rockford, Ill.). Electrophoresis was performed on a 15% SDS-PAGE gel and proteins were transferred onto a 0.2 µm PVDF membrane. Half of the blot was probed with anti-GE dog sera (6) and the other half was stained with Ponceau S. Two protein bands which matched the molecular mass of the two most immunoreactive bands on the Western blot (43 and 45 kDa) were excised. A portion of each band was used for direct N-terminal sequencing. The remaining material was digested with trypsin in situ and individual peptides were separated by RP-HPLC on a ZORBAX C18 (1 mm×150 mm) column. The peptides were analyzed and screened by MALDI-TOF mass spectrometry. Sequencing of peptides was performed by Edman degradation (Harvard Microchemistry, Cambridge, Mass.). An N-terminal peptide and two internal peptides were obtained for each protein (Table 7).

TABLE 7

Peptide Sequences from Transblotted GE Proteins

| | N-terminal (N) or Internal (I) | Homology to A. marginale MSP-2 | Location |
|---|---|---|---|
| 45 kDa | | | |
| HDDVSALETGGAGYF[a] (SEQ ID NO: 66) | N | no | MSP2-A, MSP-2C (1)[b] |
| SGDNGSLADYTDGGASQTNK (SEQ ID NO: 67) | I | no | MSP2-A |
| AVGVSHPGIDK (SEQ ID NO: 68) | I | no | MSP2-A, MSP-2C (2) |
| 43 kDa | | | |
| HDDVSALETGGAGYF (SEQ ID NO: 66) | N | no | MSP2-A, MSP-2C (1) |
| FDWNTPDPR (SEQ ID NO: 69) | I | yes | MSP2-A, MSP-2C |
| LSYQLSPVISAFAGGFYH (SEQ ID NO: 70) | I | yes | MSP2-A, MSP-2b (1) |

[a]Amino acids are shown using the single letter code.
[b]Numbers in parentheses indicate the number of amino acid changes from the sequence shown The results show that the amino-terminal peptides from the two proteins are identical. A BLAST homology search showed that two of the internal peptides from the 43 kDa protein were homologous to the MSP-2 proteins of *Anaplasma marginale*, a rickettsial hemoparasite of livestock (Palmer et al., *Infect. Immun.* 62:3808-3816 (1994)) which is phylogenetically closely related to the GE (Dumler et al., *J. Clin. Microbiol.* 33:1098-1103)(1995).

Example 9

PCR Amplification of USG3 Genomic DNA

To obtain additional sequence information for these proteins, degenerate pools of oligonucleotides were synthesized based on the reverse translation of the peptide sequences and used to amplify DNA from USG3. The reverse complement of each oligonucleotide was also synthesized with the exception of the one corresponding to the amino-terminal peptide. PCR amplifications were performed using one forward and one reverse primer set using USG3 genomic DNA as template and an annealing temperature of 55° C. Primer pairs either gave no PCR product or a single band. The primer pair that resulted in generating the longest product, 550 bp, consisted of the forward primer 5'-ACNGGNGGNGCWGGNTAY-TTY-3' (SEQ ID NO:71) (amino-terminal peptide HDDVSALETGGAGYF (SEQ ID NO:66)) and the reverse primer 5'-CCNCCRTCNGTRTARTCNGC-3' (SEQ ID NO:72) (peptide SGDNGSLADYTDGGASQTNK (SEQ ID NO:67)). This DNA was sequenced and found to contain an open reading frame with homology to the MSP-2 protein of *A. marginale* (FIG. 26). Two other peptides, one from the 45 kDa protein and one from the 43 kDa protein, were also contained within this sequence. The similarity in protein sequence between the two immunoreactive 43 and 45 kDa proteins may indicate that they are differentially modified or processed versions of the same protein or they may represent proteins expressed from two different members of a gene family.

Example 10

Isolation of Clones Using Goat Sera

A goat serum reactive against proteins of the HGE agent was obtained by immunizing animals 3 times with purified USG3 antigen. Western blot analysis showed that many proteins of various molecular mass were recognized by this serum including the 43 and 45 kDa proteins (FIG. 27, GE lanes). The USG3 genomic expression library (prepared as described in Protocol C) was screened with immune goat serum and several immunoreactive plaques were identified for further analysis. To eliminate clones previously isolated using immune dog sera, phage supernatants from the plaques were screened by PCR using primers based on the sequences of those previously identified clones. Bacteriophage were plated with XL1-Blue MRF' and induced to express protein with 10 mM IPTG (Sigma, St. Louis, Mo.). Proteins were transferred to nitrocellulose filters and the filters were washed with TBS (25 mM Tris HCl, pH 7.5, 0.5 M NaCl). Washed filters were blocked in TBS containing 0.1% polyoxyethylene 20 cetyl ether (Brij 58) and incubated with a 1:1000 dilution of goat serum depleted of anti-*E. coli* antibodies. The filters were washed and incubated with rabbit anti-goat Ig HRP conjugated antibody (1:2000 dilution), rewashed and developed with 4-chloronapthol. Positive plaques were isolated, replated and screened again. Plasmid DNA containing the putative recombinant clones was obtained by plasmid rescue (Stratagene, La Jolla, Calif.). pBluescript plasmids were rescued from the remaining clones and they were assessed for relatedness by restriction enzyme analysis. Two clones, E8 and E33, appeared to contain the same insert in opposite orientation from the lacZ promoter. Two other clones, E46 and E80, shared restriction enzyme fragments in common but E46 contained a larger insert than E80.

Example 11

DNA Sequencing and Sequence Analysis

Three clones, E8, E33, and E46, were sequenced by the primer walking method. Both strands of each insert were sequenced as described in Protocol F. The sequences of the three clones shared considerable homology. The E8 clone contained a larger version of the E33 insert but in opposite orientation with respect to the lacZ promoter (FIG. 28). Both clones contained the same open reading frame but E33 was missing 420 nucleotides from the 5' end of the gene. The deduced amino acid sequence of the E33 open reading frame was in frame with the partial β-galactosidase amino acid sequence encoded by the vector (data not shown). The nucleotide and deduced amino acid sequences of the pBluescript E8 insert (which did contain the entire gene) are shown in FIG. 29. The predicted molecular mass of the protein encoded by this gene was 45.9 kDa. The nucleotide and deduced amino acid sequences for E46 clone is shown in FIG. 30. The E46 insert contained one partial and two complete open reading frames which all shared considerable homology with the protein encoded by the E8 gene. FIG. 28 shows how the DNA sequences (+ and − strands) and deduced amino acid sequences from E46 compare with those from E8 and E33. The boxed regions represent the open reading frames and shaded areas indicate homologous sequences. As shown in FIG. 31, all three of the complete genes showed a similar pattern for the encoded proteins: a variable domain flanked by conserved regions having a consensus amino-terminal sequence as set forth in SEQ ID NOS:41-43, and/or a carboxy terminus having a consensus sequence as set forth in SEQ ID NOS:41-43. (See FIG. 31). The length of the conserved regions varied among the encoded proteins, with the longest amino and carboxy-terminal conserved regions present in the E8 protein. The sequences present in the E8, E33 and E46 pBluescript plasmids were confirmed to be derived from USG3 genomic DNA and not HL60 DNA by PCR analysis using the primers described herein. When the sequences of the three full length genes isolated by expression library cloning were compared with the sequence of the PCR product derived from the peptide analysis, it was found that the PCR fragment was contained within the E8 sequence, by 232 to 760 (FIG. 29). In fact, the amino-terminal peptide and all four internal peptides sequenced from the 43 kDa and 45 kDa proteins could be found within the amino acid sequence of the E8 protein. The sequenced peptides are underlined in FIG. 29. The amino-terminal peptide (HDDVSALE . . . ) was found beginning at amino acid 27 and this may indicate that the first 26 amino acids are part of a signal peptide which is cleaved to produce the mature protein. Since the PCR product had both nucleotide and amino acid homology to the *A. marginale* msp2 gene family, a BLAST homology search was performed to assess the relatedness of the E8 and E46 gene products to this family as well. Strong matches were observed for all of the GE proteins described here to the *A. marginals* MSP-2 proteins. A ClustalW amino acid alignment of the GE proteins (designated GE MSP-2A (E8), MSP-2B (E46#1), and MSP-2C (E46#2)) with one of the *A. marginale* MSP-2 proteins (GenBank accession number U07862) is shown in FIG. 31. The homology of the GE MSP2 proteins with *A. marginale* MSP-2 occurred primarily in the conserved regions shown in FIG. 28. Amino acid identity ranged from 40 to 50% between the proteins of the two species and amino acid similarity was close to 60%. The *A. marginale* MSP-2 proteins contain signal peptides (data not shown) and the data indicating that GE MSP-2A has a signal peptide is consistent with the homology observed between the MSP-2 proteins of the two species. The nucleotide sequences of the genes described here have been assigned the following GenBank accession numbers: GE msp2A (E8):AF029322; GE msp2B (E46#1) and GE msp2C (E46#2):AF029323.

The three GE clones E8, E33, and E46 thus appear to be part of a multigene family encoding proteins containing highly homologous amino- and carboxy-terminal regions related to the MSP-2 proteins of *A. marginale*. In addition to the three full length and one truncated msp2-like genes reported here, there are likely to be others present in the GE genome. Hybridization studies (infra) using probes from either the 5' or 3' end of the E8 msp2 gene identified multiple copies of homologous msp2 genes in the genome of USG3. Sequencing of several other GE library clones has revealed short (100 to 300 nucleotides) stretches of DNA homologous to msp2. Several different MSP-2 proteins ranging in size from 33 to 41 kDa have been reported for *A. marginale* and >1% of its genome may consist of msp2. The function of the GE MSP-2 proteins is unknown. Zhi et al., supra, demonstrated that the antigens are present in outer membrane fractions of purified granulocytic ehrlichiae. Thus, they may play a role in the interaction between the pathogen and the host cell. In *A. marginale*, expression of antigenically unique MSP-2 variants by individual organisms during acute rickettsemia in cattle suggests that the multiple msp-2 gene copies may provide a mechanism for evasion of the beneficial immune response directed against these antigens. This may explain the observation that the GE MSP-2A protein is present in purified USG3 but the MSP-2B and MSP-2C are not.

Example 12

Southern Blot Analysis

To determine whether additional copies of msp-2 were present in the genome, genomic DNA was isolated from USG3 and digested with restriction enzymes.

Digoxigenin-labeled probes were prepared by PCR using the PCR Dig Probe Synthesis kit (Boehringer Mannheim). Two sets of primers were used to generate a 240 by product (probe A) from the 5' end of the E8 gene:
(forward primer: 5'-CATGCTTGTAGCTATG-3' (SEQ ID NO:52);
reverse primer: 5'-GCAAACTGAACAATATC-3' (SEQ ID NO:53)) and a 238 by product (probe B) from the 3'-end of the E8 gene;
(forward primer: 5'-GACCTAGTACAGGAGC-3' (SEQ ID NO:54);
reverse primer: 5'-CTATAAGCAAGCTTAG-3' (SEQ ID NO:55) including the consensus sequence corresponding to the amino- and/or carboxy-terminus regions shared by E8, E46#1, and E46#2 polypeptide). Genomic DNA was prepared from USG3 or HL60 cells as described above and aliquots of 1 µg of DNA were digested with SphI, NdeI, SacI, or SspI (New England Biolabs, Beverly, Mass.). These restriction endonucleases do not cut within the sequence of E8 msp2A. Calf thymus DNA was digested identically as a control. Recombinant pBluescript E8 plasmid DNA was digested with EcoRI and used as a positive control for probe hybridization. Digested fragments were separated by gel electrophoresis in a 1% agarose gel. Southern blotting was performed under prehybridization and hybridization conditions of 65° C. in Dig Easy Hyb (Boehringer Mannheim) and hybridization was performed overnight. Two membrane washes in 2×SSC/0.1% SDS were performed at room temp for 5 min each followed by two washes in 0.5×SSC/0.1% SDS at 65° C. for 15 min each. Bound probe was detected by chemiluminescence using anti-digoxigenin alkaline phospate conjugated antibody (Boehringer Mannheim). FIG. 32 shows that multiple bands were present on the Southern blots using both probes, indicating the presence of multiple msp-2 copies. The exact number of genes cannot be determined since sequence differences may generate additional restriction enzyme sites in some of the msp-2 copies, resulting in more than one band from a single copy. Also, more than one msp-2 gene could be present on a single restriction fragment, an event which does occur with the msp-2B and msp-2C genes.

Example 13

Western Blot Analysis of Proteins Encoded by GE Clones

Bacterial lysates from the genomic library clones, E8, E33, and E46, were analyzed by SDS-PAGE and Western blotting. Individual recombinant plasmid containing cultures were induced to express protein with 5 mM IPTG. Bacterial cells were pelleted by centrifugation and resuspended in 5× Laemmli buffer (12% glycerol, 0.2M Tris-HCl, pH 6.8, 5% SDS, 5% p-mercaptoethanol) at 200 µl per 1 OD unit of culture. Samples were boiled and 10 µl of each were analyzed on NuPage gels (Novex, San Diego, Calif.). Proteins were transferred to nitrocellulose filters, the filters were blocked in TBS/Brij 58 and the blots were probed with either a 1:500 dilution of pooled sera from dogs that were infected with GE by tick exposure, a 1:500 dilution of the goat serum described above, or a 1:1000 dilution of human serum. Preimmune dog and goat sera were also used at a 1:500 dilution. Blots were washed and incubated with HRP conjugated secondary antibody (Bio-Rad, Hercules, Calif.). After several additional washes, the blots were developed using the Pierce (Rockford, Ill.) Super Signal Chemiluminescence kit and viewed by autoradiography. FIG. 27 shows that a protein of approximately 37 kDa from the E46 clone and a 45 kDa protein from the E8 clone were specifically detected by dog and goat sera (indicated by arrows on the right side of each blot). The reactivity of the sera differed somewhat in that the dog sera reacted much better than the goat sera with the E46 protein and the goat sera had better reactivity to the E8 protein. Whether the 37 kDa/E46 protein is encoded by the first or second E46 gene is unknown and the reason for the expression of two closely sized immunoreactive E33 proteins is also unclear. Preimmune sera did not detect these proteins and expression was observed in the absence of IPTG induction. The molecular mass of the proteins is consistent with the coding capacity of the msp-2 genes found in the library clones. The negative control (NEG lane) was a pBluescript library clone without an insert. FIG. 27 also shows a couple of proteins of smaller molecular mass from E46 and E8 that react specifically with the goat serum. It is not known whether they are breakdown products of the full length MSP-2 proteins or whether they are produced by internal initiation within the msp-2 genes.

Example 14

PCR Amplification of Isolated Clones

PCR primer sets were designed based on the sequences of each GE clone and are as follows:

```
                                              (SEQ ID NO: 56)
E8 (forward 5'-GCGTCACAGACGAATAAGACGG-3';

(SEQ ID NO: 57))
reverse 5'-AGCGGAGATTACAGGAGAGAGCTG-3';

(SEQ ID NO: 58)
E46.1 (forward 5'-TGTTGAATACGGGGAAAGGGAC-3';

(SEQ ID NO: 59)
reverse 5' AGCGGAGATTTCAGGAGAGAGCTG 3';

(SEQ ID NO: 60)
E46.2 (forward 5'-TGGTTTGGATTACAGTCCAGCG 3'

(SEQ ID NO: 61))
reverse 5'ACCTGCCCAGTTTCACTTACATTC 3'.
```

Each 50 µl reaction contained 0.5 µM of each primer, 1×PCR Supermix (Life Technologies, Gaithersburg, Md.) and either 100 ng USG3 DNA, 100 ng HL60 DNA or 250 ng plasmid DNA. PCR amplification was performed using the following conditions: 94° C. for 30 s, 61° C. for 30 s, and 72° C. for 1 min. After 30 cycles, a single 10 min extension at 72° C. was done. PCR products were analyzed on 4% Nusieve 3:1 agarose gels (FMC Bioproducts, Rockland, Me.).

Example 15

Recognition of MSP-2A and MSP-2B by GE-Positive Human Sera

PCR amplification of the first gene in pBluescript clone E46 was performed to generate an insert for subcloning in *E. coli*. Primer sets were designed to contain restriction sites for cloning, a translation termination codon and a six residue histidine sequence for expressed protein purification

```
                                              (SEQ ID NO: 62);
(forward 5-CCGGCATATGCTTGTAGCTATGGAAGGC-3';

(SEQ ID NO: 63))
reverse.5'-CCGGCTCGAGCTAGTGGTGGTGGTGGTGGTGAAAAGC
AAACCTAACACCAAATTCCCC-3'.
```

The 100 µl A reaction contained 500 ng of each primer, 500 ng of E46 template, and IX PCR Supermix (Life Technologies, Gaithersburg, Md.). Amplification was performed using the following conditions: 94° C. for 30 s, 58° C. for 30 s, 72° C. for 1 min. After 37 cycles a single 10 min extension at 72° C. was performed. Following analysis on a 1% TBE agarose gel, amplified product was purified using a QIAEX II gel extraction kit (QIAGEN Inc, Chatsworth, Calif.) and digested with restriction enzymes NdeI and XhoI (New England Biolabs, Beverly, Mass.) using the manufacturer's recommended conditions. The 1004 bp fragment was ligated into NdeI and XhoI digested pXA and transformed into *E. coli* strain MZ-1(19). Expression vector pXA is a pBR322-based vector containing the bacteriophage lambda pL promoter, a ribosome binding site, ATG initiation codon and transcription and translation termination signals. Recombinant MSP-2B was induced by growing the Mz-1 transformed clone to an $A_{550}$=1.0 at 30° C. and then shifting the temperature to 38° C. for an additional 2 hr. Aliquots (1.5 ml) of pre-induced and induced cells were pelleted by centrifugation and resuspended in SX Laemmli buffer.

The coding regions for MSP-2A and MSP-2B were recloned using a heat inducible *E. coli* expression system as outlined above. The expression of the MSP2A protein using this system remained low. However, the recombinant MSP-2B protein was expressed and could be detected with both dog and goat GE-positive sera (FIG. 32). The recombinant MSP-2B protein and the E33 MSP-2A protein were then tested for reactivity with human serum samples which had previously been shown to be positive for granulocytic *Ehrlichia* by immunofluorescence assay (IFA). Table 8 shows the patient profiles and diagnostic laboratory results from fourteen individuals. Ten of these individuals were clinically diagnosed with HGE (#1-9, 13), three of them participated in a seroprevalence study (#10-12), and one was a negative control (#14). Immune and preimmune dog and goat sera were also used as positive and negative controls in the Western blots. FIG. 33 shows the reactivity of each human serum sample with MSP-2A (top) and MSP-2B (bottom). All of the human samples with IFA titers of 512 or more (#7,9,10,11,13) reacted with the MSP-2 proteins as did the positive dog and goat sera. Human serum #8 also reacted faintly with both proteins. In addition, these same sera all reacted with purified GE on Western blots (data not shown). Human serum #12 reacted with an *E. coli* protein which migrates in between the two E33 MSP-2 proteins. This reactivity was seen with all of the library clones we have tested, including those which do not express any GE related proteins (data not shown). From these data it appears that the IFA assay is more sensitive than the Western blot for diagnosis of HGE.

TABLE 8

HGE Patient Profiles and Diagnostic Laboratory Test Results

| Patient | Gender | Age | Loc'n (state) | Conval. Stage (months) | Morulae | PCR[1] | IFA[2] | Peak IFA[3] |
|---|---|---|---|---|---|---|---|---|
| 1 | F | 57 | MN | 0.5 | + | ND | 320 | >2560 |
| 2 | M | 56 | WI | 12 | + | + | 160 | 640 |
| 3 | M | 59 | MN | 6 | + | ND | 320 | 320 |
| 4 | M | 74 | WI | 12 | + | + | 160 | >2560 |
| 5 | M | 40 | WI | 12 | + | + | 320 | 5120 |
| 6 | M | 71 | WI | 24 | + | + | 320 | 1280 |
| 7 | M | 80 | WI | 36 | + | − | >2560 | >2560 |
| 8 | M | 60 | MN | 6 | − | ND | 320 | >2560 |
| 9 | F | 44 | MN | 42 | − | − | >2560 | 5120 |
| 10 | M | 50 | WI | random | ND | ND | >2560 | ND |
| 11 | F | 50 | WI | random | ND | ND | >2560 | ND |
| 12 | M | 64 | WI | random | ND | ND | 60 | ND |
| 13[3] | F | 65 | RI | 1 | − | + | 512 | 1024 |
| 14 | F | 29 | MA | NA | − | ND | <32 | <32 |

[1] PCR with GE9F and GE1 OR primers (6).
[2] Polylonal IFA assay with *E. equi* antigen.
[3] Data taken from reference 27.
+ Positive, − negative, ND not done, NA not applicable.

Example 16

Characterization of Representative Clone S11

Purified GE protein preparations were obtained as described in Protocol G. Aliquots were run on four lanes to allow the staining of three lanes with Ponceau S (0.1% in 1 N acetic acid) and one lane with Coomassie blue staining. Molecular weight markers were also run in two lanes. Electrophoresis was performed on a 10% SDS-PAGE preparative gel and proteins were transferred onto a 0.2 µm PVDF membrane. The Ponceau S bands with the same molecular weight as the bands stained with Coomassie blue (five total) were cut out for sequencing. N-terminal sequence was obtained for one of the five bands. The proteins in the other four bands were digested with trypsin in situ for internal peptide sequencing. Peptides were separated by RP-HPLC on a ZORBAX C18 (1 mm×150 mm) column. Potential candidates for sequencing were screened for molecular mass by MALDI-TOF Mass Spectrometry on a Finnigan Lasermet 2000 (Hemel, UK). Protein sequencing was performed by Edman degradation.

Four of the five gel bands contained either serum proteins (probably from the fetal bovine serum used to culture the cells) or heat shock proteins. The other band appeared to contain a unique protein. Four internal peptide sequences were obtained from this gel band, representing a protein of approximately 64 kDa, that did not match any protein sequences in the database. The sequences of these peptides are shown in FIG. 34. (SEQ ID NOS:34-37). Based on these sequences, degenerate DNA oligonucleotides were designed for each peptide (both forward and reverse/complement orientation) and used in all possible combinations for PCR using GE DNA as template. One combination, primers 5F (SEQ ID NO:32) and 6R (SEQ ID NO:33) (shown in FIG. 34), produced a PCR fragment of 450 base pairs. The DNA was cloned into pCR Script SK(+) and the insert was sequenced. When the insert DNA was translated, both peptides (#24 and 25) (SEQ ID NOS:34-35) were found in the sequence, one at each end as expected.

To obtain a clone containing the entire gene represented by the PCR fragment, two primers were designed based on the DNA sequence of the PCR fragment. These primers were used in PCR reactions to screen sublibraries of the GE genomic library.

```
                                          (SEQ ID NO: 64)
Forward primer (250F2):   5' CCCCGGGCTTTACAGT 3'

(SEQ ID NO: 65)
Reverse primer (250R2):   5' CCAGCAAGCGATAACC 3'
```

The sublibraries were generated by the initial screening of the genomic library with convalescent dog sera.

When a positive phage stock was found by PCR screening, the lysate was serially diluted twice and replated with bacterial stock XL1-Blue MRF' to obtain isolated plaques. Forty-eight of these plaques were picked and lysates screened by PCR with primers 250F2 and 250R2. A positive clone was obtained which was designated S11. The plasmid DNA was rescued and restriction enzyme analysis performed to determine the size of the insert DNA and the approximate location of the gene within the insert. Results indicated that the insert size was about 8 kb and that the gene of interest was located at the T7 end of the insert relative to the pBluescript vector (FIG. 35). A 2 kb portion of the S11 insert was sequenced and found to contain an open reading frame of 545 amino acids. The complete sequence is shown in FIG. 36 (SEQ ID NO:39).

When the amino acid sequence of S11 (SEQ ID NO:39) was compared to the peptide sequences obtained from the excised gel band representing a protein of 64 kDa, all four peptide sequences were found. These are shown underlined in FIG. 36. The only difference between the nucleic acid sequence and the peptide sequences was the presence of phenylalanine (F) instead of aspartic acid (D) in position 4 of peptide #26 (SEQ ID NO:37). The reason for this difference is unknown. The calculated molecular weight of the protein encoded by the S11 gene was 58.5 kDa. A search of the nucleic acid and protein databases did not reveal any significant homology between it and other proteins in the database. There were, however, some minor similarities to outer surface proteins of some bacterial species.

All publications mentioned hereinabove are hereby incorporated in their entirety by reference. While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A purified polypeptide having an amino-terminus comprising the amino acid sequence set forth in SEQ ID NOS:27, 29, or 30 and/or having a carboxy-terminus comprising the amino acid sequence set forth in SEQ ID NOS:27, 29, or 30.

2. A method of detecting an antibody to a S2, S7, S22, S23, C6.1, C6.2, S11, E8, E46#1, or E46#2 polypeptide in a sample, comprising:
   (a) contacting said sample with a polypeptide consisting of an amino acid sequence set forth in SEQ ID NOs: 4, 6, 2, 8, 21, 22, 39, 27, 29, or 30, corresponding to S2, S7, S22, S23, C6.1, C6.2, S11, E8, E46#1, or E46#2, respectively, under conditions such that immunocomplexes form; and
   (b) detecting the presence of said polypeptide bound to said antibody.

3. A diagnostic kit comprising: a container means containing a polypeptide consisting of an amino acid sequence set forth in SEQ ID NOS: 4, 6, 2, 8, 21, 22, 39, 27, 29, or 30, or a polypeptide of claim 1.

4. A polypeptide consisting of an amino- or carboxy-terminal conserved region of granulocytic Ehrlichia E8 polypeptide.

5. The polypeptide of claim 4 which consists of the amino-terminal conserved region of granulocytic Ehrlichia E8 polypeptide.

6. The polypeptide of claim 5, wherein the amino-terminal conserved region corresponds to amino acids 1-207 of SEQ ID NO:27.

7. The polypeptide of claim 5, wherein the amino-terminal conserved region comprises the amino acid sequence of SEQ ID NO:69.

8. The polypeptide of claim 4 which consists of the carboxy-terminal conserved region of granulocytic Ehrlichia E8 polypeptide.

9. The polypeptide of claim 8, wherein the carboxy-terminal conserved region comprises the amino acid sequence of SEQ ID NO:70.

10. A polypeptide which is encoded by a nucleotide sequence contained within nucleotides 232 to 760 of SEQ ID NO:26, wherein the polypeptide is an immunogenic or antigenic epitope.

11. The polypeptide of claim 10, wherein the immunogenic or antigenic epitope comprises the amino acid sequence SEQ ID NO:69.

12. The polypeptide of claim 10, wherein the immunogenic or antigenic epitope comprises the amino acid sequence SEQ ID NO:70.

13. A diagnostic kit comprising: a container means containing the polypeptide of any one of claims 4-12.

14. A method of detecting an antibody to granulocytic Ehrlichia E8 polypeptide in a sample, comprising:
   (a) contacting said sample with the polypeptide of any one of claims 4-12, under conditions such that immunocomplexes form; and
   (b) detecting the presence of said immunocomplexes, thereby detecting said antibody to granulocytic Ehrlichia E8 polypeptide in said sample.

15. A composition comprising a polypeptide of any one of claims 4-12.

\* \* \* \* \*

SEQUENCE LISTING

<160> NUMBER OF SEQ ID NOS: 72

<210> SEQ ID NO 1
<211> LENGTH: 3147
<212> TYPE: DNA
<213> ORGANISM: Granulocytic Ehrlichia
<220> FEATURE:
<223> OTHER INFORMATION: S22 of Granulocytic Ehrlichia

<400> SEQUENCE: 1
gaattcctta cctccctata tttcgtacag gttatttcgc agtctagcta tgatgcttta 60
ccaggatacg ttaaacgttg acgttctacg ctgtcatagc cttttattct gcaaaaatag 120
cttaactgtg tcacttcctg agaaagtaag atacatattt agtttttgca cagccaaaaa 180
acttctagtg aactgtggtt tctctggaat caataacctg ttttatattc gtgcgttcta 240
taacaatcta cagctgtggt tattaggcgt ggtttcgcct gataataaag atactttaga 300
gggtataaac ttggaaaaaa taatgaaaaa ccctccttag tgcctccccg tttttgacaa 360
catactctta tggaaaagcg ttagggagtt gcttcgcttg tcacgcgtgc gttaggtttt 420
acgtatacgt gtctgggact tcacgaaaac tcgacgcagg cggattttgt actatgtttc 480
acttaacaag gtattataaa tgtttgaaca caatattcct gatacataca caggaacaac 540
tgcagaaggt tctcctggct tagcaggcgg ggattttagc ttaagttcta ttgactttac 600
aagggacttt acaattgaat cacatagagg aagctcagct gatgacccag gttacatcag 660
ctttagggat caagacggaa acgtcatgtc acgttttctt gatgtgtacg tagctaattt 720
cagcttgcga tgcaagcatt ctccctataa caacgacaga atggaaacag ctgcgttctc 780
tctaactccc gacataatag agccttctgc tttattgcaa gaatcacata gtacacaaaa 840
caatgtagaa gaggcagtac aagttacagc tcttgagtgc cctccatgta atccagtccc 900
tgccgaggaa gtagctcctc aaccgtcttt tctaagcaga ataattcagg cgttcttgtg 960
gttattcacg ccttcttcta ctaccgacac tgctgaagac agcaagtgta atagtagcga 1020
tacttcaaaa tgtacctctg ctagcagtga gtcattagag cagcaacaag aatcagtgga 1080
agtgcaacca tctgtactta tgtctactgc ccctatagca acagagcctc aaaatgcggt 1140
tgttaaccaa gtaaacacta ctgcagtaca agtagaatca tccattattg tgccagaatc 1200
gcaacacact gacgttaccg tgctcgaaga tactactgag acgataactg ttgatgggga 1260
atatggacat tttagtgaca ttgcttcagg tgaacacaat aacgatctgc ctgccatgtt 1320
gttagatgaa gcagacttca ctatgttatt agcgaacgag gagtcaaaga ccctggagtc 1380
tatgccttct gatagcctag aagacaatgt tcaggaacta ggtacattgc ctttacaaga 1440
aggtgaaaca gtttctgagg gcaacacacg agagtcacta cccactgacg tttcacaaga 1500
ctcagttggt gtaagtacag atcttgaagc tcattctcaa gaagttgaaa cagtttctga 1560
ggtcagcaca caagattcac tatccactaa catttcacaa gactcagttg gtgtaagtac 1620
agatcttgaa gctcattcta aaggagttga aatagtttct gagggcggca cacaagattc 1680
actatccgct gattttccaa taaacacagt tgaaagtgaa agtacagatc ttgaagctca 1740
ttctcaagaa gttgaaactg tttctgaatt cacacaagat tcactatcca ctaacatttc 1800
acaagactca gttggtgtaa gtacagatct tgaagttcat tctcaagaag ttgaaatagt 1860
ttctgagggc ggcacacaag attcactatc cactaacatt tcacaagact cagttggtgt 1920
aagtacagat cttgaagctc attctcaaga agttgaaact gtttctgaat tcacacaaga 1980

-continued

```
ttcactatcc actaacattt cacaagactc agttggtgta agtacagatc ttgaagttca    2040
ttctcaagaa gttgaaatag tttctgaggg cggcacacaa gattcactat ccactaacat    2100
ttcacaagac tcagttggtg taagtacaga tcttgaagct cattctaaag gagttgaaat    2160
agtttctgag ggcggcacac aagattcact atccgctgat tttccaataa acacagttga    2220
aagtgaaagt acagatcttg aagctcattc cccagaaggt gaaatagttt ctgaggtcag    2280
cacacaagat gcgccatcca ctggagtaga gatcagattt atggatcgtg attctgatga    2340
tgacgtgctc gcgttgtcaa gtgatcatgg taggggaaac agttatggcg taaagacatc    2400
tttgatgact tgtcttgcgt gaataagtag tgcaagtttt ttatgcattg atgtgcatga    2460
tcattgcccc taaggaaagc agtactaatg gtagtctaag atcttataca gggtttcgga    2520
ctaccacttt tggtgtttta aaacgtctta ttcgcgttgg gtgcttgctt acaatgtacc    2580
tgtacgtgcc caacactaaa aatggtcagt attacttagg ggagttcgta gacgaggcat    2640
ctcgatttac tctaagtaag ctacaaataa ctcagtcata tcaaggtagt tcaagatgaa    2700
agcagtgcta tgcttatcat ggagaattcc tgcggttctc ttcaaaattc tcttttcccg    2760
caagggcaga ctcttatttg ttaaaataac aaaatttctc tacaggaagc gacatttcat    2820
atcaaagctg attgtgaaat aatggcattg agtatttttc tcgccctaga agataatcat    2880
ttcggcacta tcaaagcatt tacgatattc tccattatct tgtaatcaga tggctatctt    2940
gaaagcaacc aaggatatcc gtacatggta gcttacatac tgctatcaat ctcctatacg    3000
accttcaatg aaacggtaac tgttgctgac agcttgcaca tgctgtgatt caattcctgg    3060
ttcctagatg ttctactacg tttatccggt actaatatta ttctttggcg ctctattatc    3120
tagcaactca gagtccatta ggaattc                                        3147
```

<210> SEQ ID NO 2
<211> LENGTH: 619
<212> TYPE: PRT
<213> ORGANISM: Granulocytic Ehrlichia
<220> FEATURE:
<223> OTHER INFORMATION: S22 of Granulocytic Ehrlichia

<400> SEQUENCE: 2

```
Met Phe Glu His Asn Ile Pro Asp Thr Tyr Thr Gly Thr Thr Ala Glu
1               5                   10                  15

Gly Ser Pro Gly Leu Ala Gly Gly Asp Phe Ser Leu Ser Ser Ile Asp
                20                  25                  30

Phe Thr Arg Asp Phe Thr Ile Glu Ser His Arg Gly Ser Ser Ala Asp
            35                  40                  45

Asp Pro Gly Tyr Ile Ser Phe Arg Asp Gln Asp Gly Asn Val Met Ser
        50                  55                  60

Arg Phe Leu Asp Val Tyr Val Ala Asn Phe Ser Leu Arg Cys Lys His
65                  70                  75                  80

Ser Pro Tyr Asn Asn Asp Arg Met Glu Thr Ala Phe Ser Leu Thr
                85                  90                  95

Pro Asp Ile Ile Glu Pro Ser Ala Leu Leu Gln Glu Ser His Ser Thr
            100                 105                 110

Gln Asn Asn Val Glu Glu Ala Val Gln Val Thr Ala Leu Glu Cys Pro
        115                 120                 125

Pro Cys Asn Pro Val Pro Ala Glu Glu Val Ala Pro Gln Pro Ser Phe
    130                 135                 140

Leu Ser Arg Ile Ile Gln Ala Phe Leu Trp Leu Phe Thr Pro Ser Ser
145                 150                 155                 160
```

```
Thr Thr Asp Thr Ala Glu Asp Ser Lys Cys Asn Ser Ser Asp Thr Ser
            165                 170                 175
Lys Cys Thr Ser Ala Ser Glu Ser Leu Glu Gln Gln Gln Glu Ser
        180                 185                 190
Val Glu Val Gln Pro Ser Val Leu Met Ser Thr Ala Pro Ile Ala Thr
            195                 200                 205
Glu Pro Gln Asn Ala Val Val Asn Gln Val Asn Thr Thr Ala Val Gln
        210                 215                 220
Val Glu Ser Ser Ile Ile Val Pro Glu Ser Gln His Thr Asp Val Thr
225                 230                 235                 240
Val Leu Glu Asp Thr Thr Glu Thr Ile Thr Val Asp Gly Glu Tyr Gly
            245                 250                 255
His Phe Ser Asp Ile Ala Ser Gly Glu His Asn Asn Asp Leu Pro Ala
        260                 265                 270
Met Leu Leu Asp Glu Ala Asp Phe Thr Met Leu Leu Ala Asn Glu Glu
            275                 280                 285
Ser Lys Thr Leu Glu Ser Met Pro Ser Asp Ser Leu Glu Asp Asn Val
        290                 295                 300
Gln Glu Leu Gly Thr Leu Pro Leu Gln Glu Gly Glu Thr Val Ser Glu
305                 310                 315                 320
Gly Asn Thr Arg Glu Ser Leu Pro Thr Asp Val Ser Gln Asp Ser Val
            325                 330                 335
Gly Val Ser Thr Asp Leu Glu Ala His Ser Gln Glu Val Glu Thr Val
        340                 345                 350
Ser Glu Val Ser Thr Gln Asp Ser Leu Ser Thr Asn Ile Ser Gln Asp
        355                 360                 365
Ser Val Gly Val Ser Thr Asp Leu Glu Ala His Ser Lys Gly Val Glu
        370                 375                 380
Ile Val Ser Glu Gly Gly Thr Gln Asp Ser Leu Ser Ala Asp Phe Pro
385                 390                 395                 400
Ile Asn Thr Val Glu Ser Ser Thr Asp Leu Glu Ala His Ser Gln
        405                 410                 415
Glu Val Glu Thr Val Ser Glu Phe Thr Gln Asp Ser Leu Ser Thr Asn
            420                 425                 430
Ile Ser Gln Asp Ser Val Gly Val Ser Thr Asp Leu Glu Val His Ser
        435                 440                 445
Gln Glu Val Glu Ile Val Ser Glu Gly Gly Thr Gln Asp Ser Leu Ser
        450                 455                 460
Thr Asn Ile Ser Gln Asp Ser Val Gly Val Ser Thr Asp Leu Glu Ala
465                 470                 475                 480
His Ser Gln Glu Val Glu Thr Val Ser Glu Phe Thr Gln Asp Ser Leu
            485                 490                 495
Ser Thr Asn Ile Ser Gln Asp Ser Val Gly Val Ser Thr Asp Leu Glu
        500                 505                 510
Val His Ser Gln Glu Val Glu Ile Val Ser Glu Gly Gly Thr Gln Asp
        515                 520                 525
Ser Leu Ser Thr Asn Ile Ser Gln Asp Ser Val Gly Val Ser Thr Asp
        530                 535                 540
Leu Glu Ala His Ser Lys Gly Val Glu Ile Val Ser Glu Gly Gly Thr
545                 550                 555                 560
Gln Asp Ser Leu Ser Ala Asp Phe Pro Ile Asn Thr Val Glu Ser Glu
            565                 570                 575
Ser Thr Asp Leu Glu Ala His Ser Pro Glu Gly Glu Ile Val Ser Glu
        580                 585                 590
```

Val Ser Thr Gln Asp Ala Pro Ser Thr Gly Val Glu Ile Arg Phe Met
    595                 600                 605

Asp Arg Asp Ser Asp Asp Asp Val Leu Ala Leu
    610                 615

<210> SEQ ID NO 3
<211> LENGTH: 4724
<212> TYPE: DNA
<213> ORGANISM: Granulocytic Ehrlichia
<220> FEATURE:
<223> OTHER INFORMATION: S2 of Granulocytic Ehrlichia

<400> SEQUENCE: 3

```
ggatccccg ggctgcagga attcctaaaa agatctggcg cctgagcgtc tgctacaggc      60
agattgtgcg cgctaagata ggtttagtaa gacgtgtttt ttattgaata aaggccccaa    120
caatgttgac agaagaagaa aagaaaaaga gcgccggtgc tctgcaagcc attatcacag    180
gagattacga gagtgttcag gcgtccgttc agggaatttc ttccgaagac ttaatactcc    240
cgttgattat gagggagaa cactactgca ctatgcagct tcatcccgta atggtaattt    300
ctatggcatt ctggttgaaa gaggatgtgt tactaatatc agagatgctt atggatttac    360
tccagaacaa gcacgtgaga aggcagggta tgcacgcaca cagtggtatg gagcagatgt    420
aaatgaccct ggtgtatcta ggcagttaat gacgcaagct gttcagcagt ctgcgaaagg    480
taacatgtat gctgctctcg ctatattaga ccttgtgcgt aatgacgatg caaaacattc    540
aggtcaatga ggaaagggc atagtgtttt gcatctagca tgtattgaag gcagtaatcc    600
atctttcact tcatccctca tgctaaaggg ttgttctta aacattaagg atgtagatgg    660
taatacgcca ttcatacag ctgcgttttc agtaggcaaa aatgctttag gcaatcttga    720
tgtactatgc gacaagctct tatagcagat gttaatgcta agggaccggg tggaaacact    780
ccgcttcata ttgctacgga gcgtatggct caccagaaag tagagcatct tctctcaagg    840
ttaagtgata ttagcgttgc aaatcgatgc tggtgaaacc gtttgccaca ttgttgcaaa    900
gcaatggcca aggcgggatg ttttaccata cattgacaag atgcaagaag cggtgtcgtc    960
aaatattgag ggcaatcgcg agtgtgcaga ggcactaata ttcccggata aaaagggat   1020 gagtgcagta cagtatgcta ttagaaggca tataccggag ctgagaagat cttcgagaag   1080
gccattaaca ttgcagataa agtgtatggc ttagcttctt cagaagtaga atctctcttt   1140
acatgtccta atccagagga cgcatcaacg ctggtgcatt ttgtatcttc taatgggacc   1200
ccaaattttg attctcttgc gaaaagggta ttggaggaag catatcatag gtatggagag   1260 aaaccttta ctaatttaga tgttgcaggt aatgcaccta tacatgctgc agcacaaaaa   1320
tcaacagtgg gggttttga gcaggtggta agatacactc ctgagtctgt tgtaaactca   1380
attagcaccg aatggcaaag cgcctattca catgatagtt gaggatgagc caagccataa   1440
aagcgtaagc attaaattgc agatgttgat tgggaatgtg cgtaatattc catcaatcaa   1500
tgtaccatcc ccagtgacag gtgaaacgct gcggtagctg cgtataaagg gggcaacact   1560
gaggatgtta agactatgtt acgctgtaat agcatggacg tagatgctcg gtcacatgat   1620
ggtagaacta aatacatta cgcagcaaag gatggaaatt tagagatatt gcagcaggct   1680 cttgaagga agagtagtta ttctaagttt cctgtaaagg atggtgttcc tactccaggt   1740
gtatatgcga ttcgtgaagc aagtggtgta aaagtatcgc tacaagcact tgacatgtta   1800
atgagatatg agcctcaccc gcagcatgtt gctgtcgagg cagtaagaac aggtgcagta   1860
ggtgtattgg agcaccttat taccactgaa gtgattagtg taaatgaaga aattacaact   1920
```

```
cctgaaggaa aaaagacaac tttgaccgct gaagcactaa ctagtggtaa atatggtgta   1980
gtgaaggcgt taattaaaaa cagtgctgat gtaaatgcgt ctccagaacc agctattact   2040
ttgggtatac aaggaaggtg ctttcagggg agtaaagcta taaagcattt aaagcgtgtt   2100
gtagaagctg gggcacatat aaatactcct accggatcta tgagccctttt agctgctgca   2160
gttcaagcgg caaatgaggc aagtaacctt aaagaggcta taagattgt aaatttcctt   2220
ttacatagggg gtgcagatct ttcgtctacg gaacacactg gaactccagc cttgcattta   2280
gcaacagctg ctggcaacca taggactgct atgttgctct tggataaagg ggctccagca   2340
acgcagagag atgctagggg taggacggct ttacatatag cagctgctaa tggtgacggt   2400
aagctatata ggatgattgc gaaaaaatgc ccagatagct gtcaaccact ctgttctgat   2460
atgggagata cagcgttaca tgaggcttta tattctgata atgttacaga aaaatgcttt   2520
ttaaagatgc ttaaagagtc tcgaaagcat ttgtcaaact catctttttt cggagacttg   2580
cttaatactc ctcaagaagc aaatggtgac acgttactgc atctggctgc atcgcgtggt   2640
ttcggtaaag catgtaaaat actactaaag gctgggcgt cagtatcagt cgtgaatgta   2700
gagggaaaaa caccggtaga tgttgcggat ccatcattga aaactcgtcc gtggtttttt   2760
ggaaagtccg ttgtcacaat gatggctgaa cgtgttcaag ttcctgaagg gggattccca   2820
ccatatctgc cgcctgaaag tccaactcct tctttaggat ctatttcaag ttttgcgagt   2880
gtctctgcgc tatcatcctt gggtagtggc ctagatactg caggagctga ggagtctatc   2940
tacgaagaaa ttaaggatac agcaaaaggt acaacggaag ttgaaagcac atatacaact   3000
gtaggagctg aggagtctat ctacgaagaa attaaggata cagcaaaagg tacaacggaa   3060
gttgaaagca catatacaac tgtaggagct gaaggtccga gaacaccaga aggtgaagat   3120
ctgtatgcta ctgtgggagc tgcaattact tccgaggcgc aagcatcaga tgcggcgtca   3180
tctaagggag aaaggccgga atccatttat gctgatccat ttgatatagt gaaacctagg   3240
caggaaaggc ctgaatctat ctatgctgac ccatttgctg cggaacgaac atcttctgga   3300
gtaacgacat ttggccctaa ggaagagccg atttatgcaa cagtgaaaaa gggtcctaag   3360
aagagtgata cttctcaaaa agaaggaaca gcttctgaaa aagtctgctc aacaataact   3420
gtgattaaga agaaagtgaa acctcaggtt ccagctagga caagtagttt gcctactaaa   3480
gaaggtatag gttctgataa agacctgagt tcaggaacta gtagctcttt tgcagctgag   3540
ctgcaagcac aaagggggtaa attgcgtcct gtgaagggag gtgctccgga ttctaccaaa   3600
gacaaaacag ctacttctat attctccagt aaagagttca aaaaggaact aacaaaagct   3660
gccgaaggat tacagggagc agttgaagaa gctcagaagg gtgatggagg agctgcaaag   3720
gcaaagcaag atcttggcat ggaatctggt gccccaggat ctcaaccaga agctcctcaa   3780
agtgaaggcc ctaagtctgt aaaaggaggt cgcggtaggt agaattatac cgaaaaatcg   3840
ctgaggtact ttgatcaata taattcgcgc ttctgagtat ttaggcgatg atctcgccac   3900
tttaataata ccccttttag agtacataac gctctaaagg gggcagatta ttttaagtag   3960
tagggttttg attctgagat cttttgagta caactattcc ttagtgtttt tttggaatgc   4020
tatgtgcttg ataaagaaaa aacttgctct ggggtgggat gcactcttga gtactttccg   4080
cgctctgtat attcctttttt ttgcatctgc ataatctgct gcatatgtga ttatgtgata   4140
atgacggaat tacccagaaa agccttagcg tgtgaggcct atcattctca gaaagtcaca   4200
gtaggaaact tgcattttca tcttgtattt ttgtaagttg gctaagagca ctagctataa   4260
caaatgcatc tatggcattt tttgagagtt ataataatga gagcaacaaa gggtggtact   4320
```

```
attgttcaaa atttgtttat gtgctttgtc tcacaatgga gtttaaagtc atctccgagt   4380
agtactacga ctttaagtag agaatacttt gtattttctt tatagagctc agagatatac   4440
ttcagtatgt gtcggaggtt gttcccttgg gaaaaagggc attttatcaa ctgtgaacta   4500
tcgctactat ggctgaggaa aagtagatag caacaaagat agtattctgg ttttataatc   4560
aaaccgtaat ctttcaacat gttcgaagat cgctttcact ttataatcct ttttgactgc   4620
cctgctgaaa gggctttttt gttatgaaac tatcctcgct cgattttctt atctttggat   4680
tctattacca cggataatgt ttgttggaat tattttagaa gaag                    4724

<210> SEQ ID NO 4
<211> LENGTH: 748
<212> TYPE: PRT
<213> ORGANISM: Granulocytic Ehrlichia
<220> FEATURE:
<223> OTHER INFORMATION: S22 of Granulocytic Ehrlichia

<400> SEQUENCE: 4

Met Leu Arg Cys Asn Ser Met Asp Val Asp Ala Arg Ser His Asp Gly
1               5                   10                  15

Arg Thr Ile Ile His Tyr Ala Ala Lys Asp Gly Asn Leu Glu Ile Leu
            20                  25                  30

Gln Gln Ala Leu Gly Arg Lys Ser Ser Tyr Ser Lys Phe Pro Val Lys
        35                  40                  45

Asp Gly Val Pro Thr Pro Gly Val Tyr Ala Ile Arg Glu Ala Ser Gly
    50                  55                  60

Gly Lys Val Ser Leu Gln Ala Leu Asp Met Leu Met Arg Tyr Glu Pro
65                  70                  75                  80

His Pro Gln His Val Ala Val Glu Ala Val Arg Thr Gly Ala Val Gly
                85                  90                  95

Val Leu Glu His Leu Ile Thr Thr Glu Val Ile Ser Val Asn Glu Glu
            100                 105                 110

Ile Thr Thr Pro Glu Gly Lys Lys Thr Thr Leu Thr Ala Glu Ala Leu
        115                 120                 125

Thr Ser Gly Lys Tyr Gly Val Val Lys Ala Leu Ile Lys Asn Ser Ala
    130                 135                 140

Asp Val Asn Ala Ser Pro Glu Pro Ala Ile Thr Leu Gly Ile Gln Gly
145                 150                 155                 160

Arg Cys Phe Gln Gly Ser Lys Ala Ile Lys His Leu Lys Arg Val Val
                165                 170                 175

Glu Ala Gly Ala His Ile Asn Thr Pro Thr Gly Ser Met Ser Pro Leu
            180                 185                 190

Ala Ala Ala Val Gln Ala Ala Asn Glu Ala Ser Asn Leu Lys Glu Ala
        195                 200                 205

Asn Lys Ile Val Asn Phe Leu Leu His Arg Gly Ala Asp Leu Ser Ser
    210                 215                 220

Thr Glu His Thr Gly Thr Pro Ala Leu His Leu Ala Thr Ala Ala Gly
225                 230                 235                 240

Asn His Arg Thr Ala Met Leu Leu Leu Asp Lys Gly Ala Pro Ala Thr
                245                 250                 255

Gln Arg Asp Ala Arg Gly Arg Thr Ala Leu His Ile Ala Ala Ala Asn
            260                 265                 270

Gly Asp Gly Lys Leu Tyr Arg Met Ile Ala Lys Lys Cys Pro Asp Ser
        275                 280                 285

Cys Gln Pro Leu Cys Ser Asp Met Gly Asp Thr Ala Leu His Glu Ala
```

```
                290                 295                 300
Leu Tyr Ser Asp Asn Val Thr Glu Lys Cys Phe Leu Lys Met Leu Lys
305                 310                 315                 320

Glu Ser Arg Lys His Leu Ser Asn Ser Ser Phe Phe Gly Asp Leu Leu
                325                 330                 335

Asn Thr Pro Gln Glu Ala Asn Gly Asp Thr Leu Leu His Leu Ala Ala
                340                 345                 350

Ser Arg Gly Phe Gly Lys Ala Cys Lys Ile Leu Leu Lys Ala Gly Ala
                355                 360                 365

Ser Val Ser Val Val Asn Val Glu Gly Lys Thr Pro Val Asp Val Ala
370                 375                 380

Asp Pro Ser Leu Lys Thr Arg Pro Trp Phe Phe Gly Lys Ser Val Val
385                 390                 395                 400

Thr Met Met Ala Glu Arg Val Gln Val Pro Glu Gly Gly Phe Pro Pro
                405                 410                 415

Tyr Leu Pro Pro Glu Ser Pro Thr Pro Ser Leu Gly Ser Ile Ser Ser
                420                 425                 430

Phe Glu Ser Val Ser Ala Leu Ser Ser Leu Gly Ser Gly Leu Asp Thr
                435                 440                 445

Ala Gly Ala Glu Glu Ser Ile Tyr Glu Glu Ile Lys Asp Thr Ala Lys
450                 455                 460

Gly Thr Thr Glu Val Glu Ser Thr Tyr Thr Thr Val Gly Ala Glu Glu
465                 470                 475                 480

Ser Ile Tyr Glu Glu Ile Lys Asp Thr Ala Lys Gly Thr Thr Glu Val
                485                 490                 495

Glu Ser Thr Tyr Thr Thr Val Gly Ala Glu Gly Pro Arg Thr Pro Glu
                500                 505                 510

Gly Glu Asp Leu Tyr Ala Thr Val Gly Ala Ala Ile Thr Ser Glu Ala
                515                 520                 525

Gln Ala Ser Asp Ala Ala Ser Ser Lys Gly Glu Arg Pro Glu Ser Ile
530                 535                 540

Tyr Ala Asp Pro Phe Asp Ile Val Lys Pro Arg Gln Glu Arg Pro Glu
545                 550                 555                 560

Ser Ile Tyr Ala Asp Pro Phe Ala Ala Glu Arg Thr Ser Ser Gly Val
                565                 570                 575

Thr Thr Phe Gly Pro Lys Glu Glu Pro Ile Tyr Ala Thr Val Lys Lys
                580                 585                 590

Gly Pro Lys Lys Ser Asp Thr Ser Gln Lys Glu Gly Thr Ala Ser Glu
                595                 600                 605

Lys Val Cys Ser Thr Ile Thr Val Ile Lys Lys Val Lys Pro Gln
                610                 615                 620

Val Pro Ala Arg Thr Ser Ser Leu Pro Thr Lys Glu Gly Ile Gly Ser
625                 630                 635                 640

Asp Lys Asp Leu Ser Ser Gly Thr Ser Ser Phe Ala Ala Glu Leu
                645                 650                 655

Gln Ala Gln Arg Gly Lys Leu Arg Pro Val Lys Gly Gly Ala Pro Asp
                660                 665                 670

Ser Thr Lys Asp Lys Thr Ala Thr Ser Ile Phe Ser Ser Lys Glu Phe
                675                 680                 685

Lys Lys Glu Leu Thr Lys Ala Ala Glu Gly Leu Gln Gly Ala Val Glu
                690                 695                 700

Glu Ala Gln Lys Gly Asp Gly Gly Ala Ala Lys Ala Lys Gln Asp Leu
705                 710                 715                 720
```

Gly Met Glu Ser Gly Ala Pro Gly Ser Gln Pro Glu Ala Pro Gln Ser
                725                 730                 735

Glu Gly Pro Lys Ser Val Lys Gly Gly Arg Gly Arg
            740                 745

<210> SEQ ID NO 5
<211> LENGTH: 3998
<212> TYPE: DNA
<213> ORGANISM: Granulocytic Ehrlichia
<220> FEATURE:
<223> OTHER INFORMATION: S7 of Granulocytic Ehrlichia

<400> SEQUENCE: 5

| | | | | | |
|---|---|---|---|---|---|
| gaattcctga | tagtatttta | gaggatagta | ggcaatatgg | tttaggggat | ttcttcgcat | 60 |
| acttgttatc | atcgtcctta | tttgtgctta | gttggtcgga | tatttgtgca | agttgttgta | 120 |
| aaatatgcat | attgtatgta | taggtgtgca | agatatcatc | tctttaggtg | tatcgtgtag | 180 |
| cacttaaaca | aatgctggtg | aacgtagagg | gattaaagga | ggatttgcgt | atatgtatgg | 240 |
| tatagatata | gagctaagtg | attacagaat | tggtagtgaa | accatttcca | gtggagatga | 300 |
| tggctactac | gaaggatgtg | cttgtgacaa | agatgccagc | actaatgcgt | actcgtatga | 360 |
| caagtgtagg | gtagtacggg | gaacgtggag | accgagcgaa | ctggttttat | atgttggtga | 420 |
| tgagcatgtg | gcatgtagag | atgttgcttc | gggtatgcat | catggtaatt | tgccagggaa | 480 |
| ggtgtatttt | atagaggcag | aagcgggcag | agctgctact | gctgaaggtg | gtgtttatac | 540 |
| taccgttgtg | gaggcattat | cgctggtgca | agaggaagag | ggtacaggta | tgtacttgat | 600 |
| aaacgcacca | gaaaaagcgg | tcgtaaggtt | tttcaagata | gaaaagagtg | cagcagagga | 660 |
| acctcaaaca | gtagatccta | gtgtagttga | gtcagcaaca | gggtcgggtg | tagatacgca | 720 |
| agaagaacaa | gaaatagatc | aagaagcacc | agcaattgaa | gaagttgaga | cagaagagca | 780 |
| agaagttatt | ctggaagaag | gtactttgat | agatcttgag | caacctgtag | cgcaagtacc | 840 |
| tgtagtagct | gaagcagaat | tacctggtgt | tgaagctgca | gaagcgattg | taccatcact | 900 |
| agaagaaaat | aagcttcaag | aagtggtagt | tgctccagaa | gcgcaacaac | tagaatcagc | 960 |
| tcctgaagtt | tctgcgccag | cacaacctga | gtctacagtt | cttggtgttg | ctgaaggtga | 1020 |
| tctaaagtct | gaagtatctg | tagaagctaa | tgctgatgta | ccgcaaaaag | aagtaatctc | 1080 |
| tggtcaacaa | gagcaagaaa | ttgcagaagc | actagaggga | actgaagctc | ctgtagaagt | 1140 |
| aaaagaagaa | acagaagttc | ttctaaagga | agatactttg | atagatcttg | agcaacctgt | 1200 |
| agcacaagta | cctgtagtag | ctgaagcaga | attacctggt | gttgaagctg | cagaagcgat | 1260 |
| tgtaccatca | ctagaagaaa | ataagcttca | agaagtggta | gttgctccag | aagcgcaaca | 1320 |
| actagaatca | gctcctgaag | tttctgcgcc | agcacaacct | gagtctacag | ttcttggtgt | 1380 |
| tactgaaggt | gatctgaagt | ctgaagtatc | tgtagaagct | gatgctggta | tgcagcaaga | 1440 |
| agcaggaatc | tctgatcaag | agacacaagc | aactgaagaa | gttgaaaagg | ttgaagtatc | 1500 |
| tgtagaaaca | aaaacggaag | agccagaagt | tattctagaa | gaaggtactt | tgatagatct | 1560 |
| tgagcaacct | gtagcgcaag | tacctgtagt | agctgaagca | gaattacctg | gtgttgaagc | 1620 |
| tgcagaagcg | attgtaccat | cactagaaga | aaataagctt | caagaagtgg | tagttgctcc | 1680 |
| agaagcggaa | caactagaat | cagctcctga | agtttctgcg | ccagtacaac | tgagtctac | 1740 |
| agttcttggt | gttactgaag | gtgatctgaa | gtctgaagta | tctgtagaag | ctgatgctgg | 1800 |
| tatgcagcaa | gaagcaggaa | tctctgatca | agagacacaa | gcaactgaag | aagttgagaa | 1860 |
| ggttgaagta | tctgtagaac | ctgatcctgg | tatgcagcaa | gagttagtag | atgttccgac | 1920 |

```
tgctttgccg ttaaaggatc ctgacgatga agatgttcta agttattagg atatctttct   1980
cgtgaaaagt atggggaagg ttcgatgtgt tgaaccgtgc cccatgcttt ttctttaaga   2040
tttcttcaaa aagaggtaaa actctcctat gttttttgtg agcagtaatt tcttgcagtt   2100
ttgcgactga gttgtgtgtt attgcgaagt ttttcttctg attattggac gaaggtggtg   2160
cttgtcatgt ctgtggtgcg tgctttccat gcttgataga gctcctgatt attttcttta   2220
tacgcaagcc aggtaaatcg tgtatgtggc gacttttcga atcagtgttt agattacata   2280
gaagtaattg tggcttatac gctgttaatt gcgctgcaat ctgtcaaaag tgatgcagta   2340
acttcctcta tatgtcctaa tgctgttaca tgacatgggt aatgcatagc attatcaatg   2400
gtcatggtgt ctttagtagg cataccagcg gttttatata ccagtgatgc gcgagccttg   2460
ttctccgctt tcataaaaga tttattactc aagatattgg tatacctagc gattcacgtg   2520
taatttgagt acttacctgc gtatttcgaa ggtaacgtac taatagcgta tggtaaaact   2580
atctattatc ccaatcccta agaataacta tgctgttttg gagctgttgc atgctgaaag   2640
atgtcttata gcatcgcggt tatatatttt cacattttag agattttaag agtataactt   2700
tctagcatct tagagaacta tactcaaagt taaacacaat aaaaacatga agcattaaaa   2760
ctcaagtata ctaaaccagc cttagacctt aaaggaaagt aaggaatgct tatctatgtt   2820
caattgtgcc attacttaaa aagcgaacct aacaccgaat tccccaccga cataagccat   2880
ggagaaatta gcaatagcag tatccttagt acgacccgcc ggactagtat catctacaag   2940
acgttgagcc ggcagatcat cataaacgcc atctccaaca acgcgatgat agaatccacc   3000
cgcaaaagcg gagatttcag gtgagagctg ataactcaag ccagccttta acctcaagct   3060
taggagtgat gttctagaca ccatccgtat tagtcacaga ttagcttcct ctcgaagtac   3120
agataacctc tggaaagttt tagaaaggac ggaatgtgta acgccgctcc gtgccatcaa   3180
ccacgccaac gaagttaccg cctaaaccaa cacaagcata aggaacaaca cctaaacctt   3240
cactaagaag atcataacaa gcattaacca ttacagatgt agaagaaaca gctctgatct   3300
caacaacctc tcccccttca atagttttag caagtaatcc tgctactatg gttttttcat   3360
cacgattaag acctaatagg tctttagcca tagcgtttgc attactatta ggttctccct   3420
cgacgttttg actgctgcca ttactccctc gtcccctagg ccagttttta ccttcaccga   3480
ctttcacagt attaacaaaa ccactcaacg tctttggtcc tgtcgccccc gtcgtatttc   3540
ccaaaccgct acactgtgtt gtctcctcgt tgccgtgtgt cgtcgacaac tccgcaacat   3600
acttcttccc cttagcccta gttatagcag catgatcccc actacaaacc ttcccatcaa   3660
tttcagggct ggaaattttc acagcattgg caaactgaac gatgtctttc ccagaggttt   3720
tgcaagagc agcggcaagg ttatcagtct gcccagtaac aacatcataa gctaactcct   3780
tagctagtag atatactgta tcagcttcat cttccttact accactatct ctaatacect   3840
tggtcttcct tttaataata agagttattg cataggatat tgatatacct atcgatttat   3900
aggcagttga gccggaagat catcttaaac accatctccc acaacacgat ggtaaaagcc   3960
acccgcagga attccggaat tccggaattc cggaattc                           3998
```

<210> SEQ ID NO 6
<211> LENGTH: 578
<212> TYPE: PRT
<213> ORGANISM: Granulocytic Ehrlichia
<220> FEATURE:
<223> OTHER INFORMATION: S7 of Granulocytic Ehrlichia

<400> SEQUENCE: 6

```
Met Tyr Gly Ile Asp Ile Glu Leu Ser Asp Tyr Arg Ile Gly Ser Glu
1               5                   10                  15

Thr Ile Ser Ser Gly Asp Gly Tyr Glu Gly Cys Ala Cys Asp
            20                  25                  30

Lys Asp Ala Ser Thr Asn Ala Tyr Ser Tyr Asp Lys Cys Arg Val Val
            35                  40                  45

Arg Gly Thr Trp Arg Pro Ser Glu Leu Val Leu Tyr Val Gly Asp Glu
50                      55                  60

His Val Ala Cys Arg Asp Val Ala Ser Gly Met His His Gly Asn Leu
65                      70                  75                  80

Pro Gly Lys Val Tyr Phe Ile Glu Ala Glu Ala Gly Arg Ala Ala Thr
                85                  90                  95

Ala Glu Gly Gly Val Tyr Thr Thr Val Val Glu Ala Leu Ser Leu Val
            100                 105                 110

Gln Glu Glu Glu Gly Thr Gly Met Tyr Leu Ile Asn Ala Pro Glu Lys
            115                 120                 125

Ala Val Val Arg Phe Phe Lys Ile Glu Lys Ser Ala Ala Glu Glu Pro
            130                 135                 140

Gln Thr Val Asp Pro Ser Val Val Glu Ser Ala Thr Gly Ser Gly Val
145                 150                 155                 160

Asp Thr Gln Glu Glu Gln Glu Ile Asp Gln Glu Ala Pro Ala Ile Glu
            165                 170                 175

Glu Val Glu Thr Glu Glu Gln Glu Val Ile Leu Glu Glu Gly Thr Leu
            180                 185                 190

Ile Asp Leu Glu Gln Pro Val Ala Gln Val Pro Val Val Ala Glu Ala
            195                 200                 205

Glu Leu Pro Gly Val Glu Ala Ala Glu Ala Ile Val Pro Ser Leu Glu
            210                 215                 220

Glu Asn Lys Leu Gln Glu Val Val Ala Pro Glu Ala Gln Gln Leu
225                 230                 235                 240

Glu Ser Ala Pro Glu Val Ser Ala Pro Ala Gln Pro Glu Ser Thr Val
            245                 250                 255

Leu Gly Val Ala Glu Gly Asp Leu Lys Ser Glu Val Ser Val Glu Ala
            260                 265                 270

Asn Ala Asp Val Pro Gln Lys Glu Val Ile Ser Gly Gln Gln Glu Gln
            275                 280                 285

Glu Ile Ala Glu Ala Leu Glu Gly Thr Glu Ala Pro Val Glu Val Lys
            290                 295                 300

Glu Glu Thr Glu Val Leu Leu Lys Glu Asp Thr Leu Ile Asp Leu Glu
305                 310                 315                 320

Gln Pro Val Ala Gln Val Pro Val Val Ala Glu Ala Glu Leu Pro Gly
                325                 330                 335

Val Glu Ala Ala Glu Ala Ile Val Pro Ser Leu Glu Glu Asn Lys Leu
            340                 345                 350

Gln Glu Val Val Val Ala Pro Glu Ala Gln Gln Leu Glu Ser Ala Pro
            355                 360                 365

Glu Val Ser Ala Pro Ala Gln Pro Glu Ser Thr Val Leu Gly Val Thr
            370                 375                 380

Glu Gly Asp Leu Lys Ser Glu Val Ser Val Glu Ala Asp Ala Gly Met
385                 390                 395                 400

Gln Gln Glu Ala Gly Ile Ser Asp Gln Glu Thr Gln Ala Thr Glu Glu
            405                 410                 415

Val Glu Lys Val Glu Val Ser Val Glu Thr Lys Thr Glu Glu Pro Glu
            420                 425                 430
```

```
Val Ile Leu Glu Glu Gly Thr Leu Ile Asp Leu Glu Gln Pro Val Ala
            435                 440                 445

Gln Val Pro Val Val Ala Glu Ala Glu Leu Pro Gly Val Glu Ala Ala
        450                 455                 460

Glu Ala Ile Val Pro Ser Leu Glu Glu Asn Lys Leu Gln Glu Val Val
465                 470                 475                 480

Val Ala Pro Glu Ala Gln Gln Leu Glu Ser Ala Pro Glu Val Ser Ala
                485                 490                 495

Pro Val Gln Pro Glu Ser Thr Val Leu Gly Val Thr Glu Gly Asp Leu
            500                 505                 510

Lys Ser Glu Val Ser Val Glu Ala Asp Ala Gly Met Gln Gln Glu Ala
        515                 520                 525

Gly Ile Ser Asp Gln Glu Thr Gln Ala Thr Glu Val Glu Lys Val
    530                 535                 540

Glu Val Ser Val Glu Ala Asp Ala Gly Met Gln Gln Glu Leu Val Asp
545                 550                 555                 560

Val Pro Thr Ala Leu Pro Leu Lys Asp Pro Asp Asp Glu Asp Val Leu
                565                 570                 575

Ser Tyr

<210> SEQ ID NO 7
<211> LENGTH: 5570
<212> TYPE: DNA
<213> ORGANISM: Granulocytic Ehrlichia
<220> FEATURE:
<223> OTHER INFORMATION: S23 of Granulocytic Ehrlichia

<400> SEQUENCE: 7
gaattccctg tggttattag gcgtggtttc gcctgataat aaagatactt tagagggtat      60
aaacttggaa aaataatga aaaccctcc ttagtgcctc cccgttttg acaacatact         120 cttatggaaa agcgttaggg agttgcttcg cttgtcacgc gtgcgttagg ttttacgtat     180
acgtgtctgg gacttcacga aaactcgacg caggcggatt ttgtactatg tttcacttaa     240
caaggtatta taattgtttg aacacaatat tcctgataca tacacaggaa caactgcaga     300
aggttctcct ggcttagcag gcggggattt tagtttaagt tctattgact ttacaaggga     360
ctttacaatt gaatcacata gaggaagctc agctgatgac ccaggttaca tcagctttag     420
ggatcaagac ggaaacgtca tgtcacgttt tcttgatgtg tacgtagcta atttcagctt     480
gcgatgcaag cattctccct ataacaacga cagaatggaa acagctgcgt tctctctaac     540
tcccgacata atagagcctt ctgctttatt gcaagaatca catagtacac aaaacaatgt     600
agaagaggca gtacaagtta cagctcttga gtgccctcca tgtaatccag tccctgccga     660
ggaagtagct cctcaaccgt ctttttctaag cagaataatt caggcgttct tgtggttatt     720
cacgccttct tctactaccg acactgctga agacagcaag tgtaatagta gcgatacttc     780
aaaatgtacc tctgctagca gtgagtcatt agagcagcaa caagaatcag tggaagtgca     840
accatctgta cttatgtcta ctgccccctat agcaacagag cctcaaaatg cggttgttaa     900
ccaagtaaac actactgcag tacaagtaga atcatccatt attgtgccag aatcgcaaca     960
cactgacgtt accgtgctcg aagatactac tgagacgata actgttgatg gggaatatgg    1020
acattttagt gacattgctt caggtgaaca caataacgat ctgcctgcca tgttgttaga    1080
tgaagcagac ttcactatgt tattagcgaa cgaggagtca aagaccctgg agtctatgcc    1140
ttctgatagc ctagaagaca atgttcagga actaggtaca ttgcctttac aagaaggtga    1200
```

```
aacagtttct gagggcaaca cacgagagtc actacccact gacgtttcac aagactcagt    1260
tggtgtaagt acagatcttg aagctcattc tcaagaagtt gaaacagttt ctgaggtcag    1320
cacacaagat tcactatcca ctaacatttc acaagactca gttggtgtaa gtacagatct    1380
tgaagttcat tctcaagaag ttgaaatagt ttctgagggc ggcacacaag attcactatc    1440
cactaacatt tcacaagact cagttggtgt aagtacagat cttgaagctc attctaaagg    1500
agttgaaata gtttctgagg gcggcacaca aaattcacta tccgctgatt ttccaataaa    1560
cacagttgaa agtgaaagta cagatcttga agctcattcc ccagaaggtg aaatagtttc    1620
tgaggtcagc acacaagatg cgccatccac tggagtagag atcagattta tggatcgtga    1680
ttttgatgat gacgtgctcg cgttgtgaag tgatcatggt aggggaaaca gttatggcgt    1740
aaagacatct ttgatgactt gtcttgcgtg aataagtagt gcaagttttt tatgcattga    1800
tgtgcatgat cattgcccct aaggaaagca gtactaatgg tagtctaaga tcttatacag    1860
ggtttcggac taccactttt ggtgttttaa aacgtcttat tcgcgttggg tgcttgctta    1920
caatgtacct gtacgtgccc aacactaaaa atggtcagta ttacttaggg gagttcgtag    1980
acgaggcatc tcgatttact cttggtaagc tacaaataac tcagtcatat caaggtagtt    2040
caagatgaaa gcagtcctat gcttatcatg gagaattcct gcggttctct tcaaaattct    2100
cttttcccgc aagggcagac tcttatttgt taaaataaca aaatttctct acaggaagcg    2160
acatttcata tcaaagctga ttgtgaaata atggcattga gtattttct cgccctagaa     2220 gataatcatt tcggcactat caaagcattt acgatattct ccattatctt gtaatcagat    2280
ggctatcttg aaagcaacca aggatatccg tacatggtag cttacatact gctatcaatc    2340
tcctatacga ccttcaatga aacggtaact gttgctgaca gcttgcacat gctgtgattc    2400
aattcctggt tcctagatgt tctactacgt ttatccggta ctaatattat tctttggcgc    2460
tctattatct agcaactcag agtccattat tggatctcta ataccaaggg tataagggaa    2520
agtggaagag tattattaga gagaagaagc aaatacagta tatctactag ctaaggagtt    2580
agcttatgat gttgttactg gacagactga taagcttgct gctgctcttg ccaagaccctc   2640 cgggaaagat atcgttcagt ttgctaaggc agttgagatt tcggctccta agatcgataa    2700
gcaagtttgt gtgactaata agaatgggga tagcggaaca agatatgcta agtacctcga    2760
agaagctgga acgtctagca atgctggcac gtcgttgtgt ggtggtaaaa acctaaagac    2820
gactgactcc aacacaggag tagagaaagg acaggtgtta catgactttg tttctggaac    2880
gttgagtggg gtactaagaa actggccgac atctagtgaa agtactaaag aaaataacga    2940
caacgcaggg aaggtagcta agacctgac aaaactaacc cctgaggaaa aaccatagt      3000 agcagggtta ctagctaaga ctattgaagg gggtgaagtt gttgagatca gggcggtttc    3060
ttctacttct gtgatggtta atgcttgtta tgatcttctt agtgaaggtt taggtgtcgt    3120
tccttacgct tgtgttggtc ttgggggtaa cttcgtgggg ggttgttgat ggcacgcgc     3180 agcgttacac aatccgtcct tgacctgaat actctagtta agcactaggc aaaattagtg    3240
ctggatcact tacgcaacat actacggtca gcgattttcc atactgagca ggtacgtaca    3300
gtggctttat actcttaccc agcatgaaat tacttgttat ctaagaatct ccacagctga    3360
ccttagaaag gttatctgtc cttcgagaga aagctaatct gtgtcttatg cggatggcgt    3420
tgaacgtatt acaggtccca agctgtcttg caagtttcta aggatattat aagggcacac    3480
ctataaaact gcgcaatata tcacctgcaa tacggtcccg attcgaaaac actgggaagt    3540
gcgctcatta tctatgaatc gctagctagg cataaataag agtatacgca ataacgctta    3600
```

```
ttattaaaaa caagaccaag ggtattagag atagtggtag taaggaagat gaagctgata    3660
cagtatatct actagctaag gagttagctt atgatgttgt tactgggcag actgataacc    3720
ttgctgctgc tcttgccaag acttctggta aagatattgt tcagtttgct aagactctta    3780
atatttctca ctctaatatc gatgggaagg tttgtaggag ggaaaagcat gggagtcaag    3840
gtttgactgg aaccaaagca ggttcgtgtg atagtcagcc acaaacggcg ggtttcgatt    3900
ccatgaaaca aggtttgatg gcagctttag gcgaacaagg cgctgaaaag tggcccaaaa    3960
ttaacaatgg tggccacgca acaatttata gtagtagcgc aggtccagga aatgcgtatg    4020
ctagagatgc atctactacg gtagctacag acctaacaaa gctcactact gaagaaaaaa    4080
ccatagtagc agggttacta gctagaacta ttgaaggggg tgaagttgtt gagattaggg    4140
cagtttcttc tacttctgtg atggttaatg cttgttatga tcttctgaag ggaaacgcat    4200
cacattattt atctggttgc tgtaatctga tcttcccgtt gctatgatcg catctccccc    4260
tcacttctct cgcaaactct ggattaacct ctggatgcga ataatgttta tcagctttga    4320
gaaaaacata ttagagtttt atacagcacc aatgataagc gtgggcactt aaataaaggt    4380
tcatatccct agaaatttat cccactagct aaaattattg aagggggtga ggtcgttgag    4440
ataagggcag tttcttctac ttctgtgatg gttaatgctt gttatgatct tcttagtgaa    4500
ggtttaggcg ttgttcctta tgcttgcgtg ggtcttggtg gaacttcgt gggcgtggtt    4560
gatgggcata tcacaaacca ctccatctct gaccctgtat gcactagcaa gtaactaggc    4620
aaaattattg ctgcatcact ttgaaacaaa ctacgatcag caatgttcaa tacttagcag    4680
gtctgtacag tggctttaca ctcttaccca gcatgaaata cttgctatct aagaatctcc    4740
tctaaaactt ccagaggtt atctgtactt tgagggaagc taatctgtgg ctaatgagga    4800
tggtgtctag aatatcactc ctaagcttgc ttataggtta aaggctgggt tgagttatca    4860
gctttctcct gaaatctctg cttttgtagg tggtttctat cattggtttg ttggttatgg    4920
tgtttatgat gatcttccgg ctcaacgtct tgtagatgat actagtccgg cgggtcgtac    4980
taaggatact gctattgcta acttctccat ggcctatgtt ggtgcatcat ttcagccata    5040
ttacgcagtt cttctagtag aactgtatga gtatcgataa aaagatatac gacgcagcat    5100
gctctgaaaa agtgacaggg tgaacagcag tgcagcatac attagcctgt ctgtatcagt    5160
gtgcaatctg ttacaaaact actaggatca ttcttttaac acctatcggg ttcatcaaga    5220
aaatgagtgc atacgtgacg gcaagcgcta aaacgctaaa gctgatgcat cacattaaaa    5280
tgtgttgacg ttagaccttc caagcactgt aaagtgtggc gattcccccg catacgttct    5340
tatgcgtgat tttgaaaaac ccggcgtctg caacttcgga agagaattgt ttttgtgtgg    5400
gaaaagctct tatgctttca actaagtagg aatatgcatc aatatccccg gctactattt    5460
tgccaatttt cggtataaca agaaagaat acaggtcata agctgttttg aatgcactgt    5520
cttcgagtat aggagaaaac tccaagcata aaaacctacc acatggtttc               5570
```

<210> SEQ ID NO 8
<211> LENGTH: 484
<212> TYPE: PRT
<213> ORGANISM: Granulocytic Ehrlichia
<220> FEATURE:
<223> OTHER INFORMATION: S23 of Granulocytic Ehrlichia

<400> SEQUENCE: 8

Met Phe Glu His Asn Ile Pro Asp Thr Tyr Thr Gly Thr Thr Ala Glu
1 5 10 15

Gly Ser Pro Gly Leu Ala Gly Gly Asp Phe Ser Leu Ser Ser Ile Asp

-continued

```
                    20                  25                  30
Phe Thr Arg Asp Phe Thr Ile Glu Ser His Arg Gly Ser Ser Ala Asp
                35                  40                  45
Asp Pro Gly Tyr Ile Ser Phe Arg Asp Gln Asp Gly Asn Val Met Ser
 50                  55                  60
Arg Phe Leu Asp Val Tyr Val Ala Asn Phe Ser Leu Arg Cys Lys His
 65                  70                  75                  80
Ser Pro Tyr Asn Asn Asp Arg Met Glu Thr Ala Ala Phe Ser Leu Thr
                85                  90                  95
Pro Asp Ile Ile Glu Pro Ser Ala Leu Leu Gln Glu Ser His Ser Thr
                100                 105                 110
Gln Asn Asn Val Glu Glu Ala Val Gln Val Thr Ala Leu Glu Cys Pro
                115                 120                 125
Pro Cys Asn Pro Val Pro Ala Glu Glu Val Ala Pro Gln Pro Ser Phe
                130                 135                 140
Leu Ser Arg Ile Ile Gln Ala Phe Leu Trp Leu Phe Thr Pro Ser Ser
 145                 150                 155                 160
Thr Thr Asp Thr Ala Glu Asp Ser Lys Cys Asn Ser Ser Asp Thr Ser
                165                 170                 175
Lys Cys Thr Ser Ala Ser Ser Glu Ser Leu Glu Gln Gln Gln Glu Ser
                180                 185                 190
Val Glu Val Gln Pro Ser Val Leu Met Ser Thr Ala Pro Ile Ala Thr
                195                 200                 205
Glu Pro Gln Asn Ala Val Val Asn Gln Val Asn Thr Thr Ala Val Gln
                210                 215                 220
Val Glu Ser Ser Ile Ile Val Pro Glu Ser Gln His Thr Asp Val Thr
 225                 230                 235                 240
Val Leu Glu Asp Thr Thr Glu Thr Ile Thr Val Asp Gly Glu Tyr Gly
                245                 250                 255
His Phe Ser Asp Ile Ala Ser Gly Glu His Asn Asn Asp Leu Pro Ala
                260                 265                 270
Met Leu Leu Asp Glu Ala Asp Phe Thr Met Leu Leu Ala Asn Glu Glu
                275                 280                 285
Ser Lys Thr Leu Glu Ser Met Pro Ser Asp Ser Leu Glu Asp Asn Val
                290                 295                 300
Gln Glu Leu Gly Thr Leu Pro Leu Gln Glu Gly Thr Val Ser Glu
 305                 310                 315                 320
Gly Asn Thr Arg Glu Ser Leu Pro Thr Asp Val Ser Gln Asp Ser Val
                325                 330                 335
Gly Val Ser Thr Asp Leu Glu Ala His Ser Gln Glu Val Glu Thr Val
                340                 345                 350
Ser Glu Val Ser Thr Gln Asp Ser Leu Ser Thr Asn Ile Ser Gln Asp
                355                 360                 365
Ser Val Gly Val Ser Thr Asp Leu Glu Val His Ser Gln Glu Val Glu
                370                 375                 380
Ile Val Ser Glu Gly Gly Thr Gln Asp Ser Leu Ser Thr Asn Ile Ser
 385                 390                 395                 400
Gln Asp Ser Val Gly Val Ser Thr Asp Leu Glu Ala His Ser Lys Gly
                405                 410                 415
Val Glu Ile Val Ser Glu Gly Gly Thr Gln Asp Ser Leu Ser Ala Asp
                420                 425                 430
Phe Pro Ile Asn Thr Val Glu Ser Glu Ser Thr Asp Leu Glu Ala His
                435                 440                 445
```

```
Ser Pro Glu Gly Glu Ile Val Ser Glu Val Ser Thr Gln Asp Ala Pro
        450                 455                 460

Ser Thr Gly Val Glu Ile Arg Phe Met Asp Arg Asp Ser Asp Asp Asp
465                 470                 475                 480

Val Leu Ala Leu

<210> SEQ ID NO 9
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 9

Asp Gly Arg Thr Ile Ile His Tyr Ala Ala Lys Asp Gly Asn Leu Glu
1               5                   10                  15

Ile Leu Gln Gln Ala Leu Gly Arg Lys Ser Ser Tyr Ser Lys Phe Pro
            20                  25                  30

Val

<210> SEQ ID NO 10
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 10

Lys Lys Thr Thr Leu Thr Ala Glu Ala Leu Thr Ser Gly Lys Tyr Gly
1               5                   10                  15

Val Val Lys Ala Leu Ile Lys Asn Ser Ala Asp Val Asn Ala Ser Pro
            20                  25                  30

Glu

<210> SEQ ID NO 11
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 11

Ala Val Gln Ala Ala Asn Glu Ala Ser Asn Leu Lys Glu Ala Asn Lys
1               5                   10                  15

Ile Val Asn Phe Leu Leu His Arg Gly Ala Asp Leu Ser Ser Thr Glu
            20                  25                  30

His

<210> SEQ ID NO 12
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 12

Thr Gly Thr Pro Ala Leu His Leu Ala Thr Ala Ala Gly Asn His Arg
1               5                   10                  15

Thr Ala Met Leu Leu Leu Asp Lys Gly Ala Pro Ala Thr Gln Arg Asp
            20                  25                  30

Ala
```

```
<210> SEQ ID NO 13
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 13

Arg Gly Arg Thr Ala Leu His Ile Ala Ala Asn Gly Asp Gly Lys
1               5                   10                  15

Leu Tyr Arg Met Ile Ala Lys Lys Cys Pro Asp Ser Cys Gln Pro Leu
            20                  25                  30

Cys

<210> SEQ ID NO 14
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 14

Met Gly Asp Thr Ala Leu His Glu Ala Leu Tyr Ser Asp Asn Val Thr
1               5                   10                  15

Glu Lys Cys Phe Leu Lys Met Leu Lys Glu Ser Arg Lys Arg Leu Ser
            20                  25                  30

Asn

<210> SEQ ID NO 15
<211> LENGTH: 35
<212> TYPE: PRT
<213> ORGANISM: Granulocytic Ehrlichia
<220> FEATURE:
<223> OTHER INFORMATION: proposed ankyrin repeat

<400> SEQUENCE: 15

Asn Gly Asp Thr Leu Leu His Leu Ala Ala Ser Arg Gly Phe Gly Lys
1               5                   10                  15

Ala Cys Lys Ile Leu Leu Lys Ala Gly Ala Ser Val Ser Val Val Ala
            20                  25                  30

Ser Asn Val
        35

<210> SEQ ID NO 16
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 16

Glu Gly Lys Thr Pro Val Asp Val Ala Asp Pro Ser Leu Lys Thr Arg
1               5                   10                  15

Pro Trp Phe Phe Gly Lys Ser Val Val Thr Met Met Ala Glu Arg Val
            20                  25                  30

Gln

<210> SEQ ID NO 17
<211> LENGTH: 33
<212> TYPE: PRT
<213> ORGANISM: Artificial Sequence
<220> FEATURE:
<221> NAME/KEY: VARIANT
```

```
<222> LOCATION: 1, 3, 9, 12, 13, 16, 21, 25, 27, 29, 30, 31, 32, 33
<223> OTHER INFORMATION: Xaa = Any Amino Acid
<220> FEATURE:
<223> OTHER INFORMATION: Consensus sequence of ankyrin repeats

<400> SEQUENCE: 17

Xaa Thr Xaa Ser Thr Pro Leu His Xaa Ala His Xaa Xaa Thr Thr Xaa
1               5                   10                  15

Thr His His Thr Xaa Leu Leu Thr Xaa Thr Xaa Thr Xaa Xaa Xaa Xaa
            20                  25                  30

Xaa

<210> SEQ ID NO 18
<211> LENGTH: 29
<212> TYPE: PRT
<213> ORGANISM: E. chaffeensis

<400> SEQUENCE: 18

Ser Gly Thr Asp Leu Thr Leu Glu Ser Ala Val His Ser Gln Lys Gln
1               5                   10                  15

Pro Glu Gly Val Asp Gly Glu Ile Thr Val Ser Glu Gln
            20                  25

<210> SEQ ID NO 19
<211> LENGTH: 28
<212> TYPE: PRT
<213> ORGANISM: Granulocytic Ehrlichia

<400> SEQUENCE: 19

Gln Pro Ser Val Ser Ala Leu Ser Gln Glu Val Pro Phe Val Val Ala
1               5                   10                  15

Glu Ser Ala Glu Val Leu Ser Pro Lys Gly Val Glu
            20                  25

<210> SEQ ID NO 20
<211> LENGTH: 24
<212> TYPE: PRT
<213> ORGANISM: E. chaffeensis

<400> SEQUENCE: 20

Glu Ser Ala Gly Val Ile Ser Asp Gln Pro Glu Ala Thr Gln Val Ala
1               5                   10                  15

Val Thr Thr Glu Glu Arg Val Glu
            20

<210> SEQ ID NO 21
<211> LENGTH: 406
<212> TYPE: PRT
<213> ORGANISM: Granulocytic Ehrlichia
<220> FEATURE:
<223> OTHER INFORMATION: C6.1 of Granulocytic Ehrlichia

<400> SEQUENCE: 21

Met Gly Asp Ala Val Glu Val Arg Ala Glu Asn Leu Gly Gly Glu Ser
1               5                   10                  15

Ile Leu Glu Ala Pro Ile Arg Val Met Lys Lys Val Gly Asp Thr Val
            20                  25                  30

Ser Ala Glu Asp Val Leu Phe Ile Val Glu Thr Asp Lys Thr Ser Leu
        35                  40                  45

Glu Ile Ser Ala Pro Val Ala Gly Val Leu Thr Glu Leu Arg Val Ala
    50                  55                  60

Asp Glu Glu Val Ile Thr Lys Gly Gln Val Leu Ala Ile Ile Arg Pro
```

-continued

```
                 65                  70                  75                  80
Gln Gly Glu Ala Thr Ala Glu Gly Val Asn Lys Glu Pro Ser Lys
                 85                  90                  95
Glu Glu Val Pro Ala Gln Pro Val Ala Gln Ala Val Ser Thr Gln
                100                 105                 110
Lys Pro Gln Glu Lys Thr Ile Ile Glu Gly Lys Gly Leu Val Thr Pro
                115                 120                 125
Thr Val Glu Asp Phe Val Ala Gly Ile Asn Thr Thr Pro Thr Ser Arg
                130                 135                 140
Ala Leu Gly Met Ser Ala Lys Ser Glu Gln Asp Lys Lys Ile Val Ala
145                 150                 155                 160
Ser Gln Pro Ser Lys Asp Leu Met Ser Cys His Gly Asp Val Gly
                165                 170                 175
Glu Arg Arg Val Lys Met Ser Lys Ile Arg Gln Val Ile Ala Ala Arg
                180                 185                 190
Leu Lys Glu Ser Gln Asn Thr Ser Ala Thr Leu Ser Thr Phe Asn Glu
                195                 200                 205
Val Asp Met Ser Lys Val Met Glu Leu Arg Ala Lys Tyr Lys Asp Ala
210                 215                 220
Phe Val Lys Arg Tyr Asp Val Lys Leu Gly Phe Met Ser Phe Phe Ile
225                 230                 235                 240
Arg Ala Val Val Leu Val Ser Glu Ile Pro Val Leu Asn Ala Glu
                245                 250                 255
Ile Ser Gly Asp Asp Ile Val Tyr Arg Asp Tyr Cys Asn Ile Gly Val
                260                 265                 270
Ala Val Gly Thr Asp Lys Gly Leu Val Val Pro Val Ile Arg Arg Ala
                275                 280                 285
Glu Thr Met Ser Leu Ala Glu Met Glu Gln Ala Leu Val Asp Leu Ser
                290                 295                 300
Thr Lys Ala Arg Ser Gly Lys Leu Ser Val Ser Asp Met Ser Gly Ala
305                 310                 315                 320
Thr Phe Thr Ile Thr Asn Gly Gly Val Tyr Gly Ser Leu Leu Ser Thr
                325                 330                 335
Pro Ile Ile Asn Pro Pro Gln Ser Gly Ile Leu Gly Met His Ala Ile
                340                 345                 350
Gln Gln Arg Pro Val Ala Val Asp Gly Lys Val Glu Ile Arg Pro Met
                355                 360                 365
Met Tyr Leu Ala Leu Ser Tyr Asp His Arg Ile Val Asp Gly Gln Gly
                370                 375                 380
Ala Val Thr Phe Leu Val Arg Val Lys Gln Tyr Ile Glu Asp Pro Asn
385                 390                 395                 400
Arg Leu Ala Leu Gly Ile
                405

<210> SEQ ID NO 22
<211> LENGTH: 264
<212> TYPE: PRT
<213> ORGANISM: Granulocytic Ehrlichia
<220> FEATURE:
<223> OTHER INFORMATION: C6.2 of Granulocytic Ehrlichia

<400> SEQUENCE: 22

Met Gly Arg Gly Thr Ile Thr Ile His Ser Lys Glu Asp Phe Ala Cys
1               5                   10                  15
Met Arg Arg Ala Gly Met Leu Ala Ala Lys Val Leu Asp Phe Ile Thr
                20                  25                  30
```

-continued

```
Pro His Val Val Pro Gly Val Thr Thr Asn Ala Leu Asn Asp Leu Cys
        35                  40                  45

His Asp Phe Ile Ile Ser Ala Gly Ala Ile Pro Ala Pro Leu Gly Tyr
    50                  55                  60

Arg Gly Tyr Pro Lys Ser Ile Cys Thr Ser Lys Asn Phe Val Val Cys
65                  70                  75                  80

His Gly Ile Pro Asp Asp Ile Ala Leu Lys Asn Gly Asp Ile Val Asn
                85                  90                  95

Ile Asp Val Thr Val Ile Leu Asp Gly Trp His Gly Asp Thr Ser Arg
            100                 105                 110

Met Tyr Trp Val Gly Asp Asn Val Ser Ile Lys Ala Lys Arg Ile Cys
        115                 120                 125

Glu Ala Ser Tyr Lys Ala Leu Met Ala Ala Ile Gly Val Ile Gln Pro
    130                 135                 140

Gly Lys Lys Leu Asn Ser Ile Gly Leu Ala Ile Glu Glu Glu Ile Arg
145                 150                 155                 160
Gly Tyr Gly Tyr Ser Ile Val Arg Asp Tyr Cys Gly His Gly Ile Gly
                165                 170                 175
Arg Glu Phe His Ala Ala Pro Asn Ile Val His Tyr Tyr Asp Glu Glu
            180                 185                 190
Asp Asp Val Thr Ile Gln Glu Gly Met Phe Phe Thr Val Glu Pro Met
        195                 200                 205
Ile Asn Ala Gly Lys Tyr His Thr Val Leu Asp Lys Lys Asp Gly Trp
    210                 215                 220

Thr Val Thr Thr Arg Asp Phe Ser Leu Ser Ala Gln Phe Glu His Thr
225                 230                 235                 240
Leu Gly Val Thr Glu Thr Gly Val Glu Ile Phe Thr Met Ser Pro Lys
                245                 250                 255
Asn Trp His Cys Pro Pro Tyr Leu
            260
```

<210> SEQ ID NO 23
<211> LENGTH: 2706
<212> TYPE: DNA
<213> ORGANISM: Granulocytic Ehrlichia
<220> FEATURE:
<223> OTHER INFORMATION: C6 of Granulocytic Ehrlichia

<400> SEQUENCE: 23

```
gaattccgga attccggaat tcctatggat cgtgcagtga tggaagaggg cagcatgtta     60
gctgcaggtt cactgctcac taggggtaag attgtaaaat ctggagagtt atgggcaggt    120
aggcctgcaa aatttctacg tatgatgact gaagaggaga ttttatacct acaaaaaatct    180 gctgaaaatt acatagcgtt atcgcgtgga tacttataac aaggtattca tctatggttt    240
gacattagtg tcttttggtg attacactgc ctttcaatct gtgtttttttg ttttagttct    300 ggtttgtatt tatgggtgat gctgtagaag ttagggctga gaatcttggt ggcgaatcca    360
ttctagaagc tccgattcgg gtaatgaaaa aggtgggaga tactgtatct gcagaagatg    420
tgctcttcat tgttgaaaca gacaagactt ctcttgaaat atcagcccct gttgctggtg    480
ttctcacaga gttgagagtt gcagatgaag aagtgattac caaggggcag gtcttggcta    540
tcatacggcc acagggtgag gctactgcag agggtgttaa taaggagcca gagagcaagg    600
aggaggtgcc tgctcaaccc gttgttgcac aggcagtgag cactcaaaaa ccgcaggaaa    660
agacaattat tgaaggcaaa ggtctagtaa ctcctactgt agaagatttt gttgcaggaa    720
```

| | |
|---|---|
| tcaacacaac tcctacttct agagctttgg gtatgagtgc taagagtgaa caagacaaga | 780 |
| agatagttgc tagccagccg tctaaggatc tgatgagttg ccatggcgac gtggtgggtg | 840 |
| aaagacgcgt gaagatgagc aaaatccgcc aagttatagc tgctaggctt aaggagtcac | 900 |
| aaaataccte tgctacactc agcacctttta atgaagttga tatgagcaaa gtgatggagc | 960 |
| tcagagctaa gtacaaagat gcctttgtga agaggtatga tgttaagctt gggtttatgt | 1020 |
| ccttctttat cagagcggtt gtgctagtcc tttccgaaat tcctgtgctg aatgcggaga | 1080 |
| tttcaggcga tgatatagtc tacagggact attgtaacat tggagtcgcg gtaggtaccg | 1140 |
| ataaggggtt agtggtgcct gttatcagaa gagcggaaac tatgtcactt gctgaaatgg | 1200 |
| agcaagcact tgttgactta agtacaaaag caagaagtgg caagctctct gtttctgata | 1260 |
| tgtctggtgc aaccttttact attaccaatg gtggtgtgta tggtcgcta ttgtctaccc | 1320 |
| ctataatcaa ccctcctcaa tctggaatct tgggtatgca tgctatacag cagcgtcctg | 1380 |
| tggcagtaga tggtaaggta gagataaggc ctatgtgta tttggcgcta tcatatgatc | 1440 |
| atagaatagt tgacgggcaa ggtgctgtga cgttttttggt aagagtgaag cagtacatag | 1500 |
| aagatcctaa cagattggct ctaggaattt agggggtttt tatggggcgg ggtacaataa | 1560 |
| ccatccactc caaagaggat tttgcctgta tgagaagggc tgggatgctt gcagctaagg | 1620 |
| tgcttgattt tataacgccg catgttgttc ctggtgtgac tactaatgct ctgaatgatc | 1680 |
| tatgtcacga tttcatcatt tctgccgggg ctattccagc gcctttgggc tatagagggt | 1740 |
| atcctaagtc tatttgtact tcgaagaatt tgtggtttg ccatggcatt ccagatgata | 1800 |
| ttgcattaaa aaacggcgat atagttaaca tagacgttac tgtgatcctc gatggttggc | 1860 |
| acggggatac tagtaggatg tattgggttg gtgataacgt ctctattaag gctaagcgca | 1920 |
| tttgtgaggc aagttataag gcattgatgg cggcgattgg tgtaatacag ccaggtaaga | 1980 |
| agctcaatag catagggtta gctatagagg aagaaatcag aggttatgga tactccattg | 2040 |
| ttagagatta ctgcggacat gggataggtc gcgaatttca tgctgctcct aacatagttc | 2100 |
| actactatga cgaagaggat gatgttacga ttcaggaggg aatgtttttc actgttgagc | 2160 |
| caatgatcaa tgctggaaag tatcatactg tgctagataa gaaagacgga tggacagtta | 2220 |
| caacgagaga ctttttcctt tcagcgcagt ttgaacatac cttgggtgta actgaaactg | 2280 |
| gcgttgagat ttttactatg tcgccaaaaa attggcattg tccgccatac ctttaagtag | 2340 |
| gatattttttg ttatgtgtaa agcgtgtggc agggtaatgt taggtgcatg ttctgttgac | 2400 |
| gatgtgtgct gataagaaat tgtacaatca tactgcgttg gaagttagga atatgtactt | 2460 |
| atgagtgcta ataagcttgc tgtgttatta agcgaagccg cttcagtttt gaaaagagta | 2520 |
| ggaatagata caccggggtt agacgctcga ctaattgcgg acatgttttt gggttttaagt | 2580 |
| gagcatgagg tgctaataaa tccagattta gttgttactg ctgctaaaac aaaagaattt | 2640 |
| tttgaagtta ttgcaagacg tttagccggg gtaccagttt cgcatatttt acgcagacga | 2700 |
| gaattc | 2706 |

<210> SEQ ID NO 24
<211> LENGTH: 176
<212> TYPE: PRT
<213> ORGANISM: Artificial Sequence
<220> FEATURE:
<223> OTHER INFORMATION: amino acid sequence encoded by 550 bp PCR product

<400> SEQUENCE: 24

Thr Gly Gly Ala Gly Tyr Phe Tyr Val Gly Leu Asp Tyr Ser Pro Ala

```
1               5                   10                  15
Phe Ser Lys Ile Arg Asp Phe Ser Ile Arg Glu Ser Asn Gly Glu Thr
                20                  25                  30

Lys Ala Val Tyr Pro Tyr Leu Lys Asp Gly Lys Ser Val Lys Leu Glu
            35                  40                  45

Ser His Lys Phe Asp Trp Asn Thr Pro Asp Pro Arg Ile Gly Phe Lys
        50                  55                  60

Asp Asn Met Leu Val Ala Met Glu Gly Ser Val Gly Tyr Gly Ile Gly
65                  70                  75                  80

Gly Ala Arg Val Glu Leu Glu Ile Gly Tyr Glu Arg Phe Lys Thr Lys
                85                  90                  95

Gly Ile Arg Asp Ser Gly Ser Lys Glu Asp Glu Ala Asp Thr Val Tyr
            100                 105                 110

Leu Leu Ala Lys Glu Leu Ala Tyr Asp Val Val Thr Gly Gln Thr Asp
        115                 120                 125

Asn Leu Ala Ala Ala Leu Ala Lys Thr Ser Gly Lys Asp Ile Val Gln
130                 135                 140

Phe Ala Lys Ala Val Gly Val Ser His Pro Gly Ile Asp Lys Lys Val
145                 150                 155                 160

Cys Asp Gly Gly His Ala Arg Gly Lys Lys Ser Gly Asp Asn Gly Ser
                165                 170                 175
```

<210> SEQ ID NO 25
<211> LENGTH: 181
<212> TYPE: PRT
<213> ORGANISM: A. marginale
<220> FEATURE:
<223> OTHER INFORMATION: Genbank accession number U07862

<400> SEQUENCE: 25

```
Gly Ala Gly Ala Gly Ser Phe Tyr Ile Gly Leu Asp Tyr Ser Pro Ala
1               5                   10                  15

Phe Gly Ser Ile Lys Asp Phe Lys Val Gln Glu Ala Gly Gly Thr Thr
                20                  25                  30

Arg Gly Val Phe Pro Tyr Lys Arg Asp Ala Ala Gly Arg Val Asp Phe
            35                  40                  45

Lys Val His Asn Phe Asp Trp Ser Ala Pro Glu Pro Lys Ile Ser Phe
        50                  55                  60

Lys Asp Ser Met Leu Thr Ala Leu Glu Gly Ser Ile Gly Tyr Ser Ile
65                  70                  75                  80

Gly Gly Ala Arg Val Glu Val Glu Val Gly Tyr Glu Arg Phe Val Ile
                85                  90                  95

Lys Gly Gly Lys Lys Ser Asn Glu Asp Thr Ala Ser Val Phe Leu Leu
            100                 105                 110

Gly Lys Glu Leu Ala Tyr His Thr Ala Arg Gly Gln Val Asp Arg Leu
        115                 120                 125

Ala Thr Ala Leu Gly Lys Met Thr Lys Ser Glu Ala Lys Lys Trp Gly
130                 135                 140

Asn Ala Ile Glu Ser Ala Thr Gly Thr Thr Ser Gly Asp Glu Leu Ser
145                 150                 155                 160

Lys Lys Val Cys Gly Lys Gly Thr Thr Ser Gly Ser Thr Asn Gln Cys
                165                 170                 175

Gly Thr Thr Asp Ser
            180
```

<210> SEQ ID NO 26

<211> LENGTH: 1840
<212> TYPE: DNA
<213> ORGANISM: Granulocytic Ehrlichia
<220> FEATURE:
<223> OTHER INFORMATION: E8 msp2 gene

<400> SEQUENCE: 26

```
gaggtcgacg gtatcgataa gcttgatatc gaattcctgg ctggagatgt tagagggggt     60
tagcccttga gtggaccggc tgaagtgagg agacgaagaa aaagaaggaa tttggagaag    120
ttgaaaagta tgagaaaagg aaagataatc ttaggaagcg taatgatgtc gatggctata    180
gtcatggctg ggaatgatgt cagggctcat gatgacgtta gcgctttgga gactggtggt    240
gcgggatatt tctatgttgg cttggattac agtccagcgt ttagcaagat aagagatttt    300
agtataaggg agagtaacgg agagactaag gcagtatatc catacttaaa ggatggaaag    360
agtgtaaagc tagagtcaca caagtttgac tggaacactc ctgatcctcg gattgggttt    420
aaggacaaca tgcttgtagc tatggaaggt agtgttggtt atggtattgg tggtgccagg    480
gttgagcttg agattggtta cgagcgcttc aagaccaagg gtattagaga tagtggtagt    540
aaggaagatg aagctgatac agtatatcta ctagctaagg agttagctta tgatgttgtt    600
actgggcaga ctgataacct tgctgctgct cttgccaaga cctctggtaa agatattgtt    660
cagtttgcta aggcggttgg ggtttctcat cccggtattg ataagaaggt ttgtgatggg    720
ggtcatgcac ggggaaaaaa gagtggagat aatggctcgc tggccgacta tacggatggt    780
ggcgcgtcac agacgaataa gacggctcag tgtagtggta tgggaaccgg caaagccggc    840
aagagaggat tgggcttgac tgagtttgtt aacaaaacaa aggttggaga aggtaagaat    900
tggccaacgg ggtacgttaa tgatggcgac aacgttaatg tgctcggcga tacgaatggt    960
aacgccgaag ccgtagctaa agacctagta caggagctaa cccctgaaga aaaaaccata   1020
gtagcagggt tactagctaa gactattgaa gggggtgaag ttgttgagat cagggcggtt   1080
tcttctactt ccgtaatggt caatgcttgt tatgatcttc ttagtgaagg tttaggtgtt   1140
gttccttatg cttgtgttgg tcttggcggt aacttcgtgg gcgtggttga tggccatatc   1200
actcctaagc ttgcttatag attaaaggct gggttgagtt atcagctctc tcctgtaatc   1260
tccgcttttg cgggtggatt ctaccatcgc gttgtgggag atggcgttta tgatgatctg   1320
ccggctcaac gtcttgtaga tgatactagt ccggcgggtc gtactaagga tactgctatt   1380
gctaacttct ccatggctta tgtcggtggg gaatttggtg ttaggtttgc tttttaagct   1440
tgcttatcta aagagggggg ctaagggctc cccttttcta ctttaattct acttcctgcg   1500
gtacttcacc ctcttcctga cttcttctgg ttctgctacc attaattatt actccgtgac   1560
cgttcctatt atttattttc ttgctgctca ggttagaagg tttctatcag tgcttgatgg   1620
ggatttggcg tgtttttata gtgcaaatcg catcgctccc atttgtacaa atcttgacac   1680
ttttggcttc aatgtctatt gttgagcagt taaaattctt gtgataccc atggttgaaa   1740
tgctattggt cagattgaac tgaaggactc cccctctgat aagcagcggg ctgttgatgc   1800
gcgcttttgg gcgtggatct attatgaggc tgcagaatag                         1840
```

<210> SEQ ID NO 27
<211> LENGTH: 435
<212> TYPE: PRT
<213> ORGANISM: Granulocytic Ehrlichia
<220> FEATURE:
<223> OTHER INFORMATION: E8 msp2 gene

<400> SEQUENCE: 27

```
Met Arg Lys Gly Lys Ile Ile Leu Gly Ser Val Met Ser Met Ala
1               5                   10                  15

Ile Val Met Ala Gly Asn Asp Val Arg Ala His Asp Val Ser Ala
                20                  25                  30

Leu Glu Thr Gly Gly Ala Gly Tyr Phe Tyr Val Gly Leu Asp Tyr Ser
            35                  40                  45

Pro Ala Phe Ser Lys Ile Arg Asp Phe Ser Ile Arg Glu Ser Asn Gly
    50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
                100                 105                 110

Ile Gly Gly Ala Arg Val Glu Leu Glu Ile Gly Tyr Glu Arg Phe Lys
            115                 120                 125

Thr Lys Gly Ile Arg Asp Ser Gly Ser Lys Glu Asp Glu Ala Asp Thr
    130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Ile
                165                 170                 175

Val Gln Phe Ala Lys Ala Val Gly Val Ser His Pro Gly Ile Asp Lys
                180                 185                 190

Lys Val Cys Asp Gly Gly His Ala Arg Gly Lys Lys Ser Gly Asp Asn
            195                 200                 205

Gly Ser Leu Ala Asp Tyr Thr Asp Gly Gly Ala Ser Gln Thr Asn Lys
    210                 215                 220

Thr Ala Gln Cys Ser Gly Met Gly Thr Gly Lys Ala Gly Lys Arg Gly
225                 230                 235                 240

Leu Gly Leu Thr Glu Phe Val Asn Lys Thr Lys Val Gly Glu Gly Lys
                245                 250                 255

Asn Trp Pro Thr Gly Tyr Val Asn Asp Gly Asp Asn Val Asn Val Leu
                260                 265                 270

Gly Asp Thr Asn Gly Asn Ala Glu Ala Val Ala Lys Asp Leu Val Gln
    275                 280                 285

Glu Leu Thr Pro Glu Glu Lys Thr Ile Val Ala Gly Leu Leu Ala Lys
    290                 295                 300

Thr Ile Glu Gly Gly Glu Val Val Glu Ile Arg Ala Val Ser Ser Thr
305                 310                 315                 320

Ser Val Met Val Asn Ala Cys Tyr Asp Leu Leu Ser Glu Gly Leu Gly
                325                 330                 335

Val Val Pro Tyr Ala Cys Val Gly Leu Gly Gly Asn Phe Val Gly Val
                340                 345                 350

Val Asp Gly His Ile Thr Pro Lys Leu Ala Tyr Arg Leu Lys Ala Gly
            355                 360                 365

Leu Ser Tyr Gln Leu Ser Pro Val Ile Ser Ala Phe Ala Gly Gly Phe
    370                 375                 380

Tyr His Arg Val Gly Asp Gly Val Tyr Asp Asp Leu Pro Ala Gln
385                 390                 395                 400

Arg Leu Val Asp Asp Thr Ser Pro Ala Gly Arg Thr Lys Asp Thr Ala
                405                 410                 415

Ile Ala Asn Phe Ser Met Ala Tyr Val Gly Gly Glu Phe Gly Val Arg
                420                 425                 430
```

Phe Ala Phe
    435

<210> SEQ ID NO 28
<211> LENGTH: 3435
<212> TYPE: DNA
<213> ORGANISM: Artificial Sequence
<220> FEATURE:
<223> OTHER INFORMATION: E46 gene inset in Lambda Zap II

<400> SEQUENCE: 28

| | | | | | |
|---|---|---|---|---|---|
| tttttatatc | tggagctctt | gtactgtgtt | taccacggga | tttattattg | ggtaggcttg | 60 |
| atattcaggc | tctatcaacg | cagctattca | tggcattatt | acagataaat | ttggcatttt | 120 |
| ggagataggc | gatctagggt | tctattatta | ggaatctatt | atttagatat | atagggatat | 180 |
| aagggagagt | aacggagaga | ctaaggcagt | atatccatac | ttaaaggatg | gaaagagtgt | 240 |
| aaagctagag | tcacacaagt | ttgactggaa | cactcctgat | cctcggattg | ggtttaagga | 300 |
| caacatgctt | gtagctatgg | aaggcagtgt | tggttatggt | attggtggtg | ccagggttga | 360 |
| gcttgagatt | ggttacgagc | gcttcaagac | caagggtatt | agagatagtg | gtagtaagga | 420 |
| agatgaagca | gatacagtat | atctactagc | taaggagtta | gcttatgatg | ttgttactgg | 480 |
| acagactgat | aaccttgccg | ctgctcttgc | caaaaccctcg | gggaaggaca | tcgttcagtt | 540 |
| tgccaatgct | gtgaaaattt | cttaccctaa | aattgatgag | caggtttgta | ataaaaatca | 600 |
| tacagtgttg | aatacgggga | aagggacaac | ctttaatcca | gatcccaaga | caaccgaaga | 660 |
| taatacagcg | cagtgcagtg | ggttgaacac | gaagggaacg | aataagttta | gcgattttgc | 720 |
| tgaaggtgta | ggtttgaaag | ataataagaa | ttggcctact | ggtcaggctg | ggaagagcag | 780 |
| tggtggtcct | gtggtgggtg | catctaatag | taatgccaac | gctatggcta | gagacctagt | 840 |
| agatcttaat | cgagacgaaa | aaaccatagt | agcagggtta | ctagctaaaa | ctattgaagg | 900 |
| tggtgaggtt | gttgagatta | gggcggtttc | ttctacttct | gtaatggtca | atgcttgtta | 960 |
| tgatcttctt | agtgaaggtc | taggcgttgt | tccttacgct | tgtgtcggtc | ttggaggtaa | 1020 |
| cttcgtgggc | gttgttgatg | ggcatatcac | tcctaagctt | gcttatagat | aaaggctgg | 1080 |
| gttgagttat | cagctctctc | ctgaaatctc | cgcttttgct | ggggattct | atcatcgcgt | 1140 |
| tgtgggagat | ggtgtctatg | atgatcttcc | agctcaacgt | cttgtagatg | atactagtcc | 1200 |
| ggcgggtcgt | actaaggata | ctgctattgc | taacttctcc | atggcttatg | tcggtgggga | 1260 |
| atttggtgtt | aggtttgctt | tttaaggtgg | tttgttggaa | gcggggtaag | tcaaacttac | 1320 |
| cccgcttcta | ttagggagtt | agtatatgag | atctagaagt | aagctatttt | taggaagcgt | 1380 |
| aatgatgtcg | ttggctatag | taatggctgg | gaatgatgtc | agggctcatg | atgacgttag | 1440 |
| cgctttggat | actggtggtg | cgggatattt | ctatgttggt | ttggattaca | gtccagcgtt | 1500 |
| tagcaagata | agagatttta | gtataaggga | gagtaacgga | gagactaagg | cagtatatcc | 1560 |
| atacttaaag | gatggaaaga | gtgtaaagct | agagtcacac | aagtttgact | ggaacactcc | 1620 |
| tgatcctcgg | attgggttta | aggacaacat | gcttgtagct | atggaaggta | gtgttggtta | 1680 |
| tggtattggt | ggtgccaggg | ttgagcttga | gattggttac | gagcgcttca | agaccaaggg | 1740 |
| tattagagat | agtggtagta | aggaagatga | agctgataca | gtatatctac | tagctaagga | 1800 |
| gttggcttat | gatgttgtta | ctgggcagac | tgataacctt | gccgctgctc | tggccaaaac | 1860 |
| ctccggtaaa | gactttgtcc | agtttgctaa | ggcggttggg | gtttctcatc | ctagtattga | 1920 |
| tgggaaggtt | tgtaagacga | aggcggatag | ctcgaagaaa | tttccgttat | atagtgacga | 1980 |

```
aacgcacacg aagggggcaa gtgagggag aacgtctttg tgcggtgaca atggtagttc    2040
tacgataaca aacagtggtg cgaatgtaag tgaaactggg caggttttta gggattttat    2100
cagggcaacg ctgaaagagg atggtagtaa aaactggcca acttcaagcg gcacgggaac    2160
tccaaaacct gtcacgaacg acaacgccaa agccgtagct aaagacctag tacaggagct    2220 aaccccctgaa gaaaaaacca tagtagcagg gttactagct aaaactattg aaggtggtga    2280
ggttattgaa atcagggcgg tttcttctac ttctgtgatg gtcaatgctt gttatgatct    2340
tcttagtgaa ggtttaggtg ttgtccctta tgcttgtgtt ggtctcggtg gtaacttcgt    2400
gggcgtggtt gatggaattc attacacaaa ccatctttaa ctctgaatac cctagttaag    2460
gtaagtgaag taactaggca aattagtgct gcaccactcg tgaaacaaac tacgatcagc    2520
gattcaccat acttagtaag tccgtacagt ggctttacgc tcttacccat catgaaaaat    2580
acttgctatc taggaatctc ctctaaaact ttacagaggt tatctgtact tcgagaggaa    2640
gctaatctgt ggctcatgag gatggtattt agcgtatcac aggttccagc tgtcttacag    2700
tctctggaga tgttataagg gtgcacatat aaaactatgc aatatttcgc tgcaatacga    2760
ttccgattcg aaaacactga aaagtattcc cattatctat gaatctctgt gtagatataa    2820
ataagggtat acgcagtaac tcttacttgt taaaaacaag accaatggta taaggaaaaa    2880
gcctcagtgt tgttcctcat gcttgcagct tacccgatgc actcttattt aataaggttg    2940
aatgttaatc agtgtttctg ggaagggaat atcttattgc aaaaccctca gcagctgctt    3000
agatattgaa acaaatgcga tcatgccgtc agcacaatta tgacatctct taaggctctg    3060
tagtgcgctt atttagtcta acatgtggta aagctttgcc agttctttac cacatgttca    3120
ccatcagtta attgaaagca aatcttgctc ctatgttgaa gccgtaacta gctatatttg    3180
cctttacctt ggctgcagca ccacctgcta tgtttacacg gttactagcg ggaatacctg    3240
catactgttc atcgaaaatt ccgtggtaaa aacctccagc tattaaagat atttcaggag    3300
taagcttgta acttacgcct acctttcctc tataagccaa cttacttgta acgtgatcgg    3360
cgatattaat aaagctcgcc cctaacccag cacacatgta aggagggaat tcgatatcaa    3420
gcttatcgat accgt                                                     3435
```

<210> SEQ ID NO 29
<211> LENGTH: 326
<212> TYPE: PRT
<213> ORGANISM: Granulocytic Ehrlichia
<220> FEATURE:
<223> OTHER INFORMATION: E46#1

<400> SEQUENCE: 29

Met Leu Val Ala Met Glu Gly Ser Val Gly Tyr Gly Ile Gly Gly Ala
1               5                   10                  15

Arg Val Glu Leu Glu Ile Gly Tyr Glu Arg Phe Lys Thr Lys Gly Ile
            20                  25                  30

Arg Asp Ser Gly Ser Lys Glu Asp Glu Ala Asp Thr Val Tyr Leu Leu
        35                  40                  45

Ala Lys Glu Leu Ala Tyr Asp Val Val Thr Gly Gln Thr Asp Asn Leu
    50                  55                  60

Ala Ala Ala Leu Ala Lys Thr Ser Gly Lys Asp Ile Val Gln Phe Ala
65                  70                  75                  80

Asn Ala Val Lys Ile Ser Tyr Pro Lys Ile Asp Glu Gln Val Cys Asn
                85                  90                  95

Lys Asn His Thr Val Leu Asn Thr Gly Lys Gly Thr Thr Phe Asn Pro
            100                 105                 110

Asp Pro Lys Thr Thr Glu Asp Asn Thr Ala Gln Cys Ser Gly Leu Asn
            115                 120                 125

Thr Lys Gly Thr Asn Lys Phe Ser Asp Phe Ala Glu Gly Val Gly Leu
130                 135                 140

Lys Asp Asn Lys Asn Trp Pro Thr Gly Gln Ala Gly Lys Ser Ser Gly
145                 150                 155                 160

Gly Pro Val Val Gly Ala Ser Asn Ser Asn Ala Asn Ala Met Ala Arg
                165                 170                 175

Asp Leu Val Asp Leu Asn Arg Asp Glu Lys Thr Ile Val Ala Gly Leu
            180                 185                 190

Leu Ala Lys Thr Ile Glu Gly Glu Val Val Glu Ile Arg Ala Val
        195                 200                 205

Ser Ser Thr Ser Val Met Val Asn Ala Cys Tyr Asp Leu Leu Ser Glu
        210                 215                 220

Gly Leu Gly Val Val Pro Tyr Ala Cys Val Gly Leu Gly Gly Asn Phe
225                 230                 235                 240

Val Gly Val Val Asp Gly His Ile Thr Pro Lys Leu Ala Tyr Arg Leu
                245                 250                 255

Lys Ala Gly Leu Ser Tyr Gln Leu Ser Pro Glu Ile Ser Ala Phe Ala
            260                 265                 270

Gly Gly Phe Tyr His Arg Val Val Gly Asp Gly Val Tyr Asp Asp Leu
        275                 280                 285

Pro Ala Gly Arg Leu Val Asp Asp Thr Ser Pro Ala Gly Arg Thr Lys
        290                 295                 300

Asp Thr Ala Ile Ala Asn Phe Ser Met Ala Tyr Val Gly Gly Glu Phe
305                 310                 315                 320

Gly Val Arg Phe Ala Phe
                325

<210> SEQ ID NO 30
<211> LENGTH: 364
<212> TYPE: PRT
<213> ORGANISM: Granulocytic Ehrlichia
<220> FEATURE:
<223> OTHER INFORMATION: E46#2

<400> SEQUENCE: 30

Met Arg Ser Arg Ser Lys Leu Phe Leu Gly Ser Val Met Met Ser Leu
1               5                   10                  15

Ala Ile Val Met Ala Gly Asn Asp Val Arg Ala His Asp Asp Val Ser
            20                  25                  30

Ala Leu Asp Thr Gly Gly Ala Gly Tyr Phe Tyr Val Gly Leu Asp Tyr
        35                  40                  45

Ser Pro Ala Phe Ser Lys Ile Arg Asp Phe Ser Ile Arg Glu Ser Asn
50                  55                  60

Gly Glu Thr Lys Ala Val Tyr Pro Tyr Leu Lys Asp Gly Lys Ser Val
65                  70                  75                  80

Lys Leu Glu Ser His Lys Phe Asp Trp Asn Thr Pro Asp Pro Arg Ile
            85                  90                  95

Gly Phe Lys Asp Asn Met Leu Val Ala Met Glu Gly Ser Val Gly Tyr
                100                 105                 110

Gly Ile Gly Gly Ala Arg Val Glu Leu Glu Ile Gly Tyr Glu Arg Phe
            115                 120                 125

Lys Thr Lys Gly Ile Arg Asp Ser Gly Ser Lys Glu Asp Glu Ala Asp
        130                 135                 140

```
Thr Val Tyr Leu Leu Ala Lys Glu Leu Ala Tyr Asp Val Val Thr Gly
145                 150                 155                 160

Gln Thr Asp Asn Leu Ala Ala Leu Ala Lys Thr Ser Gly Lys Asp
            165                 170                 175

Phe Val Gln Phe Ala Lys Ala Val Gly Val Ser His Pro Ser Ile Asp
            180                 185                 190

Gly Lys Val Cys Lys Thr Lys Ala Asp Ser Ser Lys Lys Phe Pro Leu
            195                 200                 205

Tyr Ser Asp Glu Thr His Thr Lys Gly Ala Ser Glu Gly Arg Thr Ser
            210                 215                 220

Leu Cys Gly Asp Asn Gly Ser Ser Thr Ile Thr Asn Ser Gly Ala Asn
225                 230                 235                 240

Val Ser Glu Thr Gly Gln Val Phe Arg Asp Phe Ile Arg Ala Thr Leu
            245                 250                 255

Lys Glu Asp Gly Ser Lys Asn Trp Pro Thr Ser Ser Gly Thr Gly Thr
            260                 265                 270

Pro Lys Pro Val Thr Asn Asp Asn Ala Lys Ala Val Ala Lys Asp Leu
            275                 280                 285

Val Gln Glu Leu Thr Pro Glu Glu Lys Thr Ile Val Ala Gly Leu Leu
            290                 295                 300

Ala Lys Thr Ile Glu Gly Gly Glu Val Ile Glu Ile Arg Ala Val Ser
305                 310                 315                 320

Ser Thr Ser Val Met Val Asn Ala Cys Tyr Asp Leu Leu Ser Glu Gly
            325                 330                 335

Leu Gly Val Val Pro Tyr Ala Cys Val Gly Leu Gly Gly Asn Phe Val
            340                 345                 350

Gly Val Val Asp Gly Ile His Tyr Thr Asn His Leu
            355                 360

<210> SEQ ID NO 31
<211> LENGTH: 409
<212> TYPE: PRT
<213> ORGANISM: A. marginale
<220> FEATURE:
<223> OTHER INFORMATION: msp-2 gene

<400> SEQUENCE: 31

Met Ser Ala Val Ser Asn Arg Lys Leu Pro Leu Gly Gly Val Leu Met
1               5                   10                  15

Ala Leu Ala Ala Ala Val Ala Pro Ile His Ser Leu Leu Ala Ala Pro
            20                  25                  30

Ala Ala Gly Ala Gly Ala Gly Gly Glu Gly Leu Phe Ser Gly Ala Gly
            35                  40                  45

Ala Gly Ser Phe Tyr Ile Gly Leu Asp Tyr Ser Pro Ala Phe Gly Ser
            50                  55                  60

Ile Lys Asp Phe Lys Val Gln Glu Ala Gly Gly Thr Thr Arg Gly Val
65                  70                  75                  80

Phe Pro Tyr Lys Arg Asp Ala Ala Gly Arg Val Asp Phe Lys Val His
            85                  90                  95

Asn Phe Asp Trp Ser Ala Pro Glu Pro Lys Ile Ser Phe Lys Asp Ser
            100                 105                 110

Met Leu Thr Ala Leu Glu Gly Ser Ile Gly Tyr Ser Ile Gly Gly Ala
            115                 120                 125

Arg Val Glu Val Glu Val Gly Tyr Glu Arg Phe Val Ile Lys Gly Gly
            130                 135                 140

Lys Lys Ser Asn Glu Asp Thr Ala Ser Val Phe Leu Leu Gly Lys Glu
```

```
            145                 150                 155                 160
Leu Ala Tyr His Thr Ala Arg Gly Gln Val Asp Arg Leu Ala Thr Ala
                165                 170                 175
Leu Gly Lys Met Thr Lys Ser Glu Ala Lys Lys Trp Gly Asn Ala Ile
            180                 185                 190
Glu Ser Ala Thr Gly Thr Thr Ser Gly Asp Glu Leu Ser Lys Lys Val
        195                 200                 205
Cys Gly Lys Gly Thr Thr Ser Gly Ser Thr Asn Gln Cys Gly Thr Thr
    210                 215                 220
Asp Ser Thr Ala Thr Thr Lys Ile Ser Ala Val Phe Thr Glu Asp Ala
225                 230                 235                 240
Ala Ala Gln Leu Ser Thr Met Asp Asn Thr Thr Ile Asn Thr Thr Gly
                245                 250                 255
Met Ala Asn Asn Ile Asn Ser Leu Thr Lys Asp Glu Lys Ala Ile Val
            260                 265                 270
Ala Gly Ala Phe Ala Arg Ala Val Glu Gly Ala Glu Val Ile Glu Val
        275                 280                 285
Arg Ala Ile Gly Ser Thr Ser Val Met Leu Asn Ala Cys Tyr Asp Leu
    290                 295                 300
Leu Thr Asp Gly Ile Gly Val Val Pro Tyr Ala Cys Ala Gly Ile Gly
305                 310                 315                 320
Gly Asn Phe Val Ser Val Asp Gly His Ile Asn Pro Lys Phe Ala
                325                 330                 335
Tyr Arg Val Lys Ala Gly Leu Ser Tyr Ala Leu Thr Pro Glu Ile Ser
                340                 345                 350
Ala Phe Ala Gly Ala Phe Tyr His Lys Val Leu Gly Asp Gly Asp Tyr
            355                 360                 365
Asp Glu Leu Pro Leu Ser His Ile Ser Asp Tyr Thr Gly Thr Ala Gly
        370                 375                 380
Lys Asn Lys Asp Thr Gly Ile Ala Ser Phe Asn Phe Ala Tyr Phe Gly
385                 390                 395                 400
Gly Glu Leu Gly Val Arg Phe Ala Phe
                405

<210> SEQ ID NO 32
<211> LENGTH: 20
<212> TYPE: DNA
<213> ORGANISM: Artificial Sequence
<220> FEATURE:
<221> NAME/KEY: misc_feature
<222> LOCATION: 3, 18
<223> OTHER INFORMATION: n = A,T,C or G
<220> FEATURE:
<223> OTHER INFORMATION: Synthetic nucleotide - degenerate primer

<400> SEQUENCE: 32
ccnttycaya tgtayccngg                                                       20

<210> SEQ ID NO 33
<211> LENGTH: 20
<212> TYPE: DNA
<213> ORGANISM: Artificial Sequence
<220> FEATURE:
<221> NAME/KEY: misc_feature
<222> LOCATION: 3, 6, 15, 18
<223> OTHER INFORMATION: n = A,T,C or G
<220> FEATURE:
<223> OTHER INFORMATION: Synthetic nucleotide - degenerate primer

<400> SEQUENCE: 33
```
ggnckngcrt aytcnccngc                                           20

<210> SEQ ID NO 34
<211> LENGTH: 24
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 34

Pro Phe His Met Tyr Pro Gly Ser Glu Asn Leu Phe Arg Ser Thr Arg
1               5                   10                  15

Asp Leu Arg Gly Val Ser Gly Val
            20

<210> SEQ ID NO 35
<211> LENGTH: 13
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 35

Phe Arg Leu Ser Leu Ala Gly Glu Tyr Ala Arg Pro Lys
1               5                   10

<210> SEQ ID NO 36
<211> LENGTH: 9
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 36

Glu Leu Val Val Gly Glu Asn Thr Leu
1               5

<210> SEQ ID NO 37
<211> LENGTH: 14
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 37

Glu Asp Thr Val Arg Asp Gly Ile Ala Gly Phe Asp Ser Leu
1               5                   10

<210> SEQ ID NO 38
<211> LENGTH: 2097
<212> TYPE: DNA
<213> ORGANISM: Granulocytic Ehrlichia
<220> FEATURE:
<221> NAME/KEY: CDS
<222> LOCATION: (338)...(1972)
<223> OTHER INFORMATION: S11 of Granulocytic Ehrlichia

<400> SEQUENCE: 38
gaattcctag caacaagggt ggatatttca cgcttgctag gctgagtgat ttaggactga      60
gggtgagcta tgagatgtat aggggggaga gtatgcgctg cgtgcttttt actcagcttc    120
ataagatagc ggcgagctac agctttgcta cggggttcgt agaaaagcgt tatttgtcgct   180 ataacactcg tgatgtatat catcgtgatg tcggttataa ggatcatgga tgtgctatgg    240

```
ttaagccttt gaagtatgac tttggcttga tggctttagg tgtgaagctg gtcttctaag      300
aagagtgtgg gtgtttgtgg attttttgaag gttttgt atg aga ggt tct ctg gta      355
                                         Met Arg Gly Ser Leu Val
                                         1               5 gtt gtg agt atg gcg atg ctt ctc ctg ggg tcc tct ggt ggt gta gtt      403
Val Val Ser Met Ala Met Leu Leu Leu Gly Ser Ser Gly Gly Val Val
            10                  15                  20 gct gca tct tct gga ggg ggg ttt gaa gga gag cgt gcg tcg gta acg      451
Ala Ala Ser Ser Gly Gly Gly Phe Glu Gly Glu Arg Ala Ser Val Thr
            25                  30                  35 ggt aag gtg tta tct tat gcc tgg ttg ttg agt gat cgg gct gta aaa      499
Gly Lys Val Leu Ser Tyr Ala Trp Leu Leu Ser Asp Arg Ala Val Lys
    40                  45                  50 ggg caa ggt aac agt gaa ggt cag aag ctc gcg ctg gaa atg tat ggc      547
Gly Gln Gly Asn Ser Glu Gly Gln Lys Leu Ala Leu Glu Met Tyr Gly
55              60                  65                  70 gca aag ttg ggc tat aag ggt tat ggt tat cca gga gtt gga gat gtc      595
Ala Lys Leu Gly Tyr Lys Gly Tyr Gly Tyr Pro Gly Val Gly Asp Val
                75                  80                  85 ttt tct tcg ccg ttg gag cat ggt ctt gat tct tgg gga gct agc tat      643
Phe Ser Ser Pro Leu Glu His Gly Leu Asp Ser Trp Gly Ala Ser Tyr
            90                  95                  100 gat gcg atg tta tct ctt gga ttg cgt acg ggt cgt gat gtg cta ggt      691
Asp Ala Met Leu Ser Leu Gly Leu Arg Thr Gly Arg Asp Val Leu Gly
            105                 110                 115 acc caa tat ggg gca aat ttt tcc ctt atg gtt cct gcg ggt tct ggt      739
Thr Gln Tyr Gly Ala Asn Phe Ser Leu Met Val Pro Ala Gly Ser Gly
    120                 125                 130 gga tct atg gtg ttt cat ggt gcg cct ggt ata gag agc agg gtt ttt      787
Gly Ser Met Val Phe His Gly Ala Pro Gly Ile Glu Ser Arg Val Phe
135             140                 145                 150 gct gat act tcc ttg gga aat ttt tct gtt ggt tac cag gaa ggt gtc      835
Ala Asp Thr Ser Leu Gly Asn Phe Ser Val Gly Tyr Gln Glu Gly Val
                155                 160                 165 gag tca aaa atg aag gtg gat gtc ttc ggt ggc tta tca ggt gaa aat      883
Glu Ser Lys Met Lys Val Asp Val Phe Gly Gly Leu Ser Gly Glu Asn
            170                 175                 180 gga agc gct tgg ggt cgg tac ttg cgt ggc ttt tta aag tat gcg aag      931
Gly Ser Ala Trp Gly Arg Tyr Leu Arg Gly Phe Leu Lys Tyr Ala Lys
        185                 190                 195 ggt gta cct ttt cac atg tat cca ggg ctt tac agt gag aat tta ttc      979
Gly Val Pro Phe His Met Tyr Pro Gly Leu Tyr Ser Glu Asn Leu Phe
    200                 205                 210 cgg tct aca aga gac tta cgg ggt gtt agt ggt gtt tct gcg aag aca     1027
Arg Ser Thr Arg Asp Leu Arg Gly Val Ser Gly Val Ser Ala Lys Thr
215                 220                 225                 230 aag gat gtc tta aat tct atg ccg ctg agg ttt tct ttt gag tct gct     1075
Lys Asp Val Leu Asn Ser Met Pro Leu Arg Phe Ser Phe Glu Ser Ala
                235                 240                 245 agg ttg ggt ggc ttg tct gtt ggt ttt agt tac tct cca acg gga tat     1123
Arg Leu Gly Gly Leu Ser Val Gly Phe Ser Tyr Ser Pro Thr Gly Tyr
        250                 255                 260 cgg gat gat atg tac aag ggt gga gag ttt act gta cgg gat ggt att     1171
Arg Asp Asp Met Tyr Lys Gly Gly Glu Phe Thr Val Arg Asp Gly Ile
    265                 270                 275 gct ggt ttc gat tcc ttg ggt aca gta aat tta ttc gcg aag acg ggg     1219
Ala Gly Phe Asp Ser Leu Gly Thr Val Asn Leu Phe Ala Lys Thr Gly
280                 285                 290 gtt aag ttt ggc aaa atg att gcc gtg gtg cct cct cgt ttt gat tct     1267
```

```
Val Lys Phe Gly Lys Met Ile Ala Val Val Pro Pro Arg Phe Asp Ser
295                 300                 305                 310 ggt ccg gta tat aaa aac ata gta agc ggt gct gcg aat tac gag tac    1315
Gly Pro Val Tyr Lys Asn Ile Val Ser Gly Ala Ala Asn Tyr Glu Tyr
                315                 320                 325 gag tta gcc gat att gct aag ttt agg tta tcg ctt gct ggt gag tat    1363
Glu Leu Ala Asp Ile Ala Lys Phe Arg Leu Ser Leu Ala Gly Glu Tyr
            330                 335                 340 gca aga ccg aag aag gct agg gat ata gtg cca gaa gga aga aga aag    1411
Ala Arg Pro Lys Lys Ala Arg Asp Ile Val Pro Glu Gly Arg Arg Lys
        345                 350                 355 gaa gaa att tat gta gct gat tac aat gat ttg tcc gcg ttt tcc agt    1459
Glu Glu Ile Tyr Val Ala Asp Tyr Asn Asp Leu Ser Ala Phe Ser Ser
    360                 365                 370 ggc tta gaa ata gac ttg ggt agg ttg cgg ttt gct gtt ggc ggt gga    1507
Gly Leu Glu Ile Asp Leu Gly Arg Leu Arg Phe Ala Val Gly Gly Gly
375                 380                 385                 390 tac ctt ggg aag tct ggt agt cct aaa atg tac ata tta aag gat gta    1555
Tyr Leu Gly Lys Ser Gly Ser Pro Lys Met Tyr Ile Leu Lys Asp Val
                395                 400                 405 aga cat aag gta cct tat gtg aaa aag aag ggt ttg ccg tct cat tat    1603
Arg His Lys Val Pro Tyr Val Lys Lys Lys Gly Leu Pro Ser His Tyr
            410                 415                 420 gtg act tca gcg gtt tcc tat acg att ggt tct ttc tct gct aca gtt    1651
Val Thr Ser Ala Val Ser Tyr Thr Ile Gly Ser Phe Ser Ala Thr Val
        425                 430                 435 gct tac ttt atg agt agg tta acg cac att ccg cct gct acg gta tct    1699
Ala Tyr Phe Met Ser Arg Leu Thr His Ile Pro Pro Ala Thr Val Ser
    440                 445                 450 cat aag atc cca ggg aag tat gag ttg gat tcc gtt gtg gat ggg gag    1747
His Lys Ile Pro Gly Lys Tyr Glu Leu Asp Ser Val Val Asp Gly Glu
455                 460                 465                 470 aat acg ttg aag gat ttg gtt gta gga gtc ggt tat aac ctt ttt agt    1795
Asn Thr Leu Lys Asp Leu Val Val Gly Val Gly Tyr Asn Leu Phe Ser
                475                 480                 485 aag gga agt acg agc tta gaa gta ttt cta aat tgt cac atg ttc tct    1843
Lys Gly Ser Thr Ser Leu Glu Val Phe Leu Asn Cys His Met Phe Ser
            490                 495                 500 gtg caa cat aaa ttc aac atc cat gag tac aaa tct act gag agt agt    1891
Val Gln His Lys Phe Asn Ile His Glu Tyr Lys Ser Thr Glu Ser Ser
        505                 510                 515 ggg ttt gta ttg aaa gaa ggt gga gag cgt gca aat act aat aat ggc    1939
Gly Phe Val Leu Lys Glu Gly Gly Glu Arg Ala Asn Thr Asn Asn Gly
    520                 525                 530 gct gtg gcg tta tta gga atg aag ttt gcg ttt taataacaag gggttgttgc   1992
Ala Val Ala Leu Leu Gly Met Lys Phe Ala Phe
535                 540                 545 aagaatactc ttgtggttta tttagccaag tcttcttatt ggggcgtgta ctgaggtacg   2052
gcgccccttt ttttgtggag agtctaaggt ttgttatgtt gtaga                   2097

<210> SEQ ID NO 39
<211> LENGTH: 545
<212> TYPE: PRT
<213> ORGANISM: Granulocytic Ehrlichia
<220> FEATURE:
<223> OTHER INFORMATION: open reading frame of Granulocytic Ehrlichia
      S11

<400> SEQUENCE: 39

Met Arg Gly Ser Leu Val Val Ser Met Ala Met Leu Leu Leu Gly
1               5                   10                  15
```

Ser Ser Gly Gly Val Ala Ala Ser Ser Gly Gly Phe Glu Gly
        20                  25                  30

Glu Arg Ala Ser Val Thr Gly Lys Val Leu Ser Tyr Ala Trp Leu Leu
            35                  40                  45

Ser Asp Arg Ala Val Lys Gly Gln Gly Asn Ser Glu Gly Gln Lys Leu
50                  55                  60

Ala Leu Glu Met Tyr Gly Ala Lys Leu Gly Tyr Lys Gly Tyr Gly Tyr
65                  70                  75                  80

Pro Gly Val Gly Asp Val Phe Ser Ser Pro Leu Glu His Gly Leu Asp
                85                  90                  95

Ser Trp Gly Ala Ser Tyr Asp Ala Met Leu Ser Leu Gly Leu Arg Thr
                100                 105                 110

Gly Arg Asp Val Leu Gly Thr Gln Tyr Gly Ala Asn Phe Ser Leu Met
                115                 120                 125

Val Pro Ala Gly Ser Gly Ser Met Val Phe His Gly Ala Pro Gly
130                 135                 140

Ile Glu Ser Arg Val Phe Ala Asp Thr Ser Leu Gly Asn Phe Ser Val
145                 150                 155                 160

Gly Tyr Gln Glu Gly Val Glu Ser Lys Met Lys Val Asp Val Phe Gly
                165                 170                 175

Gly Leu Ser Gly Glu Asn Gly Ser Ala Trp Gly Arg Tyr Leu Arg Gly
                180                 185                 190

Phe Leu Lys Tyr Ala Lys Gly Val Pro Phe His Met Tyr Pro Gly Leu
        195                 200                 205

Tyr Ser Glu Asn Leu Phe Arg Ser Thr Arg Asp Leu Arg Gly Val Ser
        210                 215                 220

Gly Val Ser Ala Lys Thr Lys Asp Val Leu Asn Ser Met Pro Leu Arg
225                 230                 235                 240

Phe Ser Phe Glu Ser Ala Arg Leu Gly Gly Leu Ser Val Gly Phe Ser
                245                 250                 255

Tyr Ser Pro Thr Gly Tyr Arg Asp Asp Met Tyr Lys Gly Gly Glu Phe
                260                 265                 270

Thr Val Arg Asp Gly Ile Ala Gly Phe Asp Ser Leu Gly Thr Val Asn
                275                 280                 285

Leu Phe Ala Lys Thr Gly Val Lys Phe Gly Lys Met Ile Ala Val Val
        290                 295                 300

Pro Pro Arg Phe Asp Ser Gly Pro Val Tyr Lys Asn Ile Val Ser Gly
305                 310                 315                 320

Ala Ala Asn Tyr Glu Tyr Glu Leu Ala Asp Ile Ala Lys Phe Arg Leu
                325                 330                 335

Ser Leu Ala Gly Glu Tyr Ala Arg Pro Lys Lys Ala Arg Asp Ile Val
                340                 345                 350

Pro Glu Gly Arg Arg Lys Glu Glu Ile Tyr Val Ala Asp Tyr Asn Asp
                355                 360                 365

Leu Ser Ala Phe Ser Ser Gly Leu Glu Ile Asp Leu Gly Arg Leu Arg
        370                 375                 380

Phe Ala Val Gly Gly Gly Tyr Leu Gly Lys Ser Gly Ser Pro Lys Met
385                 390                 395                 400

Tyr Ile Leu Lys Asp Val Arg His Lys Val Pro Tyr Val Lys Lys Lys
                405                 410                 415

Gly Leu Pro Ser His Tyr Val Thr Ser Ala Val Ser Tyr Thr Ile Gly
                420                 425                 430

Ser Phe Ser Ala Thr Val Ala Tyr Phe Met Ser Arg Leu Thr His Ile

```
                    435                 440                 445
Pro Pro Ala Thr Val Ser His Lys Ile Pro Gly Lys Tyr Glu Leu Asp
    450                 455                 460

Ser Val Val Asp Gly Glu Asn Thr Leu Lys Asp Leu Val Val Gly Val
465                 470                 475                 480

Gly Tyr Asn Leu Phe Ser Lys Gly Ser Thr Ser Leu Glu Val Phe Leu
                    485                 490                 495

Asn Cys His Met Phe Ser Val Gln His Lys Phe Asn Ile His Glu Tyr
                500                 505                 510

Lys Ser Thr Glu Ser Ser Gly Phe Val Leu Lys Glu Gly Gly Glu Arg
            515                 520                 525

Ala Asn Thr Asn Asn Gly Ala Val Ala Leu Leu Gly Met Lys Phe Ala
    530                 535                 540

Phe
545

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
ctgcaggttt gatcctgg                                             18

<210> SEQ ID NO 41
<211> LENGTH: 22
<212> TYPE: DNA
<213> ORGANISM: Artificial Sequence
<220> FEATURE:
<223> OTHER INFORMATION: Synthetic primer

<400> SEQUENCE: 41
ggatcctacc ttgttacgac tt                                        22

<210> SEQ ID NO 42
<211> LENGTH: 15
<212> TYPE: DNA
<213> ORGANISM: Artificial Sequence
<220> FEATURE:
<223> OTHER INFORMATION: Synthetic primer

<400> SEQUENCE: 42
cacgccttct tctac                                                15

<210> SEQ ID NO 43
<211> LENGTH: 18
<212> TYPE: DNA
<213> ORGANISM: Artificial Sequence
<220> FEATURE:
<223> OTHER INFORMATION: Synthetic primer

<400> SEQUENCE: 43
ctctgttgct atagggggc                                            18

<210> SEQ ID NO 44
<211> LENGTH: 19
<212> TYPE: DNA
<213> ORGANISM: Artificial Sequence
<220> FEATURE:
<223> OTHER INFORMATION: Synthetic primer

<400> SEQUENCE: 44
```
gatgttgctt cgggtatgc                                                19

<210> SEQ ID NO 45
<211> LENGTH: 22
<212> TYPE: DNA
<213> ORGANISM: Artificial Sequence
<220> FEATURE:
<223> OTHER INFORMATION: Synthetic primer

<400> SEQUENCE: 45
cagagattac ttcttttgc gg                                             22

<210> SEQ ID NO 46
<211> LENGTH: 16
<212> TYPE: DNA
<213> ORGANISM: Artificial Sequence
<220> FEATURE:
<223> OTHER INFORMATION: Synthetic primer

<400> SEQUENCE: 46
gcgtctccag aaccag                                                   16

<210> SEQ ID NO 47
<211> LENGTH: 16
<212> TYPE: DNA
<213> ORGANISM: Artificial Sequence
<220> FEATURE:
<223> OTHER INFORMATION: Synthetic primer

<400> SEQUENCE: 47
cctatatagc ttaccg                                                   16

<210> SEQ ID NO 48
<211> LENGTH: 23
<212> TYPE: DNA
<213> ORGANISM: Artificial Sequence
<220> FEATURE:
<223> OTHER INFORMATION: Synthetic primer

<400> SEQUENCE: 48
caggcagtga gcactcaaaa acc                                           23

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
gcgactccaa tgttacaata gtccc                                         25

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
tgtgatcctc gatggttggc                                               20

<210> SEQ ID NO 51
<211> LENGTH: 24
<212> TYPE: DNA
<213> ORGANISM: Artificial Sequence
<220> FEATURE:
<223> OTHER INFORMATION: Synthetic primer

<400> SEQUENCE: 51
ccctcctgaa tcgtaacatc atcc          24

<210> SEQ ID NO 52
<211> LENGTH: 16
<212> TYPE: DNA
<213> ORGANISM: Artificial Sequence
<220> FEATURE:
<223> OTHER INFORMATION: Synthetic primer

<400> SEQUENCE: 52
catgcttgta gctatg          16

<210> SEQ ID NO 53
<211> LENGTH: 17
<212> TYPE: DNA
<213> ORGANISM: Artificial Sequence
<220> FEATURE:
<223> OTHER INFORMATION: Synthetic primer

<400> SEQUENCE: 53
gcaaactgaa caatatc          17

<210> SEQ ID NO 54
<211> LENGTH: 16
<212> TYPE: DNA
<213> ORGANISM: Artificial Sequence
<220> FEATURE:
<223> OTHER INFORMATION: Synthetic primer

<400> SEQUENCE: 54
gacctagtac aggagc          16

<210> SEQ ID NO 55
<211> LENGTH: 16
<212> TYPE: DNA
<213> ORGANISM: Artificial Sequence
<220> FEATURE:
<223> OTHER INFORMATION: Synthetic primer

<400> SEQUENCE: 55
ctataagcaa gcttag          16

<210> SEQ ID NO 56
<211> LENGTH: 22
<212> TYPE: DNA
<213> ORGANISM: Artificial Sequence
<220> FEATURE:
<223> OTHER INFORMATION: Synthetic primer

<400> SEQUENCE: 56
gcgtcacaga cgaataagac gg          22

<210> SEQ ID NO 57
<211> LENGTH: 24
<212> TYPE: DNA
<213> ORGANISM: Artificial Sequence
<220> FEATURE:
<223> OTHER INFORMATION: Synthetic primer

<400> SEQUENCE: 57
agcggagatt acaggagaga gctg          24

```
<210> SEQ ID NO 58
<211> LENGTH: 22
<212> TYPE: DNA
<213> ORGANISM: Artificial Sequence
<220> FEATURE:
<223> OTHER INFORMATION: Synthetic primer

<400> SEQUENCE: 58
tgttgaatac ggggaaaggg ac                                              22

<210> SEQ ID NO 59
<211> LENGTH: 24
<212> TYPE: DNA
<213> ORGANISM: Artificial Sequence
<220> FEATURE:
<223> OTHER INFORMATION: Synthetic primer

<400> SEQUENCE: 59
agcggagatt tcaggagaga gctg                                            24

<210> SEQ ID NO 60
<211> LENGTH: 22
<212> TYPE: DNA
<213> ORGANISM: Artificial Sequence
<220> FEATURE:
<223> OTHER INFORMATION: Synthetic primer

<400> SEQUENCE: 60
tggtttggat tacagtccag cg                                              22

<210> SEQ ID NO 61
<211> LENGTH: 24
<212> TYPE: DNA
<213> ORGANISM: Artificial Sequence
<220> FEATURE:
<223> OTHER INFORMATION: Synthetic primer

<400> SEQUENCE: 61
acctgcccag tttcacttac attc                                            24

<210> SEQ ID NO 62
<211> LENGTH: 28
<212> TYPE: DNA
<213> ORGANISM: Artificial Sequence
<220> FEATURE:
<223> OTHER INFORMATION: Synthetic primer

<400> SEQUENCE: 62
ccggcatatg cttgtagcta tggaaggc                                        28

<210> SEQ ID NO 63
<211> LENGTH: 58
<212> TYPE: DNA
<213> ORGANISM: Artificial Sequence
<220> FEATURE:
<223> OTHER INFORMATION: Synthetic primer

<400> SEQUENCE: 63
ccggctcgag ctagtggtgg tggtggtggt gaaaagcaaa cctaacacca aattcccc       58

<210> SEQ ID NO 64
<211> LENGTH: 16
<212> TYPE: DNA
<213> ORGANISM: Artificial Sequence
<220> FEATURE:
<223> OTHER INFORMATION: Synthetic primer

<400> SEQUENCE: 64
```

```
ccccgggctt tacagt                                                        16
```

<210> SEQ ID NO 65
<211> LENGTH: 16
<212> TYPE: DNA
<213> ORGANISM: Artificial Sequence
<220> FEATURE:
<223> OTHER INFORMATION: Synthetic primer

<400> SEQUENCE: 65

```
ccagcaagcg ataacc                                                        16
```

<210> SEQ ID NO 66
<211> LENGTH: 15
<212> TYPE: PRT
<213> ORGANISM: Granulocytic Ehrlichia

<400> SEQUENCE: 66

```
His Asp Asp Val Ser Ala Leu Glu Thr Gly Gly Ala Gly Tyr Phe
1               5                   10                  15
```

<210> SEQ ID NO 67
<211> LENGTH: 20
<212> TYPE: PRT
<213> ORGANISM: Granulocytic Ehrlichia

<400> SEQUENCE: 67

```
Ser Gly Asp Asn Gly Ser Leu Ala Asp Tyr Thr Asp Gly Gly Ala Ser
1               5                   10                  15

Gln Thr Asn Lys
            20
```

<210> SEQ ID NO 68
<211> LENGTH: 11
<212> TYPE: PRT
<213> ORGANISM: Granulocytic Ehrlichia

<400> SEQUENCE: 68

```
Ala Val Gly Val Ser His Pro Gly Ile Asp Lys
1               5                   10
```

<210> SEQ ID NO 69
<211> LENGTH: 9
<212> TYPE: PRT
<213> ORGANISM: Granulocytic Ehrlichia

<400> SEQUENCE: 69

```
Phe Asp Trp Asn Thr Pro Asp Pro Arg
1               5
```

<210> SEQ ID NO 70
<211> LENGTH: 18
<212> TYPE: PRT
<213> ORGANISM: Granulocytic Ehrlichia

<400> SEQUENCE: 70

```
Leu Ser Tyr Gln Leu Ser Pro Val Ile Ser Ala Phe Ala Gly Gly Phe
1               5                   10                  15

Tyr His
```

<210> SEQ ID NO 71
<211> LENGTH: 21
<212> TYPE: DNA
<213> ORGANISM: Artificial Sequence

```
<220> FEATURE:
<221> NAME/KEY: misc_feature
<222> LOCATION: 3, 6, 9, 15
<223> OTHER INFORMATION: n = A,T,C or G
<220> FEATURE:
<223> OTHER INFORMATION: Synthetic nucleotide - degenerate primer

<400> SEQUENCE: 71 acngnggng cwggntaytt y                                              21

<210> SEQ ID NO 72
<211> LENGTH: 20
<212> TYPE: DNA
<213> ORGANISM: Artificial Sequence
<220> FEATURE:
<221> NAME/KEY: misc_feature
<222> LOCATION: 3, 9, 18
<223> OTHER INFORMATION: n = A,T,C or G
<220> FEATURE:
<223> OTHER INFORMATION: Synthetic nucleotide - degenerate primer

<400> SEQUENCE: 72
ccnccrtcng trtartcngc                                               20
```